United States Patent
Charnley et al.

(10) Patent No.: US 12,247,033 B2
(45) Date of Patent: Mar. 11, 2025

(54) TRIAZOLE-SUBSTITUTED IMIDAZO[1,2-A]PYRIMIDINES AS cGAS INHIBITORS

(71) Applicant: GlaxoSmithKline Intellectual Property Development Limited, Stevenage (GB)

(72) Inventors: Adam K. Charnley, Collegeville, PA (US); Janos Botyanszki, Collegeville, PA (US); Xiaoyang Dong, Collegeville, PA (US); Philip Gareth Humphreys, Stevenage (GB); Bryan Wayne King, Collegeville, PA (US); Kimberly Katherine Marcus, Collegeville, PA (US); Joseph Pero, Collegeville, PA (US); Alexander Joseph Reif, Collegeville, PA (US); Daohua Zhang, Collegeville, PA (US); Attiq Rahman, Collegeville, PA (US); Kenneth Allen Newlander, Collegeville, PA (US); Kenneth Wiggall, Collegeville, PA (US); Joshi Ramanjulu, Collegeville, PA (US)

(73) Assignee: GlaxoSmithKline Intellectual Property Development Limited (GB)

( * ) Notice: Subject to any disclaimer, the term of this patent is extended or adjusted under 35 U.S.C. 154(b) by 0 days.

(21) Appl. No.: 18/586,620

(22) Filed: Feb. 26, 2024

(65) Prior Publication Data
US 2024/0228503 A1 Jul. 11, 2024

Related U.S. Application Data

(63) Continuation of application No. PCT/EP2023/078739, filed on Oct. 17, 2023.

(60) Provisional application No. 63/379,950, filed on Oct. 18, 2022.

(51) Int. Cl.
C07D 487/04 (2006.01)
C07D 403/14 (2006.01)
C07D 471/04 (2006.01)
C07D 471/14 (2006.01)
C07F 9/6561 (2006.01)

(52) U.S. Cl.
CPC ......... C07D 487/04 (2013.01); C07D 403/14 (2013.01); C07D 471/04 (2013.01); C07D 471/14 (2013.01); C07F 9/6561 (2013.01)

(58) Field of Classification Search
CPC .................................................. C07D 487/04
See application file for complete search history.

(56) References Cited

FOREIGN PATENT DOCUMENTS

WO 2022/137082 A1 6/2022
WO 2022/137085 A1 6/2022

OTHER PUBLICATIONS

Tully et al.: "2-(oxadiazolyl)- and 2-(thiazolyl)imidazo[1,2-a]pyrimidines as Agonists and Inverse Agonists at Benzodiazepine Receptors", J. Med. Chem., vol. 34, Jan. 1, 1991 (Jan. 1, 1991), pp. 2060-2067, XP002910638,ISSN: 0022-2623, DOI: 10.1021/JM00111A021 Abstract; p. 2063, table 4: compound 34.

*Primary Examiner* — Brian E McDowell
(74) *Attorney, Agent, or Firm* — W. Brett Stauffer

(57) ABSTRACT

The present invention relates to compounds of Formula (I), (I)

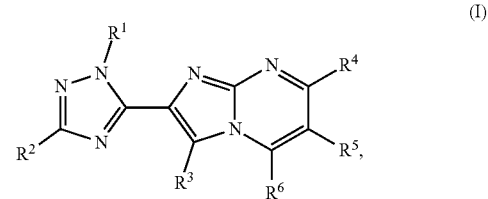

compositions containing them, and to their use in the treatment of various disorders, in particular autoimmune, autoinflammatory or immune-mediated conditions, such as systemic lupus erythematosus (SLE), cutaneous lupus erythematosus (CLE) and lupus nephritis.

28 Claims, No Drawings

TRIAZOLE-SUBSTITUTED IMIDAZO[1,2-A]PYRIMIDINES AS cGAS INHIBITORS

CROSS-REFERENCE TO RELATED APPLICATIONS

This application is a Continuation of PCT/EP2023/078739 filed Oct. 17, 2023, which claims the benefit of U.S. Provisional 63/379,950 filed Oct. 18, 2022, the contents of which are incorporated herein by reference in their entirety.

FIELD OF THE INVENTION

The present invention relates to compounds, compositions containing them, and to their use in the treatment of various disorders, in particular autoimmune, autoinflammatory or immune-mediated conditions, such as systemic lupus erythematosus (SLE), cutaneous lupus erythematosus (CLE), lupus nephritis, Sjogren's syndrome, dermatomyositis, scleroderma, amyotrophic lateral sclerosis (ALS), Parkinson's disease (PD) and Alzheimer's disease (AD), acute kidney injury, chronic kidney disease, diabetic kidney disease or injury, APOL1 nephropathy, focal segmental glomerulosclerosis, membranous nephropathy, idiopathic pulmonary fibrosis, interstitial lung disease, myocardial infarction, stroke, heart hypertrophy/heart failure, nonalcoholic steatohepatitis (NASH) and nonalcoholic fatty liver disease (NAFLD), particularly systemic lupus erythematosus, cutaneous lupus erythematosus and lupus nephritis.

BACKGROUND TO THE INVENTION

Cyclic GMP-AMP synthase (cGAS) is a cytosolic DNA sensor that mediates the production of type I interferons and inflammatory cytokines in response to dsDNA (Sun et al. Science, 33(6121) 786-791, 2013; Cai et al. Mol Cell, 54(2) 289-296, 2014). In the absence of DNA, cGAS exists in an autoinhibited state. Binding to DNA induces a conformational change in the active site, which catalyzes the synthesis of cyclic GMP-AMP (cGAMP) from ATP and GTP (Zhang et al. Cell Rep, 6(3) 421-430, 2014; Gao et al. Cell, 153(5) 1094-1107, 2013; Civril et al. Nature, 498(7454) 332-337, 2013). The generated cGAMP functions as a second messenger that binds and activates stimulator of interferon genes (STING). Activated STING recruits TANK-binding kinase 1 (TBK1), which phosphorylates STING and subsequently the transcription factor IFN regulatory factor 3 (IRF3). Phosphorylated IRF3 dimerizes and translocates into the nucleus, where it functions together with nuclear factor kB (NF-kB), a transcription factor also activated by STING, to turn on the expression of type I IFNs and inflammatory cytokines (Ablasser and Chen, Science, 363(6431) eaat8657, 2019).

While the cGAS-STING pathway has evolved as a major defense mechanism for the detection of microbial infection, activation of cGAS by self-DNA has been linked to a number of monogenic diseases (AGS, FCL, RVCL) as well as multifactorial autoimmune/inflammatory diseases.

Therapeutic targeting of the cGAS-STING pathway with small molecule cGAS inhibitors could be beneficial in a broad array of autoinflammatory, autoimmune and immune-mediated diseases. Therefore, there exists a need for novel chemical compounds which are capable of inhibiting the cGAS pathway.

SUMMARY OF THE INVENTION

In a first aspect, the present invention provides a compound of Formula (I) or a tautomer thereof, or a pharmaceutically acceptable salt of said compound or tautomer thereof,

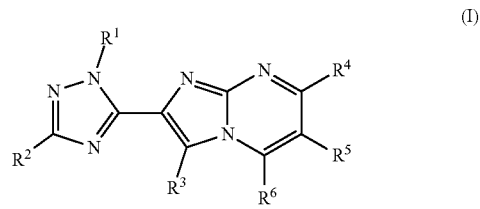

wherein
$R^1$ is hydrogen or a prodrug moiety;
$R^2$ is selected from the group consisting of hydrogen, halo, cyano, nitro, $C_{1-3}$ alkyl, halo($C_{1-3}$)alkyl, halo($C_{1-3}$)alkoxy, —S(O)$R^7$, —SO$_2R^7$, —C(O)NR$^7R^8$, —NR$^7$C(O)R$^8$—CO$_2R^7$, wherein $C_{1-3}$ alkyl, halo($C_{1-3}$)alkyl, and halo($C_{1-3}$)alkoxy is optionally substituted by hydroxyl or —NR$^7R^8$;
$R^3$ is a 5- or 6-membered heteroaryl optionally substituted by $C_{1-3}$ alkyl, —C(O)R$^8$ or a prodrug moiety;
each $R^4$, $R^5$ and $R^6$ is independently -L-Y;
each L is independently selected from a bond, —(CR$^aR^b)_n$—, —O—, (CR$^aR^b)_n$O—, —O(R$^aR^b)_n$—, or —(CR$^aR^b)_nO(CR$^aR^b)_m$—;
wherein each n or m is independently 1, 2 or 3;
each $R^a$ and $R^b$ is independently selected from hydrogen, halo and methyl; each Y is independently selected from the group consisting of hydrogen, halo, hydroxyl, cyano, $C_{1-4}$ alkyl, $C_{1-4}$ alkoxy, $C_{3-7}$cycloalkyl, $C_{2-4}$ alkenyl, $C_{1-6}$ hydroxyalkyl, $C_{1-4}$ cyanoalkyl, halo($C_{1-4}$)alkyl, halo($C_{2-4}$)alkenyl, —NR$^9R^{10}$, —C(O)NR$^9R^{10}$, —CO$_2R^{10}$, —C(O)R$^{10}$, —SO$_2R^{10}$, —OSO$_2R^{10}$, —S(O)R$^{10}$, —SO$_2NR^9R^{10}$, —N(R$^{10}$)SO$_2R^{10}$, —CF$_2$CH$_2$OR$^{10}$, phenyl, 5- or 6-membered heteroaryl, and 4- to 10-membered heterocycloalkyl ring containing one, two or three heteroatoms independently selected from N, O and S, wherein the $C_{3-7}$cycloalkyl, phenyl, heteroaryl and heterocycloalkyl groups are optionally substituted with one, two or three substituents independently selected from halo, hydroxyl, —C(O)R$^{10}$, oxo, $C_{1-4}$ alkyl, halo($C_{1-4}$)alkyl and $C_{1-4}$ hydroxyalkyl; or
$R^4$ and $R^5$ taken together with the carbon atoms to which they are attached form a 5- to 8-membered monocyclic or bicyclic ring which optionally contains one or two heteroatoms independently selected from N, O and S, wherein the ring is optionally substituted with one, two or three substituents independently selected from halo, $C_{1-4}$ alkyl, oxo, —C(O)R$^{10}$ and —SO$_2R^{10}$;
$R^7$ and $R^8$ are independently selected from hydrogen and $C_{1-4}$ alkyl;
$R^9$ is independently selected from the group consisting of hydrogen, $C_{1-4}$ alkyl, —C(O)C$_{1-4}$ alkyl and halo($C_{1-4}$) alkyl; and
$R^{10}$ is independently selected from hydrogen and $C_{1-6}$ alkyl; or
wherein $R^9$ and $R^{10}$ taken together with the nitrogen atom to which they are attached form a 5- to 8-membered heterocycloalkyl ring containing one or two heteroatoms independently selected from N, O and S, wherein the heterocycloalkyl is optionally substituted with oxo.

In a second aspect, the present invention provides a compound of Formula (I) or a tautomer thereof, or a pharmaceutically acceptable salt of said compound or tautomer thereof,

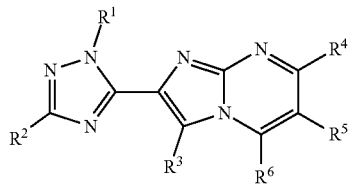

(I)

wherein
R$^1$ is hydrogen or a prodrug moiety;
R$^2$ is selected from the group consisting of hydrogen, halo, cyano, nitro, C$_{1-3}$ alkyl, halo(C$_{1-3}$)alkyl, halo(C$_{1-3}$)alkoxy, —S(O)R$^7$, —SO$_2$R$^7$, —C(O)NR$^7$R$^8$, —NR$^7$C(O)R$^8$ —CO$_2$R$^7$, wherein C$_{1-3}$ alkyl, halo(C$_{1-3}$)alkyl, and halo(C$_{1-3}$)alkoxy is optionally substituted by hydroxyl or —NR$^7$R$^8$;
R$^3$ is imidazolyl or pyrazolyl, where R$^3$ is optionally substituted by C$_{1-3}$ alkyl, —C(O)R$^8$ or a prodrug moiety;
each R$^4$, R$^5$ and R$^6$ is independently -L-Y;
each L is independently selected from a bond, —(CR$^a$R$^b$)$_n$—, —O—, —(CR$^a$R$^b$)$_n$O—, —O(R$^a$R$^b$)$_n$—, or —(CR$^a$R$^b$)$_n$O(CR$^a$R$^b$)$_m$—;
wherein each n or m is independently 1, 2 or 3;
each R$^a$ and R$^b$ is independently selected from hydrogen or methyl; each Y is independently selected from the group consisting of hydrogen, halo, hydroxyl, cyano, C$_{1-4}$ alkyl, C$_{1-4}$ alkoxy, C$_{3-7}$cycloalkyl, C$_{2-4}$ alkenyl, C$_{1-4}$ thioalkyl, C$_{1-6}$ hydroxyalkyl, C$_{1-4}$ cyanoalkyl, halo(C$_{1-4}$)alkyl, halo(C$_{2-4}$)alkenyl, —NR$^9$R$^{10}$, —C(O)NR$^9$R$^{10}$, —CO$_2$R$^{10}$, —C(O)R$^{10}$, —SO$_2$R$^{10}$, —OSO$_2$R$^{10}$, —S(O)R$^{10}$, —SO$_2$NR$^9$R$^{10}$, —N(R$^{10}$)SO$_2$R$^{10}$, —CF$_2$CH$_2$OR$^{10}$, phenyl, 5- or 6-membered heteroaryl, and 4- to 10-membered heterocycloalkyl ring containing one, two or three heteroatoms independently selected from N, O and S, wherein the C$_{3-7}$cycloalkyl, phenyl, heteroaryl and heterocycloalkyl groups are optionally substituted with one, two or three substituents independently selected from halo, hydroxyl, —C(O)R$^{10}$, oxo, C$_{1-4}$ alkyl, halo(C$_{1-4}$)alkyl and C$_{1-4}$ hydroxyalkyl; or
R$^4$ and R$^5$ taken together with the carbon atoms to which they are attached form a 5- to 8-membered monocyclic or bicyclic ring which optionally contains one or two heteroatoms independently selected from N, O and S, wherein the ring is optionally substituted with one, two or three substituents independently selected from halo, C$_{1-4}$ alkyl, oxo, —C(O)R$^{10}$ and —SO$_2$R$^{10}$;
R$^7$ and R$^8$ are independently selected from hydrogen and C$_{1-3}$ alkyl;
R$^9$ is independently selected from the group consisting of hydrogen, C$_{1-4}$ alkyl, —C(O)C$_{1-4}$ alkyl and halo(C$_{1-4}$) alkyl; and
R$^{10}$ is independently selected from hydrogen and C$_{1-6}$ alkyl; or wherein R$^9$ and R$^{10}$ taken together with the nitrogen atom to which they are attached form a 5- to 8-membered heterocycloalkyl ring containing one or two heteroatoms independently selected from N, O and S, wherein the heterocycloalkyl is optionally substituted with oxo.

In a third aspect, the present invention provides a pharmaceutical composition comprising a compound of the invention, and a pharmaceutically acceptable excipient.

In a fourth aspect, the present invention provides a method of treatment of an autoimmune, autoinflammatory or immune-mediated condition in a human in need thereof comprising administering to said human a therapeutically effective amount of a compound of the invention as disclosed herein.

In a fifth aspect, the present invention provides a compound of the invention as disclosed herein, for use in therapy.

In a sixth aspect, the present invention provides the use of a compound of the invention disclosed herein in the manufacture of a medicament for use in the treatment of an autoimmune, autoinflammatory or immune-mediated condition.

DETAILED DESCRIPTION

Definitions

As used herein, the term halo refers to chloro, fluoro, bromo, or iodo substituents.

As used herein, the term cyano refers to the group —CN.

As used herein, the term nitro refers to the group —NO$_2$.

As used herein, the term hydroxyl refers to the group —OH.

As used herein, the term "prodrug" refers to compounds that readily undergo chemical changes under physiological conditions to provide a pharmacologically active parent compound. The term "prodrug moiety" refers to the chemical moiety of a prodrug that is released under physiological conditions to form the active parent compound.

As used herein, the term "alkyl" refers to a saturated hydrocarbon radical, straight or branched, having the specified number of carbon atoms. For example, the term "C$_{1-6}$ alkyl" refers to an alkyl group having 1 to 6 carbon atoms. Exemplary groups include, but are not limited to, methyl, ethyl, propyl (n-propyl and isopropyl), butyl (n-butyl, sec-butyl, isobutyl and tert-butyl), pentyl, and hexyl. The term "C$_{1-4}$ alkyl" refers to an alkyl group having 1 to 4 carbon atoms.

As used herein, the term "cycloalkyl" refers to a non-aromatic, saturated, monocyclic, hydrocarbon ring containing the specified number of carbon atoms. For example, "C$_{3-7}$ cycloalkyl" refers to a cycloalkyl group containing 3 to 7 carbon atoms. Exemplary groups include cyclopropyl, cyclobutyl, cyclopentyl, cyclohexyl, cycloheptyl or cyclooctyl.

As used herein, the term "alkylene" refers to a divalent radical derived from a straight or branched, saturated hydrocarbon group of, for example, 1 to 6 carbon atoms (C$_{1-6}$ alkylene). Exemplary groups include, but are not limited to, —CH$_2$— (methylene), —CH$_2$CH$_2$— (ethylene), —CH$_2$CH$_2$CH$_2$— (propylene) and —CH$_2$CH(CH$_3$)$_2$— (iso-butylene).

As used herein, the term "C$_{2-4}$ alkenyl" refers to a straight or branched hydrocarbon radical containing the specified number of carbon atoms and at least 1 double bond. For example, "C$_{2-4}$ alkenyl" has 2 to 4 carbon atoms. Exemplary groups include, but are not limited to, ethenyl and propenyl.

As used herein, the term "alkoxy" refers to an —O-alkyl group, i.e. an alkyl group which is attached through an oxygen linking atom, wherein "alkyl" is defined above. For example, the term "$C_{1-4}$ alkoxy" refers to an alkoxy group having 1 to 4 carbon atoms. Exemplary groups include, but are not limited to, methoxy, ethoxy, n-propoxy, isopropoxy, n-butoxy, s-butoxy, isobutoxy, and t-butoxy.

As used herein, the term "halo($C_{1-4}$)alkyl" is intended to mean a radical having one or more halogen atoms, which may be the same or different, at one or more carbon atoms of an alkyl moiety containing from 1 to 4 carbon atoms, which is a straight or branched chain carbon radical. Exemplary groups include, but are not limited to, —$CF_3$ (trifluoromethyl), —$CCl_3$ (trichloromethyl), 1,1-difluoroethyl, 2,2,2-trifluoroethyl, and hexafluoroisopropyl. It follows that the term halo($C_{1-2}$)alkyl refers to a radical having one or more halogen atoms, which may be the same or different, at one or more carbon atoms of an alkyl moiety containing from 1 to 2 carbon atoms.

As used herein, the term "halo($C_{1-4}$)alkoxy" refers to a straight or branched chain hydrocarbon radical, having at least 1 and up to 4 carbon atoms with one or more halogen atoms, which may be the same or different, attached to one or more carbon atoms, which radical is attached through an oxygen linking atom. Exemplary groups include, but are not limited to, —$OCHF_2$ (difluoromethoxy), —$OCF_3$ (trifluoromethoxy), and —$OCH(CF_3)_2$ (hexafluoroisopropoxy).

As used herein, the term "$C_{1-4}$ thioalkyl" refers to refers to an —S-alkyl group, i.e. an alkyl group which is attached through a sulfur linking atom, wherein "alkyl" is defined above. For example, the term "$C_{1-4}$ thioalkyl" refers to a thioalkyl group having 1 to 4 carbon atoms.

Exemplary groups include, but are not limited to, thiomethyl, thioethyl, thiopropyl, thio-isopropyl, and so on.

As used herein, the term "$C_{1-6}$ hydroxyalkyl" is intended to mean a radical having one or more hydroxy groups at one or more carbon atoms of an alkyl moiety containing from 1 to 6 carbon atoms, which is a straight or branched chain carbon radical. Exemplary groups include, but are not limited to, hydroxymethyl (—$CH_2OH$), 2-hydroxyethyl (—$CH_2CH_2OH$), and hydroxy-isopropyl.

As used herein, the term "$C_{1-4}$ cyanoalkyl" is intended to mean a radical having one or more cyano groups at one or more carbon atoms of an alkyl moiety containing 1 to 4 carbon atoms, which is a straight or branched chain carbon radical.

As used herein, the term "halo($C_{2-4}$)alkenyl" refers to a straight or branched chain hydrocarbon radical, having at least 2 and up to 4 carbon atoms and at least one double bond, with one or more halogen atoms, which may be the same or different, attached to one or more carbon atoms. Exemplary groups include, but are not limited to, —CH=CHF, —CH=$CF_2$ and —CF=$CF_2$.

As used herein, the term "5- or 6-membered heteroaryl" refers to a group or moiety comprising an aromatic monovalent monocyclic radical, containing 5 or 6 ring atoms, including at least one carbon atom and at least one heteroatom independently selected from nitrogen, oxygen, and sulfur. Selected 5-membered heteroaryl groups contain one nitrogen, oxygen, or sulfur ring heteroatom, and optionally contain 1, 2, or 3 additional nitrogen ring atoms. Selected 6-membered heteroaryl groups contain 1, 2, or 3 nitrogen ring heteroatoms. Exemplary groups include, but are not limited to furanyl, thienyl, pyrrolyl, imidazolyl, pyrazolyl, triazolyl, tetrazolyl, oxazolyl, thiazolyl, isoxazolyl, isothiazolyl, oxadiazolyl, thiadiazolyl, pyridinyl, pyridazinyl, pyrazinyl, pyrimidinyl, and triazinyl.

As used herein, the term "5-membered nitrogen containing heteroaryl" refers to a group or moiety comprising an aromatic monovalent monocyclic radical, containing 5 ring atoms, containing at least one carbon atom, at least one nitrogen and optionally at least one other heteroatom independently selected from nitrogen, oxygen, and sulfur. Exemplary groups include, but are not limited to, pyrrolyl, imidazolyl, pyrazolyl, triazolyl, tetrazolyl, oxazolyl, thiazolyl, isoxazolyl, isothiazolyl, oxadiazolyl and thiadiazolyl.

As used herein, the term "heteroarylene" refers to a group or moiety comprising an aromatic divalent monocyclic or bicyclic radical, containing 5 to 10 ring atoms, including at least one heteroatom independently selected from nitrogen, oxygen and sulfur. For example, the term "heteroarylene" refers to a group or moiety comprising an aromatic divalent monocyclic or bicyclic radical, containing 5 to 10 ring atoms, including one or two heteroatoms independently selected from nitrogen, oxygen and sulfur.

As used herein, the term "heterocycloalkyl" refers to a non-aromatic, saturated, monocyclic or bicyclic radical containing the specified number of atoms and including at least one heteroatom independently selected from nitrogen, oxygen and sulfur. For example, the term "4- to 10-membered heterocycloalkyl" refers to a heterocycloalkyl group having 4 to 10 atoms.

As used herein, the term "5- to 8-membered monocyclic or bicyclic ring" refers to a ring, which may be saturated or unsaturated, containing 5 to 8 ring atoms.

As used herein, the term "bicyclic ring" may refer to a bridged, fused or spiro bicyclic group.

As used herein, the term "optionally substituted" indicates that a group may be unsubstituted or substituted with one or more substituents as defined herein. The term "substituted" in reference to a group indicates that a hydrogen atom attached to a member atom within a group is replaced by one of the defined substituents. In the case where groups may be selected from a number of alternative groups, the selected groups may be the same or different.

As used herein, the term "pharmaceutically acceptable salt" refers to salts that retain the desired biological activity of the subject compound and exhibit minimal undesired toxicological effects. Such pharmaceutically acceptable salt may be prepared in situ during the final isolation and purification of the compound, or by separately reacting the purified compound in its free acid or free base form with a suitable base or acid, respectively.

The term "treatment" refers to ameliorating or stabilising the specified condition, reducing or eliminating the symptoms of the condition, slowing or eliminating the progression of the condition, and preventing or delaying reoccurrence of the condition in a previously afflicted patient or subject.

The term "prevention" refers to avoidance of the stated disease in a subject who is not suffering from the stated disease.

The term "compound(s) of the invention" refers to a compound of Formula (I) or a tautomer thereof, or a pharmaceutically acceptable salt of said compound or tautomer thereof.

The term "therapeutically effective amount" refers to the quantity of a compound of the invention, which will elicit the desired biological response in a human body. It may vary depending on the compound, the disease and its severity, and the age and weight of the subject to be treated.

A reference to a compound of Formula (I) encompasses a reference to any one of Formulae (IA), (IAA), (IB), (IBB), (IC) and (ICC).

STATEMENT OF INVENTION

In a first aspect, the present invention provides a compound of Formula (I) or a tautomer thereof, or a pharmaceutically acceptable salt of said compound or tautomer thereof,

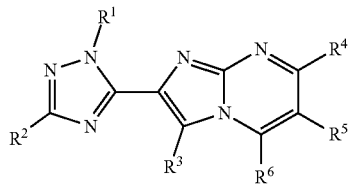

(I)

wherein
- $R^1$ is hydrogen or a prodrug moiety;
- $R^2$ is selected from the group consisting of hydrogen, halo, cyano, nitro, $C_{1-3}$ alkyl, halo($C_{1-3}$)alkyl, halo($C_{1-3}$)alkoxy, —S(O)$R^7$, —SO$_2$$R^7$, —C(O)NR$^7$$R^8$, —NR$^7$C(O)R$^8$ —CO$_2$$R^7$, wherein $C_{1-3}$ alkyl, halo($C_{1-3}$)alkyl, and halo($C_{1-3}$)alkoxy is optionally substituted by hydroxyl or —NR$^7$$R^8$;
- $R^3$ is a 5- or 6-membered heteroaryl optionally substituted by $C_{1-3}$ alkyl, —C(O)R$^8$ or a prodrug moiety;
- each $R^4$, $R^5$ and $R^6$ is independently -L-Y;
- each L is independently selected from a bond, —(CR$^a$R$^b$)$_n$—, —O—, (CR$^a$R$^b$)$_n$O—, —O(R$^a$R$^b$)$_n$—, or —(CR$^a$R$^b$)$_n$O(CR$^a$R$^b$)$_m$—;
- wherein each n or m is independently 1, 2 or 3;
- each $R^a$ and $R^b$ is independently selected from hydrogen, halo and methyl; each Y is independently selected from the group consisting of hydrogen, halo, hydroxyl, cyano, $C_{1-4}$ alkyl, $C_{1-4}$ alkoxy, $C_{3-7}$cycloalkyl, $C_{2-4}$ alkenyl, $C_{1-4}$ thioalkyl, $C_{1-6}$ hydroxyalkyl, $C_{1-4}$ cyanoalkyl, halo($C_{1-4}$)alkyl, halo($C_{2-4}$)alkenyl, —NR$^9$$R^{10}$, —C(O)NR$^9$$R^{10}$, —CO$_2$$R^{10}$, —C(O)R$^{10}$, —SO$_2$$R^{10}$, —OSO$_2$$R^{10}$, —S(O)R$^{10}$, —SO$_2$NR$^9$$R^{10}$, —N(R$^{10}$)SO$_2$$R^{10}$, —CF$_2$CH$_2$OR$^{10}$, phenyl, 5- or 6-membered heteroaryl, and 4- to 10-membered heterocycloalkyl ring containing one, two or three heteroatoms independently selected from N, O and S, wherein the $C_{3-7}$cycloalkyl, phenyl, heteroaryl and heterocycloalkyl groups are optionally substituted with one, two or three substituents independently selected from halo, hydroxyl, —C(O)R$^{10}$, oxo, $C_{1-4}$ alkyl, halo($C_{1-4}$)alkyl and $C_{1-4}$ hydroxyalkyl; or
- $R^4$ and $R^5$ taken together with the carbon atoms to which they are attached form a 5- to 8-membered monocyclic or bicyclic ring which optionally contains one or two heteroatoms independently selected from N, O and S, wherein the ring is optionally substituted with one, two or three substituents independently selected from halo, $C_{1-4}$ alkyl, oxo, —C(O)R$^{10}$ and —SO$_2$$R^{10}$;
- $R^7$ and $R^8$ are independently selected from hydrogen and $C_{1-4}$ alkyl;
- $R^9$ is independently selected from the group consisting of hydrogen, $C_{1-4}$ alkyl, —C(O)$C_{1-4}$ alkyl and halo($C_{1-4}$) alkyl; and
- $R^{10}$ is independently selected from hydrogen and $C_{1-6}$ alkyl; or
- wherein $R^9$ and $R^{10}$ taken together with the nitrogen atom to which they are attached form a 5- to 8-membered heterocycloalkyl ring containing one or two heteroatoms independently selected from N, O and S, wherein the heterocycloalkyl is optionally substituted with oxo.

In an embodiment, $R^3$ is a 5-membered heteroaryl optionally substituted by $C_{1-3}$ alkyl, —C(O)R$^8$ or a prodrug moiety.

In an embodiment, $R^3$ is a 5-membered nitrogen containing heteroaryl optionally substituted by $C_{1-3}$ alkyl, —C(O)R$^8$ or a prodrug moiety.

In an embodiment, $R^3$ is a 5-membered nitrogen containing heteroaryl optionally containing one, two or three additional heteroatoms selected from N, O and S, wherein the heteroaryl is optionally substituted by $C_{1-3}$ alkyl, —C(O)R$^8$ or a prodrug moiety.

In an embodiment, $R^3$ is imidazolyl or pyrazolyl, where $R^3$ is optionally substituted by $C_{1-3}$ alkyl, —C(O)R$^8$ or a prodrug moiety.

In a second aspect, the present invention provides a compound of Formula (I) or a tautomer thereof, or a pharmaceutically acceptable salt of said compound or tautomer thereof,

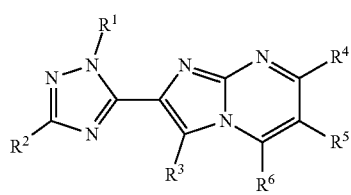

(I)

wherein
- $R^1$ is hydrogen or a prodrug moiety;
- $R^2$ is selected from the group consisting of hydrogen, halo, cyano, nitro, $C_{1-3}$ alkyl, halo($C_{1-3}$)alkyl, halo($C_{1-3}$)alkoxy, —S(O)$R^7$, —SO$_2$$R^7$, —C(O)NR$^7$$R^8$, —NR$^7$C(O)R$^8$—CO$_2$$R^7$, wherein $C_{1-3}$ alkyl, halo($C_{1-3}$)alkyl, and halo($C_{1-3}$)alkoxy is optionally substituted by hydroxyl or —NR$^7$$R^8$;
- $R^3$ is imidazolyl or pyrazolyl, where $R^3$ is optionally substituted by $C_{1-3}$ alkyl, —C(O)R$^8$ or a prodrug moiety;
- each $R^4$, $R^5$ and $R^6$ is independently -L-Y;
- each L is independently selected from a bond, —(CR$^a$R$^b$)$_n$—, —O—, —(CR$^a$R$^b$)$_n$O—, —O(R$^a$R$^b$)$_n$—, or —(CR$^a$R$^b$)$_n$O(CR$^a$R$^b$)$_m$—;
- wherein each n or m is independently 1, 2 or 3;
- each $R^a$ and $R^b$ is independently selected from hydrogen or methyl; each Y is independently selected from the group consisting of hydrogen, halo, hydroxyl, cyano, $C_{1-4}$ alkyl, $C_{1-4}$ alkoxy, $C_{3-7}$cycloalkyl, $C_{2-4}$ alkenyl, $C_{1-4}$ thioalkyl, $C_{1-6}$ hydroxyalkyl, $C_{1-4}$ cyanoalkyl, halo($C_{1-4}$)alkyl, halo($C_{2-4}$)alkenyl, —NR$^9$$R^{10}$, —C(O)NR$^9$$R^{10}$, —CO$_2$$R^{10}$, —C(O)R$^{10}$, —SO$_2$$R^{10}$, —OSO$_2$$R^{10}$, —S(O)R$^{10}$, —SO$_2$NR$^9$$R^{10}$, —N(R$^{10}$)SO$_2$$R^{10}$, —CF$_2$CH$_2$OR$^{10}$, phenyl, 5- or 6-membered heteroaryl, and 4- to 10-membered heterocycloalkyl ring containing one, two or three heteroatoms independently selected from N, O and S, wherein the $C_{3-7}$cycloalkyl, phenyl, heteroaryl and heterocycloalkyl groups are optionally substituted with one, two or three substituents independently selected from halo, hydroxyl, —C(O)R$^{10}$, oxo, $C_{1-4}$ alkyl, halo($C_{1-4}$)alkyl and $C_{1-4}$ hydroxyalkyl; or
- $R^4$ and $R^5$ taken together with the carbon atoms to which they are attached form a 5- to 8-membered monocyclic or bicyclic ring which optionally contains one or two heteroatoms independently selected from N, O and S, wherein the ring is optionally substituted with one, two or three substituents independently selected from halo, $C_{1-4}$ alkyl, oxo, —C(O)$R^{10}$ and —SO$_2$$R^{10}$;

$R^7$ and $R^8$ are independently selected from hydrogen and $C_{1-3}$ alkyl;

$R^9$ is independently selected from the group consisting of hydrogen, $C_{1-4}$ alkyl, —C(O)$C_{1-4}$ alkyl and halo($C_{1-4}$) alkyl; and $R^{10}$ is independently selected from hydrogen and $C_{1-6}$ alkyl; or wherein $R^9$ and $R^{10}$ taken together with the nitrogen atom to which they are attached form a 5- to 8-membered heterocycloalkyl ring containing one or two heteroatoms independently selected from N, O and S, wherein the heterocycloalkyl is optionally substituted with oxo.

In an embodiment, only one of $R^1$ and $R^3$ comprises a prodrug moiety. In an embodiment, a prodrug moiety is at $R^1$ and not at $R^3$. In another embodiment, a prodrug moiety is at $R^3$ and not at $R^1$. In an embodiment, $R^1$ is a prodrug moiety and $R^3$ is a 5-membered heteroaryl optionally substituted by $C_{1-3}$ alkyl or —C(O)$R^8$. In an embodiment, $R^1$ is a prodrug moiety and $R^3$ is a 5-membered nitrogen containing heteroaryl optionally substituted by $C_{1-3}$ alkyl or —C(O)$R^8$. In an embodiment, $R^1$ is a prodrug moiety and $R^3$ is imidazolyl or pyrazolyl, where $R^3$ is optionally substituted by $C_{1-3}$ alkyl or —C(O)$R^8$.

In an embodiment, each $R^a$ and $R^b$ is independently selected from hydrogen, fluoro and methyl.

In an embodiment, each $R^a$ and $R^b$ is independently selected from hydrogen and methyl.

In an embodiment, $R^1$ is a prodrug moiety.

In an embodiment, the prodrug moiety is a phosphate ester, ester or an amino acid type prodrug.

In an embodiment, the prodrug moiety is a phosphate ester.

In an embodiment, $R^1$ is a phosphate ester prodrug.

In an embodiment, each prodrug moiety is independently selected from the group consisting of —CH($R^c$)O—P(O)(O$R^d$)(O$R^e$), —CH($R^c$)O—C(O)—$C_{1-6}$ alkylene-O—P(O)(O$R^d$)(O$R^e$), —CH($R^c$)O—C(O)—$C_{1-6}$ alkylene-P(O)(O$R^d$)(O$R^e$), —CH($R^c$)O—C(O)—$C_{1-6}$ alkylene-CO$_2$H, —CH($R^c$)O—C(O)$R^d$, —CH($R^c$)O—C(O)O—$C_{1-6}$ alkylene-CO$_2$H, —CH($R^c$)O—C(O)—$C_{1-6}$ alkylene-N$R^d$$R^e$, —CH($R^c$)O—C(O)O—$C_{1-6}$ alkylene-N$R^d$$R^e$, —C(O)$R^d$, —CH($R^c$)O—C(O)—$C_{1-6}$ alkylene-heterocycloalkyl, —CH($R^c$)O—C(O)—$C_{1-6}$ alkylene-heterocycloalkyl and —C$R^d$$R^e$—O—(C(O)—N$R^d$-heteroarylene-CH$_2$O—C(O)—CH$_2$—N$R^d$$R^e$; wherein $R^c$ is independently selected from hydrogen and methyl; $R^d$ and $R^e$ are each independently hydrogen or $C_{1-6}$ alkyl; each heterocycloalkyl is 4- to 6-membered and contains one or two heteroatoms independently selected from N, O and S; and each heteroarylene is 5- or 6-membered and contains one or two heteroatoms independently selected from N, O and S.

In an embodiment, $R^c$ is independently selected from hydrogen, halo and $C_{1-3}$ alkyl.

In an embodiment, $R^c$ is independently selected from hydrogen, fluoro and methyl.

In an embodiment, $R^c$ is independently selected from hydrogen and methyl.

In an embodiment, $R^c$ is hydrogen.

In an embodiment, each prodrug moiety is independently selected from the group consisting of —CH$_2$O—P(O)(O$R^d$)(O$R^e$), —CH$_2$O—C(O)—$C_{1-6}$ alkylene-O—P(O)(O$R^d$)(O$R^e$), —CH$_2$O—C(O)—$C_{1-6}$ alkylene-P(O)(O$R^d$)(O$R^e$), —CH$_2$O—C(O)—$C_{1-6}$ alkylene-CO$_2$H, —CH$_2$O—C(O)$R^d$, —CH$_2$O—C(O)O—$C_{1-6}$ alkylene-CO$_2$H, —CH$_2$O—C(O)—$C_{1-6}$alkylene-N$R^d$$R^e$, —CH$_2$O—C(O)O—$C_{1-6}$alkylene-N$R^d$$R^e$, —C(O)$R^d$, —CH$_2$O—C(O)—$C_{1-6}$alkylene-heterocycloalkyl, —CH$_2$O—C(O)—$C_{1-6}$alkylene-heterocycloalkyl and —C$R^d$$R^e$—O—(C(O)—N$R^d$-heteroarylene-CH$_2$O—C(O)—CH$_2$—N$R^d$$R^e$; wherein $R^d$ and $R^e$ are each independently hydrogen or $C_{1-6}$ alkyl; each heterocycloalkyl is 4- to 6-membered and contains one or two heteroatoms independently selected from N, O and S; and each heteroarylene is 5- or 6-membered and contains one or two heteroatoms independently selected from N, O and S.

In an embodiment, each prodrug moiety is independently selected from the group consisting of —CH$_2$O—P(O)(O$R^d$)(O$R^e$), —CH$_2$O—C(O)—$C_{1-6}$ alkylene-O—P(O)(O$R^d$)(O$R^e$), —CH$_2$O—C(O)—$C_{1-6}$ alkylene-P(O)(O$R^d$)(O$R^e$), —CH$_2$O—C(O)—$C_{1-6}$ alkylene-CO$_2$H, —CH$_2$O—C(O)$R^d$, —CH$_2$O—C(O)O—$C_{1-6}$ alkylene-CO$_2$H, —CH$_2$O—C(O)—$C_{1-6}$ alkylene-N$R^d$$R^e$, —CH$_2$O—C(O)O—$C_{1-6}$ alkylene-N$R^d$$R^e$ and —C(O)$R^d$.

In an embodiment, each prodrug moiety is independently selected from the group consisting of —CH$_2$O—P(O)(O$R^d$)(O$R^e$), —CH$_2$O—C(O)—$C_{1-6}$ alkylene-O—P(O)(O$R^d$)(O$R^e$), —CH$_2$O—C(O)—$C_{1-6}$ alkylene-P(O)(O$R^d$)(O$R^e$), —CH$_2$O—C(O)—$C_{1-6}$ alkylene-CO$_2$H, —CH$_2$O—C(O) O— $C_{1-6}$ alkylene-CO$_2$H, —CH$_2$O—C(O)—$C_{1-6}$ alkylene-N$R^d$$R^e$ and —CH$_2$O—C(O)O—$C_{1-6}$ alkylene-N$R^d$$R^e$.

In an embodiment, each prodrug moiety is independently selected from the group consisting of —CH$_2$O—P(O)(O$R^d$)(O$R^e$), —CH$_2$O—C(O)—$C_{1-3}$ alkylene-O—P(O)(O$R^d$)(O$R^e$), —CH$_2$O—C(O)—$C_{1-3}$ alkylene-P(O)(O$R^d$)(O$R^e$), —CH$_2$O—C(O)—$C_{1-3}$ alkylene-CO$_2$H, —CH$_2$O—C(O)$R^d$, —CH$_2$O—C(O)O—$C_{1-3}$ alkylene-CO$_2$H, —CH$_2$O—C(O)—$C_{1-3}$alkylene-N$R^d$$R^e$, —CH$_2$O—C(O)O—$C_{1-3}$alkylene-N$R^d$$R^e$, —C(O)$R^d$, —CH$_2$O—C(O)—$C_{1-3}$alkylene-heterocycloalkyl, —CH$_2$O—C(O)—$C_{1-3}$alkylene-heterocycloalkyl and —C$R^d$$R^e$—O—(C(O)—N$R^d$-heteroarylene-CH$_2$O—C(O)—CH$_2$—N$R^d$$R^e$; wherein $R^d$ and $R^e$ are each independently hydrogen or $C_{1-6}$ alkyl; each heterocycloalkyl is 4- to 6-membered and contains one or two heteroatoms independently selected from N, O and S; and each heteroarylene is 5- or 6-membered and contains one or two heteroatoms independently selected from N, O and S.

In an embodiment, each prodrug moiety is independently selected from the group consisting of —CH$_2$O—P(O)(O$R^d$)(O$R^e$), —CH$_2$O—C(O)—$C_{1-3}$ alkylene-O—P(O)(O$R^d$)(O$R^e$), —CH$_2$O—C(O)—$C_{1-3}$ alkylene-P(O)(O$R^d$)(O$R^e$), —CH$_2$O—C(O)—$C_{1-3}$ alkylene-CO$_2$H, —CH$_2$O—C(O)$R^d$, —CH$_2$O—C(O)O—$C_{1-3}$ alkylene-CO$_2$H, —CH$_2$O—C(O)—$C_{1-3}$ alkylene-N$R^d$$R^e$, —CH$_2$O—C(O)O—$C_{1-3}$ alkylene-N$R^d$$R^e$ and —C(O)$R^d$.

In an embodiment, each prodrug moiety is independently selected from the group consisting of —CH$_2$O—P(O)(O$R^d$)(O$R^e$), —CH$_2$O—C(O)—$C_{1-3}$ alkylene-O—P(O)(O$R^d$)(O$R^e$), —CH$_2$O—C(O)—$C_{1-3}$ alkylene-P(O)(O$R^d$)(O$R^e$), —CH$_2$O—C(O)—$C_{1-3}$alkylene-CO$_2$H, —CH$_2$O—C(O) O— $C_{1-3}$alkylene-CO$_2$H, —CH$_2$O—C(O)—$C_{1-3}$ alkylene-N$R^d$$R^e$ and —CH$_2$O—C(O)O—$C_{1-3}$ alkylene-N$R^d$$R^e$.

In an embodiment, each prodrug moiety is independently selected from

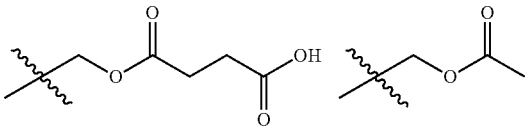

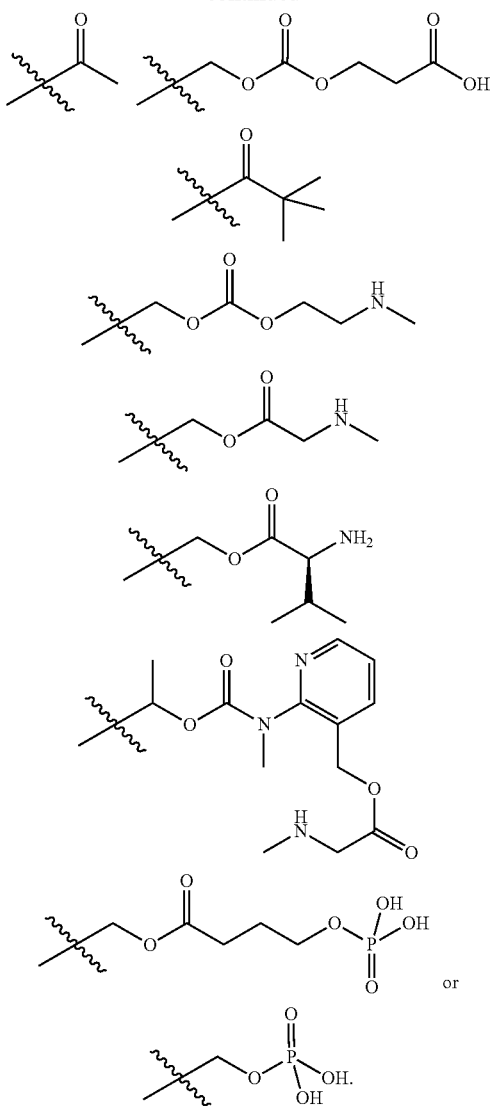

In an embodiment, each prodrug moiety is independently selected from

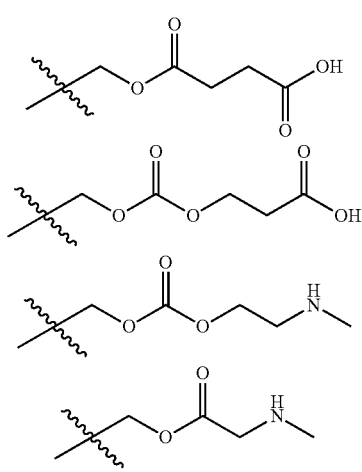

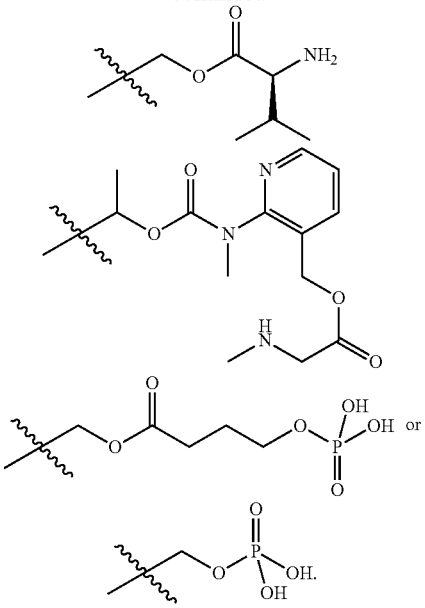

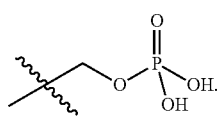

In an embodiment, each prodrug moiety is —CH$_2$O—P(O)(OR$^d$)(OR$^e$), where R$^d$ and R$^e$ are as defined above.

In an embodiment, each prodrug moiety is

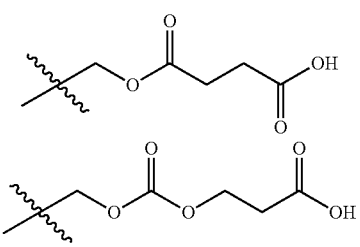

In an embodiment, R$^1$ is a prodrug moiety, as defined according to any one of the above embodiments. In an embodiment, R$^1$ is independently selected from the group consisting of —CH$_2$O—P(O)(OR$^d$)(OR$^e$), —CH$_2$O—C(O)—C$_{1-6}$ alkylene-O—P(O)(OR$^d$)(OR$^e$), —CH$_2$O—C(O)—C$_{1-6}$ alkylene-P(O)(OR$^d$)(OR$^e$), —CH$_2$O—C(O)—C$_{1-6}$ alkylene-CO$_2$H, —CH$_2$O—C(O)R$^d$, —CH$_2$O—C(O)O—C$_{1-6}$ alkylene-CO$_2$H, —CH$_2$O—C(O)—C$_{1-6}$alkylene-NR$^d$R$^e$, —CH$_2$O—C(O)O—C$_{1-6}$alkylene-NR$^d$R$^e$, —C(O)R$^d$, —CH$_2$O—C(O)—C$_{1-6}$ alkylene-heterocycloalkyl, —CH$_2$O—C(O)—C$_{1-6}$alkylene-heterocycloalkyl and —CR$^d$R$^e$—O—(C(O)—NR$^d$-heteroarylene-CH$_2$O—C(O)—CH$_2$—NR$^d$R$^e$; wherein R$^d$ and R$^e$ are each independently hydrogen or C$_{1-6}$ alkyl; each heterocycloalkyl is 4- to 6-membered and contains one or two heteroatoms independently selected from N, O and S; and each heteroarylene is 5- or 6-membered and contains one or two heteroatoms independently selected from N, O and S.

In an embodiment, R$^1$ is independently selected from

-continued

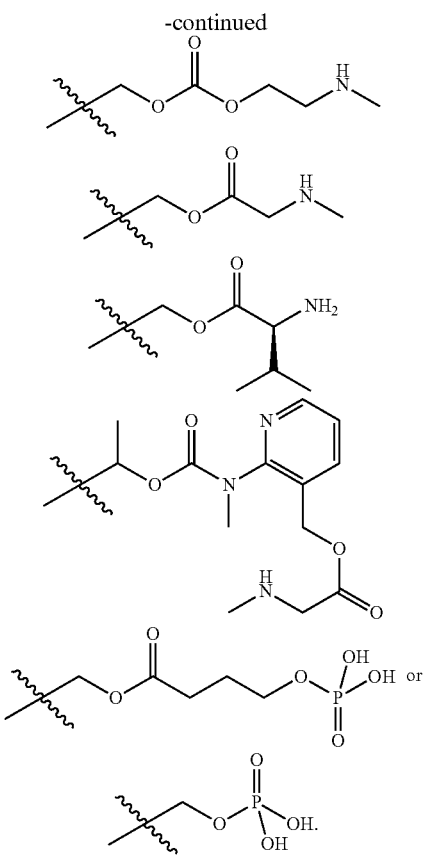

In an embodiment, R¹ is —CH₂O—P(O)(OR^d)(OR^e), where R^d and R^e are as defined above.

In an embodiment, R¹ is

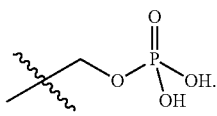 [SMILES: *COP(=O)(O)O]

In an embodiment, the compound of Formula (I) is a compound of Formula (IA) or a tautomer thereof, or a pharmaceutically acceptable salt of said compound or tautomer thereof:

(IA)

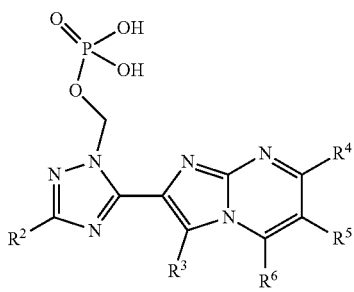

wherein R², R³, R⁴, R⁵ and R⁶ are as defined herein in relation to Formula (I).

In an embodiment, R¹ is hydrogen.

In an embodiment, the compound of Formula (I) is a compound of Formula (IAA) or a tautomer thereof, or a pharmaceutically acceptable salt of said compound or tautomer thereof:

(IAA)

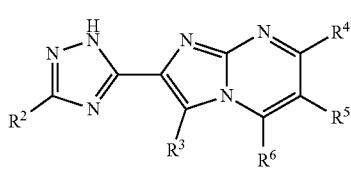

wherein R², R³, R⁴, R⁵ and R⁶ are as defined herein in relation to Formula (I).

In an embodiment, R² is selected from the group consisting of halo, cyano, halo(C₁₋₃)alkyl, halo(C₁₋₃)alkoxy, —S(O)R⁷, —C(O)NR⁷R⁸ and CO₂R⁷, wherein halo(C₁₋₃) alkyl, and halo(C₁₋₃)alkoxy is optionally substituted by hydroxyl or —NR⁷R⁸;

In an embodiment, R² is selected from the group consisting of halo, cyano, —C(O)NH₂, halo(C₁₋₄)alkoxy, halo(C₁₋₂)alkyl, —CF₂CH₂NH₂, —CF₂CH₂OH, and —S(O)CH₃.

In an embodiment, R² is selected from the group consisting of Br, cyano, —C(O)NH₂, —CF₂CH₂NH₂, —CF₂CH₂OH, —CH₂F, —CHF₂, —CF₃, —CF₂CF₃, —CF₂CH₃, —CF₂CHF₂, —OCHF₂ and —S(O)CH₃.

In an embodiment, R² is selected from hydrogen, halo, C₁₋₃alkyl, halo(C₁₋₃)alkyl and halo(C₁₋₃)alkoxy.

In an embodiment, R² is selected from hydrogen, Br, —CF₃, —CHF₂, —CH₃ and —OCHF₂.

In an embodiment, R² is CF₃.

In an embodiment, the compound of Formula (I) is a compound of Formula (IB) or Formula (IBB) or a tautomer thereof, or a pharmaceutically acceptable salt of said compound or tautomer thereof:

(IB)

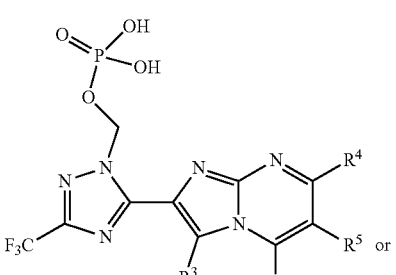

or (IBB)

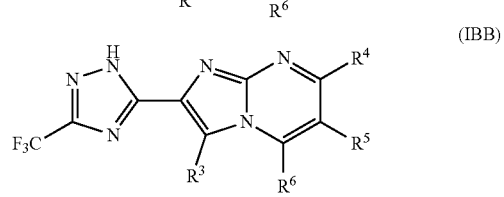

wherein R³, R⁴, R⁵ and R⁶ are as defined herein in relation to Formula (I).

In an embodiment, R³ is imidazolyl or pyrazolyl. In an embodiment, R³ is imidazolyl. For the avoidance of doubt, in an embodiment, R³ is unsubstituted imidazolyl.

In an embodiment, R³ is imidazolyl or pyrazolyl linked through carbon, i.e. a C-linked imidazolyl or C-linked pyrazolyl. In an embodiment, R³ is a C-linked imidazolyl. In an embodiment, $R^3$ is imidazol-4-yl or imidazol-5-yl. In an embodiment, $R^3$ is imidazol-5-yl.

In an embodiment, $R^1$ is a prodrug moiety and $R^3$ is imidazolyl, in particular C-linked imidazolyl.

In an embodiment, $R^1$ is H and $R^3$ is substituted by a prodrug moiety.

In an embodiment, $R^1$ is

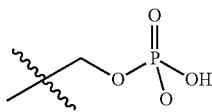

and $R^3$ is imidazolyl, in particular C-linked imidazolyl.

In an alternative embodiment, $R^1$ is hydrogen and $R^3$ is imidazolyl, in particular C-linked imidazolyl.

In an embodiment, the compound of Formula (I) is a compound of Formula (IC) or Formula (ICC) or a tautomer thereof, or a pharmaceutically acceptable salt of said compound or tautomer thereof:

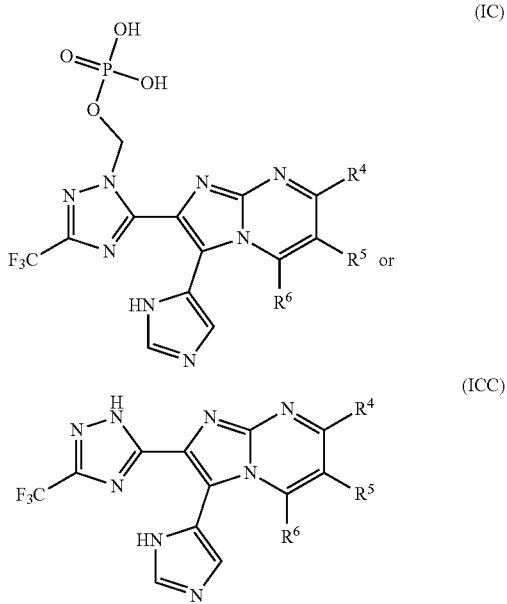

wherein $R^4$, $R^5$ and $R^6$ are as defined above in relation to Formula (I).

In an embodiment, each $R^4$, $R^5$ and $R^6$ is independently -L-Y and each L is a bond.

In an embodiment, each L is a bond; and each Y is independently selected from the group consisting of hydrogen, halo, hydroxyl, cyano, $C_{1-4}$ alkyl, $C_{3-7}$cycloalkyl, $C_{1-4}$ alkoxy, $C_{1-4}$thioalkyl, $C_{1-6}$hydroxyalkyl, $C_{1-4}$ cyanoalkyl, halo($C_{1-4}$)alkyl, —$NR^9R^{10}$, —$C(O)NR^9R^{10}$, —$CO_2R^{10}$, —$C(O)R^{10}$, —$SO_2R^{10}$, —$OSO_2R^{10}$, —$CF_2CH_2OR^{10}$, phenyl, 5- or 6-membered heteroaryl, and 5- or 6-membered heterocycloalkyl ring containing one or two heteroatoms independently selected from N, O and S, wherein the heterocycloalkyl is optionally substituted with one, two or three substituents independently selected from halo, hydroxyl, —$C(O)R^{10}$, and $C_{1-4}$ alkyl; or $R^4$ and $R^5$ taken together with the carbon atoms to which they are attached form a 5- to 8-membered monocyclic heterocycloalkyl ring containing one or two heteroatoms independently selected from N, O and S, wherein the ring is optionally substituted with up to three substituents independently selected from halo, $C_{1-4}$ alkyl, oxo, —$C(O)R^{10}$ and —$SO_2R^{10}$.

In an embodiment, each L is selected from a bond, —$(CR^aR^b)_n$—, —O—, —$(CR^aR^b)_nO$—, —$O(CH_2)_n$—, or —$(CR^aR^b)_nO(CR^aR^b)_m$—; and each Y is independently selected from the group consisting of hydrogen, halo, hydroxyl, cyano, $C_{1-4}$ alkyl, $C_{3-7}$cycloalkyl, $C_{1-4}$ alkoxy, $C_{1-4}$thioalkyl, $C_{1-6}$ hydroxyalkyl, $C_{1-4}$ cyanoalkyl, halo($C_{1-4}$)alkyl, —$NR^9R^{10}$, —$C(O)NR^9R^{10}$, —$CO_2R^{10}$, —$C(O)R^{10}$, —$SO_2R^{10}$, —$OSO_2R^{10}$, —$CF_2CH_2OR^{10}$, phenyl, 5- or 6-membered heteroaryl, and 5- or 6-membered heterocycloalkyl ring containing one or two heteroatoms independently selected from N, O and S, wherein the $C_{3-7}$cycloalkyl, phenyl, heteroaryl and heterocycloalkyl are optionally substituted with one, two or three substituents independently selected from halo, hydroxyl, —$C(O)R^{10}$, and $C_{1-4}$ alkyl.

In an embodiment, each L is independently selected from a bond, —$(CH_2)_n$—, —O—, —$(CH_2)_nO$—, —$O(CH_2)_n$—, and —$(CH_2)_nO(CH_2)_m$—; and each Y is independently selected from the group consisting of hydrogen, halo, cyano, $C_{1-4}$ alkyl, $C_{1-4}$ alkoxy, $C_{3-7}$cycloalkyl, $C_{1-4}$thioalkyl, $C_{1-6}$hydroxyalkyl, $C_{1-4}$ cyanoalkyl, halo($C_{1-4}$)alkyl, —$NR^9R^{10}$, —$CO_2R^{10}$, —$C(O)R^{10}$, —$CF_2CH_2OR^{10}$, and 4- to 10-membered heterocycloalkyl ring containing one, two or three heteroatoms independently selected from N, O and S where the heterocycloalkyl and $C_{3-7}$cycloalkyl are optionally substituted with one, two or three substituents independently selected from halo, hydroxyl, —$C(O)R^{10}$, oxo, $C_{1-4}$ alkyl, halo($C_{1-4}$)alkyl and $C_{1-4}$ hydroxyalkyl.

In an embodiment, each L is a bond; and each Y is independently selected from the group consisting of hydrogen, halo, hydroxyl, cyano, $C_{1-4}$ alkyl, $C_{3-7}$cycloalkyl, $C_{1-4}$ alkoxy, $C_{1-4}$thioalkyl, $C_{1-6}$hydroxyalkyl, $C_{1-4}$ cyanoalkyl, halo($C_{1-4}$)alkyl, —$NR^9R^{10}$, —$C(O)NR^9R^{10}$, —$CO_2R^{10}$, —$C(O)R^{10}$, —$SO_2R^{10}$, —$OSO_2R^{10}$, —$CF_2CH_2OR^{10}$, phenyl, 5- or 6-membered heteroaryl, and 5- or 6-membered heterocycloalkyl ring containing one or two heteroatoms independently selected from N, O and S, wherein the $C_{3-7}$cycloalkyl, phenyl, heteroaryl and heterocycloalkyl are optionally substituted with one, two or three substituents independently selected from halo, hydroxyl, —$C(O)R^{10}$, and $C_{1-4}$ alkyl. In an embodiment, $R^4$, $R^5$ and $R^6$ are independently selected from hydrogen, halogen, $CO_2R^{10}$ and halo($C_{1-4}$)alkyl.

In an embodiment, $R^6$ is hydrogen.

In an embodiment, $R^4$ and $R^5$ are independently selected from hydrogen, halogen, $CO_2R^{10}$ and halo($C_{1-4}$)alkyl and $R^6$ is hydrogen.

In an embodiment, $R^4$ and $R^6$ are hydrogen.

In an embodiment, $R^4$, $R^5$ and $R^6$ are hydrogen.

In an embodiment, $R^4$ and $R^6$ are hydrogen and $R^5$ is halo.

In an embodiment $R^4$ and $R^6$ are hydrogen and $R^5$ is fluoro.

In an embodiment, $R^a$ and $R^b$ are hydrogen.

In an embodiment, $R^4$ and $R^5$ taken together with the carbon atoms to which they are attached form a 5- to 8-membered monocyclic or bicyclic ring which optionally contains one or two heteroatoms independently selected from N, O and S, wherein the ring is optionally substituted with up to three substituents independently selected from halo, $C_{1-4}$ alkyl, oxo, —$C(O)R^8$ and —$SO_2R^8$.

In an embodiment, $R^4$ and $R^5$ taken together with the carbon atoms to which they are attached form a 5-membered monocyclic ring. In an embodiment, $R^4$ and $R^5$ taken together with the carbon atoms to which they are attached form a 5-membered monocyclic ring containing one heteroatom selected from N and O. In an embodiment, $R^4$ and $R^5$ taken together with the carbon atoms to which they are attached form a 6-membered monocyclic ring. In an embodiment, $R^4$ and $R^5$ taken together with the carbon atoms to which they are attached form a 6-membered monocyclic ring containing one heteroatom selected from N and O.

In an embodiment, each L is independently selected from a bond, —$(CH_2)_n$— and —$(CH_2)_nO$—.

In an embodiment, each Y is independently selected from hydrogen, halogen, $CO_2R^{10}$ and halo$(C_{1-4})$alkyl.

In an embodiment, the present invention provides a compound of Formula (I) or a tautomer thereof, or a pharmaceutically acceptable salt of said compound or tautomer thereof,

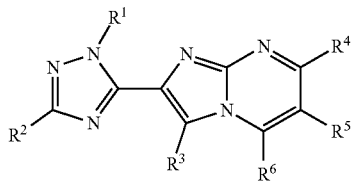

(I)

wherein
- $R^1$ is hydrogen or a prodrug moiety;
- $R^2$ is selected from the group consisting of hydrogen, halo, $C_{1-3}$ alkyl and halo$(C_{1-3})$alkyl;
- $R^3$ is imidazolyl or pyrazolyl, where $R^3$ is optionally substituted by a prodrug moiety; each $R^4$, $R^5$ and $R^6$ is independently -L-Y;
- each L is independently selected from a bond, —$(CR^aR^b)_n$— or —O—;
- wherein each n is independently 1, 2 or 3;
- each $R^a$ and $R^b$ is independently selected from hydrogen or methyl; and each Y is independently selected from the group consisting of hydrogen, halo, $C_{1-4}$ alkyl, $C_{3-7}$cycloalkyl, $C_{1-4}$ thioalkyl, $C_{1-6}$ hydroxyalkyl, halo$(C_{1-4})$alkyl, —$CO_2R^{10}$, —$COR^{10}$, —$SO_2R^{10}$, —$OSO_2R^{10}$, —$CF_2CH_2OR^{10}$; or
- $R^4$ and $R^5$ taken together with the carbon atoms to which they are attached form a 5- to 8-membered monocyclic or bicyclic ring which optionally contains one or two heteroatoms independently selected from N, O and S, wherein the ring is optionally substituted with one, two or three substituents independently selected from halo, $C_{1-4}$alkyl, —$C(O)R^{10}$ and —$SO_2R^{10}$;
- $R^{10}$ is independently selected from hydrogen and $C_{1-6}$ alkyl. In an embodiment, the compound of Formula (I) is selected from the group consisting of:

5-[3-(1H-imidazol-4-yl)imidazo[1,2-a]pyrimidin-2-yl]-3-(trifluoromethyl)-1H-1,2,4-triazole;

5-[6-fluoro-3-(1H-imidazol-5-yl)imidazo[1,2-a]pyramidin-2-yl]-3-(trifluoromethyl)-1H-1,2,4-triazole;

5-[3-(1H-imidazol-5-yl)-7-(trifluoromethyl)imidazo[1,2-a]pyrimidin-2-yl]-3-(trifluoromethyl)-1H-1,2,4-triazole;

5-[6-chloro-3-(1H-imidazol-4-yl)imidazo[1,2-a]pyrimidin-2-yl]-3-(difluoromethyl)-1H-1,2,4-triazole;

3-(difluoromethyl)-5-[6-fluoro-3-(1H-imidazol-4-yl)imidazo[1,2-a]pyrimidin-2-yl]-1H-1,2,4-triazole;

5-[7-chloro-3-(1H-imidazol-5-yl)imidazo[1,2-a]pyrimidin-2-yl]-3-(trifluoromethyl)-1H-1,2,4-triazole;

3-(difluoromethyl)-5-[7-(difluoromethyl)-3-(1H-imidazol-5-yl)imidazo[1,2-a]pyrimidin-2-yl]-1H-1,2,4-triazole;

5-[3-(1H-pyrazol-4-yl)imidazo[1,2-a]pyrimidin-2-yl]-3-(trifluoromethyl)-1H-1,2,4-triazole;

{4-oxo-4-[(4-{2-[3-(trifluoromethyl)-1H-1,2,4-triazol-5-yl]imidazo[1,2-a]pyrimidin-3-yl}-1H-imidazol-1-yl)methoxy]butoxy}phosphonic acid;

{4-oxo-4-[(5-{3-[1-({[4-(phosphonooxy)butanoyl]oxy}methyl)-1H-imidazol-4-yl]imidazo[1,2-a]pyrimidin-2-yl}-3-(trifluoromethyl)-1H-1,2,4-triazol-1-yl)methoxy]butoxy}phosphonic acid;

({5-[6-fluoro-3-(1H-imidazol-5-yl)imidazo[1,2-a]pyrimidin-2-yl]-3-(trifluoromethyl)-1H-1,2,4-triazol-1-yl}methoxy)phosphonic acid;

methyl 2-(3-bromo-1H-1,2,4-triazol-5-yl)-3-(1H-pyrazol-4-yl)imidazo[1,2-a]pyrimidine-7-carboxylate;

methyl 2-(3-bromo-1H-1,2,4-triazol-5-yl)-3-(1H-imidazol-4-yl)imidazo[1,2-a]pyrimidine-7-carboxylate;

3-bromo-5-[3-(1H-imidazol-4-yl)imidazo[1,2-a]pyrimidin-2-yl]-1H-1,2,4-triazole;

5-[6-fluoro-3-(1H-pyrazol-4-yl)imidazo[1,2-a]pyrimidin-2-yl]-3-(trifluoromethyl)-1H-1,2,4-triazole;

5-[6-chloro-3-(1H-imidazol-5-yl)imidazo[1,2-a]pyrimidin-2-yl]-3-(trifluoromethyl)-1H-1,2,4-triazole;

3-(difluoromethyl)-5-[3-(1H-imidazol-5-yl)imidazo[1,2-a]pyrimidin-2-yl]-1H-1,2,4-triazole;

5-[3-(1H-imidazol-5-yl)-6-(trifluoromethyl)imidazo[1,2-a]pyrimidin-2-yl]-3-(trifluoromethyl)-1H-1,2,4-triazole;

5-[6-bromo-3-(1H-imidazol-5-yl)imidazo[1,2-a]pyrimidin-2-yl]-3-(trifluoromethyl)-1H-1,2,4-triazole;

3-(difluoromethyl)-5-[3-(1H-imidazol-5-yl)-7-(trifluoromethyl)imidazo[1,2-a]pyrimidin-2-yl]-1H-1,2,4-triazole;

3-bromo-5-[3-(1H-imidazol-5-yl)-7-(trifluoromethyl)imidazo[1,2-a]pyrimidin-2-yl]-1H-1,2,4-triazole;

5-[3-(1H-pyrazol-4-yl)-7-(trifluoromethyl)imidazo[1,2-a]pyrimidin-2-yl]-3-(trifluoromethyl)-1H-1,2,4-triazole;

5-[7-(difluoromethyl)-3-(1H-imidazol-5-yl)imidazo[1,2-a]pyrimidin-2-yl]-3-(trifluoromethyl)-1H-1,2,4-triazole;

5-[3-(1H-imidazol-5-yl)-7-(trifluoromethyl)imidazo[1,2-a]pyrimidin-2-yl]-1H-1,2,4-triazole;

5-[3-(1H-imidazol-5-yl)-7-(trifluoromethyl)imidazo[1,2-a]pyrimidin-2-yl]-3-methyl-1H-1,2,4-triazole;

methyl 3-(1H-imidazol-4-yl)-2-[3-(trifluoromethyl)-1H-1,2,4-triazol-5-yl]imidazo[1,2-a]pyrimidine-7-carboxylate;

3-(1H-imidazol-4-yl)-2-[3-(trifluoromethyl)-1H-1,2,4-triazol-5-yl]imidazo[1,2-a]pyrimidine-7-carboxylic acid;

3-(difluoromethoxy)-5-[3-(1H-imidazol-5-yl)imidazo[1,2-a]pyrimidin-2-yl]-1H-1,2,4-triazole;

5-[6-(difluoromethyl)-3-(1H-imidazol-4-yl)imidazo[1,2-a]pyrimidin-2-yl]-3-(trifluoromethyl)-1H-1,2,4-triazole;

5-[6-fluoro-3-(1H-imidazol-5-yl)-7-(trifluoromethyl)imidazo[1,2-a]pyrimidin-2-yl]-3-(trifluoromethyl)-1H-1,2,4-triazole;

5-[6-chloro-3-(1H-imidazol-5-yl)-7-(trifluoromethyl)imidazo[1,2-a]pyrimidin-2-yl]-3-(trifluoromethyl)-1H-1,2,4-triazole;

5-[3-(2-methyl-1H-imidazol-4-yl)imidazo[1,2-a]pyrimidin-2-yl]-3-(trifluoromethyl)-1H-1,2,4-triazole;

5-[3-(1-methyl-1H-pyrazol-4-yl)imidazo[1,2-a]pyrimidin-2-yl]-3-(trifluoromethyl)-1H-1,2,4-triazole; and 3-bromo-5-[6-fluoro-3-(1H-imidazol-4-yl)imidazo[1,2-a]pyrimidin-2-yl]-1H-1,2,4-triazole, or a tautomer thereof, or a pharmaceutically acceptable salt of said compound or tautomer thereof.

In an embodiment, the compound of Formula (I) is

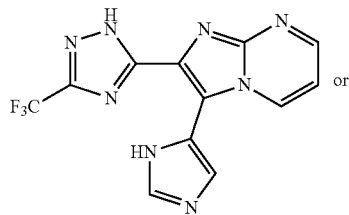

or

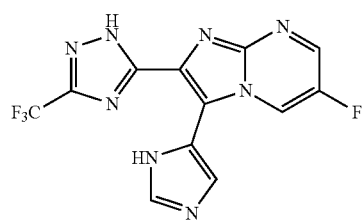

or a tautomer thereof, or a pharmaceutically acceptable salt of said compound or tautomer thereof.

In an embodiment, the compound of Formula (I) is depicted by one of the following structures, depicting the available tautomers when $R^3$ is imidazolyl, $R^2$ is $CF_3$:

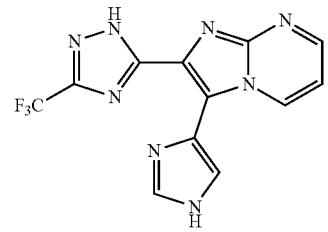

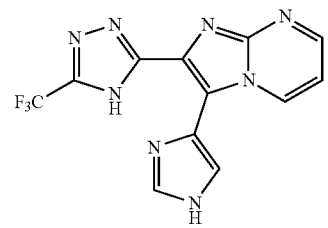

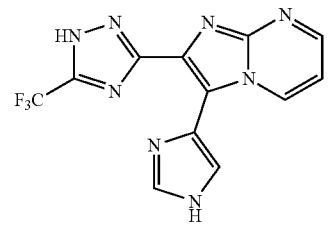

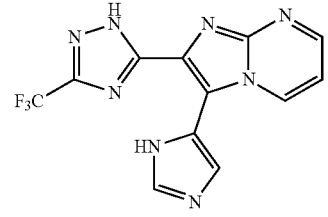

-continued

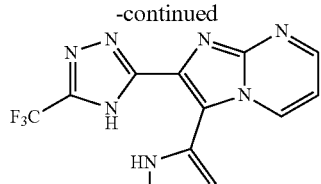

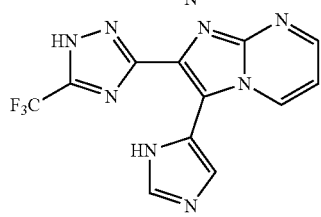

or a tautomer thereof, or a pharmaceutically acceptable salt of said compound or tautomer thereof.

In an embodiment, the compound of Formula (I) is depicted by one of the following structures, depicting the available tautomers when $R^3$ is imidazolyl, $R^2$ is $CF_3$:

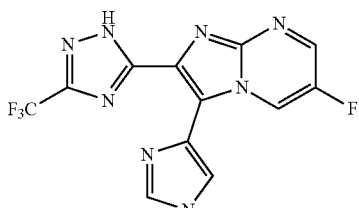

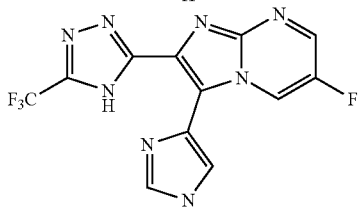

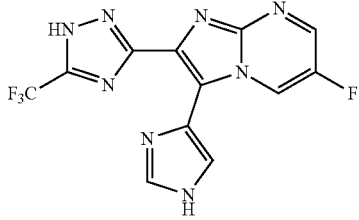

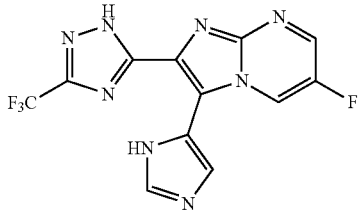

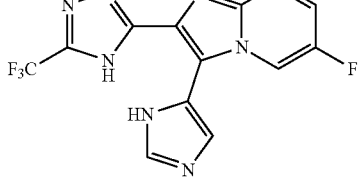

-continued

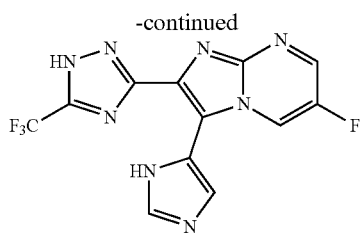

or a pharmaceutically acceptable salt thereof.

In an embodiment, the compound of Formula (I) is a prodrug of

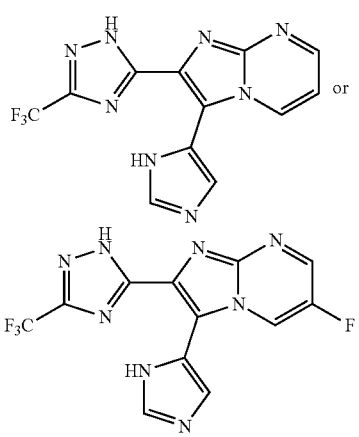

or a tautomer thereof, or a pharmaceutically acceptable salt of said compound or tautomer thereof.

In an embodiment, the compound of Formula (I) is

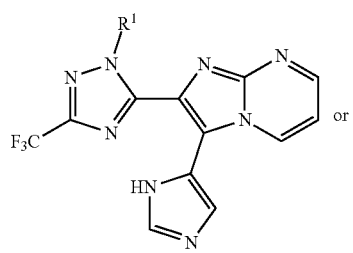

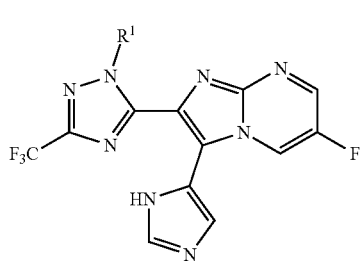

wherein $R^1$ is a prodrug moiety, or a tautomer thereof, or a pharmaceutically acceptable salt of said compound or tautomer thereof.

In an embodiment, the compound of Formula (I) is

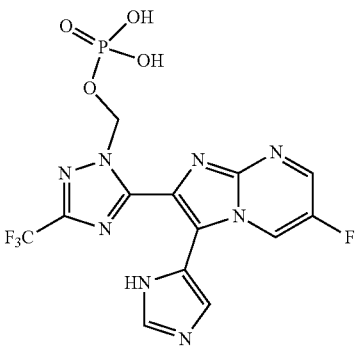 [SMILES: O=P(O)(O)OCn1nc(C(F)(F)F)nc1-c1nc2ncc(F)cn2c1-c1cnc[nH]1]

or a tautomer thereof, or a pharmaceutically acceptable salt of said compound or tautomer thereof.

In an embodiment, the compound of Formula (I) is depicted by one of the following structures, depicting the available tautomers when $R^3$ is imidazolyl:

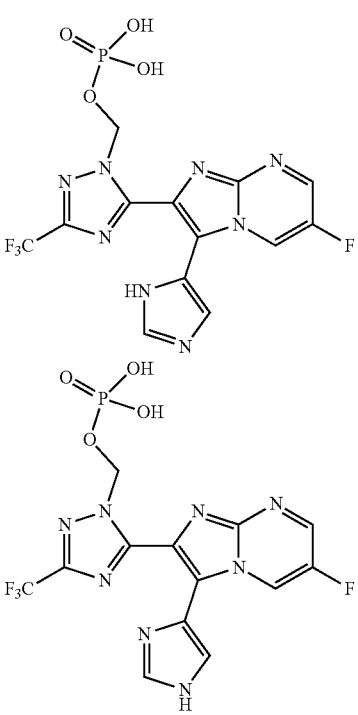

or a pharmaceutically acceptable salt thereof.

In an embodiment, a compound of Formula (I) is in the form of a free base. In one embodiment, the compound of Formula (I) in the form of a free base is any one of the compounds of Examples 1 to 165.

In an embodiment, a compound of Formula (I) is in the form of a pharmaceutically acceptable salt. In one embodiment, the compound of Formula (I) in the form of a pharmaceutically acceptable salt is any one of compounds of Examples 1 to 165.

Compounds of Formula (I) or a tautomer thereof may contain an acidic or basic functional group and, thus, a person of skill in the art will appreciate that pharmaceutically acceptable salts of the compounds of Formula (I) may be prepared.

Pharmaceutically acceptable salts include, amongst others, those described in Berge, J.

Pharm. Sci., 1977, 66, 1-19, or those listed in P H Stahl and C G Wermuth, editors, Handbook of Pharmaceutical Salts; Properties, Selection and Use, Second Edition Stahl/Wermuth: Wiley-VCH/VHCA, 2011 (see http://www.wiley.com/WileyCDA/WileyTitle/productCd-3906390519.html).

Suitable pharmaceutically acceptable salts can include acid or base addition salts.

Such base addition salts can be formed by reaction of a compound of formula (I) (which, for example, contains a carboxylic acid or other acidic functional group) with the appropriate base, optionally in a suitable solvent such as an organic solvent, to give the salt.

Such acid addition salts can be formed by reaction of a compound of formula (I) (which, for example contains a basic amine or other basic functional group) with the appropriate acid, optionally in a suitable solvent such as an organic solvent, to give the salt.

Salts may be prepared in situ during the final isolation and purification of a compound of formula (I). If a basic compound of formula (I) is isolated as a salt, the corresponding free base form of that compound may be prepared by any suitable method known to the art, including treatment of the salt with an inorganic or organic base. Similarly, if a compound of formula (I) containing a carboxylic acid or other acidic functional group is isolated as a salt, the corresponding free acid form of that compound may be prepared by any suitable method known to the art, including treatment of the salt with an inorganic or organic acid.

It will be understood that if a compound of Formula (I) contains two or more basic moieties, the stoichiometry of salt formation may include 1, 2 or more equivalents of acid. Such salts would contain 1, 2 or more acid counterions, for example, a dihydrochloride salt.

Stoichiometric and non-stoichiometric forms of a pharmaceutically acceptable salt of a compound of formula (I) are included within the scope of the invention, including sub-stoichiometric salts.

Representative pharmaceutically acceptable acid addition salts include, but are not limited to, 4-acetamidobenzoate, acetate, adipate, alginate, ascorbate, aspartate, benzenesulfonate (besylate), benzoate, bisulfate, bitartrate, butyrate, calcium edetate, camphorate, camphorsulfonate (camsylate), caprate (decanoate), caproate (hexanoate), caprylate (octanoate), cinnamate, citrate, cyclamate, digluconate, 2,5-dihydroxybenzoate, disuccinate, dodecylsulfate (estolate), edetate (ethylenediaminetetraacetate), estolate (lauryl sulfate), ethane-1,2-disulfonate (edisylate), ethanesulfonate (esylate), formate, fumarate, galactarate (mucate), gentisate (2,5-dihydroxybenzoate), glucoheptonate (gluceptate), gluconate, glucuronate, glutamate, glutarate, glycerophosphorate, glycolate, hexylresorcinate, hippurate, hydrabamine (N,N'-di(dehydroabietyl)-ethylenediamine), hydrobromide, hydrochloride, hydroiodide, hydroxynaphthoate, isobutyrate, lactate, lactobionate, laurate, malate, maleate, malonate, mandelate, methanesulfonate (mesylate), methylsulfate, mucate, naphthalene-1,5-disulfonate (napadisylate), naphthalene-2-sulfonate (napsylate), nicotinate, nitrate, oleate, palmitate, p-aminobenzenesulfonate, p-aminosalicylate, pamoate (embonate), pantothenate, pectinate, persulfate, phenylacetate, phenylethylbarbiturate, phosphate, polygalacturonate, propionate, p-toluenesulfonate (tosylate), pyroglutamate, pyruvate, salicylate, sebacate, stearate, subacetate, succinate, sulfamate, sulfate, tannate, tartrate, teoclate (8-chlorotheophyllinate), thiocyanate, triethiodide, undecanoate, undecylenate, and valerate.

Representative pharmaceutically acceptable base addition salts include, but are not limited to, aluminium, 2-amino-2-(hydroxymethyl)-1,3-propanediol (TRIS, tromethamine), arginine, benethamine (N-benzylphenethylamine), benzathine (N,N'-dibenzylethylenediamine), bis-(2-hydroxyethyl)amine, bismuth, calcium, chloroprocaine, choline, clemizole (1-p chlorobenzyl-2-pyrrolildine-1'-ylmethylbenzimidazole), cyclohexylamine, dibenzylethylenediamine, diethylamine, diethyltriamine, dimethylamine, dimethylethanolamine, dopamine, ethanolamine, ethylenediamine, L-histidine, iron, isoquinoline, lepidine, lithium, lysine, magnesium, meglumine (N-methylglucamine), piperazine, piperidine, potassium, procaine, quinine, quinoline, sodium, strontium, t-butylamine, and zinc.

The compounds of the invention may exist in tautomeric forms. It is to be understood that any reference to a named compound or a structurally depicted compound is intended to encompass all tautomers of such compound.

For example, when $R^1$ is hydrogen, the following tautomers exist:

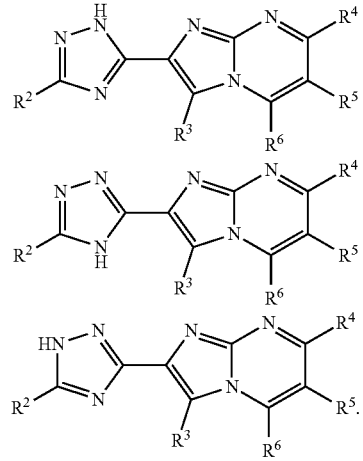

For example, when $R^1$ is a prodrug moiety and $R^3$ is imidazolyl (bonded through carbon), the following tautomers exist:

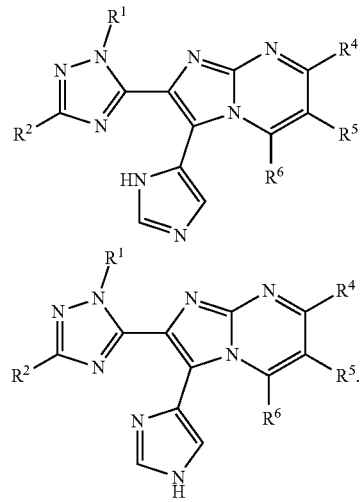

In an embodiment, when $R^1$ is hydrogen and $R^3$ is imidazolyl (bonded through C), the following tautomers exist:

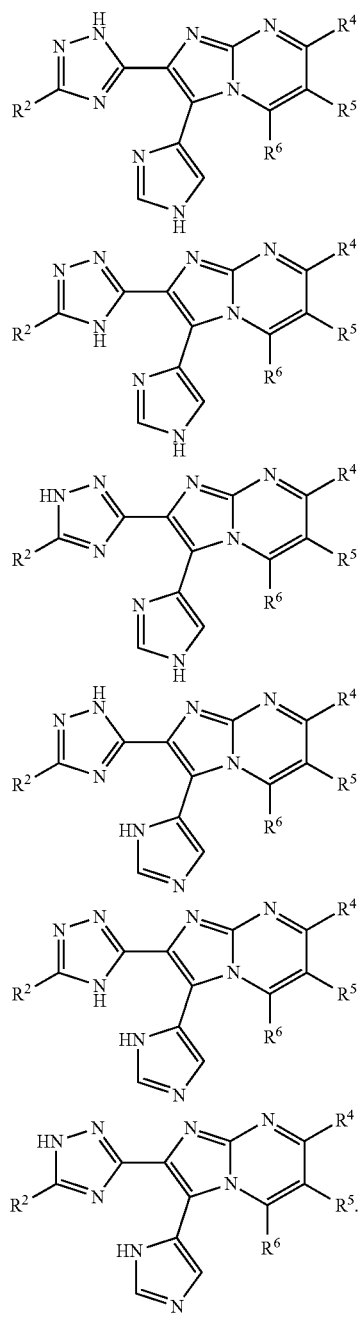

The present invention also includes all suitable isotopic variations of a compound of the invention. An isotopic variation of a compound of the invention, is defined as one in which at least one atom is replaced by an atom having the same atomic number but an atomic mass different from the atomic mass usually found in nature.

Examples of isotopes that can be incorporated into compounds of the invention include isotopes of hydrogen, carbon, nitrogen, oxygen, fluorine and chlorine such as 2H, 3H, 13C, 14C, 15N, 17O, 18O, 18F and 36Cl, respectively. Certain isotopic variations of a compound of formula (I) or a salt or solvate thereof, for example, those in which a radioactive isotope such as 3H or 14C is incorporated, are useful in drug and/or substrate tissue distribution studies. Tritiated, i.e., 3H, and carbon-14, i.e., 14C, isotopes are particularly preferred for their ease of preparation and detectability. Further, substitution with isotopes such as deuterium, i.e., 2H, may afford certain therapeutic advantages resulting from greater metabolic stability, for example, increased in vivo half-life or reduced dosage requirements and hence may be preferred in some circumstances. Thus, in one embodiment, the present invention includes a compound of the invention, wherein one or more hydrogen atoms attached to carbon atoms are replaced by deuterium. Isotopic variations of a compound of the invention, can generally be prepared by conventional procedures such as by the illustrative methods or by the preparations described in the Examples hereafter using appropriate isotopic variations of suitable reagents.

In an embodiment, the present invention includes

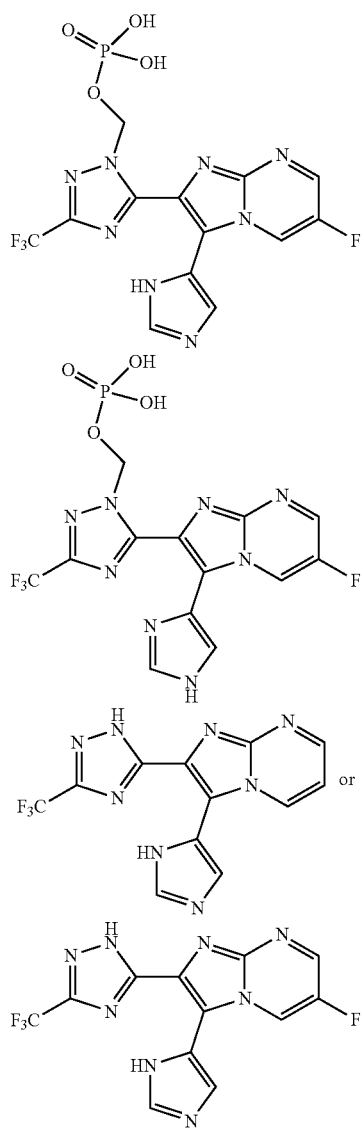

Wherein One or More Hydrogen Atoms Attached to Carbon Atoms are Replaced by Deuterium.

Representative compounds of Formula (I) are listed in Table 1 below:

TABLE 1

| Compound No. / Example No. | Chemical Name | Structure |
|---|---|---|
| 1 | 5-[3-(1H-imidazol-4-yl)imidazo[1,2-a]pyrimidin-2-yl]-3-(trifluoromethyl)-1H-1,2,4-triazole | 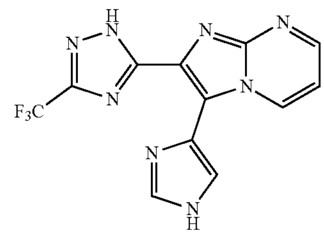 [SMILES: FC(F)(F)c1n[nH]c(-c2nc3ncccn3c2-c2c[nH]cn2)n1] |
| 2 | 5-[6-fluoro-3-(1H-imidazol-5-yl)imidazo[1,2-a]pyrimidin-2-yl]-3-(trifluoromethyl)-1H-1,2,4-triazole | 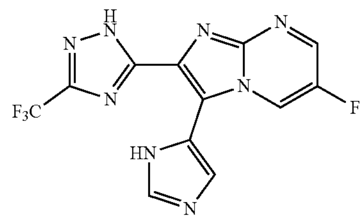 [SMILES: Fc1cnc2nc(-c3nc(C(F)(F)F)n[nH]3)c(-c3cnc[nH]3)n2c1] |
| 3 | 5-[3-(1H-imidazol-5-yl)-7-(trifluoromethyl)imidazo[1,2-a]pyrimidin-2-yl]-3-(trifluoromethyl)-1H-1,2,4-triazole | 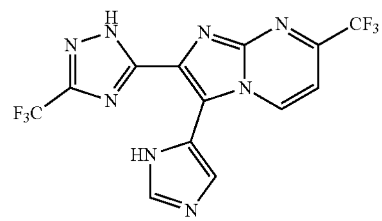 [SMILES: FC(F)(F)c1ccn2c(-c3cnc[nH]3)c(-c3nc(C(F)(F)F)n[nH]3)nc2n1] |
| 4 | 5-[6-chloro-3-(1H-imidazol-4-yl)imidazo[1,2-a]pyrimidin-2-yl]-3-(difluoromethyl)-1H-1,2,4-triazole | 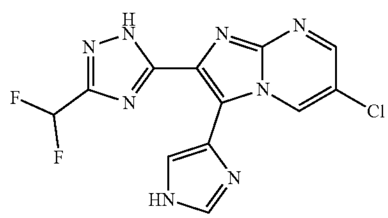 [SMILES: FC(F)c1n[nH]c(-c2nc3ncc(Cl)cn3c2-c2c[nH]cn2)n1] |
| 5 | 3-(difluoromethyl)-5-[6-fluoro-3-(1H-imidazol-4-yl)imidazo[1,2-a]pyrimidin-2-yl]-1H-1,2,4-triazole | 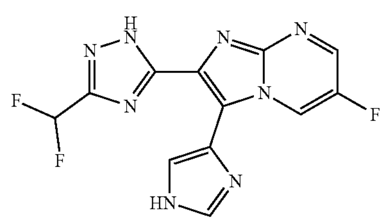 [SMILES: Fc1cnc2nc(-c3nc(C(F)F)n[nH]3)c(-c3c[nH]cn3)n2c1] |
| 6 | 2,2-difluoro-2-[3-(1H-imidazol-5-yl)-2-[3-(trifluoromethyl)-1H-1,2,4-triazol-5-yl]imidazo[1,2-a]pyrimidin-7-yl]ethan-1-ol | 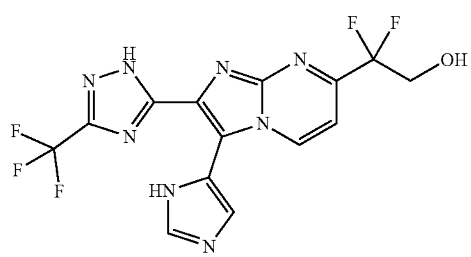 [SMILES: OCC(F)(F)c1ccn2c(-c3cnc[nH]3)c(-c3nc(C(F)(F)F)n[nH]3)nc2n1] |

TABLE 1-continued

| Compound No. / Example No. | Chemical Name | Structure |
|---|---|---|
| 7 | 5-[7-chloro-3-(1H-imidazol-5-yl)imidazo[1,2-a]pyrimidin-2-yl]-3-(trifluoromethyl)-1H-1,2,4-triazole | 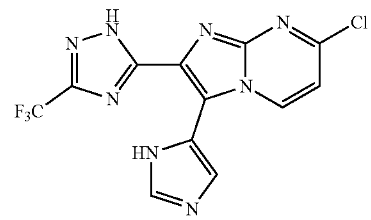 [SMILES: FC(F)(F)c1n[nH]c(-c2nc3nc(Cl)ccn3c2-c2cnc[nH]2)n1] |
| 8 | 3-(difluoromethyl)-5-[7-(difluoromethyl)-3-(1H-imidazol-5-yl)imidazo[1,2-a]pyrimidin-2-yl]-1H-1,2,4-triazole | 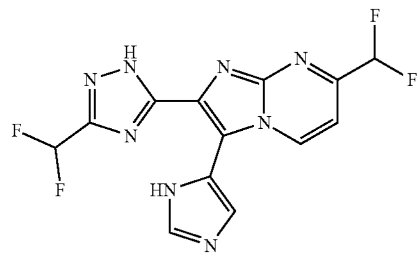 [SMILES: FC(F)c1ccn2c(-c3cnc[nH]3)c(-c3nc(C(F)F)n[nH]3)nc2n1] |
| 9 | [3-(1H-imidazol-5-yl)-2-[3-(trifluoromethyl)-1H-1,2,4-triazol-5-yl]imidazo[1,2-a]pyrimidin-7-yl]methanol | 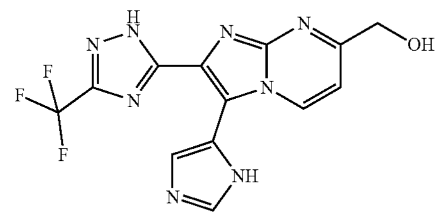 [SMILES: OCc1ccn2c(-c3cnc[nH]3)c(-c3nc(C(F)(F)F)n[nH]3)nc2n1] |
| 10 | 12-(1H-imidazol-4-yl)-11-[3-(trifluoromethyl)-1H-1,2,4-triazol-5-yl]-5-oxa-1,8,10-triazatricyclo[7.3.0.0$^{3,7}$]dodeca-2,7,9,11-tetraene | 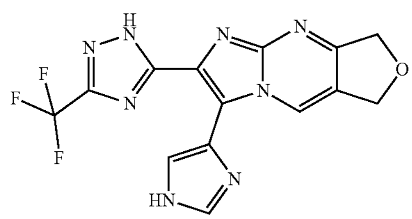 [SMILES: FC(F)(F)c1n[nH]c(-c2nc3nc4c(cn3c2-c2c[nH]cn2)COC4)n1] |
| 11 | 5-[3-(1H-pyrazol-4-yl)imidazo[1,2-a]pyrimidin-2-yl]-3-(trifluoromethyl)-1H-1,2,4-triazole | 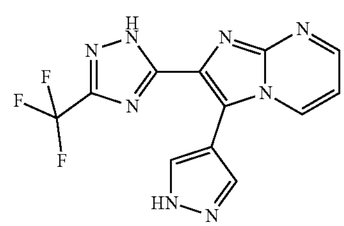 [SMILES: FC(F)(F)c1n[nH]c(-c2nc3ncccn3c2-c2cn[nH]c2)n1] |
| 12 | 5-[3-(1H-imidazol-5-yl)-7-(2,2,2-trifluoroethoxy)imidazo[1,2-a]pyrimidin-2-yl]-3-(trifluoromethyl)-1H-1,2,4-triazole | 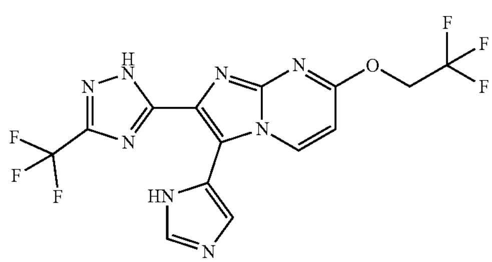 [SMILES: FC(F)(F)COc1ccn2c(-c3cnc[nH]3)c(-c3nc(C(F)(F)F)n[nH]3)nc2n1] |

TABLE 1-continued

| Compound No. / Example No. | Chemical Name | Structure |
|---|---|---|
| 13 | 1-[3-(1H-imidazol-5-yl)-2-[3-(trifluoromethyl)-1H-1,2,4-triazol-5-yl]imidazo[1,2-a]pyrimidin-7-yl]ethan-1-ol | 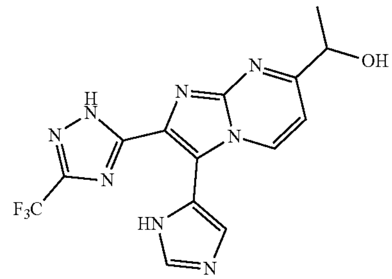 [SMILES: CC(O)c1ccn2c(-c3cnc[nH]3)c(-c3nc(C(F)(F)F)n[nH]3)nc2n1] |
| 14 | 1-[3-(1H-imidazol-5-yl)-2-[3-(trifluoromethyl)-1H-1,2,4-triazol-5-yl]imidazo[1,2-a]pyrimidin-7-yl]ethan-1-one | 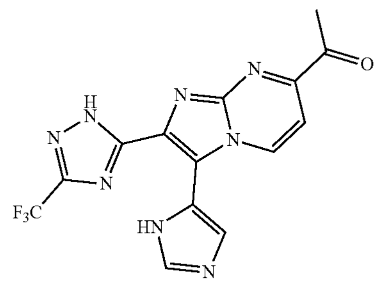 [SMILES: CC(=O)c1ccn2c(-c3cnc[nH]3)c(-c3nc(C(F)(F)F)n[nH]3)nc2n1] |
| 15 | 5-[6-(cyclohexylmethyl)-3-(1H-imidazol-5-yl)imidazo[1,2-a]pyrimidin-2-yl]-3-(trifluoromethyl)-1H-1,2,4-triazole | 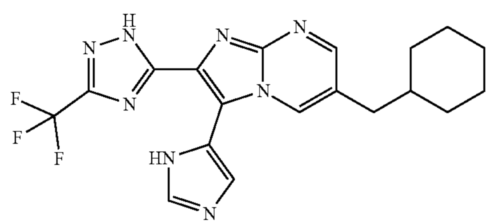 [SMILES: FC(F)(F)c1n[nH]c(-c2nc3ncc(CC4CCCCC4)cn3c2-c2cnc[nH]2)n1] |
| 16 | 5-[6-cyclopentyl-3-(1H-imidazol-5-yl)imidazo[1,2-a]pyrimidin-2-yl]-3-(trifluoromethyl)-1H-1,2,4-triazole | 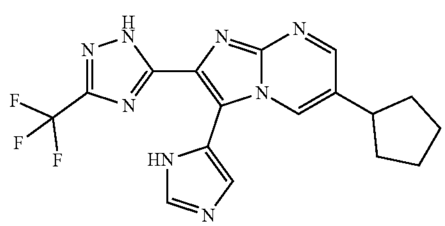 [SMILES: FC(F)(F)c1n[nH]c(-c2nc3ncc(C4CCCC4)cn3c2-c2cnc[nH]2)n1] |
| 17 | 5-[6-(cyclopentylmethyl)-3-(1H-imidazol-5-yl)imidazo[1,2-a]pyrimidin-2-yl]-3-(trifluoromethyl)-1H-1,2,4-triazole | 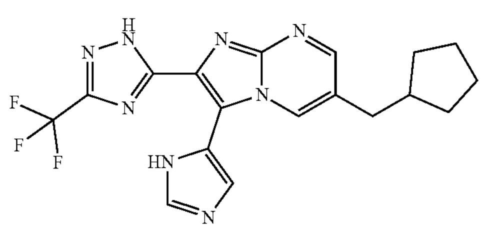 [SMILES: FC(F)(F)c1n[nH]c(-c2nc3ncc(CC4CCCC4)cn3c2-c2cnc[nH]2)n1] |
| 18 | 13,13-difluoro-6-(1H-imidazol-5-yl)-11-methyl-5-[3-(trifluoromethyl)-1H-1,2,4-triazol-5-yl]-2,4,7,11-tetraazatricyclo[7.4.0.0$^{3,7}$]tridec a-1,3,5,8-tetraene | 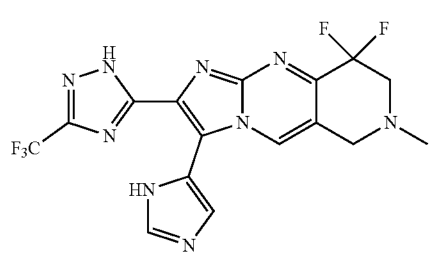 [SMILES: CN1Cc2cn3c(-c4cnc[nH]4)c(-c4nc(C(F)(F)F)n[nH]4)nc3nc2C(F)(F)C1] |

TABLE 1-continued

| Compound No. / Example No. | Chemical Name | Structure |
|---|---|---|
| 19 | 5-[7-(1, 1-difluoro-2-methoxyethyl)-3-(1H-imidazol-5-yl)imidazo[1,2-a]pyrimidin-2-yl]-3-(trifluoromethyl)-1H-1,2,4-triazole | 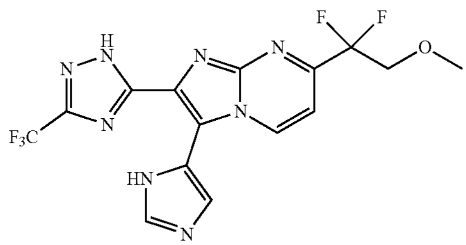 [SMILES: COCC(F)(F)c1ccn2c(-c3cnc[nH]3)c(-c3nc(C(F)(F)F)n[nH]3)nc2n1] |
| 20 | 3-(1H-imidazol-5-yl)-2-[3-(trifluoromethyl)-1H-1,2,4-triazol-5-yl]imidazo[1,2-a]pyrimidin-6-yl methanesulfonate | 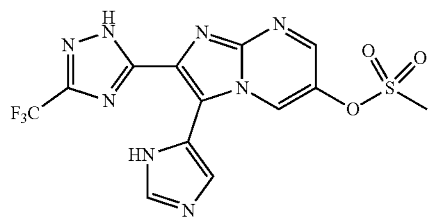 [SMILES: CS(=O)(=O)Oc1cnc2nc(-c3nc(C(F)(F)F)n[nH]3)c(-c3cnc[nH]3)n2c1] |
| 21 | 5-[3-(1H-imidazol-5-yl)-7-(methylsulfanyl)imidazo[1,2-a]pyrimidin-2-yl]-3-(trifluoromethyl)-1H-1,2,4-triazole | 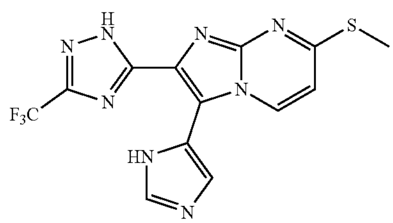 [SMILES: CSc1ccn2c(-c3cnc[nH]3)c(-c3nc(C(F)(F)F)n[nH]3)nc2n1] |
| 22 | 5-[3-(1H-imidazol-5-yl)-6-methanesulfonylimidazo[1,2-a]pyrimidin-2-yl]-3-(trifluoromethyl)-1H-1,2,4-triazole | 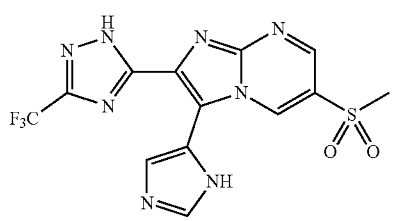 [SMILES: CS(=O)(=O)c1cnc2nc(-c3nc(C(F)(F)F)n[nH]3)c(-c3cnc[nH]3)n2c1] |
| 23 | 4-oxo-4-[(4-{2-[3-(trifluoromethyl)-1H-1,2,4-triazol-5-yl]imidazo[1,2-a]pyrimidin-3-yl}-1H-imidazol-1-yl)methoxy]butanoic acid | 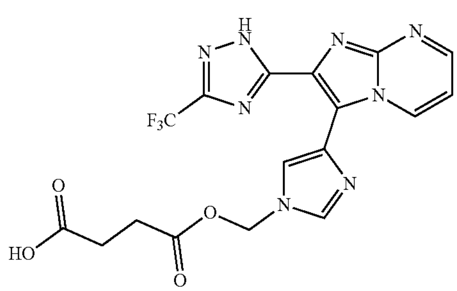 [SMILES: O=C(O)CCC(=O)OCn1cnc(-c2c(-c3nc(C(F)(F)F)n[nH]3)nc3ncccn23)c1] |

TABLE 1-continued

| Compound No. / Example No. | Chemical Name | Structure |
|---|---|---|
| 24 | (4-{2-[1-({[(2S)-2-amino-3-methylbutanoyl]oxy}methyl)-3-(trifluoromethyl)-1H-1,2,4-triazol-5-yl]imidazo[1,2-a]pyrimidin-3-yl}-1H-imidazol-1-yl)methyl (2S)-2-amino-3-methylbutanoate | 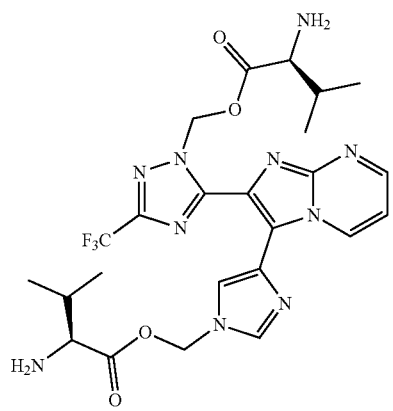 [SMILES: CC(C)[C@H](N)C(=O)OCn1cnc(-c2c(-c3nc(C(F)(F)F)nn3COC(=O)[C@@H](N)C(C)C)nc3ncccn23)c1] |
| 25 | {2-[methyl({[1-(5-{2-[3-(trifluoromethyl)-1H-1,2,4-triazol-5-yl]imidazo[1,2-a]pyrimidin-3-yl}-1H-imidazol-1-yl)ethoxy]carbonyl})amino]pyridin-3-yl}methyl 2-(methylamino)acetate | 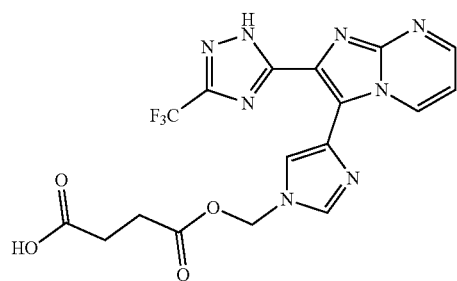 [SMILES: O=C(O)CCC(=O)OCn1cnc(-c2c(-c3nc(C(F)(F)F)n[nH]3)nc3ncccn23)c1] |
| 26 | 2-(methylamino)ethyl (4-{2-[3-(trifluoromethyl)-1H-1,2,4-triazol-5-yl]imidazo[1,2-a]pyrimidin-3-yl}-1H-imidazol-1-yl)methyl carbonate | 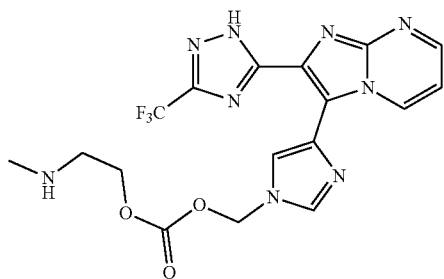 [SMILES: CNCCOC(=O)OCn1cnc(-c2c(-c3nc(C(F)(F)F)n[nH]3)nc3ncccn23)c1] |
| 27 | [4-(2-{1-[({{[2-(methylamino)ethoxy]carbonyl}oxy)methyl]-3-(trifluoromethyl)-1H-1,2,4-triazol-5-yl}imidazo[1,2-a]pyrimidin-3-yl)-1H-imidazol-1-yl]methyl 2-(methylamino)ethyl carbonate | 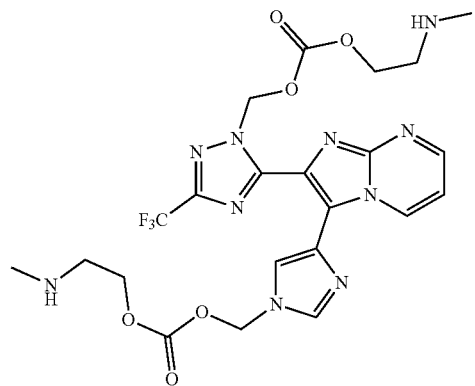 |

TABLE 1-continued

| Compound No. / Example No. | Chemical Name | Structure |
|---|---|---|
| 28 | {5-[3-(1H-imidazol-5-yl)imidazo[1,2-a]pyrimidin-2-yl]-3-(trifluoromethyl)-1H-1,2,4-triazol-1-yl}methyl 2-(methylamino)ethyl carbonate | 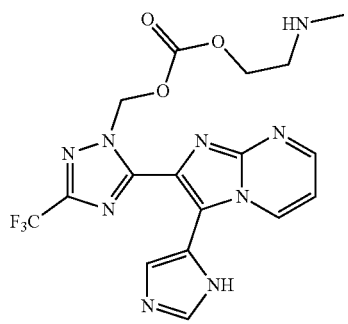 [SMILES: CNCCOC(=O)OCn1nc(C(F)(F)F)nc1-c1nc2ncccn2c1-c1cnc[nH]1] |
| 29 | {4-oxo-4-[(4-{2-[3-(trifluoromethyl)-1H-1,2,4-triazol-5-yl]imidazo[1,2-a]pyrimidin-3-yl}-1H-imidazol-1-yl)methoxy]butoxy}phosphonic acid | 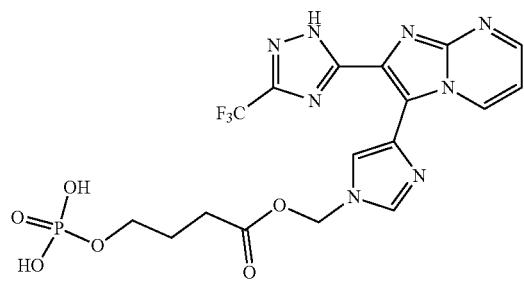 [SMILES: O=C(CCCOP(=O)(O)O)OCn1cnc(-c2c(-c3nc(C(F)(F)F)n[nH]3)nc3ncccn23)c1] |
| 30 | {4-oxo-4-[(5-{3-[1-({[4-(phosphonooxy)butanoyl]oxy}methyl)-1H-imidazol-4-yl]imidazo[1,2-a]pyrimidin-2-yl}-3-(trifluoromethyl)-1H-1,2,4-triazol-1-yl)methoxy]butoxy}phosphonic acid | 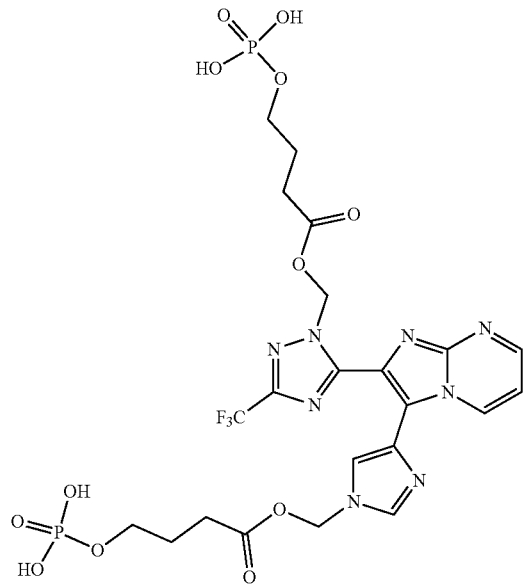 [SMILES: O=C(CCCOP(=O)(O)O)OCn1cnc(-c2c(-c3nc(C(F)(F)F)nn3COC(=O)CCCOP(=O)(O)O)nc3ncccn23)c1] |

TABLE 1-continued

| Compound No. / Example No. | Chemical Name | Structure |
|---|---|---|
| 31 | 3-({[(4-{2-[1-({[(2-carboxyethoxy)carbonyl]oxy}methyl)-3-(trifluoromethyl)-1H-1,2,4-triazol-5-yl]imidazo[1,2-a]pyrimidin-3-yl}-1H-imidazol-1-yl)methoxy]carbonyl}oxy)propanoic acid | 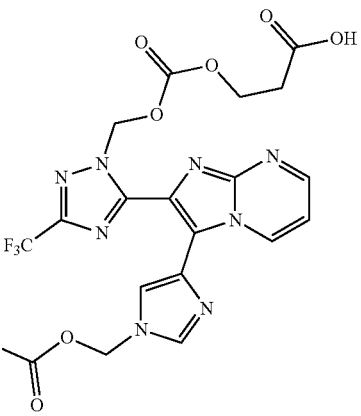 |
| 32 | 3-({[(4-{2-[3-(trifluoromethyl)-1H-1,2,4-triazol-5-yl]imidazo[1,2-a]pyrimidin-3-yl}-1H-imidazol-1-yl)methoxy]carbonyl}oxy)propanoic acid | 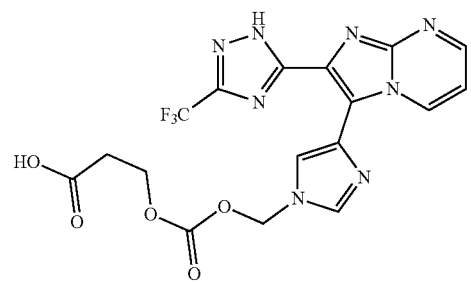 [SMILES: O=C(O)CCOC(=O)OCn1cnc(-c2c(-c3nc(C(F)(F)F)n[nH]3)nc3ncccn23)c1] |
| 33 | 3-{[{5-[{5-[3-(1H-imidazol-5-yl)imidazo[1,2-a]pyrimidin-2-yl]-3-(trifluoromethyl)-1H-1,2,4-triazol-1-yl}methoxy)carbonyl]oxy}propanoic acid | 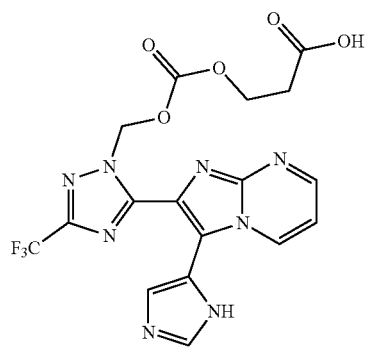 [SMILES: O=C(O)CCOC(=O)OCn1nc(C(F)(F)F)nc1-c1nc2ncccn2c1-c1cnc[nH]1] |
| 34 | ({5-[6-fluoro-3-(1H-imidazol-5-yl)imidazo[1,2-a]pyrimidin-2-yl]-3-(trifluoromethyl)-1H-1,2,4-triazol-1-yl}methoxy)phosphonic acid | 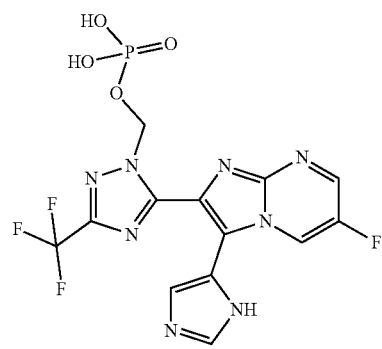 [SMILES: O=P(O)(O)OCn1nc(C(F)(F)F)nc1-c1nc2ncc(F)cn2c1-c1cnc[nH]1] |

TABLE 1-continued

| Compound No. / Example No. | Chemical Name | Structure |
|---|---|---|
| 35 | methyl 2-(3-bromo-1H-1,2,4-triazol-5-yl)-3-(1H-pyrazol-4-yl)imidazo[1,2-a]pyrimidine-7-carboxylate | 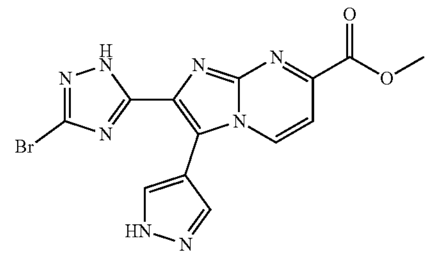 [SMILES: COC(=O)c1ccn2c(-c3cn[nH]c3)c(-c3nc(Br)n[nH]3)nc2n1] |
| 36 | methyl 2-(3-bromo-1H-1,2,4-triazol-5-yl)-3-(1H-imidazol-4-yl)imidazo[1,2-a]pyrimidine-7-carboxylate | 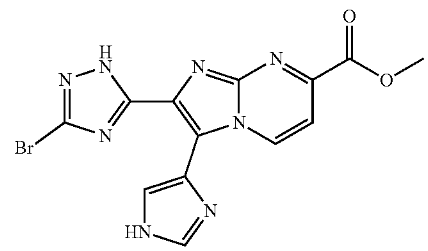 [SMILES: COC(=O)c1ccn2c(-c3c[nH]cn3)c(-c3nc(Br)n[nH]3)nc2n1] |
| 37 | 3-bromo-5-[3-(1H-imidazol-4-yl)imidazo[1,2-a]pyrimidin-2-yl]-1H-1,2,4-triazole | 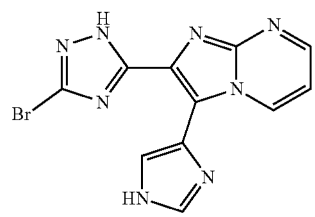 [SMILES: Brc1n[nH]c(-c2nc3ncccn3c2-c2c[nH]cn2)n1] |
| 38 | 5-[6-fluoro-3-(1H-pyrazol-4-yl)imidazo[1,2-a]pyrimidin-2-yl]-3-(trifluoromethyl)-1H-1,2,4-triazole | 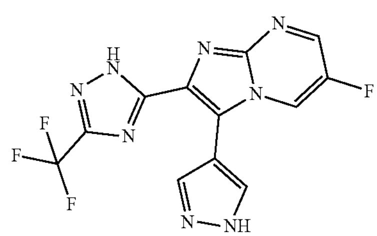 [SMILES: Fc1cnc2nc(-c3nc(C(F)(F)F)n[nH]3)c(-c3cn[nH]c3)n2c1] |
| 39 | 2-(3-bromo-1H-1,2,4-triazol-5-yl)-3-(1H-imidazol-4-yl)-7H,8H-imidazo[1,2-a]pyrimidin-7-one | 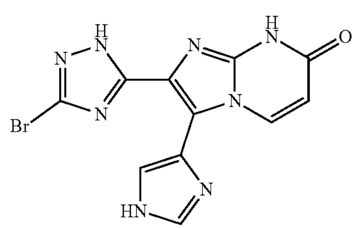 [SMILES: O=c1ccn2c(-c3c[nH]cn3)c(-c3nc(Br)n[nH]3)nc2[nH]1] |
| 40 | 3-bromo-5-[3-(1H-imidazol-4-yl)-7-(propan-2-yloxy)imidazo[1,2-a]pyrimidin-2-yl]-1H-1,2,4-triazole | 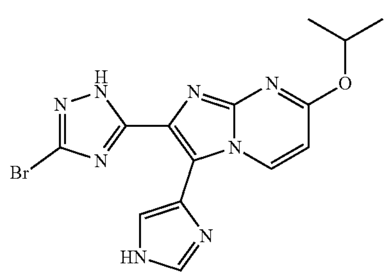 [SMILES: CC(C)Oc1ccn2c(-c3c[nH]cn3)c(-c3nc(Br)n[nH]3)nc2n1] |

TABLE 1-continued

| Compound No. / Example No. | Chemical Name | Structure |
|---|---|---|
| 41 | 5-[3-(1H-imidazol-4-yl)-7-methylimidazo[1,2-a]pyrimidin-2-yl]-3-(trifluoromethyl)-1H-1,2,4-triazole | 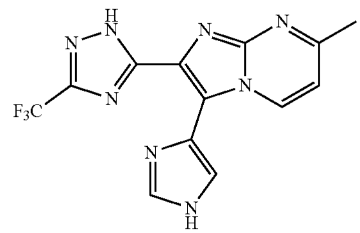 [SMILES: Cc1ccn2c(-c3c[nH]cn3)c(-c3nc(C(F)(F)F)n[nH]3)nc2n1] |
| 42 | 4-[3-(1H-imidazol-4-yl)-2-[3-(trifluoromethyl)-1H-1,2,4-triazol-5-yl]imidazo[1,2-a]pyrimidin-7-yl]morpholine | 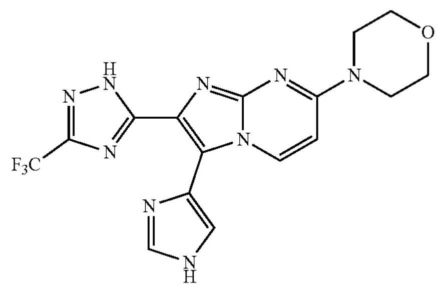 [SMILES: FC(F)(F)c1n[nH]c(-c2nc3nc(N4CCOCC4)ccn3c2-c2c[nH]cn2)n1] |
| 43 | 3-(1H-imidazol-5-yl)-N,N-dimethyl-2-[3-(trifluoromethyl)-1H-1,2,4-triazol-5-yl]imidazo[1,2-a]pyrimidin-7-amine | 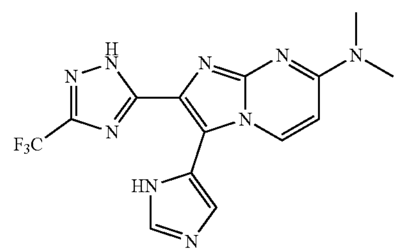 [SMILES: CN(C)c1ccn2c(-c3cnc[nH]3)c(-c3nc(C(F)(F)F)n[nH]3)nc2n1] |
| 44 | 5-[3-(1H-imidazol-4-yl)-7-methoxyimidazo[1,2-a]pyrimidin-2-yl]-3-(trifluoromethyl)-1H-1,2,4-triazole | 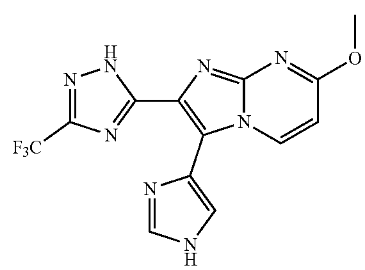 [SMILES: COc1ccn2c(-c3c[nH]cn3)c(-c3nc(C(F)(F)F)n[nH]3)nc2n1] |
| 45 | 5-[6-chloro-3-(1H-imidazol-5-yl)imidazo[1,2-a]pyrimidin-2-yl]-3-(trifluoromethyl)-1H-1,2,4-triazole | 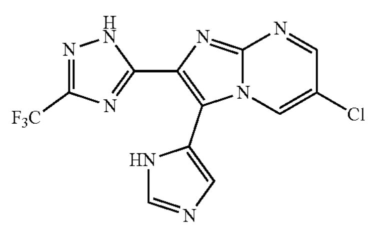 |
| 46 | 4-[6-fluoro-3-(1H-imidazol-4-yl)-2-[3-(trifluoromethyl)-1H-1,2,4-triazol-5-yl]imidazo[1,2-a]pyrimidin-7-yl]morpholine | 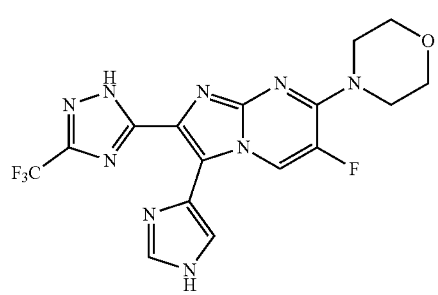 [SMILES: Fc1cn2c(-c3c[nH]cn3)c(-c3nc(C(F)(F)F)n[nH]3)nc2nc1N1CCOCC1] |

TABLE 1-continued

| Compound No. / Example No. | Chemical Name | Structure |
|---|---|---|
| 47 | 5-[7-ethyl-3-(1H-imidazol-5-yl)-6-methylimidazo[1,2-a]pyrimidin-2-yl]-3-(trifluoromethyl)-1H-1,2,4-triazole | 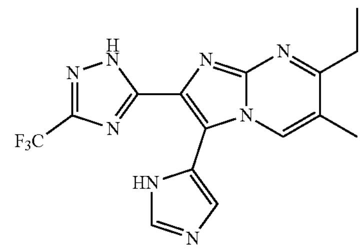 [SMILES: CCc1nc2nc(-c3nc(C(F)(F)F)n[nH]3)c(-c3cnc[nH]3)n2cc1C] |
| 48 | 12-(1H-imidazol-5-yl)-11-[3-(trifluoromethyl)-1H-1,2,4-triazol-5-yl]-6-oxa-1,8,10-triazatricyclo[7.3.0.0$^{3,7}$]dodeca-2,7,9,11-tetraene | 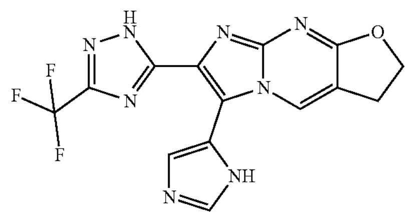 [SMILES: FC(F)(F)c1n[nH]c(-c2nc3nc4c(cn3c2-c2cnc[nH]2)CCO4)n1] |
| 49 | 5-[3-(1H-imidazol-4-yl)-5,7-dimethoxyimidazo[1,2-a]pyrimidin-2-yl]-3-(trifluoromethyl)-1H-1,2,4-triazole | 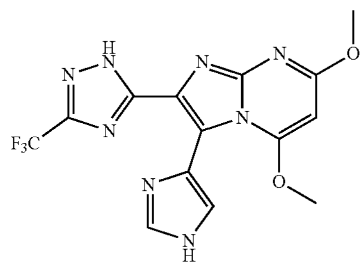 [SMILES: COc1cc(OC)n2c(-c3c[nH]cn3)c(-c3nc(C(F)(F)F)n[nH]3)nc2n1] |
| 50 | 3-(difluoromethyl)-5-[3-(1H-imidazol-5-yl)imidazo[1,2-a]pyrimidin-2-yl]-1H-1,2,4-triazole | 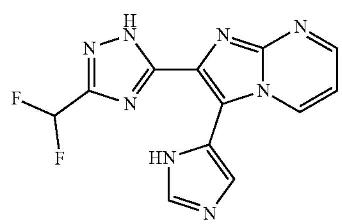 [SMILES: FC(F)c1n[nH]c(-c2nc3ncccn3c2-c2cnc[nH]2)n1] |
| 51 | 5-[3-(1H-imidazol-4-yl)-6-methoxy-7-methylimidazo[1,2-a]pyrimidin-2-yl]-3-(trifluoromethyl)-1H-1,2,4-triazole | 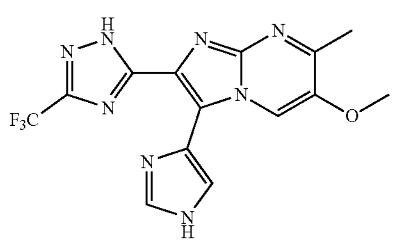 [SMILES: COc1cn2c(-c3c[nH]cn3)c(-c3nc(C(F)(F)F)n[nH]3)nc2nc1C] |
| 52 | 5-[3-(1H-imidazol-5-yl)-6,7-dimethylimidazo[1,2-a]pyrimidin-2-yl]-3-(trifluoromethyl)-1H-1,2,4-triazole | 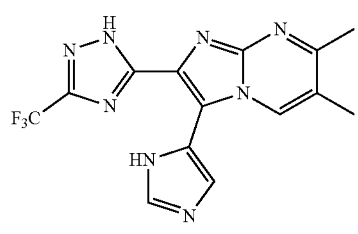 [SMILES: Cc1cn2c(-c3cnc[nH]3)c(-c3nc(C(F)(F)F)n[nH]3)nc2nc1C] |

TABLE 1-continued

| Compound No. / Example No. | Chemical Name |
|---|---|
| 53 | 1-[3-(1H-imidazol-5-yl)-2-[3-(trifluoromethyl)-1H-1,2,4-triazol-5-yl]imidazo[1,2-a]pyrimidin-7-yl]pyrrolidin-3-ol |
| 54 | 5-[3-(1H-imidazol-5-yl)-6-methylimidazo[1,2-a]pyrimidin-2-yl]-3-(trifluoromethyl)-1H-1,2,4-triazole |
| 55 | 5-[3-(1H-imidazol-5-yl)-7-(propan-2-yl)imidazo[1,2-a]pyrimidin-2-yl]-3-(trifluoromethyl)-1H-1,2,4-triazole |
| 56 | 1-[3-(1H-imidazol-5-yl)-2-[3-(trifluoromethyl)-1H-1,2,4-triazol-5-yl]imidazo[1,2-a]pyrimidin-7-yl]piperidin-3-ol |
| 57 | 11-(3-bromo-1H-1,2,4-triazol-5-yl)-12-(1H-imidazol-5-yl)-6-oxa-1,8,10-triazatricyclo[7.3.0.0$^{3,7}$]dodeca-2,7,9,11-tetraene |
| 58 | 5-[3-(1H-imidazol-5-yl)-6-methoxyimidazo[1,2-a]pyrimidin-2-yl]-3-(trifluoromethyl)-1H-1,2,4-triazole |

TABLE 1-continued

| Compound No. / Example No. | Chemical Name | Structure |
|---|---|---|
| 59 | 5-[3-(1H-imidazol-5-yl)-7-methoxy-6-methylimidazo[1,2-a]pyrimidin-2-yl]-3-(trifluoromethyl)-1H-1,2,4-triazole | 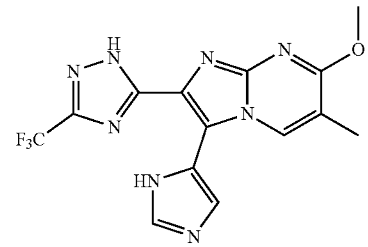 [SMILES: COc1nc2nc(-c3nc(C(F)(F)F)n[nH]3)c(-c3cnc[nH]3)n2cc1C] |
| 60 | 3-(1H-imidazol-5-yl)-2-[3-(trifluoromethyl)-1H-1,2,4-triazol-5-yl]imidazo[1,2-a]pyrimidin-6-ol | 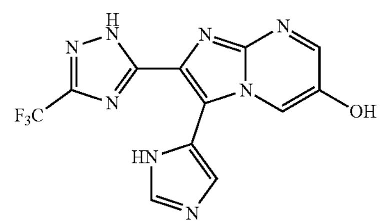 [SMILES: Oc1cnc2nc(-c3nc(C(F)(F)F)n[nH]3)c(-c3cnc[nH]3)n2c1] |
| 61 | [3-(1H-imidazol-5-yl)-2-[3-(trifluoromethyl)-1H-1,2,4-triazol-5-yl]imidazo[1,2-a]pyrimidin-6-yl]methanol | 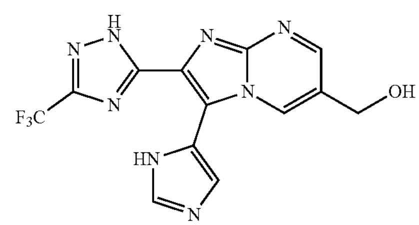 [SMILES: OCc1cnc2nc(-c3nc(C(F)(F)F)n[nH]3)c(-c3cnc[nH]3)n2c1] |
| 62 | 1-(4-{2-[3-(trifluoromethyl)-1H-1,2,4-triazol-5-yl]imidazo[1,2-a]pyrimidin-3-yl}-1H-imidazol-1-yl)ethan-1-one | 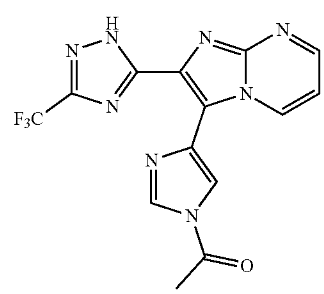 [SMILES: CC(=O)n1cnc(-c2c(-c3nc(C(F)(F)F)n[nH]3)nc3ncccn23)c1] |
| 63 | 12-(1H-imidazol-5-yl)-11-[3-(trifluoromethyl)-1H-1,2,4-triazol-5-yl]-1,5,8,10-tetraazatricyclo[7.3.0.0$^{3,7}$]dodeca-2,7,9,11-tetraene | 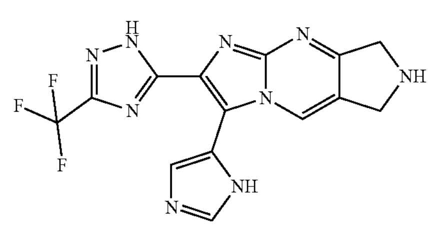 [SMILES: FC(F)(F)c1n[nH]c(-c2nc3nc4c(cn3c2-c2cnc[nH]2)CNC4)n1] |
| 64 | 5-[3-(1H-imidazol-5-yl)-6-(trifluoromethyl)imidazo[1,2-a]pyrimidin-2-yl]-3-(trifluoromethyl)-1H-1,2,4-triazole | 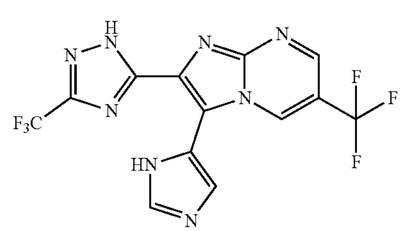 [SMILES: FC(F)(F)c1cnc2nc(-c3nc(C(F)(F)F)n[nH]3)c(-c3cnc[nH]3)n2c1] |

TABLE 1-continued

| Compound No. / Example No. | Chemical Name | Structure |
|---|---|---|
| 65 | 5-[3-(1H-imidazol-4-yl)-6-[(oxan-4-yloxy)methyl]imidazo[1,2-a]pyrimidin-2-yl]-3-(trifluoromethyl)-1H-1,2,4-triazole | 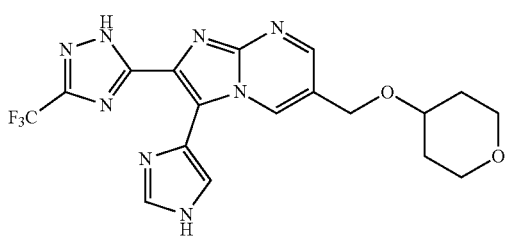 [SMILES: FC(F)(F)c1n[nH]c(-c2nc3ncc(COC4CCOCC4)cn3c2-c2c[nH]cn2)n1] |
| 66 | 5-[3-(1H-imidazol-5-yl)-6-(oxolan-3-yl)imidazo[1,2-a]pyrimidin-2-yl]-3-(trifluoromethyl)-1H-1,2,4-triazole | 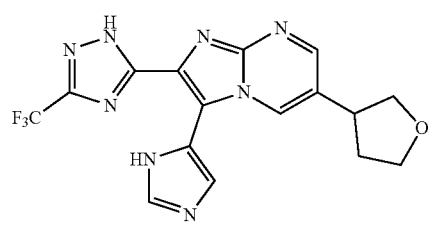 [SMILES: FC(F)(F)c1n[nH]c(-c2nc3ncc(C4CCOC4)cn3c2-c2cnc[nH]2)n1] |
| 67 | 12-(1H-imidazol-5-yl)-5-methanesulfonyl-11-[3-(trifluoromethyl)-1H-1,2,4-triazol-5-yl]-1,5,8,10-tetraazatricyclo[7.3.0.0³,⁷]dodeca-2,7,9,11-tetraene | 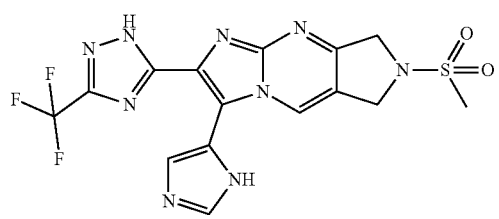 [SMILES: CS(=O)(=O)N1Cc2cn3c(-c4cnc[nH]4)c(-c4nc(C(F)(F)F)n[nH]4)nc3nc2C1] |
| 68 | 1-[12-(1H-imidazol-5-yl)-11-[3-(trifluoromethyl)-1H-1,2,4-triazol-5-yl]-1,5,8,10-tetraazatricyclo[7.3.0.0³,⁷]dodeca-2,7,9,11-tetraen-5-yl]ethan-1-one | 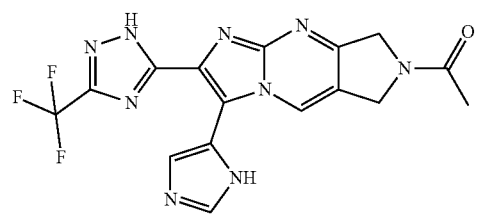 [SMILES: CC(=O)N1Cc2cn3c(-c4cnc[nH]4)c(-c4nc(C(F)(F)F)n[nH]4)nc3nc2C1] |
| 69 | 5-[3-(1H-imidazol-5-yl)-6-(methoxymethyl)imidazo[1,2-a]pyrimidin-2-yl]-3-(trifluoromethyl)-1H-1,2,4-triazole | 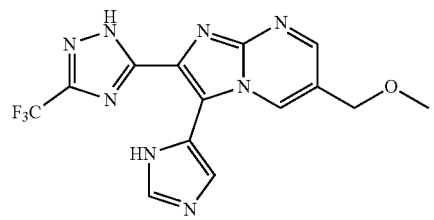 [SMILES: COCc1cnc2nc(-c3nc(C(F)(F)F)n[nH]3)c(-c3cnc[nH]3)n2c1] |
| 70 | 4-{[3-(1H-imidazol-4-yl)-2-[3-(trifluoromethyl)-1H-1,2,4-triazol-5-yl]imidazo[1,2-a]pyrimidin-6-yl]methyl}morpholine | 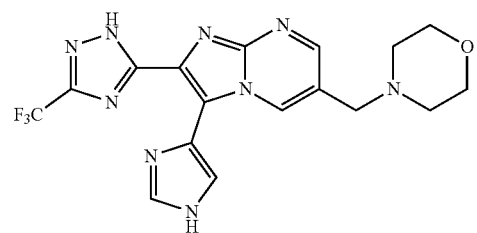 [SMILES: FC(F)(F)c1n[nH]c(-c2nc3ncc(CN4CCOCC4)cn3c2-c2c[nH]cn2)n1] |

TABLE 1-continued

| Compound No. / Example No. | Chemical Name | Structure |
|---|---|---|
| 71 | 6-(1H-imidazol-5-yl)-5-[3-(trifluoromethyl)-1H-1,2,4-triazol-5-yl]-11-oxa-2,4,7-triazatricyclo[7.4.0.0³,⁷]trideca-1,3,5,8-tetraene | 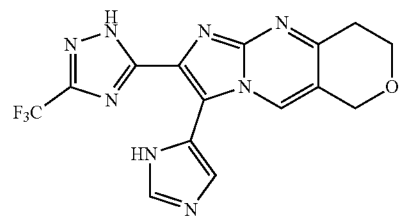 [SMILES: FC(F)(F)c1n[nH]c(-c2nc3nc4c(cn3c2-c2cnc[nH]2)COCC4)n1] |
| 72 | 6-(1H-pyrazol-4-yl)-5-[3-(trifluoromethyl)-1H-1,2,4-triazol-5-yl]-11-oxa-2,4,7-triazatricyclo[7.4.0.0³,⁷]trideca-1,3,5,8-tetraene | 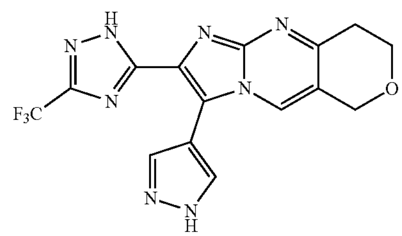 [SMILES: FC(F)(F)c1n[nH]c(-c2nc3nc4c(cn3c2-c2cn[nH]c2)COCC4)n1] |
| 73 | 6-(1H-imidazol-5-yl)-11-methyl-5-[3-(trifluoromethyl)-1H-1,2,4-triazol-5-yl]-2,4,7,11-tetraazatricyclo[7.4.0.0³,⁷]trideca-1,3,5,8-tetraene | 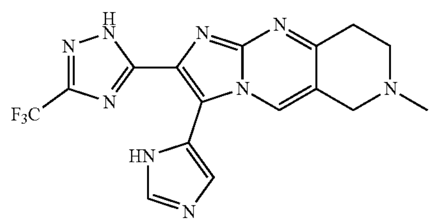 [SMILES: CN1CCc2nc3nc(-c4nc(C(F)(F)F)n[nH]4)c(-c4cnc[nH]4)n3cc2C1] |
| 74 | 6-(1H-imidazol-5-yl)-5-[3-(trifluoromethyl)-1H-1,2,4-triazol-5-yl]-2,4,7,11-tetraazatricyclo[7.4.0.0³,⁷]trideca-1,3,5,8-tetraene | 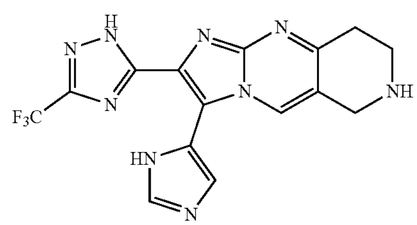 [SMILES: FC(F)(F)c1n[nH]c(-c2nc3nc4c(cn3c2-c2cnc[nH]2)CNCC4)n1] |
| 75 | {[3-(1H-imidazol-5-yl)-2-[3-(trifluoromethyl)-1H-1,2,4-triazol-5-yl]imidazo[1,2-a]pyrimidin-6-yl]methyl}(methyl)amine | 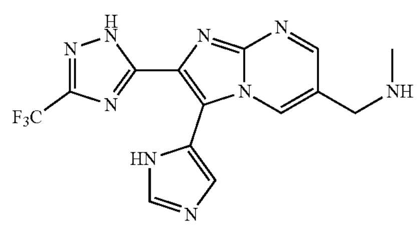 [SMILES: CNCc1cnc2nc(-c3nc(C(F)(F)F)n[nH]3)c(-c3cnc[nH]3)n2c1] |
| 76 | N-{[3-(1H-imidazol-5-yl)-2-[3-(trifluoromethyl)-1H-1,2,4-triazol-5-yl]imidazo[1,2-a]pyrimidin-6-yl]methyl}-N-methylacetamide | 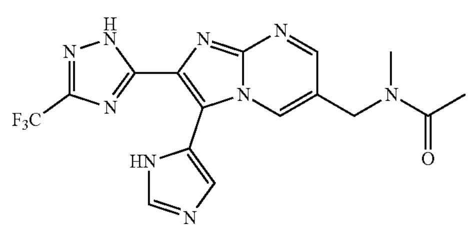 [SMILES: CC(=O)N(C)Cc1cnc2nc(-c3nc(C(F)(F)F)n[nH]3)c(-c3cnc[nH]3)n2c1] |

TABLE 1-continued

| Compound No. / Example No. | Chemical Name |
|---|---|
| 77 | 5-[6-bromo-3-(1H-imidazol-5-yl)imidazo[1,2-a]pyrimidin-2-yl]-3-(trifluoromethyl)-1H-1,2,4-triazole |
| 78 | 5-[3-(1H-imidazol-5-yl)-6-[(oxolan-3-yloxy)methyl]imidazo[1,2-a]pyrimidin-2-yl]-3-(trifluoromethyl)-1H-1,2,4-triazole |
| 79 | 5-[6-(ethoxymethyl)-3-(1H-imidazol-5-yl)imidazo[1,2-a]pyrimidin-2-yl]-3-(trifluoromethyl)-1H-1,2,4-triazole |
| 80 | 5-[3-(1H-imidazol-5-yl)-6-[(pyrrolidin-3-yloxy)methyl]imidazo[1,2-a]pyrimidin-2-yl]-3-(trifluoromethyl)-1H-1,2,4-triazole |
| 81 | 2,2-dimethyl-1-(4-{2-[3-(trifluoromethyl)-1H-1,2,4-triazol-5-yl]imidazo[1,2-a]pyrimidin-3-yl}-1H-imidazol-1-yl)propan-1-one |
| 82 | 5-[3-(1H-imidazol-5-yl)-6-(oxolan-2-yl)imidazo[1,2-a]pyrimidin-2-yl]-3-(trifluoromethyl)-1H-1,2,4-triazole |

TABLE 1-continued

| Compound No. / Example No. | Chemical Name |
|---|---|
| 83 | 13, 13-difluoro-6-(1H-imidazol-5-yl)-5-[3-(trifluoromethyl)-1H-1,2,4-triazol-5-yl]-2,4,7,11-tetraazatricyclo[7.4.0.0³,⁷]trideca-1,3,5,8-tetraene |
| 84 | [5-(3-{1-[(acetyloxy)methyl]-1H-imidazol-4-yl}imidazo[1,2-a]pyrimidin-2-yl)-3-(trifluoromethyl)-1H-1,2,4-triazol-1-yl]methyl acetate |
| 85 | 3-(difluoromethyl)-5-[6-(ethoxymethyl)-3-(1H-imidazol-5-yl)imidazo[1,2-a]pyrimidin-2-yl]-1H-1,2,4-triazole |
| 86 | 3-(difluoromethyl)-5-[3-(1H-imidazol-5-yl)-6-(methoxymethyl)imidazo[1,2-a]pyrimidin-2-yl]-1H-1,2,4-triazole |
| 87 | 1-[13, 13-difluoro-6-(1H-imidazol-5-yl)-5-[3-(trifluoromethyl)- 1H-1,2,4-triazol-5-yl]-2,4,7,11-tetraazatricyclo[7.4.0.0³,⁷]trideca-1,3,5,8-tetraen-11-yl]ethan-1-one |

TABLE 1-continued

| Compound No. / Example No. | Chemical Name | Structure |
|---|---|---|
| 88 | 3-(difluoromethyl)-5-[3-(1H-imidazol-5-yl)-7-(trifluoromethyl)imidazo[1,2-a]pyrimidin-2-yl]-1H-1,2,4-triazole | 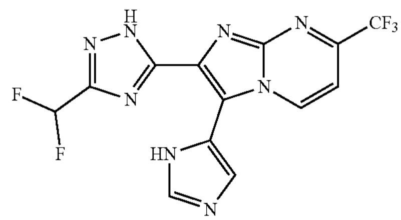 [SMILES: FC(F)c1n[nH]c(-c2nc3nc(C(F)(F)F)ccn3c2-c2cnc[nH]2)n1] |
| 89 | 5-[6-benzyl-3-(1H-imidazol-5-yl)imidazo[1,2-a]pyrimidin-2-yl]-3-(trifluoromethyl)-1H-1,2,4-triazole | 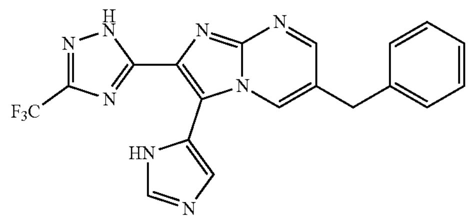 [SMILES: FC(F)(F)c1n[nH]c(-c2nc3ncc(Cc4ccccc4)cn3c2-c2cnc[nH]2)n1] |
| 90 | 3-(difluoromethyl)-5-[3-(1H-pyrazol-4-yl)imidazo[1,2-a]pyrimidin-2-yl]-1H-1,2,4-triazole | 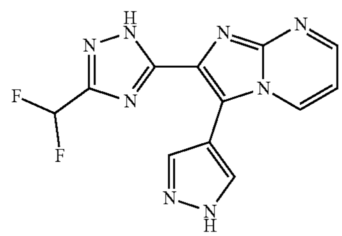 [SMILES: FC(F)c1n[nH]c(-c2nc3ncccn3c2-c2cn[nH]c2)n1] |
| 91 | 3-bromo-5-[3-(1H-imidazol-5-yl)-7-(trifluoromethyl)imidazo[1,2-a]pyrimidin-2-yl]-1H-1,2,4-triazole | 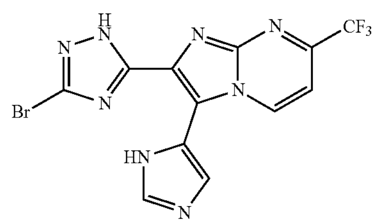 [SMILES: FC(F)(F)c1ccn2c(-c3cnc[nH]3)c(-c3nc(Br)n[nH]3)nc2n1] |
| 92 | 2-[3-(1H-imidazol-5-yl)-2-[3-(trifluoromethyl)-1H-1,2,4-triazol-5-yl]imidazo[1,2-a]pyrimidin-6-yl]acetic acid | 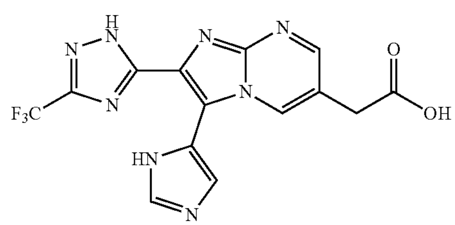 [SMILES: O=C(O)Cc1cnc2nc(-c3nc(C(F)(F)F)n[nH]3)c(-c3cnc[nH]3)n2c1] |
| 93 | 5-[3-(1H-pyrazol-4-yl)-7-(trifluoromethyl)imidazo[1,2-a]pyrimidin-2-yl]-3-(trifluoromethyl)-1H-1,2,4-triazole | 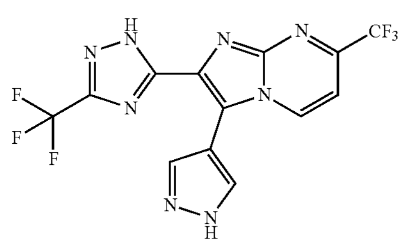 [SMILES: FC(F)(F)c1ccn2c(-c3cn[nH]c3)c(-c3nc(C(F)(F)F)n[nH]3)nc2n1] |

TABLE 1-continued

| Compound No. / Example No. | Chemical Name | Structure |
|---|---|---|
| 94 | N-(2,2-dimethylpropyl)-3-(1H-imidazol-5-yl)-2-[3-(trifluoromethyl)-1H-1,2,4-triazol-5-yl]imidazo[1,2-a]pyrimidine-6-carboxamide | 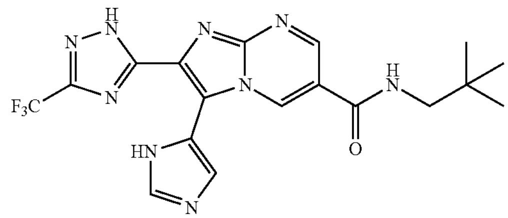 [SMILES: CC(C)(C)CNC(=O)c1cnc2nc(-c3nc(C(F)(F)F)n[nH]3)c(-c3cnc[nH]3)n2c1] |
| 95 | 5-[7-(difluoromethyl)-3-(1H-imidazol-5-yl)imidazo[1,2-a]pyrimidin-2-yl]-3-(trifluoromethyl)-1H-1,2,4-triazole | 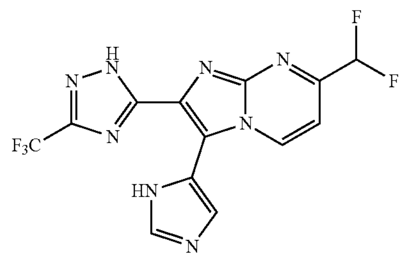 [SMILES: FC(F)c1ccn2c(-c3cnc[nH]3)c(-c3nc(C(F)(F)F)n[nH]3)nc2n1] |
| 96 | 5-[3-(1H-imidazol-5-yl)-6-(2-phenylethyl)imidazo[1,2-a]pyrimidin-2-yl]-3-(trifluoromethyl)-1H-1,2,4-triazole | 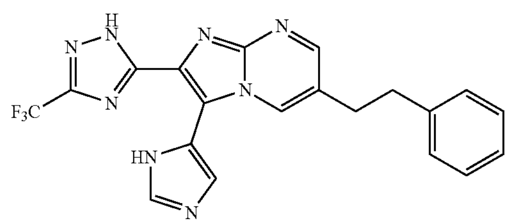 [SMILES: FC(F)(F)c1n[nH]c(-c2nc3ncc(CCc4ccccc4)cn3c2-c2cnc[nH]2)n1] |
| 97 | 5-[3-(1H-imidazol-5-yl)-7-(trifluoromethyl)imidazo[1,2-a]pyrimidin-2-yl]-1H-1,2,4-triazole | 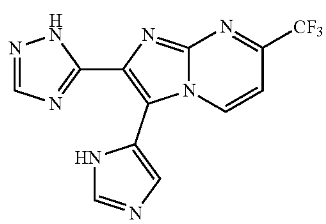 [SMILES: FC(F)(F)c1ccn2c(-c3cnc[nH]3)c(-c3ncn[nH]3)nc2n1] |
| 98 | 5-[3-(1H-imidazol-5-yl)-7-(trifluoromethyl)imidazo[1,2-a]pyrimidin-2-yl]-3-methyl-1H-1,2,4-triazole | 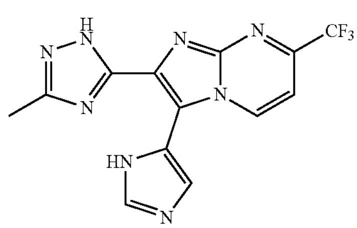 [SMILES: Cc1n[nH]c(-c2nc3nc(C(F)(F)F)ccn3c2-c2cnc[nH]2)n1] |
| 99 | 5-[3-(1H-imidazol-5-yl)-6-[(2-methanesulfonylethoxy)methyl]imidazo[1,2-a]pyrimidin-2-yl]-3-(trifluoromethyl)-1H-1,2,4-triazole | 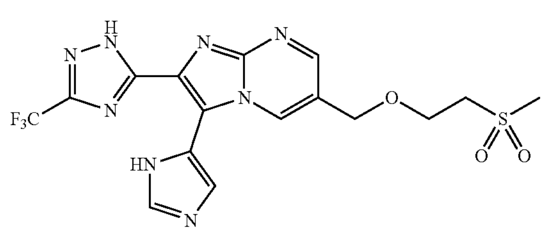 [SMILES: CS(=O)(=O)CCOCc1cnc2nc(-c3nc(C(F)(F)F)n[nH]3)c(-c3cnc[nH]3)n2c1] |

TABLE 1-continued

| Compound No. / Example No. | Chemical Name | Structure |
|---|---|---|
| 100 | methyl 3-(1H-imidazol-4-yl)-2-[3-(trifluoromethyl)-1H-1,2,4-triazol-5-yl]imidazo[1,2-a]pyrimidine-7-carboxylate | 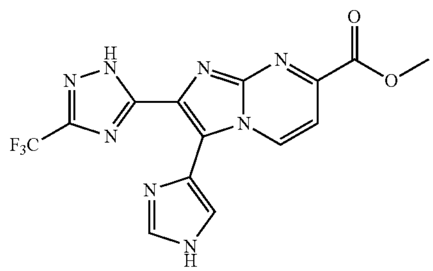 [SMILES: COC(=O)c1ccn2c(-c3c[nH]cn3)c(-c3nc(C(F)(F)F)n[nH]3)nc2n1] |
| 101 | 5-{6-[(2,2-difluoroethoxy)methyl]-3-(1H-imidazol-5-yl)imidazo[1,2-a]pyrimidin-2-yl}-3-(trifluoromethyl)-1H-1,2,4-triazole | 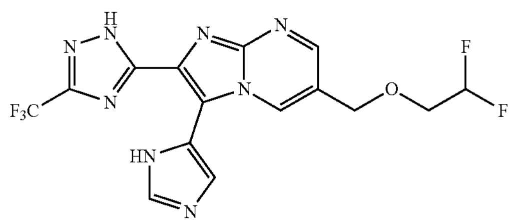 [SMILES: FC(F)COCc1cnc2nc(-c3nc(C(F)(F)F)n[nH]3)c(-c3cnc[nH]3)n2c1] |
| 102 | 3-(1H-imidazol-4-yl)-2-[3-(trifluoromethyl)-1H-1,2,4-triazol-5-yl]imidazo[1,2-a]pyrimidine-7-carboxylic acid | 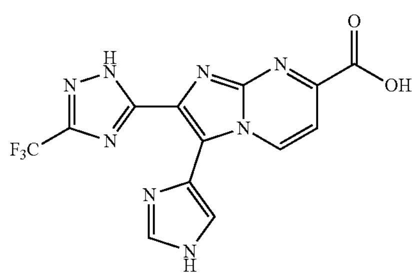 [SMILES: O=C(O)c1ccn2c(-c3c[nH]cn3)c(-c3nc(C(F)(F)F)n[nH]3)nc2n1] |
| 103 | 6-(1H-imidazol-5-yl)-5-[3-(trifluoromethyl)-1H-1,2,4-triazol-5-yl]-11-thia-2,4,7-triazatricyclo[7.4.0.0$^{3,7}$]trideca-1,3,5,8-tetraene | 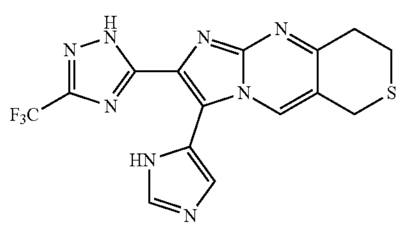 [SMILES: FC(F)(F)c1n[nH]c(-c2nc3nc4c(cn3c2-c2cnc[nH]2)CSCC4)n1] |
| 104 | 6-(1H-imidazol-5-yl)-5-[3-(trifluoromethyl)- 1H-1,2,4-triazol-5-yl]-11λ$^6$-thia-2,4,7-triazatricyclo[7.4.0.0$^{3,7}$]trideca-1,3,5,8-tetraene-11,11-dione | 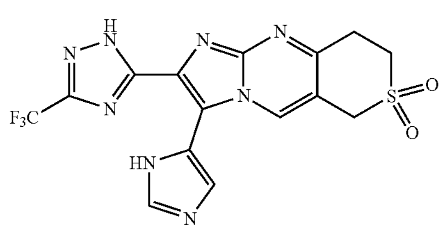 [SMILES: O=S1(=O)CCc2nc3nc(-c4nc(C(F)(F)F)n[nH]4)c(-c4cnc[nH]4)n3cc2C1] |
| 105 | 3-{[3-(1H-imidazol-5-yl)-2-[3-(trifluoromethyl)-1H-1,2,4-triazol-5-yl]imidazo[1,2-a]pyrimidin-6-yl]methoxy}propanenitrile | 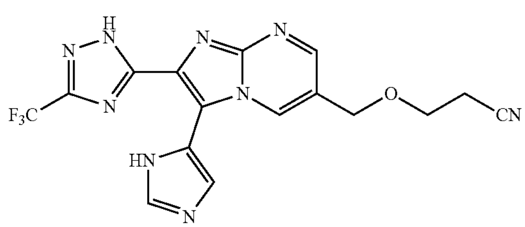 [SMILES: N#CCCOCc1cnc2nc(-c3nc(C(F)(F)F)n[nH]3)c(-c3cnc[nH]3)n2c1] |

TABLE 1-continued

| Compound No. / Example No. | Chemical Name | Structure |
|---|---|---|
| 106 | 3-({[3-(1H-imidazol-5-yl)-2-[3-(trifluoromethyl)-1H-1,2,4-triazol-5-yl]imidazo[1,2-a]pyrimidin-6-yl]methoxy}methyl)pyridine | 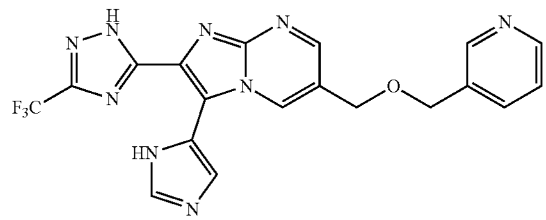 [SMILES: FC(F)(F)c1n[nH]c(-c2nc3ncc(COCc4cccnc4)cn3c2-c2cnc[nH]2)n1] |
| 107 | 3-(1H-imidazol-5-yl)-2-[3-(trifluoromethyl)-1H-1,2,4-triazol-5-yl]imidazo[1,2-a]pyrimidin-7-amine | 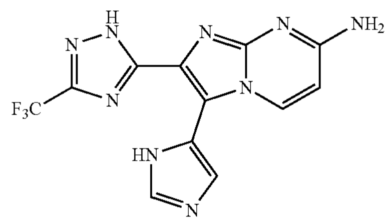 [SMILES: Nc1ccn2c(-c3cnc[nH]3)c(-c3nc(C(F)(F)F)n[nH]3)nc2n1] |
| 108 | 11-ethyl-13, 13-difluoro-6-(1H-imidazol-5-yl)-5-[3-(trifluoromethyl)-1H-1,2,4-triazol-5-yl]-2,4,7, 11-tetraazatricyclo[7.4.0.0$^{3,7}$]trideca-1,3,5,8-tetraene | 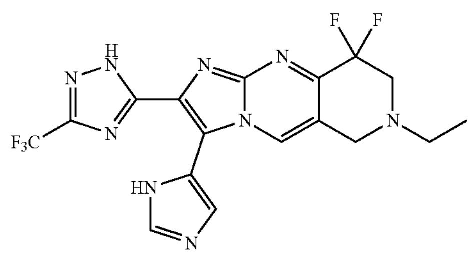 [SMILES: CCN1Cc2cn3c(-c4cnc[nH]4)c(-c4nc(C(F)(F)F)n[nH]4)nc3nc2C(F)(F)C1] |
| 109 | 5-[6-tert-butyl-3-(1H-imidazol-4-yl)imidazo[1,2-a]pyrimidin-2-yl]-3-(trifluoromethyl)-1H-1,2,4-triazole | 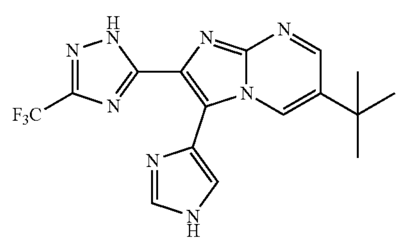 [SMILES: CC(C)(C)c1cnc2nc(-c3nc(C(F)(F)F)n[nH]3)c(-c3c[nH]cn3)n2c1] |
| 110 | 3-(1H-imidazol-5-yl)-2-[3-(trifluoromethyl)-1H-1,2,4-triazol-5-yl]imidazo[1,2-a]pyrimidine-6-carbonitrile | 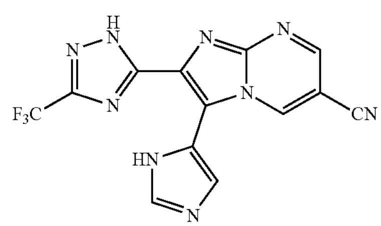 [SMILES: N#Cc1cnc2nc(-c3nc(C(F)(F)F)n[nH]3)c(-c3cnc[nH]3)n2c1] |
| 111 | 5-[3-(1H-imidazol-5-yl)-6-[(2,2,2-trifluoroethoxy)methyl]imidazo[1,2-a]pyrimidin-2-yl]-3-(trifluoromethyl)-1H-1,2,4-triazole | 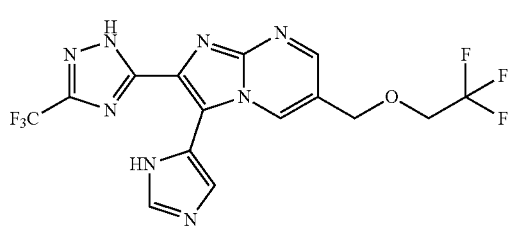 [SMILES: FC(F)(F)COCc1cnc2nc(-c3nc(C(F)(F)F)n[nH]3)c(-c3cnc[nH]3)n2c1] |

TABLE 1-continued

| Compound No. / Example No. | Chemical Name | Structure |
|---|---|---|
| 112 | 1-{[3-(1H-imidazol-5-yl)-2-[3-(trifluoromethyl)-1H-1,2,4-triazol-5-yl]imidazo[1,2-a]pyrimidin-6-yl]methoxy}butane-2,3-diol | 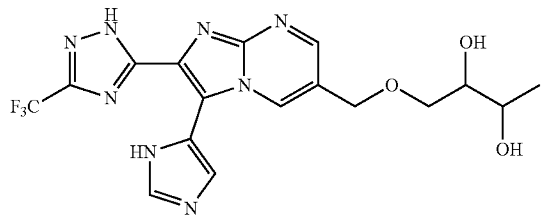 [SMILES: CC(O)C(O)COCc1cnc2nc(-c3nc(C(F)(F)F)n[nH]3)c(-c3cnc[nH]3)n2c1] |
| 113 | 3-(difluoromethoxy)-5-[3-(1H-imidazol-5-yl)imidazo[1,2-a]pyrimidin-2-yl]-1H-1,2,4-triazole | 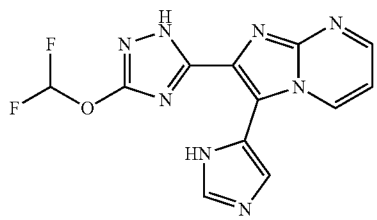 [SMILES: FC(F)Oc1n[nH]c(-c2nc3ncccn3c2-c2cnc[nH]2)n1] |
| 114 | 5-[3-(1H-imidazol-5-yl)-6-(methoxymethyl)-7-(trifluoromethyl)imidazo[1,2-a]pyrimidin-2-yl]-3-(trifluoromethyl)-1H-1,2,4-triazole | 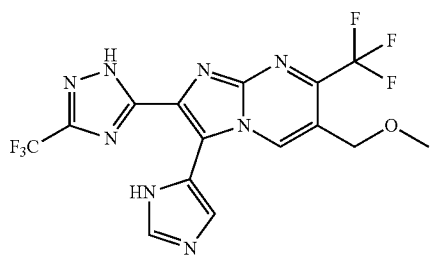 [SMILES: COCc1cn2c(-c3cnc[nH]3)c(-c3nc(C(F)(F)F)n[nH]3)nc2nc1C(F)(F)F] |
| 115 | 5-[6-(ethoxymethyl)-3-(1H-imidazol-5-yl)-7-(trifluoromethyl)imidazo[1,2-a]pyrimidin-2-yl]-3-(trifluoromethyl)-1H-1,2,4-triazole | 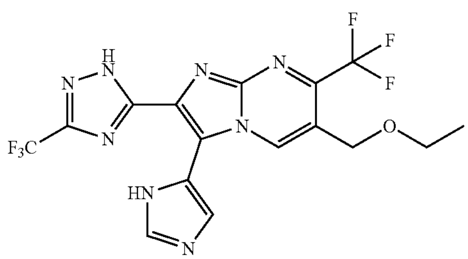 [SMILES: CCOCc1cn2c(-c3cnc[nH]3)c(-c3nc(C(F)(F)F)n[nH]3)nc2nc1C(F)(F)F] |
| 116 | 6-(1H-imidazol-5-yl)-5-[3-(trifluoromethyl)-1H-1,2,4-triazol-5-yl]-11$\lambda^4$-thia-2,4,7-triazatricyclo[7.4.0.0$^{3,7}$]trideca-1,3,5,8-tetraen-11-one | 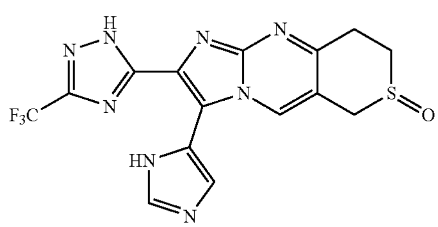 [SMILES: O=S1CCc2nc3nc(-c4nc(C(F)(F)F)n[nH]4)c(-c4cnc[nH]4)n3cc2C1] |
| 117 | 3-(difluoromethyl)-5-[6-(ethoxymethyl)-3-(1H-imidazol-5-yl)-7-(trifluoromethyl)imidazo[1,2-a]pyrimidin-2-yl]-1H-1,2,4-triazole | 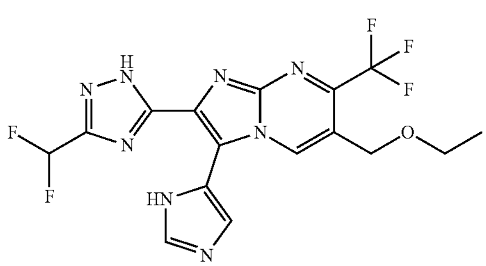 [SMILES: CCOCc1cn2c(-c3cnc[nH]3)c(-c3nc(C(F)F)n[nH]3)nc2nc1C(F)(F)F] |

TABLE 1-continued

| Compound No. / Example No. | Chemical Name | Structure |
|---|---|---|
| 118 | {[3-(1H-imidazol-4-yl)-2-[3-(trifluoromethyl)-1H-1,2,4-triazol-5-yl]imidazo[1,2-a]pyrimidin-7-yl]methyl}(1,1,1-trifluoropropan-2-yl) amine | 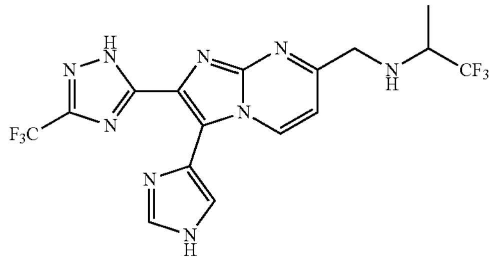 [SMILES: CC(NCc1ccn2c(-c3c[nH]cn3)c(-c3nc(C(F)(F)F)n[nH]3)nc2n1)C(F)(F)F] |
| 119 | 3-{[3-(1H-imidazol-5-yl)-2-[3-(trifluoromethyl)-1H-1,2,4-triazol-5-yl]imidazo[1,2-a]pyrimidin-6-yl]methoxy}pyridine | 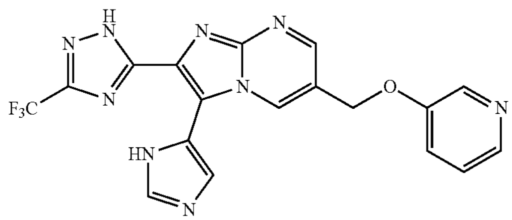 [SMILES: FC(F)(F)c1n[nH]c(-c2nc3ncc(COc4cccnc4)cn3c2-c2cnc[nH]2)n1] |
| 120 | 5-[6-(difluoromethyl)-3-(1H-imidazol-4-yl)imidazo[1,2-a]pyrimidin-2-yl]-3-(trifluoromethyl)-1H-1,2,4-triazole | 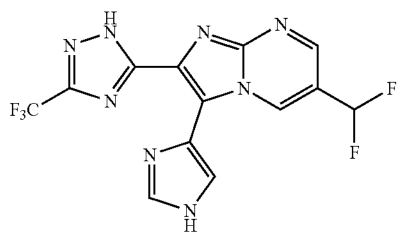 [SMILES: FC(F)c1cnc2nc(-c3nc(C(F)(F)F)n[nH]3)c(-c3c[nH]cn3)n2c1] |
| 121 | 3-(difluoromethyl)-5-[3-(1H-imidazol-5-yl)-6-(methoxymethyl)-7-(trifluoromethyl)imidazo[1,2-a]pyrimidin-2-yl]-1H-1,2,4-triazole | 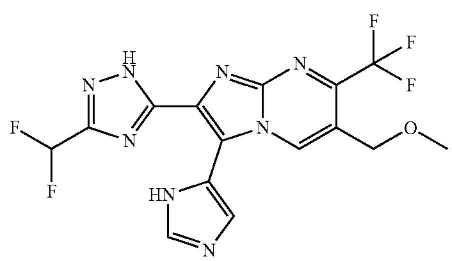 [SMILES: COCc1cn2c(-c3cnc[nH]3)c(-c3nc(C(F)F)n[nH]3)nc2nc1C(F)(F)F] |
| 122 | 4-{2-[3-(1H-imidazol-5-yl)-2-[3-(trifluoromethyl)-1H-1,2,4-triazol-5-yl]imidazo[1,2-a]pyrimidin-6-yl]ethyl}morpholine | 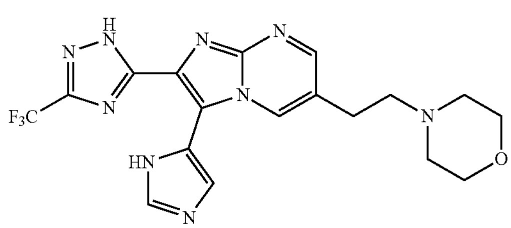 [SMILES: FC(F)(F)c1n[nH]c(-c2nc3ncc(CCN4CCOCC4)cn3c2-c2cnc[nH]2)n1] |
| 123 | 5-{6-[(2,2,3,3,4,4,4-heptafluorobutoxy)methyl]-3-(1H-imidazol-5-yl)imidazo[1,2-a]pyrimidin-2-yl}-3-(trifluoromethyl)-1H-1,2,4-triazole | 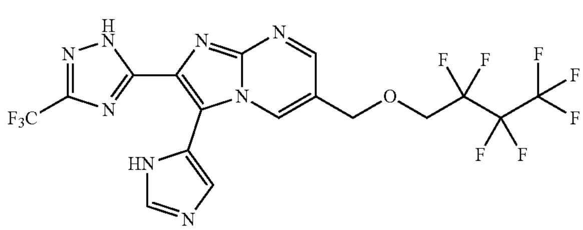 [SMILES: FC(F)(F)c1n[nH]c(-c2nc3ncc(COCC(F)(F)C(F)(F)C(F)(F)F)cn3c2-c2cnc[nH]2)n1] |

TABLE 1-continued

| Compound No. / Example No. | Chemical Name | Structure |
|---|---|---|
| 124 | 3-(1H-imidazol-4-yl)-2-[3-(trifluoromethyl)-1H-1,2,4-triazol-5-yl]imidazo[1,2-a]pyrimidine-7-carbonitrile | 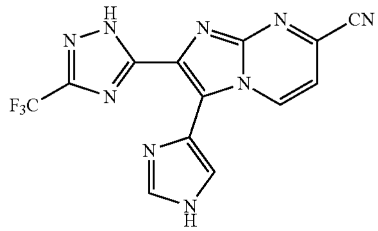 [SMILES: N#Cc1ccn2c(-c3c[nH]cn3)c(-c3nc(C(F)(F)F)n[nH]3)nc2n1] |
| 125 | 5-[6-fluoro-3-(1H-imidazol-5-yl)-7-(trifluoromethyl)imidazo[1,2-a]pyrimidin-2-yl]-3-(trifluoromethyl)-1H-1,2,4-triazole | 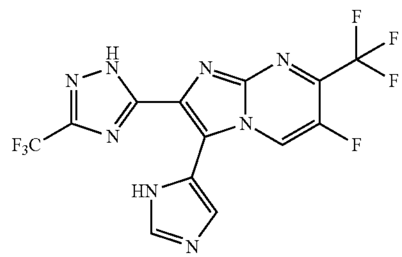 [SMILES: Fc1cn2c(-c3cnc[nH]3)c(-c3nc(C(F)(F)F)n[nH]3)nc2nc1C(F)(F)F] |
| 126 | 5-[3-(1H-imidazol-5-yl)-6-{[(oxolan-3-yl)methoxy]methyl}imidazo[1,2-a]pyrimidin-2-yl]-3-(trifluoromethyl)-1H-1,2,4-triazole | 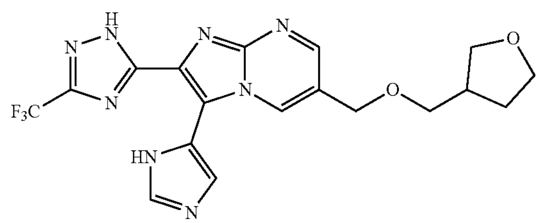 [SMILES: FC(F)(F)c1n[nH]c(-c2nc3ncc(COCC4CCOC4)cn3c2-c2cnc[nH]2)n1] |
| 127 | 5-[3-(1H-imidazol-5-yl)-6-[(3-methoxy-2-methylpropoxy)methyl]imidazo[1,2-a]pyrimidin-2-yl]-3-(trifluoromethyl)-1H-1,2,4-triazole | 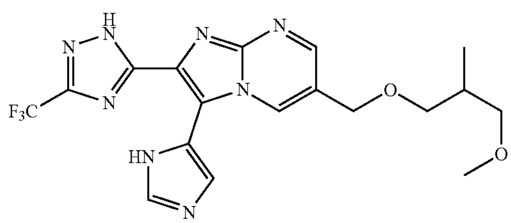 [SMILES: COCC(C)COCc1cnc2nc(-c3nc(C(F)(F)F)n[nH]3)c(-c3cnc[nH]3)n2c1] |
| 128 | 5-[6-chloro-3-(1H-imidazol-5-yl)-7-(trifluoromethyl)imidazo[1,2-a]pyrimidin-2-yl]-3-(trifluoromethyl)-1H-1,2,4-triazole | 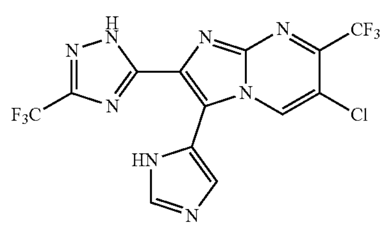 [SMILES: FC(F)(F)c1n[nH]c(-c2nc3nc(C(F)(F)F)c(Cl)cn3c2-c2cnc[nH]2)n1] |
| 129 | 5-{6-[(2-ethoxyethoxy)methyl]-3-(1H-imidazol-5-yl)imidazo[1,2-a]pyrimidin-2-yl}-3-(trifluoromethyl)-1H-1,2,4-triazole | 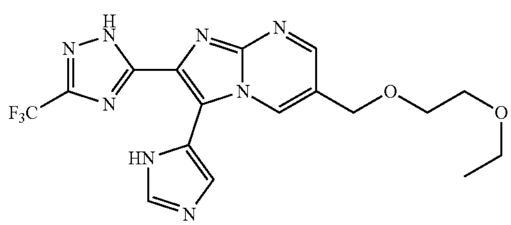 [SMILES: CCOCCOCc1cnc2nc(-c3nc(C(F)(F)F)n[nH]3)c(-c3cnc[nH]3)n2c1] |

TABLE 1-continued

| Compound No. / Example No. | Chemical Name | Structure |
|---|---|---|
| 130 | 5-[3-(2-methyl-1H-imidazol-4-yl)imidazo[1,2-a]pyrimidin-2-yl]-3-(trifluoromethyl)-1H-1,2,4-triazole | 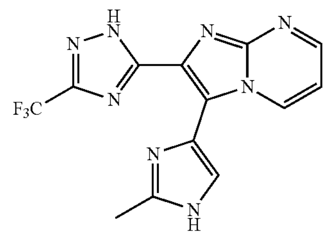 [SMILES: Cc1nc(-c2c(-c3nc(C(F)(F)F)n[nH]3)nc3ncccn23)c[nH]1] |
| 131 | 5-[3-(1-methyl-1H-pyrazol-4-yl)imidazo[1,2-a]pyrimidin-2-yl]-3-(trifluoromethyl)-1H-1,2,4-triazole | 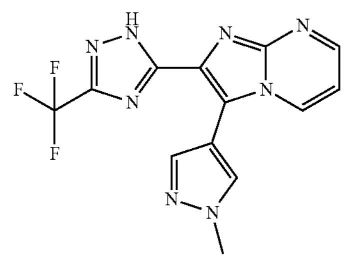 [SMILES: Cn1cc(-c2c(-c3nc(C(F)(F)F)n[nH]3)nc3ncccn23)cn1] |
| 132 | 4-{[3-(1H-imidazol-4-yl)-2-[3-(trifluoromethyl)-1H-1,2,4-triazol-5-yl]imidazo[1,2-a]pyrimidin-7-yl]oxy}-1-methylpiperidine | 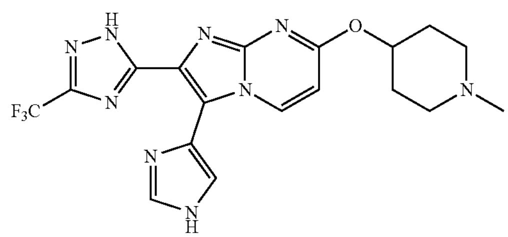 [SMILES: CN1CCC(Oc2ccn3c(-c4c[nH]cn4)c(-c4nc(C(F)(F)F)n[nH]4)nc3n2)CC1] |
| 133 | 12-(1H-imidazol-5-yl)-11-[3-(trifluoromethyl)-1H-1,2,4-triazol-5-yl]-1,8,10-triazatricyclo[7.3.0.0$^{3,7}$]dodeca-2,7,9,11-tetraene | 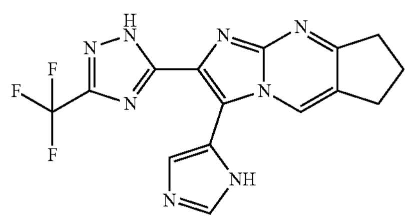 [SMILES: FC(F)(F)c1n[nH]c(-c2nc3nc4c(cn3c2-c2cnc[nH]2)CCC4)n1] |
| 134 | 5-[3-(1H-imidazol-5-yl)-6H,7H,8H,9H-imidazo[2,1-b]quinazolin-2-yl]-3-(trifluoromethyl)-1H-1,2,4-triazole | 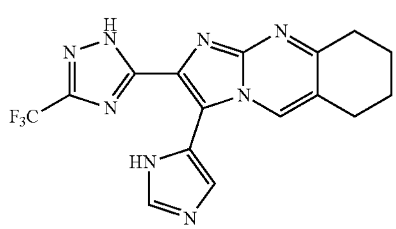 [SMILES: FC(F)(F)c1n[nH]c(-c2nc3nc4c(cn3c2-c2cnc[nH]2)CCCC4)n1] |
| 135 | 5-[3-(1H-imidazol-4-yl)-6-[(oxolan-3-yl)methoxy]imidazo[1,2-a]pyrimidin-2-yl]-3-(trifluoromethyl)-1H-1,2,4-triazole | 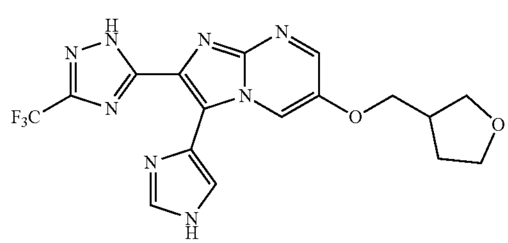 [SMILES: FC(F)(F)c1n[nH]c(-c2nc3ncc(OCC4CCOC4)cn3c2-c2c[nH]cn2)n1] |

TABLE 1-continued

| Compound No. / Example No. | Chemical Name | Structure |
|---|---|---|
| 136 | 5-(1H-imidazol-4-yl)-6-[3-(trifluoromethyl)-1H-1,2,4-triazol-5-yl]-15-oxa-4,7,9-triazatetracyclo[10.2.1.0²,¹⁰.0⁴,⁸]pentadeca-2,5,7,9-tetraene | 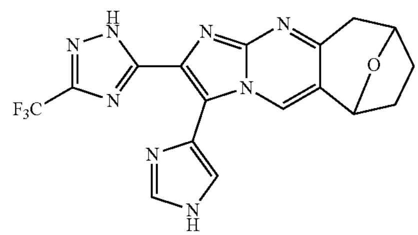 [SMILES: FC(F)(F)c1n[nH]c(-c2nc3nc4c(cn3c2-c2c[nH]cn2)C2CCC(C4)O2)n1] |
| 137 | 6-(1H-imidazol-4-yl)-12,12-dimethyl-5-[3-(trifluoromethyl)-1H-1,2,4-triazol-5-yl]-11-oxa-2,4,7-triazatricyclo[7.4.0.0³,⁷]trideca-1,3,5,8-tetraene | 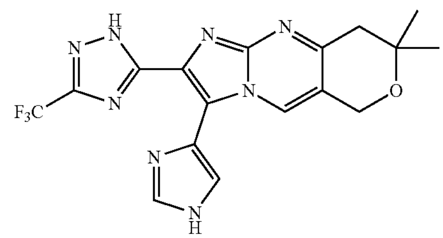 [SMILES: CC1(C)Cc2nc3nc(-c4nc(C(F)(F)F)n[nH]4)c(-c4c[nH]cn4)n3cc2CO1] |
| 138 | 5-[3-(1H-imidazol-4-yl)-5,7-dimethylimidazo[1,2-a]pyrimidin-2-yl]-3-(trifluoromethyl)-1H-1,2,4-triazole | 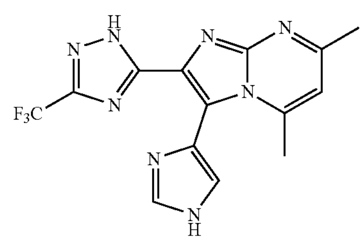 [SMILES: Cc1cc(C)n2c(-c3c[nH]cn3)c(-c3nc(C(F)(F)F)n[nH]3)nc2n1] |
| 139 | 5-[3-(1H-imidazol-5-yl)-6-{[2-(oxolan-3-yl)ethoxy]methyl}imidazo[1,2-a]pyrimidin-2-yl]-3-(trifluoromethyl)-1H-1,2,4-triazole | 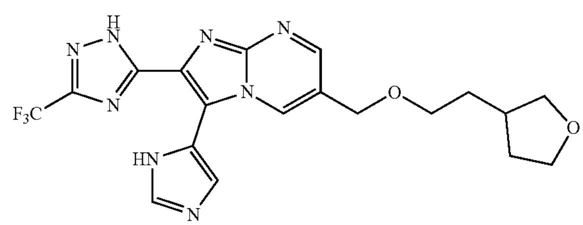 [SMILES: FC(F)(F)c1n[nH]c(-c2nc3ncc(COCCC4CCOC4)cn3c2-c2cnc[nH]2)n1] |
| 140 | 5-[3-(1H-imidazol-5-yl)-6-{[3-(oxolan-2-yl)propoxy]methyl}imidazo[1,2-a]pyrimidin-2-yl]-3-(trifluoromethyl)-1H-1,2,4-triazole | 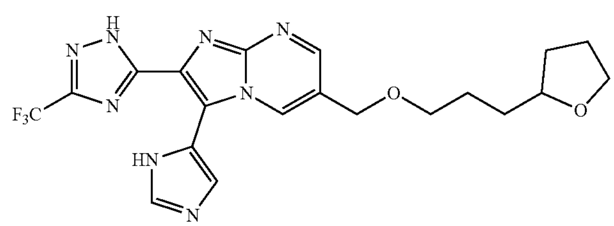 [SMILES: FC(F)(F)c1n[nH]c(-c2nc3ncc(COCCCC4CCCO4)cn3c2-c2cnc[nH]2)n1] |
| 141 | 5-[3-(1H-imidazol-5-yl)-6-{[2-(oxolan-2-yl)ethoxy]methyl}imidazo[1,2-a]pyrimidin-2-yl]-3-(trifluoromethyl)-1H-1,2,4-triazole | 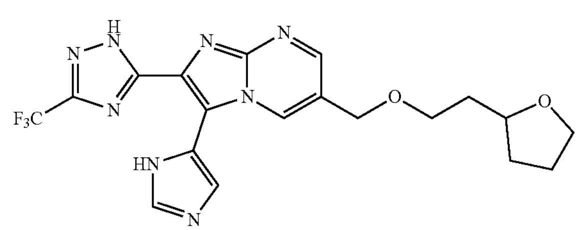 [SMILES: FC(F)(F)c1n[nH]c(-c2nc3ncc(COCCC4CCCO4)cn3c2-c2cnc[nH]2)n1] |

TABLE 1-continued

| Compound No. / Example No. | Chemical Name | Structure |
|---|---|---|
| 142 | 5-{[3-(1H-imidazol-5-yl)-2-[3-(trifluoromethyl)-1H-1,2,4-triazol-5-yl]imidazo[1,2-a]pyrimidin-6-yl]methoxy}pentan-1-ol | 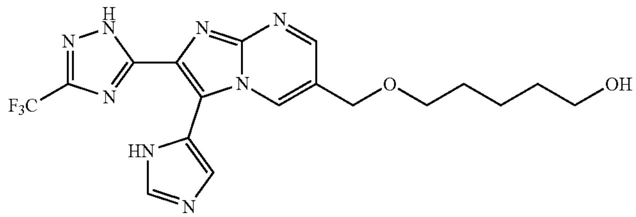 [SMILES: OCCCCCOCc1cnc2nc(-c3nc(C(F)(F)F)n[nH]3)c(-c3cnc[nH]3)n2c1] |
| 143 | 5-(6-{[2-(1H-imidazol-1-yl)propoxy]methyl}-3-(1H-imidazol-4-yl)imidazo[1,2-a]pyrimidin-2-yl)-3-(trifluoromethyl)-1H-1,2,4-triazole | 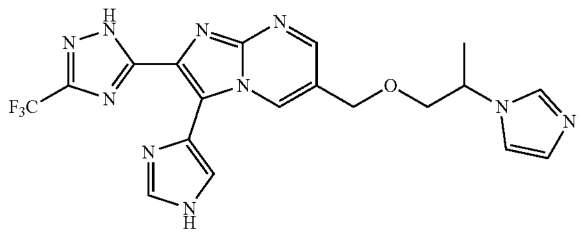 [SMILES: CC(COCc1cnc2nc(-c3nc(C(F)(F)F)n[nH]3)c(-c3c[nH]cn3)n2c1)n1ccnc1] |
| 144 | 5-[3-(1H-imidazol-5-yl)-6-[1-(trifluoromethyl)cyclopropyl]imidazo[1,2-a]pyrimidin-2-yl]-3-(trifluoromethyl)-1H-1,2,4-triazole | 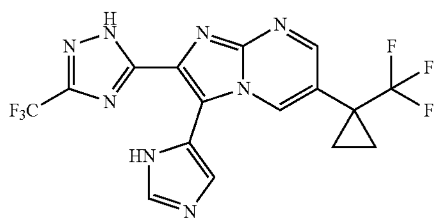 [SMILES: FC(F)(F)c1n[nH]c(-c2nc3ncc(C4(C(F)(F)F)CC4)cn3c2-c2cnc[nH]2)n1] |
| 145 | 5-(6-{[2-(1,4-dioxan-2-yl)ethoxy]methyl}-3-(1H-imidazol-4-yl)imidazo[1,2-a]pyrimidin-2-yl)-3-(trifluoromethyl)-1H-1,2,4-triazole | 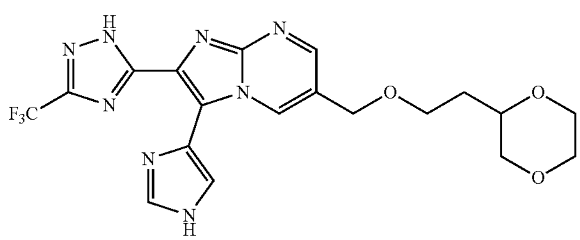 [SMILES: FC(F)(F)c1n[nH]c(-c2nc3ncc(COCCC4COCCO4)cn3c2-c2c[nH]cn2)n1] |
| 146 | 5-[3-(1H-imidazol-4-yl)-6-{[2-(1H-pyrazol-1-yl)ethoxy]methyl}imidazo[1,2-a]pyrimidin-2-yl]-3-(trifluoromethyl)-1H-1,2,4-triazole | 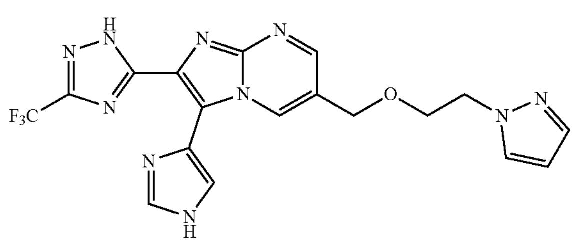 [SMILES: FC(F)(F)c1n[nH]c(-c2nc3ncc(COCCn4cccn4)cn3c2-c2c[nH]cn2)n1] |
| 147 | 2-{[3-(1H-imidazol-4-yl)-2-[3-(trifluoromethyl)-1H-1,2,4-triazol-5-yl]imidazo[1,2-a]pyrimidin-6-yl]methoxy}-1-(pyrrolidin-1-yl)ethan-1-one | 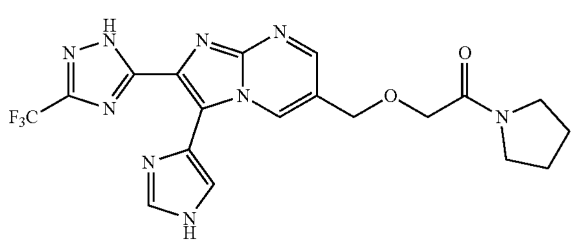 [SMILES: O=C(COCc1cnc2nc(-c3nc(C(F)(F)F)n[nH]3)c(-c3c[nH]cn3)n2c1)N1CCCC1] |

TABLE 1-continued

| Compound No. / Example No. | Chemical Name | Structure |
|---|---|---|
| 148 | 5-[3-(1H-imidazol-4-yl)-6-{[2-(3-methyl-1H-pyrazol-1-yl)ethoxy]methyl}imidazo[1,2-a]pyrimidin-2-yl]-3-(trifluoromethyl)-1H-1,2,4-triazole | 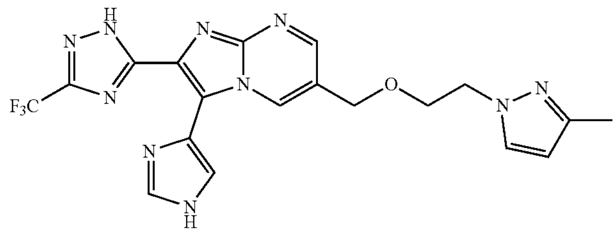 [SMILES: Cc1ccn(CCOCc2cnc3nc(-c4nc(C(F)(F)F)n[nH]4)c(-c4c[nH]cn4)n3c2)n1] |
| 149 | 1-[3-({[3-(1H-imidazol-4-yl)-2-[3-(trifluoromethyl)-1H-1,2,4-triazol-5-yl]imidazo[1,2-a]pyrimidin-6-yl]methoxy}methyl)pyrrolidin-1-yl]ethan-1-one | 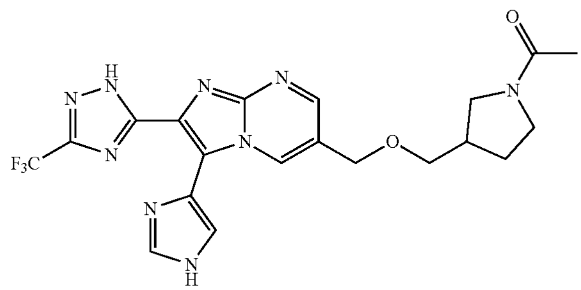 [SMILES: CC(=O)N1CCC(COCc2cnc3nc(-c4nc(C(F)(F)F)n[nH]4)c(-c4c[nH]cn4)n3c2)C1] |
| 150 | 5-(6-{[2-(1H-imidazol-1-yl)-2-methylpropoxy]methyl}-3-(1H-imidazol-4-yl)imidazo[1,2-a]pyrimidin-2-yl)-3-(trifluoromethyl)-1H-1,2,4-triazole | 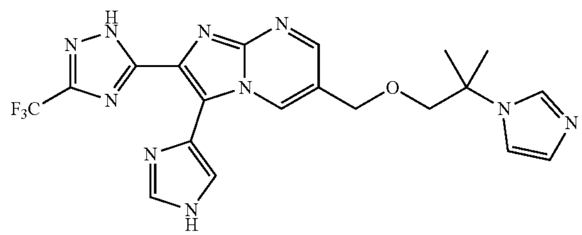 [SMILES: CC(C)(COCc1cnc2nc(-c3nc(C(F)(F)F)n[nH]3)c(-c3c[nH]cn3)n2c1)n1ccnc1] |
| 151 | 5-(6-{[2-(4-chloro-1H-pyrazol-1-yl)ethoxy]methyl}-3-(1H-imidazol-4-yl)imidazo[1,2-a]pyrimidin-2-yl)-3-(trifluoromethyl)-1H-1,2,4-triazole | 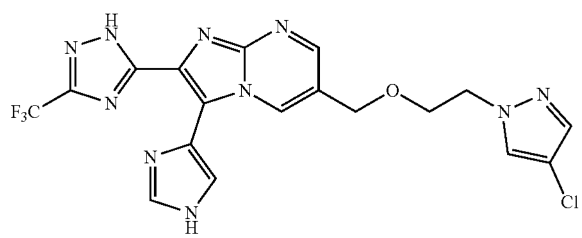 [SMILES: FC(F)(F)c1n[nH]c(-c2nc3ncc(COCCn4cc(Cl)cn4)cn3c2-c2c[nH]cn2)n1] |
| 152 | 2-{[3-(1H-imidazol-4-yl)-2-[3-(trifluoromethyl)-1H-1,2,4-triazol-5-yl]imidazo[1,2-a]pyrimidin-6-yl]methoxy}-1-(piperidin-1-yl)ethan-1-one | 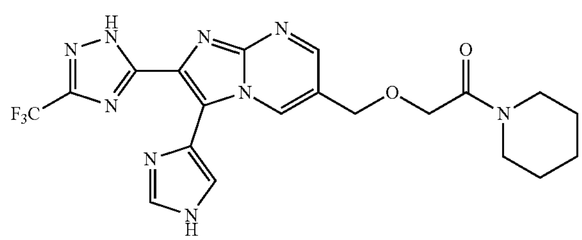 [SMILES: O=C(COCc1cnc2nc(-c3nc(C(F)(F)F)n[nH]3)c(-c3c[nH]cn3)n2c1)N1CCCCC1] |
| 153 | 5-[3-(1H-imidazol-4-yl)-6-[(2-propoxyethoxy)methyl]imidazo[1,2-a]pyrimidin-2-yl]-3-(trifluoromethyl)-1H-1,2,4-triazole | 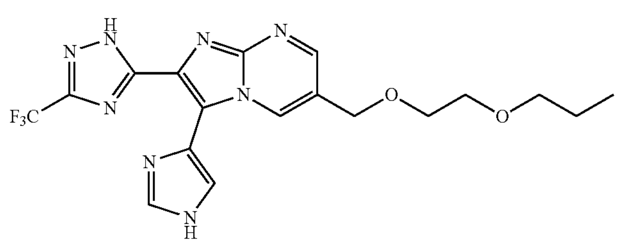 [SMILES: CCCOCCOCc1cnc2nc(-c3nc(C(F)(F)F)n[nH]3)c(-c3c[nH]cn3)n2c1] |

TABLE 1-continued

| Compound No. / Example No. | Chemical Name | Structure |
|---|---|---|
| 154 | 5-[3-(1H-imidazol-5-yl)-6-propoxyimidazo[1,2-a]pyrimidin-2-yl]-3-(trifluoromethyl)-1H-1,2,4-triazole | 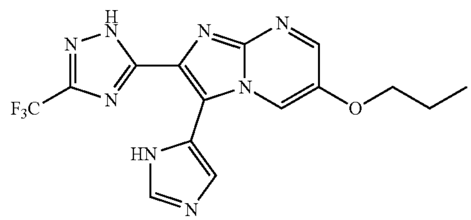 [SMILES: CCCOc1cnc2nc(-c3nc(C(F)(F)F)n[nH]3)c(-c3cnc[nH]3)n2c1] |
| 155 | 5-[3-(1H-imidazol-4-yl)-6-[{{5-oxaspiro[2.4]heptan-1-yl}methoxy)methyl]imidazo[1,2-a]pyrimidin-2-yl]-3-(trifluoromethyl)-1H-1,2,4-triazole | 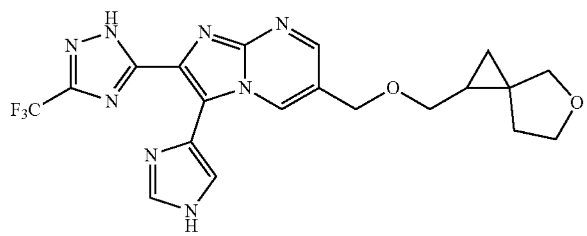 [SMILES: FC(F)(F)c1n[nH]c(-c2nc3ncc(COCC4CC45CCOC5)cn3c2-c2c[nH]cn2)n1] |
| 156 | 5-[3-(1H-imidazol-4-yl)-6-{[(4-methyloxolan-2-yl)methoxy]methyl}imidazo[1,2-a]pyrimidin-2-yl]-3-(trifluoromethyl)-1H-1,2,4-triazole | 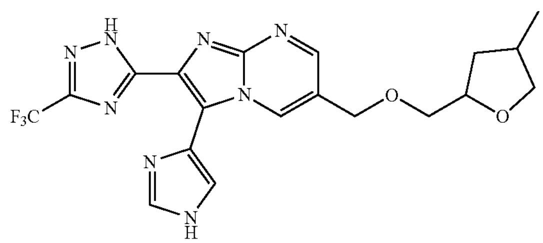 [SMILES: CC1COC(COCc2cnc3nc(-c4nc(C(F)(F)F)n[nH]4)c(-c4c[nH]cn4)n3c2)C1] |
| 157 | 5-[6-(cyclobutoxymethyl)-3-(1H-imidazol-4-yl)imidazo[1,2-a]pyrimidin-2-yl]-3-(trifluoromethyl)-1H-1,2,4-triazole | 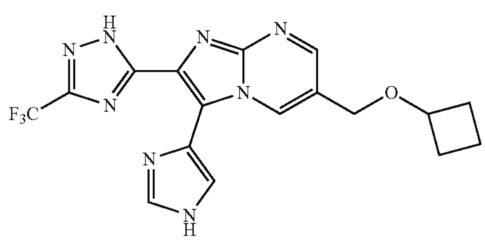 [SMILES: FC(F)(F)c1n[nH]c(-c2nc3ncc(COC4CCC4)cn3c2-c2c[nH]cn2)n1] |
| 158 | 5-(6-{[(1,4-dimethyl-1H-imidazol-2-yl)methoxy]methyl}-3-(1H-imidazol-4-yl)imidazo[1,2-a]pyrimidin-2-yl)-3-(trifluoromethyl)-1H-1,2,4-triazole | 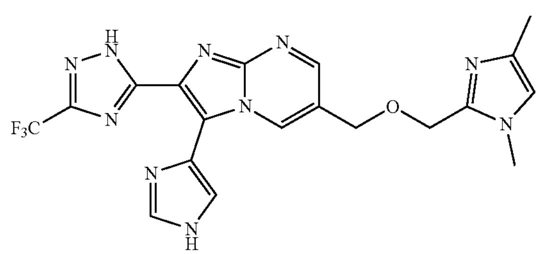 [SMILES: Cc1cn(C)c(COCc2cnc3nc(-c4nc(C(F)(F)F)n[nH]4)c(-c4c[nH]cn4)n3c2)n1] |
| 159 | 3-bromo-5-[6-fluoro-3-(1H-imidazol-4-yl)imidazo[1,2-a]pyrimidin-2-yl]-1H-1,2,4-triazole | 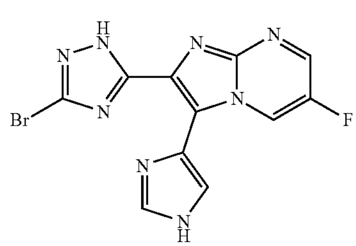 [SMILES: Fc1cnc2nc(-c3nc(Br)n[nH]3)c(-c3c[nH]cn3)n2c1] |

TABLE 1-continued

| Compound No. / Example No. | Chemical Name |
|---|---|
| 160 | 5-[3-(1H-imidazol-5-yl)-6-(2,2,2-trifluoroethoxy)imidazo[1,2-a]pyrimidin-2-yl]-3-(trifluoromethyl)-1H-1,2,4-triazole |
| 161 | 5-[3-(1H-imidazol-5-yl)-6-(oxolan-3-yloxy)imidazo[1,2-a]pyrimidin-2-yl]-3-(trifluoromethyl)-1H-1,2,4-triazole |
| 162 | 5-(6-{[1-(2,2-difluoroethyl)azetidin-3-yl]oxy}-3-(1H-imidazol-5-yl)imidazo[1,2-a]pyrimidin-2-yl)-3-(trifluoromethyl)-1H-1,2,4-triazole |
| 163 | 5-[6-ethoxy-3-(1H-imidazol-5-yl)imidazo[1,2-a]pyrimidin-2-yl]-3-(trifluoromethyl)-1H-1,2,4-triazole |
| 164 | (1-{[3-(1H-imidazol-4-yl)-2-[3-(trifluoromethyl)-1H-1,2,4-triazol-5-yl]imidazo[1,2-a]pyrimidin-7-yl]methyl}azetidin-3-yl)methanol |
| 165 | 5-[3-(1H-imidazol-4-yl)-6-(1-methoxyethyl)imidazo[1,2-a]pyrimidin-2-yl]-3-(trifluoromethyl)-1H-1,2,4-triazole |

Statement of Use

Therapeutic targeting of the cGAS-STING pathway with small molecule cGAS inhibitors could be beneficial in a broad array of autoinflammatory, autoimmune and immune-mediated diseases.

In an embodiment, "treatment" refers to ameliorating or stabilising the specified condition, reducing or eliminating the symptoms of the condition and slowing or eliminating the progression of the condition.

Compounds of the invention may be useful in the prevention of a condition in which cGAS or downstream elements of its pathway may play a known or expected role, such as in immune conditions, inflammatory conditions, auto-immune conditions, auto-inflammatory conditions, Type I interferonopathies, allergies, infectious conditions, organ injuries, tissue damage and other cGAS-dependent or related conditions.

Compounds of the invention are useful in the treatment of a condition in which cGAS or downstream elements of its pathway may play a known or expected role. Compounds of the invention may therefore be useful in the treatment of a number of immune conditions, inflammatory conditions, auto-immune conditions, auto-inflammatory conditions, Type I interferonopathies, allergies, infectious conditions, organ injuries, tissue damage and other cGAS-dependent or related conditions.

Compounds of the invention are useful in the treatment of a cGAS-related disease or disorder.

Compounds of the invention are useful in the prevention of a cGAS-related disease or disorder.

Compounds of the invention may be useful in the treatment of an autoimmune disease selected from, but not limited to, STING associated vasculitis with onset at infancy (SAVI), Aicardi Goutieres syndrome (AGS), familial chilblain lupus, ataxia telangiectasia (also referred to as Louis-Bar Syndrome), retinal vasculopathy with cerebral leukodystrophy (RVCL), systemic lupus erythematosus (SLE), cutaneous lupus, lupus nephritis (LN), psoriasis, diabetes mellitus including insulin-dependent diabetes mellitus (IDDM), dermatomyositis, human immunodeficiency virus (HIV), AIDS, polymyositis, systemic sclerosis (scleroderma), and Sjogren's syndrome (SS), rheumatoid arthritis (RA), psoriatic arthritis, polyarthritis, myasthenia gravis, polyarteritis nodosa, vasculitis, cutaneous vasculitis, anti-neutrophil cytoplasmic antibody (ANCA)-associated vasculitis, Henoch-Schonlein purpura, autoimmune hepatitis, primary sclerosing cholangitis, Wegener's granulomatosis, microscopic polyangiitis, Behcet's disease, spondylitis, giant cell arteritis, polymyalgia rheumatic, Raynaud's phenomenon, primary biliary cirrhosis, primary angiitis of the central nervous system microscopic polyangiitis, neuromyelitis optica and mixed connective tissue disease.

Compounds of the invention may be useful in the treatment of acute or chronic inflammation of any tissue or organ of the human body including, but not limited to, musculoskeletal inflammation, vascular inflammation, cardiovascular inflammation, neural inflammation, digestive system inflammation, respiratory system inflammation, renal system inflammation, inflammation of the reproductive system, ocular inflammation, periodontal inflammation, and other inflammation, as exemplified below, and the consequent tissue and organ damage.

Compounds of the invention may be useful in the treatment of musculoskeletal inflammation (i.e. any inflammatory condition of the musculoskeletal system) including, but not limited to conditions affecting skeletal joints, including joints of the hand, wrist, elbow, shoulder, jaw, spine, neck, hip, knee, ankle, and foot, and conditions affecting tissues connecting muscles to bones such as tendons. Examples of musculoskeletal inflammation which may be treated with compounds of the invention include arthritis (including, for example, osteoarthritis, rheumatoid arthritis, psoriatic arthritis, ankylosing spondylitis, acute and chronic infectious arthritis, arthritis associated with gout and pseudogout, and juvenile idiopathic arthritis), tendonitis, synovitis, tenosynovitis, bursitis, fibrositis (fibromyalgia), epicondylitis, myositis, and osteitis (including, for example, Paget's disease, osteitis pubis, and osteitis fibrosa cystic).

Compounds of the invention may be useful in the treatment of inflammation of the vasculature or lymphatic system including, but not limited to atherosclerosis, arthritis, phlebitis, vasculitis, and lymphangitis.

Compounds of the invention may be useful in the treatment of Cardiovascular conditions and cardiomyopathies including, but not limited to heart failure, myocardial infarction, cardiac hypertrophy, cardiac fibrosis, endomyocardial fibrosis, and aortic aneurysm and dissection (AAD).

Compounds of the invention may be useful in the treatment of inflammation of the nervous system including, but not limited to encephalitis, sepsis-associated encephalopathy (SAE), cerebral ischemic stroke, traumatic brain injury (TBI), ataxia-telangiectasia, Guillain-Barre syndrome, meningitis, neuromyotonia, narcolepsy, multiple sclerosis, myelitis, CNS vasculitis, and schizophrenia.

Compounds of the invention may be useful in the treatment of inflammatory conditions of the digestive system including, but not limited to cholangitis, cholecystitis, enteritis, enterocolitis, gastritis, gastroenteritis, inflammatory bowel disease (such as Crohn's disease and ulcerative colitis), ileitis, proctitis and colorectal cancer.

Compounds of the invention may be useful in the treatment of inflammation of the respiratory system including, but not limited to lung inflammation, chronic lung inflammation, cystic fibrosis, chronic obstructive pulmonary disease (COPD), idiopathic pulmonary fibrosis (IPF), silicosis, asthma and COVID-19. The compounds of this invention may be used to ameliorate lung inflammation, endothelial and vascular damage, and skin lesions derived from COVID-19 infections.

Compounds of the invention may be useful in the treatment of inflammatory conditions and diseases of the liver and kidney including, but not limited to cirrhosis, liver fibrosis, viral hepatitis, nonalcoholic fatty liver disease (NAFLD), steatosis, nonalcoholic steatohepatitis (NASH), alcoholic-related liver disease (ALD), primary hepatocellular cancer (HCC), hepatic ischemia-reperfusion injury (IRI), acute kidney injury (AKI), chronic kidney disease (CKD), and renal fibrosis.

Compounds of the invention may be useful in the treatment of metabolic disorders including, but not limited to diabetes melitus, obesity, insulin resistance and glucose intolerance.

Compounds of the invention may be useful in the treatment of inflammatory conditions of the reproductive system including, but not limited to, cervicitis, chorioamnionitis, endometritis, epididymitis, omphalitis, oophoritis, orchitis, salpingitis, tubo-ovarian abscess, urethritis, vaginitis, vulvitis, and vulvodynia.

Compounds of the invention may be useful in the treatment of ocular inflammation including, but not limited to inflammation of any structure of the eye, including the eye lids. Examples of ocular inflammation which may be treated with the compounds of the invention include blepharitis, blepharochalasis, conjunctivitis, dacryoadenitis, keratitis, fungal keratitis, keratoconjunctivitis sicca (dry eye), scleritis, trichiasis, and uveitis. In addition, other eye related disorders might be treated, including age-related macular degeneration (AMD).

Compounds of the invention may be useful in the treatment of inflammatory periodontal disease (also known as gum disease) including, but not limited to gingivitis, odontoblast inflammation, chronic periodontitis, aggressive periodontitis, necrotizing ulcerative gingivitis/periodontitis and combined periodontic-endodontic lesions.

Compounds of the invention may be useful in the treatment of autoimmune conditions having an inflammatory component including, but not limited to acute disseminated alopecia universalis, Behcet's disease, Chagas disease, STING associated vasculitis with onset at infancy (SAVI), Aicardi Goutieres syndrome (AGS), chilblain lupus, ataxia telangiectasia (also referred to as Louis-Bar Syndrome), retinal vasculopathy with cerebral leukodystrophy (RCVL), ANCA)-associated vasculitis, chronic fatigue syndrome, dysautonomia, encephalomyelitis, ankylosing spondylitis, aplastic anemia, hidradenitis suppurativa, autoimmune hepatitis, autoimmune oophoritis, celiac disease, Crohn's disease, diabetes mellitus type 1, giant cell arteritis, Goodpasture's syndrome, Grave's disease, Guillain-Barre syndrome, Hashimoto's disease, Henoch-Schonlein purpura, Kawasaki's disease, lupus erythematosus, microscopic colitis, microscopic polyarteritis, mixed connective tissue disease, multiple sclerosis, myasthenia gravis, opsoclonus myoclonus syndrome, optic neuritis, Ord's thyroiditis, pemphigus, polyarteritis nodosa, polymyalgia, rheumatoid arthritis, Reiter's syndrome, Sjogren's syndrome, temporal arteritis, Wegener's granulomatosis, warm autoimmune hemolytic anemia, interstitial cystitis, Lyme disease, morphea, psoriasis, sarcoidosis, scleroderma, ulcerative colitis, and vitiligo.

Compounds of the invention may be useful in the treatment of T-cell mediated hypersensitivity diseases having an inflammatory component including, but not limited to contact hypersensitivity, contact dermatitis (including that due to poison ivy), urticaria, skin allergies, respiratory allergies (hay fever, allergic rhinitis) and gluten-sensitive enteropathy (Celiac disease).

Compounds of the invention may be useful in the treatment of other inflammatory conditions including, but not limited to, appendicitis, dermatitis, dermatomyositis, endocarditis, fibrositis, gingivitis, glossitis, hepatitis, hidradenitis suppurativa, iritis, laryngitis, mastitis, myocarditis, nephritis, otitis, pancreatitis, parotitis, pericarditis, peritonitis, pharyngitis, pleuritis, pneumonitis, prostatitis, pyelonephritis, and stomatitis, transplant rejection (involving organs such as kidney, liver, heart, lung, pancreas (e.g., islet cells), bone marrow, cornea, small bowel, skin allografts, skin homografts, and heart valve xenografts, serum sickness, and graft vs host disease), acute pancreatitis, chronic pancreatitis, acute respiratory syndrome, Sezary's syndrome, congenital adrenal hyperplasia, nonsuppurative thyroiditis, hypercalcemia associated with cancer, pemphigus, bullous dermatitis herpetiformis, severe erythema multiforme, exfoliative dermatitis, seborrheic dermatitis, seasonal or perennial allergic rhinitis, bronchial asthma, contact dermatitis, atopic dermatitis, drug hypersensitivity reactions, allergic conjunctivitis, keratitis, herpes zoster ophthalmicus, iritis and iridocyclitis, chorioretinitis, optic neuritis, symptomatic sarcoidosis, fulminating or disseminated pulmonary tuberculosis chemotherapy, idiopathic thrombocytopenic purpura in adults, secondary thrombocytopenia in adults, acquired (autoimmune) hemolytic anemia, leukemia and lymphomas in adults, acute leukemia of childhood, regional enteritis, autoimmune vasculitis, multiple sclerosis, chronic obstructive pulmonary disease, solid organ transplant rejection, sepsis.

Compounds of the invention may be useful in the treatment of one or more diseases afflicting humans which are characterized by cellular proliferation in the area of disorders associated with neo-vascularization and/or vascular permeability including blood vessel proliferative disorders including arthritis (rheumatoid arthritis) and restenosis; fibrotic disorders including hepatic cirrhosis and atherosclerosis; mesangial cell proliferative disorders include glomerulonephritis, diabetic nephropathy, malignant nephrosclerosis, thrombotic microangiopathy syndromes, proliferative retinopathies, organ transplant rejection and glomerulopathies; and other disorders including psoriasis, diabetes mellitus and chronic wound healing.

Compounds of the invention be useful in the treatment of neurodegenerative conditions including, but not limited to, multiple sclerosis, Huntington's disease, Alzheimer's disease, Parkinson's disease, amyotrophic lateral sclerosis (ALS) and frontotemporal dementia (FTD).

Compounds of the invention may be useful in the treatment of inflammatory conditions derived from an infectious disease, which is any disease instigated by or coincident with an infection from a pathogen. Pathogens may be broadly defined as any species or organism that is foreign to a human tissue environment. Common disease causing pathogens include bacteria (many like TB), viruses (many like HBV, HIV, flu) and parasitic protozoans (like *P. falciparum* that causes malaria). The compounds of this invention may be used to treat infectious diseases derived from bacteria, such as TB infection {*Mycobacterium tuberculosis*}, *Chlamydia*, Tularemia infection {*Francisella tularensis*}, plasmodium infection or infections from DNA or RNA virus. The compounds of this invention may be used to treat infectious diseases derived from the DNA virus families: Herpesviridae (herpes simplex virus-1, Kaposi's sarcoma-associated virus and Epstein-Barr virus), Papillomaviridae (human papilloma virus), Adenovirus and Hepadnaviridae (Hepatitis B virus). Examples of RNA virus families include Retroviridae (human immunodeficiency virus) Flaviviridae (Dengue virus, Zika virus, Hepatitis C virus), Orthomyxoviridae (influenza), and Coronaviridae (human coronavirus, MERS, SARS and SARS-CoV2 coronavirus).

Compounds of the invention may be useful on the amelioration of organ injury or damage sustained as a result of a cGAS mediated disease or disorder, for example, acute kidney injury, liver injury, pulmonary injury, heart injury, etc.

Compounds of the invention may be particularly useful in the treatment of systemic lupus erythematosus (SLE), cutaneous lupus erythematosus (CLE), lupus nephritis, Sjogren's syndrome, dematomyositis and scleroderma, particularly systemic lupus erythematosus and lupus nephritis.

Compounds of the invention may be particularly useful in the treatment of neurodegenerative diseases such as amyotrophic lateral sclerosis (ALS), Parkinson's disease (PD) and Alzheimer's disease (AD), acute kidney injury, chronic kidney disease, diabetic kidney disease or injury, myocardial infarction, stroke, heart hypertrophy/heart failure, nonalcoholic steatohepatitis (NASH) and nonalcoholic fatty liver disease (NAFLD).

Aicardi-Goutieres syndrome (AGS) is an early onset disease, demonstrating characteristics of both autoinflammatory and autoimmune diseases, that manifests with progressive encephalopathy and chilblain skin lesions, and is biochemically characterized by an increase in type I interferons (Stetson et al. Cell 134(4) 587-598, 2008; Crow et al. Nat Rev Immunol 15(7) 429-440, 2015; Uggenti et al. Annu Rev Immunol 37:247-267, 2019). Many AGS patients show features of systemic autoimmunity such as anti-nuclear and anti-DNA autoantibodies, similar to SLE. More than 75% of AGS patients carry mutations in Trex1 or RnaseH2, resulting in the accumulation of cytoplasmic DNA due to the insufficient DNA clearance (Trex1) or DNA damage-driven micronuclei formation (RnaseH2). Importantly, knocking out these nucleases and/or knocking in inactivating AGS mutations causes in mice lethal autoimmune disease, which can be rescued by cGAS or STING deficiency (Gray et al. 2015 J Immunol 195(5) 1939-1943, 2015; Gao et al. PNAS USA 112(42) E5699-E5705, 2015; Pokatayevet et al. J Exp Med 213(3) 329-336, 2016; Mackenzie et al. EMBO J 35(8) 831-844, 2016). In addition to AGS, Trex1 mutations have been linked to familial chilblain lupus (FCL), a cutaneous form of systemic lupus erythematosus, and retinal vasculopathy with cerebral leukodystrophy (RVCL) (Rice et al. J Clin Immunol 35(3) 235-243, 2015). Recently, biallelic mutations in LSM11 and RNU7-1 genes, encoding components of the histone pre-mRNA processing complex, have been identified in genetically uncharacterized AGS patients and linked to excessive cGAS signaling (Uggenti et al. Nat Genet 52(12) 1364-1372, 2020).

Direct evidence that activation of STING causes inflammatory disease came from the identification of gain-of-function mutations in the TMEM173 gene encoding STING in patients presenting with early-onset vasculopathy and pulmonary inflammation (Liu et al. N Engl J Med 371(6) 507-518, 2014). The diseases caused by such mutations, now categorized as SAVI (STING associated vasculopathy with onset in infancy), is characterized by recurrent fevers, ulcerative skin lesions, vasculitis and interstitial lung disease. It is thought that SAVI-associated STING mutations lead to spontaneous dimerization and activation of STING in the absence of cGAMP (Ergun et al. Cell, 178(2) 290-301, 2019).

COPA Syndrome, named for a defect in the COPa protein that participates in Golgi-to-ER trafficking, has been also linked to aberrant cGAS-STING signaling. It is thought that due to the COPA mutations STING spends a proportionally greater time in the activated state in the Golgi apparatus, resulting in constitutive signaling (Lepelley et al. J Exp Med 217(11) e20200600, 2020; Mukai et al. Nat Commun 12(1) 61, 2021). While all COPA patients present with lung disease, a smaller subset of patients develop arthritis and kidney disease.

DNA cell deficiency has been first described in 2017 in humans. Affected patients demonstrate severe neonatal anemia, membranoproliferative glomerulonephritis, deforming arthropathy and increased levels of anti-dsDNA antibodies (Rodero et al. Nature Communications 8(1) 2176, 2017). While DNAseII is an endosomal nuclease, it is speculated that accumulation of dsDNA in the endo-lysosomes ultimately results in their rupture, exposing DNA to cGAS. DnaseII-deficient mice die during embryonic development owing to severe anemia and if crossed with IFNAR null mice, develop chronic polyarthritis (Kawane et al. Science 292(5521) 1546-1549, 2001; Yoshida et al. Nat Immunol 6(1) 49-56, 2005). Interestingly, deletion of cGAS or STING completely rescues DnaseII-deficient mice from both, embryonic lethality and chronic arthritis (Gao et al. PNAS USA 112(42) E5699-E5705, 2015).

Multiple lines of evidence suggest that the same mechanisms implicated in the pathogenesis of monogenic diseases contribute to the development of complex autoimmune diseases such as SLE. Missense Trex1 mutations have been identified in 0.5-2% of SLE patients, and lupus-like phenotype has been recapitulated in mice carrying the Trex1 D18N mutation that causes familial chilblain lupus (Namjou et al. Genes and Immunity 12(4) 270-279, 2011; Lee-Kirsch et al. Nat Genet 39(9) 1065-1067, 2007; Barizzone et al. Biomed Res Int 2013:471703, 2013). Similarly, mutations that impair RnaseH2 function have been linked to SLE in addition to AGS (Gunther et al. J Clin Invest 125(1) 413-424, 2015). Moreover, elevated cGAMP levels have been reported in 15% of SLE patients, and cGAMP-positive patients presented with higher SLEDAI score (An et al Arthritis Rheumatol 69(4) 800-807, 2017).

Based on the presence of interferon signature and overlapping clinical manifestations, diseases including various subtypes of cutaneous lupus erythematosus (CLE), lupus nephritis (LN) and dermatomyositis, are predicted to be driven (at least in part) by the same mechanisms implicated in the pathogenesis of SLE. UV-induced DNA damage may also activate cGAS-STING pathway and contribute to disease pathology (Skopelja-Gardner et al. Sci Rep 10(1) 7908, 2020).

Excessive cGAS-STING activation and cGAS-STING-dependent pathogenesis have been implied in several other autoimmune diseases, including rheumatoid arthritis (RA), psoriasis and inflammatory bowel disease (IBD). cGAS deficiency rescues polyarthritis phenotype of DnaseII-KO mice and reduces joint swelling in the K/BxN arthritis mouse model (Gao et al. PNAS USA 112(42) E5699-E5705, 2015; Willemsen et al. Cell Rep 37(6) 109977, 2021). Likewise, STING deficiency attenuates IMQ-induced psoriatic symptoms and skin inflammation (Yu et al. J Invest Dermatol 142(3) 898-906, 2022). In IBD, the cGAS-STING pathway plays both protective and detrimental roles. While elimination of cGAS reduces intestinal inflammation and ameliorates colitis associated with IL-10 deficiency, other studies underscore the beneficial role of cGAS and STING in intestinal homeostasis (Ahn et al. Cell Reports 21(13) 3873-3884, 2017; Canesso et al. Mucosal Immunol 11(3) 820-834, 2018; Hu et al. PNAS 118(23) e2105747118, 2021).

Inflammation is a prominent hallmark of several neurodegenerative diseases, including Parkinson disease, amyotrophic lateral sclerosis (ALS), Huntington disease (HD) and Alzheimer disease. In the case of Parkinson's disease, mutations in the PARKIN and PINK1 genes lead to defective mitophagy, mtDNA leakage into the cytosol and cGAS-STING-dependent cytokine production. Importantly, the motor deficit and neuronal cell loss seen in Parkin mutator mice, can be rescued by STING ablation (Slitter et al. Nature 561(7722) 258-262, 2018). Recently, cGAS-STING pathway has been implicated in the neuropathological processes associated with ALS and frontotemporal lobar degeneration. In a preclinical model of ALS driven by overexpression of human TDP-43 (A315T) allele, STING ablation dampens neuroinflammation, mitigates rapid disease progression and protects from early death (Yu et al. Cell 183(3) 636-649, 2020). Furthermore, administration of cGAS or STING inhibitors ameliorates the ongoing inflammation, improves motor function and increases survival in the SOD1-ALS mouse model (Tan et al. iScience 25:104404, 2022). Lastly, ALS patients with C9orf72 repeat expansion present with an enhanced type I interferon signature that is driven at least partly by STING activation (McCauley et al. Nature 585 (7823) 96-101, 2020). Increased cGAS activity has been also associated with inflammatory responses in HD striatal cells, and activation of microglia with Tau has been linked to the PQBP1-cGAS-STING pathway (Sharma et al. PNAS 117(27) 5989-15999, 2020; Jin et al. Nat Commun 12(1) 6565, 2021).

Activation of the cGAS-STING pathway with mtDNA has been proposed as a potential mechanism underlying obesity-induced inflammation and metabolic dysfunction. STING deficiency and/or inhibition prevents (at least partially) diet-induced adipose tissue inflammation, obesity, insulin resistance and glucose intolerance, and reduces senescence of pancreatic b-cells (Mao et al. Arterioscler Thromb Vasc Biol 37(5) 920-929, 2017; Hu et al FASEB J 36(5) e22266, 2022). In addition, excessive cGAS-STING signaling has been implicated in other metabolic diseases such as NAFLD and NASH. Independent labs have demonstrated that STING deficiency decreases severity of hepatic steatosis, inflammation and fibrosis in both methionine/choline-deficient diet (MCD) and high-fat diet (HFD) murine models (Luo et al Gastroenterology 155(6) 1971-1984, 2018; Yu et al. J Clin Invest 129(2) 546-555, 2019; Zhang et a. Front Immunol 13:931176, 2022).

Increased cGAS-STING signaling has been demonstrated in acute kidney injury (AKI), chronic kidney (CKD) and other indications associated with fibrosis. Cisplatin induced mtDNA leakage triggers tubular inflammation and acute kidney injury progression, which can be rescued by STING deficiency or treatment with STING inhibitor (Maekawa et al. Cell Rep 29(5) 1261-1273, 2019; Gong et al, Am J Physiol Renal Physiol 320(4) F608-F616, 2021). Chronic kidney disease (CKD), characterized by renal injury, inflammation, and tissue fibrosis, has been associated with compromised mitochondrial integrity and mtDNA release. Moreover, genetic ablation or pharmacological inhibition of STING ameliorates both TFAM-loss-induced and FA-induced kidney inflammation and fibrosis, and improves kidney function in APOL1 transgenic mice expressing G2 risk allele (Chung et al. Cell Metab 30(4) 784-799, 2019; Wu et al. J Clin Invest 131(20) e136329, 2021). Recently, Zhang et al. proposed that cGAS-STING-driven fibrosis is facilitated by a noncanonical cGAS-STING-PERK pathway (Zhang et al. Nat Cell Biol 24(5) 766-782, 2022).

Idiopathic pulmonary fibrosis (IPF) is characterized by progressive lung scarring. It is believed that the physiopathology relies on repetitive local micro-injuries leading to DNA damage, cell death and fibrosis. In the classical bleomycin-induced murine model of lung fibrosis, contribution of the cGAS-STING pathway to disease pathology is controversial. While Savigny et al. suggest that STING plays a protective role in the bleomycin model by limiting lung fibrosis, Zhang et al. report less severe fibrotic phenotype in STING-deficient mice in comparison to WT mice in response to bleomycin (Savigny et al. Front Immunol 11:588799, 2021; Zhang et al. Nat Cell Biol 24(5) 766-782, 2022). Administration of STING inhibitor also improves intestinal ischemia-reperfusion-mediated acute lung injury as demonstrated by reduced lung injury scores and attenuated fibrosis (Yang et a. Eur J Med Res 27(1) 79, 2022). In addition, cGAS-STING signaling induces lung inflammation in response to cigarette smoke exposure, a leading cause of chronic obstructive pulmonary disease (COPD), and silica particles (Nascimento et al. Sci Rep 9(1) 14848, 2019; Benmerzoug et al. Nat Com 9(1) 5226, 2018).

Myocardial infarction (MI) causes ischemic cell death in the heart, releasing debris from dying cells. The released cardiomyocyte DNA is phagocytosed by infiltrating macrophages, leading to cGAS-STING-mediated type I IFN production. Genetic or pharmacological blockade of the cGAS-STING pathway protects against MI-induced adverse ventricular remodeling, improves contractile function and increases survival after myocardial infarction (King et al. Nat Med 23(12) 1481-1487, 2017; Cao at al. Circulation 137(24) 2613-2634, 2018; Lai et al. J Am Heart Assoc 10(15) e020754, 2021; Rech et al. Life Sci 291:120263, 2022). Furthermore, cGAS-STING knockdown blunts pressure overload-induced cardiac hypertrophy and improves cardiac function in the mouse transverse aortic constriction (TAC) model (Hu et al. Am J Physiol Heart circ Physiol 318(6) H1525-H1537, 2020). Activation of the cGAS-STING pathway has been also implicated in the development of atherosclerosis and ischemic stroke brain injury (Pham et al. Eur Heart J 42(42) 4336-4348, 2021; Li et al., EMBO Mol Med 12(4) e11002, 2020).

Excessive cGAS-STING signaling contributes to acute and chronic inflammation in multiple tissues, and, in addition to the above mentioned diseases, cGAS-STING pathway has been linked to the pathogenesis of age-related macular degeneration (AMD) (Kerur et al. Nat Med 24(1) 50-61, 2018), acute pancreatitis (Zhao et al. Gastroenterology 154(6): 1822-1835, 2018), acne (Fischer et al. Front Immunol 11:571334, 2020) and sepsis (Hu et al., EBioMedicme 41:497-508, 2019).

In the last 5 years, several studies have shown that release of chromatin fragments into the cytosol can activate cGAS-STING pathway and induce senescence (Yang et al. PNAS Sci USA 114(23) E4612-E4620, 2017; Gluck et al. Nat Cell Biol 19(9) 1061-1070, 2017). Senescent cells have a distinctive secretory phenotype (senescence-associated secretory phenotype), which is defined by changes in the expression of proinflammatory cytokines, chemokines, extracellular matrix components, and matrix metalloproteinases (MMPs). The senescence-associated secretory phenotype is thought to contribute to many chronic diseases associated with aging, including atherosclerosis and cardiovascular disease, arthritis, type 2 diabetes, neurodegenerative and other diseases. Inhibition of cGAS can reduce chronic inflammation and provide benefit in many indications associated with elderly patient population.

Infection with Severe Acute Respiratory Syndrome Coronavirus 2 (SARS-CoV-2) is the cause of COVID-19 disease. The interaction of SARS-CoV-2 with the host cell has been reported to activate the cGAS-STING pathway through the noncanonical pathway (Neufeldt et al. 2022, Commun Biol 5(1) 45, 2022; Di Domizio et al. Nature 603(7899) 145-151, 2022). Fusion of SARS-CoV-2 with the host cell results in cytosolic micronuclei that bind and activate cGAS to induce an interferon response (Liu et al. Sci Signal 5(729) eabg8744, 2022). While activation of the cGAS-STING pathway during a SARS-CoV-2 infection will produce cytokines that can inhibit viral replication, extensive activation will lead to uncontrolled immune responses causative of COVID-19 immunopathology (Di Domizio et al. Nature 603(7899) 145-151, 2022). Pharmacological inhibition of the cGAS-STING pathway is expected to modulate the immune response after infection, which therefore may mitigate the immunopathology associated with disease symptoms. SARS-CoV-2-infected mice that were administered a STING antagonist two-days post-infection demonstrate reduced pathology and decreased levels of Type I IFNs and other cytokines in their lungs (Di Domizio et al. Nature 603(7899) 145-151, 2022). Activation of the cGAS-STING pathway has also been associated with a variety of other viral and bacterial pathogens.

Multiple labs have studied the role of the cGAS-STING pathway in cancer. Many cancer cells present with genomic instability, which leads to the formation of micronuclei and cGAS activation. The induced cGAS-STING signaling results in either antitumor or pro-tumorigenic processes, depending on the context. On the one hand, cytokines, such as type I IFN, produced by the activated cGAS-STING pathway boost natural killer (NK) cell responses and prime CD8+ T cells for a more potent tumor surveillance (Marcus et al. Immunity 9(4) 754-763, 2018; Woo et al. Immunity 41(5) 830-842, 2014). On the other hand, activation of the cGAS-STING pathway has been linked to metastasis and immune evasion. It has been proposed that tumor cells with high genomic instability, which is the hallmark of metastatic tumors, utilize the cGAS-STING pathway to facilitate cellular invasion (Bakhoum et al. Nature 553(7689) 467-472, 2018). Furthermore, cGAS and STING shape the immunosuppressive tumor microenvironment by recruiting regulatory T cells and myeloid suppressor cells, as well as upregulating immune checkpoint inhibitors, such as programmed death ligand 1 (PD-L1) (Ding et al. Biochim Biophys Acta 1852(11) 2494-2503, 2015; Liang et al. Nat Commun 8(1) 1736, 2017; Nakamura et al. J Immunother Cancer 9(7) e002852, 2021).

In an embodiment, the present invention relates to compounds, compositions containing them, and to their use in the treatment of various disorders, in particular autoimmune, autoinflammatory or immune-mediated conditions, such as systemic lupus erythematosus (SLE), cutaneous lupus erythematosus (CLE), lupus nephritis, Sjogren's syndrome, dermatomyositis, scleroderma, amyotrophic lateral sclerosis (ALS), Parkinson's disease (PD) and Alzheimer's disease (AD), acute kidney injury, chronic kidney disease, diabetic kidney disease or injury, APOL1 nephropathy, focal segmental glomerulosclerosis, membranous nephropathy, idiopathic pulmonary fibrosis, interstitial lung disease, myocardial infarction, stroke, heart hypertrophy/heart failure, nonalcoholic steatohepatitis (NASH) and nonalcoholic fatty liver disease (NAFLD), particularly systemic lupus erythematosus, cutaneous lupus erythematosus and lupus nephritis.

In an embodiment, the present invention relates to compounds, compositions containing them, and to their use in the treatment of various disorders, in particular autoimmune, autoinflammatory or immune-mediated conditions, such as systemic lupus erythematosus (SLE), cutaneous lupus erythematosus (CLE), lupus nephritis, Sjogren's syndrome, dermatomyositis, scleroderma, amyotrophic lateral sclerosis (ALS), Parkinson's disease (PD) and Alzheimer's disease (AD), acute kidney injury, chronic kidney disease, diabetic kidney injury, myocardial infarction, stroke, heart hypertrophy/heart failure, nonalcoholic steatohepatitis (NASH) and nonalcoholic fatty liver disease (NAFLD), particularly systemic lupus erythematosus.

In an aspect of the invention, there is provided a method of treatment of an autoimmune, autoinflammatory or immune-mediated condition in a human in need thereof comprising administering to said human a therapeutically effective amount of a compound of Formula (I) or a tautomer thereof, or a pharmaceutically acceptable salt of said compound or tautomer thereof.

In a further aspect, there is provided a compound of Formula (I) or a tautomer thereof, or a pharmaceutically acceptable salt of said compound or tautomer thereof for use in therapy.

In a further aspect, there is provided a compound of Formula (I) or a tautomer thereof, or a pharmaceutically acceptable salt of said compound or tautomer thereof for use in the treatment of an autoimmune, autoinflammatory or immune-mediated condition.

In a further aspect, there is provided the use of a compound of Formula (I) or a tautomer thereof, or a pharmaceutically acceptable salt of said compound or tautomer thereof in the manufacture of a medicament for use in the treatment of an autoimmune, autoinflammatory or immune-mediated condition.

In an embodiment, the autoimmune, autoinflammatory or immune-mediated condition is selected from the group consisting of systemic lupus erythematosus (SLE), cutaneous lupus erythematosus (CLE), lupus nephritis, Sjogren's syndrome, dematomyositis and scleroderma, particularly systemic lupus erythematosus.

In an embodiment, the autoimmune, autoinflammatory or immune-mediated condition is systemic lupus erythematosus (SLE). In an embodiment, the systemic lupus erythematosus is characterised as moderate to severe.

In an embodiment, the autoimmune, autoinflammatory or immune-mediated condition is lupus nephritis.

In an embodiment, the autoimmune, autoinflammatory or immune-mediated condition is selected from the group consisting of amyotrophic lateral sclerosis (ALS), Parkinson's disease (PD) and Alzheimer's disease (AD), acute kidney injury, chronic kidney disease, diabetic kidney injury, myocardial infarction, stroke, heart hypertrophy/heart failure, nonalcoholic steatohepatitis (NASH) and nonalcoholic fatty liver disease (NAFLD).

In an embodiment, there is provided a method of treatment of systemic lupus erythematosus in a human in need thereof comprising administering to said human a therapeutically effective amount of a compound of Formula (I) or a tautomer thereof, or a pharmaceutically acceptable salt of said compound or tautomer thereof.

In an embodiment, there is provided a compound of Formula (I) or a tautomer thereof, or a pharmaceutically acceptable salt of said compound or tautomer thereof for use in the treatment of systemic lupus erythematosus.

In an embodiment, the systemic lupus erythematosus is characterised as moderate to severe.

Therefore, in an embodiment, there is provided a compound of Formula (I) or a tautomer thereof, or a pharmaceutically acceptable salt of said compound or tautomer thereof for use in the treatment of moderate to severe systemic lupus erythematosus.

In an embodiment, the systemic lupus erythematosus is characterised as active systemic lupus erythematosus.

In an embodiment, the systemic lupus erythematosus is active, moderate to severe systemic lupus erythematosus.

In an embodiment, there is provided a compound of Formula (I) or a tautomer thereof, or a pharmaceutically acceptable salt of said compound or tautomer thereof for use in the treatment of lupus nephritis.

In an embodiment, there is provided a compound of Formula (I) or a tautomer thereof, or a pharmaceutically acceptable salt of said compound or tautomer thereof for use in the treatment of lupus nephritis identified via biopsy.

In an embodiment, there is provided a compound of Formula (I) or a tautomer thereof, or a pharmaceutically acceptable salt of said compound or tautomer thereof for use in the treatment of cutaneous lupus erythematosus. In an embodiment, the cutaneous lupus erythematosus is subacute or chronic.

In a further embodiment, there is provided the use of a compound of Formula (I) or a tautomer thereof, or a pharmaceutically acceptable salt of said compound or tautomer thereof in the manufacture of a medicament for use in the treatment of systemic lupus erythematosus.

In a further embodiment, there is provided the use of a compound of Formula (I) or a tautomer thereof, or a pharmaceutically acceptable salt of said compound or tautomer thereof in the manufacture of a medicament for use in the treatment of lupus nephritis.

In a further embodiment, there is provided the use of a compound of Formula (I) or a tautomer thereof, or a pharmaceutically acceptable salt of said compound or tautomer thereof in the manufacture of a medicament for use in the treatment of cutaneous lupus erythematosus.

In an embodiment, there is provided a compound having the following structure or a tautomer thereof, or a pharmaceutically acceptable salt of said compound or tautomer thereof

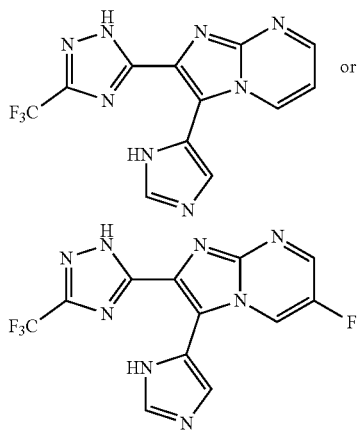

or

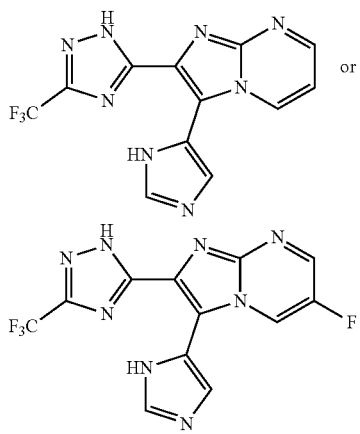

for use in the treatment of systemic lupus erythematosus.

In an embodiment, there is provided a compound having the following structure or a tautomer thereof, or a pharmaceutically acceptable salt of said compound or tautomer thereof

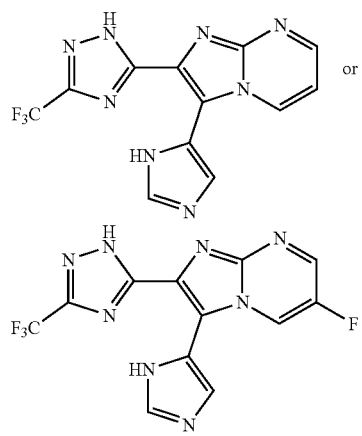

for use in the treatment of lupus nephritis.

In an embodiment, there is provided a compound having the following structure or a tautomer thereof, or a pharmaceutically acceptable salt of said compound or tautomer thereof for use in the treatment of cutaneous lupus erythematosus.

In an embodiment, there is provided a compound having the following structure or a tautomer thereof, or a pharmaceutically acceptable salt of said compound or tautomer thereof

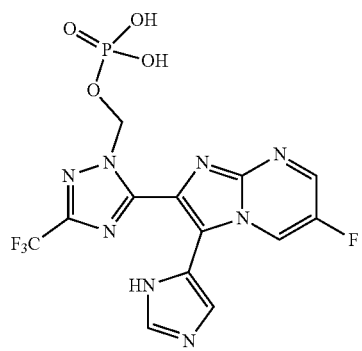 [SMILES: O=P(O)(O)OCn1nc(C(F)(F)F)nc1-c1nc2ncc(F)cn2c1-c1cnc[nH]1]

for use in the treatment of systemic lupus erythematosus.

In an embodiment, there is provided a compound having the following structure or a tautomer thereof, or a pharmaceutically acceptable salt of said compound or tautomer thereof

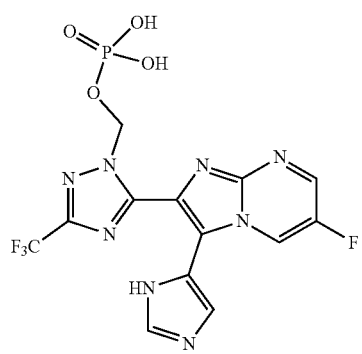 [SMILES: O=P(O)(O)OCn1nc(C(F)(F)F)nc1-c1nc2ncc(F)cn2c1-c1cnc[nH]1]

for use in the treatment of lupus nephritis.

In an embodiment, there is provided a compound having the following structure or a tautomer thereof, or a pharmaceutically acceptable salt of said compound or tautomer thereof

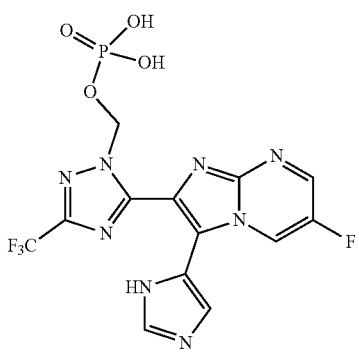 [SMILES: O=P(O)(O)OCn1nc(C(F)(F)F)nc1-c1nc2ncc(F)cn2c1-c1cnc[nH]1]

for use in the treatment of cutaneous lupus erythematosus.

Pharmaceutical Compositions/Routes of Administration/Dosages

While it is possible that for use in therapy, compounds of the invention may be administered as the raw chemical, it is common to present the active ingredient as a pharmaceutical composition.

In a further aspect, the present invention provides a pharmaceutical composition comprising (a) a compound of Formula (I) or a tautomer thereof, or a pharmaceutically acceptable salt of said compound or tautomer thereof; and (b) a pharmaceutically acceptable excipient.

The excipient(s) must be acceptable in the sense of being compatible with the other ingredients of the composition and not deleterious to the recipient thereof.

Pharmaceutical compositions may be adapted for administration by any appropriate route, for example by the oral (including buccal or sublingual), rectal, inhaled, intranasal, topical (including buccal, sublingual or transdermal), ocular (including topical, intraocular, subconjunctival, episcleral, sub-Tenon), parenteral (including subcutaneous, intramuscular, intravenous or intradermal) route. Such compositions may be prepared by any method known in the art of pharmacy, for example by bringing into association the active ingredient with the excipient(s).

In one embodiment, the pharmaceutical composition is presented for oral administration, for example as a tablet or capsule. Other suitable compositions for oral administration may be powders or granules; solutions or suspensions in aqueous or non-aqueous liquids; edible foams or whips; or oil-in-water liquid emulsions or water-in-oil liquid emulsions.

A compound of Formula (I) or a tautomer thereof, or a pharmaceutically acceptable salt of said compound or tautomer thereof may be employed alone or in combination with other therapeutic agents. Combination therapies according to the present invention thus comprise the administration of at least one compound of Formula (I) or pharmaceutically acceptable salt or tautomer thereof, and the use of at least one other therapeutically active agent. A compound of Formula (I) or pharmaceutically acceptable salt or tautomer thereof, and the other therapeutically active agent(s) may be formulated and administered together in a single pharmaceutical composition or may be formulated and administered separately. When formulated and administered separately, administration may occur simultaneously or sequentially in any order.

A compound of Formula (I) or a tautomer thereof, or a pharmaceutically acceptable salt of said compound or tautomer thereof may be used in combination with one or more other therapeutic agents which may be useful in the treatment of autoimmune, autoinflammatory or immune-mediated conditions.

Therefore, in a further aspect of the invention, there is provided a combination of (i) a compound of Formula (I) or a tautomer thereof, or a pharmaceutically acceptable salt of said compound or tautomer thereof; and (ii) an immune modulatory agent.

In an embodiment, the immune modulatory agent is belimumab also known as BENLYSTA.

In an embodiment, the present invention provides a pharmaceutical combination comprising a compound of Formula (I) or a tautomer thereof, or a pharmaceutically acceptable salt of said compound or tautomer thereof together with an immune modulatory agent.

In one embodiment, the present invention provides a compound of Formula (I) or a tautomer thereof, or a pharmaceutically acceptable salt of said compound or tautomer thereof together with an immune modulatory agent for use in combination therapy in the treatment of an autoimmune, autoinflammatory or immune-mediated condition, particularly systemic lupus erythematosus.

In one embodiment, the present invention provides a method of treatment of an autoimmune, autoinflammatory or immune-mediated condition, comprising administering a compound of Formula (I) or a tautomer thereof, or a pharmaceutically acceptable salt of said compound or tautomer thereof together with an immune modulatory agent.

In an embodiment, a compound of Formula (I) or a tautomer thereof, or a pharmaceutically acceptable salt of said compound or tautomer thereof may be used in combination with one or more other therapeutic agents useful in the standard of care for the treatment of systemic lupus erythematosus, such as for example antimalarials, steroids and immunosuppressants.

In an embodiment, a compound of Formula (I) or a tautomer thereof, or a pharmaceutically acceptable salt of said compound or tautomer thereof may be used in the treatment of SLE patients who have failed to respond to standard of care.

In an embodiment, a compound of Formula (I) or a tautomer thereof, or a pharmaceutically acceptable salt of said compound or tautomer thereof may be used in the treatment of patients with SLE receiving standard of care and have failed to respond to at least one immunosuppressant.

In an embodiment, a compound of Formula (I) or a tautomer thereof, or a pharmaceutically acceptable salt of said compound or tautomer thereof may be used in the treatment of patients with active, moderate to severe SLE receiving standard of care and have failed to respond to at least one immunosuppressant.

In an embodiment, a compound of Formula (I) or a tautomer thereof, or a pharmaceutically acceptable salt of said compound or tautomer thereof may be used in the treatment of patients with having SLE which is not controlled through treatment with standard of care alone.

EXAMPLES

General Synthetic Methods

The compounds of this invention may be prepared using synthetic procedures illustrated in the reaction schemes below and knowledge of a skilled organic chemist. The syntheses provided in these schemes are applicable for producing compounds of the invention having a variety of different substituent groups employing appropriate precursors, which are suitably protected if needed, to achieve compatibility with the reactions outlined herein.

Subsequent deprotection, where needed, affords compounds of the nature generally disclosed. Suitable protecting groups and the methods for protecting and de-protecting different substituents using such suitable protecting groups are well known to those skilled in the art; examples of which may be found in "Greene's Protective Groups in Organic Synthesis' (Peter G. M. Nuts, 5th edition, J. Wiley and Sons, 2014). Intermediates (compounds used in the preparation of the compounds of the invention) may also be present as salts.

General Method 1 (Scheme 1)

A suitably protected haloketone triazole compound (A) and pyrimidin-2-amine (B) are combined in a suitable solvent such as EtOH and heated to provide the resulting imidazopyrimidine (C). Halogenation of the imidazopyrimidine with a suitable reagent such as N-bromosuccinimide affords (D), where X is halogen. Catalyst mediated coupling of (D) with suitable reagents such as boronate (E) delivers substituted imidazopyrimidine (F), where -G-Z is $R^3$ protected with a suitable protecting group. Removal of the triazole protecting group (Y), and any other potential protecting groups, by any appropriate method, such as acidic hydrolysis affords the desired 1H-triazole of Formula (I).

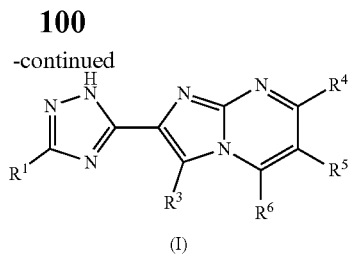

(I)

General Method 2 (Scheme 2)

Bromoimidazopyrimidine (H) which can be prepared via General Method 1 (where $R^5$ is Br), is coupled with an appropriate partner via catalyst mediated coupling (i.e., alkyl halide with photocatalysis) to afford J, where -G-Z is $R^3$ protected with a suitable protecting group. Removal of the triazole protecting group (Y), and any other potential protecting groups, by an appropriate method, such as acidic hydrolysis affords the desired 1H-triazole of Formula (I).

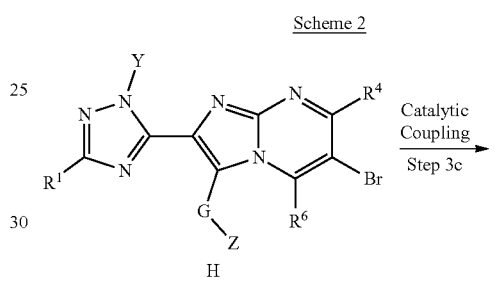

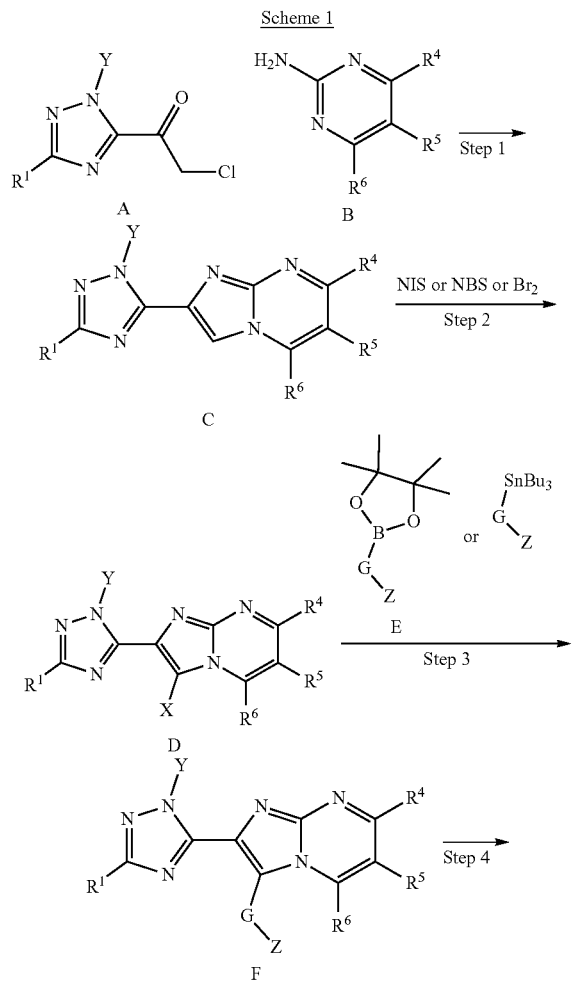

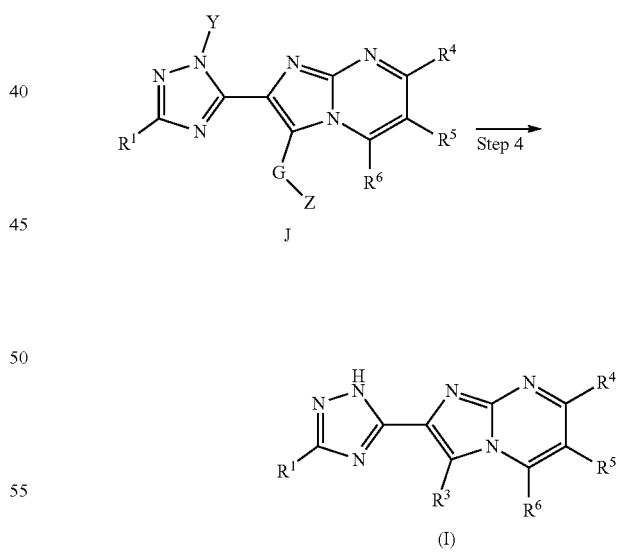

General Method 3 (Scheme 3)

An imidazopyrimidine (K) with suitably protected functional groups (PG=Protection Group) on $R^4$, $R^5$ or $R^6$ ($R^5$ as shown), prepared via Method 1, can be selectively deprotected to afford L and then further functionalized (for example by electrophilic alkylation) to afford M. Removal of the remaining protecting groups (Y and Z) affords compounds of Formula (I).

Scheme 3

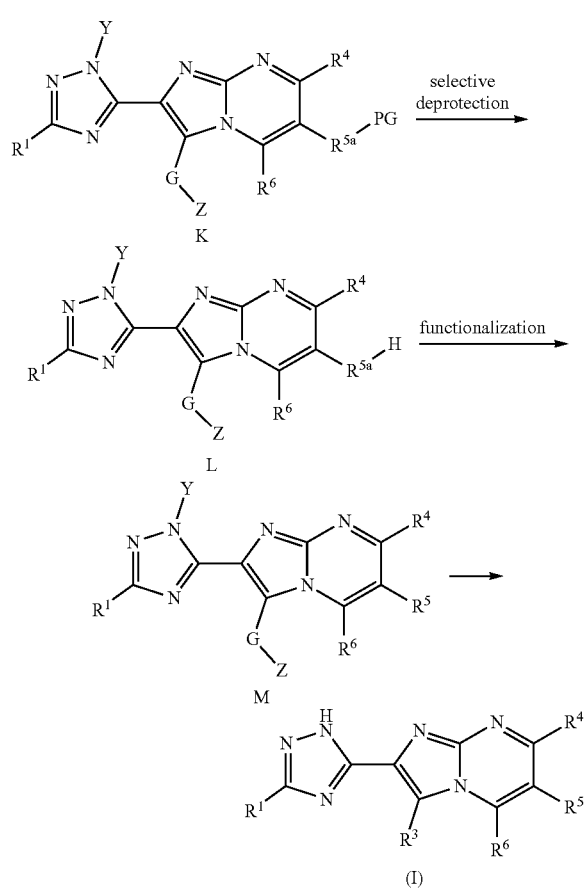

General Method 4 (Scheme 4)

An imidazopyrimidine (N) bearing a primary alcohol on any one (or more) of positions bearing $R^4$, $R^5$ or $R^6$ ($R^5$ as shown), synthesized via Method 1, is converted to a leaving group (such as mesylate) and displaced by an appropriate nucleophile to deliver P. Further elaboration is possible, prior to removal of the remaining protecting groups (Y and Z) to afford compounds of Formula (I).

Scheme 4

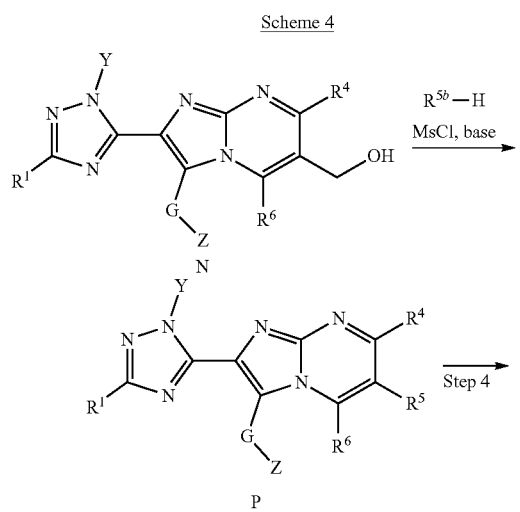

General Method 5 (Scheme 5)

Method 5 is an extension of Method 1, with additional functionalization steps following imidazopyrimidine formation. When $R^{5a}$ can be further functionalized (such as introduction of a new substituent via catalyst mediated coupling, or electrophilic alkylation) reaction affords substituted imidazopyrimidine (R). This group can be further modified by known methods to afford the desired $R^5$ group. Subsequent, halogenation of the imidazopyrimidine with a suitable reagent such as N-bromosuccinimide affords (S). Catalyst mediated coupling of (S) with suitable reagents such as boronate (E) affords substituted imidazopyrimidine (T). Removal of the triazole protecting group (Y), and any other potential protecting groups (for example, Z), by any appropriate method, such as acidic hydrolysis affords 1H-triazole compounds of Formula (I). This method would also apply to molecules where groups at $R^4$ or $R^6$ positions can be modified as above.

Scheme 5

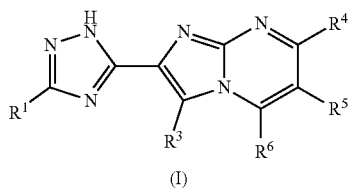

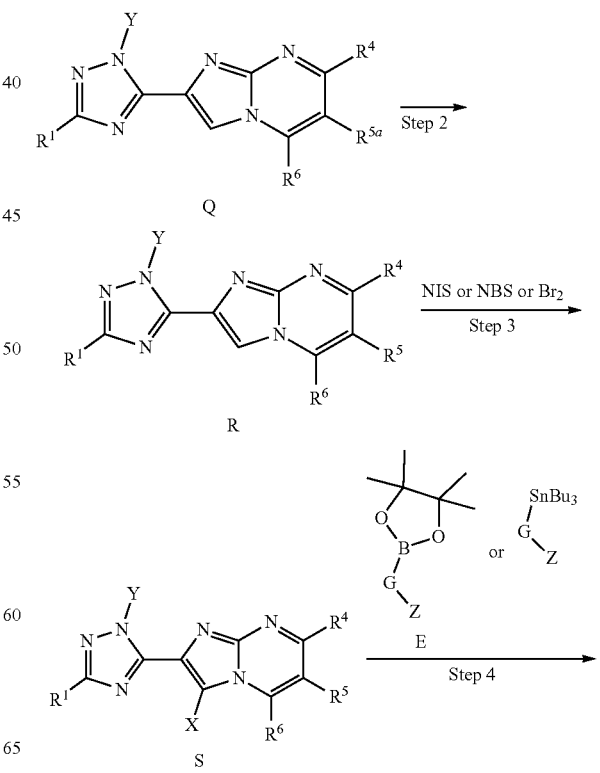

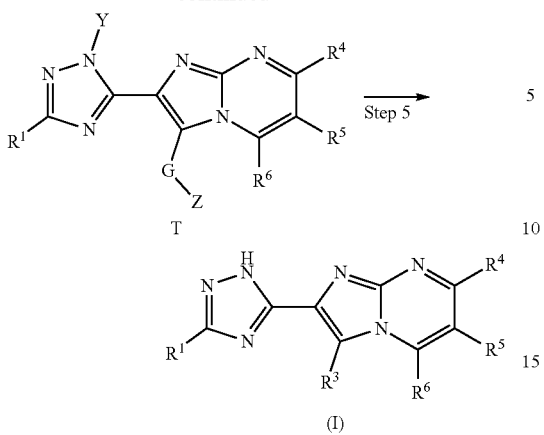

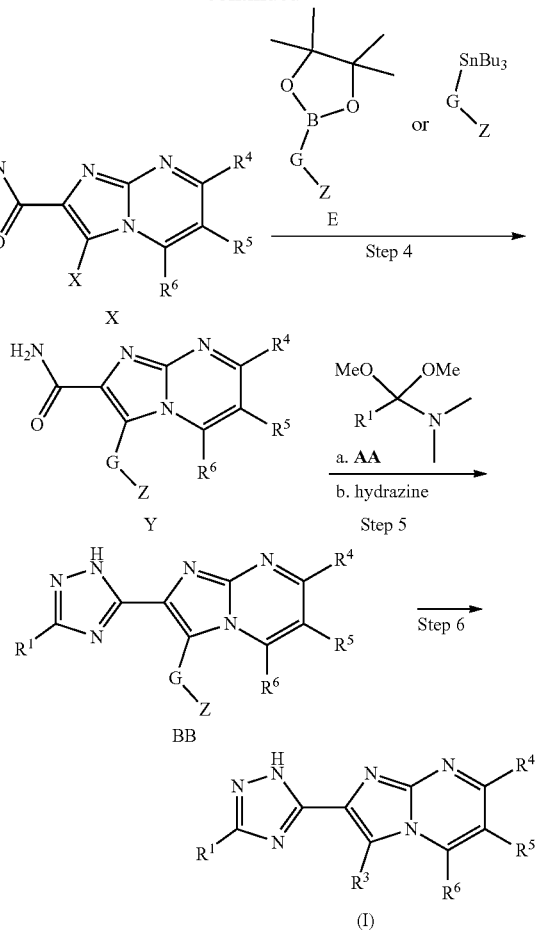

General Method 6 (Scheme 6)

General Method 6 employs a synthetic strategy of late-stage triazole formation. Imidazopyrimidine (W) is formed by reaction of U and V. Amide formation and subsequent halogenation of the imidazopyrimidine with a suitable reagent such as N-bromosuccinimide affords X. Catalyst-mediated coupling of X with a suitable reagent such as boronate E delivers substituted imidazopyrimidine Y. Two step triazole formation via condensation with a reagent comprising $R^1$ (AA) to form the amidine followed by condensation with hydrazine and cyclization to the triazole (BB). Removal of the protecting group Z can be achieved either in this step or with a separate deprotection step to afford 1H-triazole compounds of Formula (I).

General Method for Prodrug Preparation (Scheme 7)

Triazole (I) which can be prepared via one of the described General Methods, is reacted with an appropriate reagent to afford a prodrug of Formula (I) (PM=Prodrug Moiety) which may contain further protecting groups. If protecting groups are present, removal by an appropriate method in Step 6 will complete the synthesis. Prodrug moieties may also be incorporated at an earlier stage in the synthesis.

Scheme 6

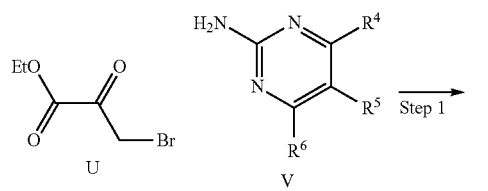

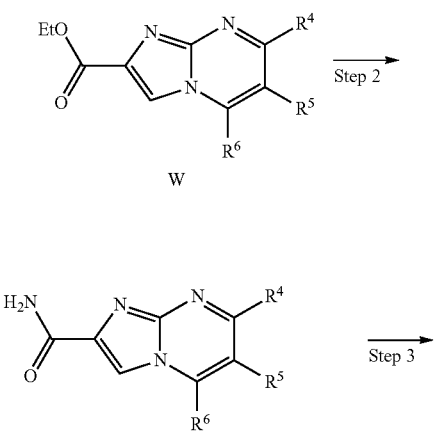

Scheme 7

From General Method 1

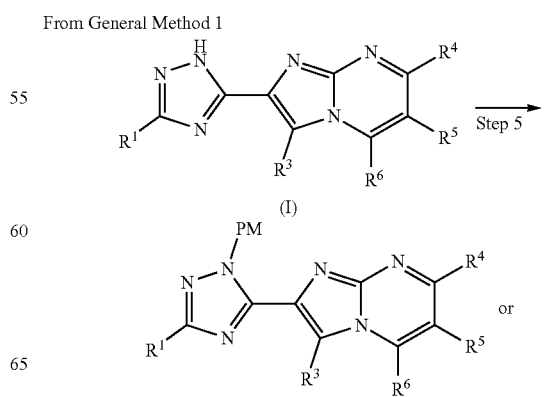

-continued

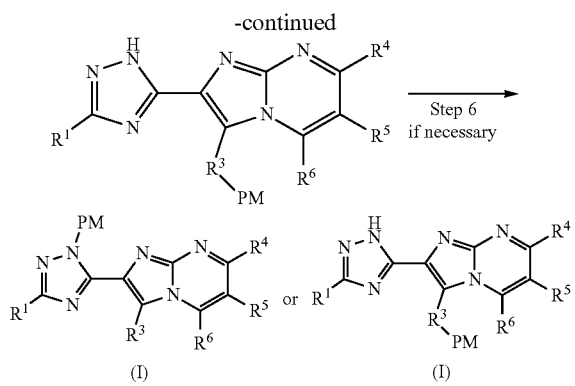

Mass Directed Autopreparative HPLC (MDAP)

Mass directed autopreparative HPLC was used for preparation of the compounds of this invention, and the conditions are given below. The UV detection was an averaged signal from wavelength of 210 nm to 350 nm and mass spectra were recorded on a mass spectrometer using alternate-scan positive and negative mode electrospray ionization.

MDAP Method A

Method A was conducted on a Xselect CSH $C_{18}$ column (typically 150 mm×30 mm i.d. 5 μm packing diameter) at ambient temperature. The solvents employed were:

A=0.1% v/v solution of trifluoroacetic acid in water
B=0.1% v/v solution of trifluoroacetic acid in acetonitrile.
The gradient employed was:

| Time (min) | Flow rate (mL/min) | % A | % B |
|---|---|---|---|
| 0 | 40 | 95 | 5 |
| 3 | 40 | 95 | 5 |
| 12 | 40 | 65 | 35 |
| 12.5 | 40 | 1 | 99 |
| 17 | 40 | 1 | 99 |

MDAP Method B

Method B was conducted on a Xselect CSH $C_{18}$ column (typically 150 mm×30 mm i.d. 5 μm packing diameter) at ambient temperature. The solvents employed were:

A=0.1% v/v solution of formic acid in water
B=0.1% v/v solution of formic acid in acetonitrile.
The gradient employed was:

| Time (min) | Flow rate (mL/min) | % A | % B |
|---|---|---|---|
| 0 | 40 | 85 | 15 |
| 1 | 40 | 85 | 15 |
| 10 | 40 | 45 | 55 |
| 10.5 | 40 | 1 | 99 |
| 15 | 40 | 1 | 99 |

MDAP Method C

Method C was conducted on a Xselect CSH $C_{18}$ column (typically 150 mm×30 mm i.d. 5 μm packing diameter) at ambient temperature. The solvents employed were:

A=0.1% v/v solution of formic acid in water
B=0.1% v/v solution of formic acid in acetonitrile.
The gradient employed was:

| Time (min) | Flow rate (mL/min) | % A | % B |
|---|---|---|---|
| 0 | 40 | 95 | 5 |
| 3 | 40 | 95 | 5 |
| 22 | 40 | 65 | 35 |
| 22.5 | 40 | 1 | 99 |
| 27 | 40 | 1 | 99 |

MDAP Method D

Method D was conducted on a Xselect CSH $C_{18}$ column (typically 150 mm×30 mm i.d. 5 μm packing diameter) at ambient temperature. The solvents employed were:

A=0.1% v/v solution of formic acid in water
B=0.1% v/v solution of formic acid in acetonitrile.
The gradient employed was:

| Time (min) | Flow rate (mL/min) | % A | % B |
|---|---|---|---|
| 0 | 40 | 95 | 5 |
| 3 | 40 | 95 | 5 |
| 12 | 40 | 65 | 35 |
| 12.5 | 40 | 1 | 99 |
| 17 | 40 | 1 | 99 |

MDAP Method E

Method E was conducted on a Xselect CSH $C_{18}$ column (typically 150 mm×30 mm i.d. 5 μm packing diameter) at ambient temperature. The solvents employed were:

A=0.1% v/v solution of trifluoroacetic acid in water
B=0.1% v/v solution of trifluoroacetic acid in acetonitrile.
The gradient employed was:

| Time (min) | Flow rate (mL/min) | % A | % B |
|---|---|---|---|
| 0 | 40 | 85 | 15 |
| 1 | 40 | 85 | 15 |
| 10 | 40 | 45 | 55 |
| 10.5 | 40 | 1 | 99 |
| 15 | 40 | 1 | 99 |

MDAP Method F

Method F was conducted on a Xselect CSH $C_{18}$ column (typically 150 mm×30 mm i.d. 5 μm packing diameter) at ambient temperature. The solvents employed were:

A=0.1% v/v solution of formic acid in water
B=0.1% v/v solution of formic acid in acetonitrile.
The gradient employed was:

| Time (min) | Flow rate (mL/min) | % A | % B |
|---|---|---|---|
| 0 | 40 | 70 | 30 |
| 1 | 40 | 70 | 30 |
| 10 | 40 | 15 | 85 |
| 10.5 | 40 | 1 | 99 |
| 15 | 40 | 1 | 99 |

MDAP Method G

Method G was conducted on a Xselect CSH $C_{18}$ column (typically 150 mm×30 mm i.d. 5 μm packing diameter) at ambient temperature. The solvents employed were:

A=0.1% v/v solution of formic acid in water
B=0.1% v/v solution of formic acid in acetonitrile.

The gradient employed was:

| Time (min) | Flow rate (mL/min) | % A | % B |
|---|---|---|---|
| 0 | 40 | 50 | 50 |
| 1 | 40 | 50 | 50 |
| 10 | 40 | 1 | 99 |
| 10.5 | 40 | 1 | 99 |
| 15 | 40 | 1 | 99 |

MDAP Method H

Method H was conducted on a Xselect CSH $C_{18}$ column (typically 150 mm×30 mm i.d. 5 μm packing diameter) at ambient temperature. The solvents employed were:

A=0.1% v/v solution of trifluoroacetic acid in water
B=0.1% v/v solution of trifluoroacetic acid in acetonitrile.

The gradient employed was:

| Time (min) | Flow rate (mL/min) | % A | % B |
|---|---|---|---|
| 0 | 40 | 70 | 30 |
| 1 | 40 | 70 | 30 |
| 10 | 40 | 15 | 85 |
| 10.5 | 40 | 1 | 99 |
| 15 | 40 | 1 | 99 |

Unless otherwise stated starting materials for the preparation of Intermediates and Examples are commercially available from, for example, PharmaTech and Sigma Aldrich.

Intermediate 1

1-(3-Bromo-1-(4-methoxybenzyl)-1H-1,2,4-triazol-5-yl)-2-chloroethanone

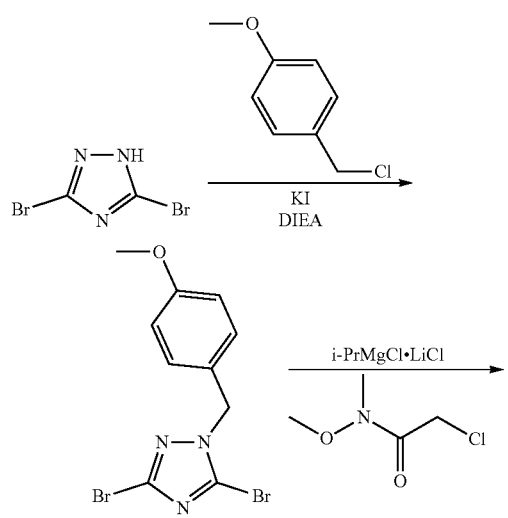

Step 1:
3,5-Dibromo-1-(4-methoxybenzyl)-1H-1,2,4-triazole

To a solution of 3,5-dibromo-1H-1,2,4-triazole (200 g, 882 mmol) in AcCN (300 mL) at RT were added DIEA (308 mL, 176 mmol), 1-(chloromethyl)-4-methoxybenzene (143 mL, 1058 mmol) and KI (14.63 g, 88 mmol). After 16 hr, the reaction mixture was diluted with water (200 mL) and extracted with EtOAc (2×500 mL). The combined organic layers were washed with water (500 mL) and brine (500 mL), dried over $Na_2SO_4$ and concentrated. The residue was dissolved in DCM (250 mL) and adsorbed onto silica (100 g), then purified by column chromatography (100-200 mesh silica gel [1 kg]), eluting with 5-10% EtOAc in hexane to yield the title compound (190 g, 531 mmol, 60% yield) as an off white solid. LCMS: $[M+H]^+=347.92$

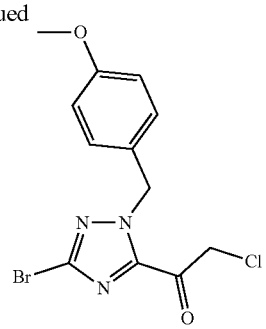

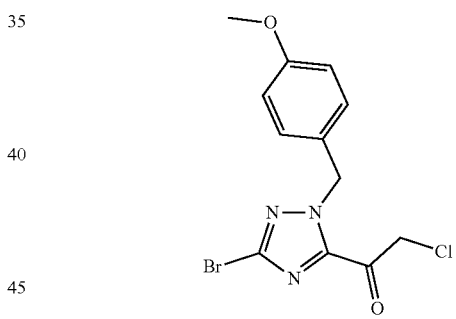

Step 2: 1-(3-Bromo-1-(4-methoxybenzyl)-1H-1,2,4-triazol-5-yl)-2-chloroethanone

To 3,5-dibromo-1-(4-methoxybenzyl)-1H-1,2,4-triazole (100 g, 280 mmol) in THF (800 mL) at −40° C. was added isopropylmagnesium lithium chloride (1M in THF) (559 mL, 559 mmol). After 2 hr 2-chloro-N-methoxy-N-methylacetamide (42.3 g, 307 mmol) in THF (200 mL) was added. After 1 hr, the reaction was quenched with sat'd aq $NH_4Cl$ (500 mL) and extracted with EtOAc (2×1 L). The combined organic extracts were washed with brine (500 mL), dried over $Na_2SO_4$ and concentrated. The residue was adsorbed onto silica (100 g) and purified by column chromatography (100-200 mesh silica gel [400 g]), eluting with 10-20% EtOAc in hexane to yield the title compound (23.45 g, 66.5 mmol, 24% yield) as an off white solid. $^1H$ NMR (400 MHz, $CDCl_3$) δ ppm 7.33-7.41 (m, 2H), 6.83-6.90 (m, 2H), 5.66 (s, 2H), 4.87 (s, 2H), 3.78 (s, 3H). LCMS: $[M+H]^+=345.92$ Intermediate 2

N,N-Dimethyl-4-(4,4,5,5-tetramethyl-1,3,2-dioxaborolan-2-yl)-1H-imidazole-1-sulfonamide

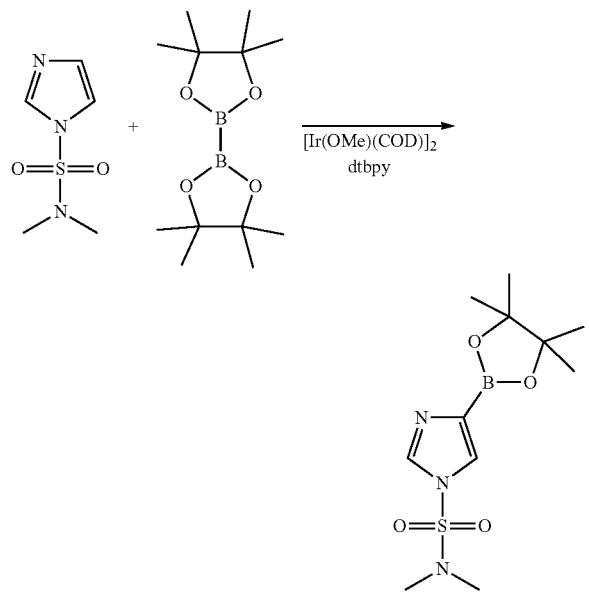

A mixture of (1,5-cyclooctadiene)(methoxy)iridium(I) dimer (3.0 g, 4.53 mmol) and bis(pinacolato)diboron (44.0 g, 173 mmol) in THF (150 mL) was stirred at 45° C. for 20 min, then treated with a solution of 4,4'-di-tert-butyl-2,2'-dipyridyl (1.50 g, 5.59 mmol) in THF (50 mL). After 20 min a solution of N,N-dimethyl-1H-imidazole-1-sulfonamide (20.0 g, 114 mmol) in THF (80 mL) was added, and the temperature was raised to 65° C. After 2 hr the reaction was concentrated, and the resulting residue was triturated with pentane to yield the title compound (32.2 g, 102 mmol, 89% yield) as a brown solid. $^1$H NMR (400 MHz, CDCl$_3$) b ppm 8.02 (d, J=1.01 Hz, 1H), 7.73 (d, J=1.01 Hz, 1H), 2.89 (s, 6H), 1.39 (s, 12H). LCMS: [M+H]$^+$=220.1 (boronic acid)

Intermediate 3

2-Chloro-1-(1-(4-methoxybenzyl)-3-(trifluoromethyl)-1H-1,2,4-triazol-5-yl)ethan-1-one

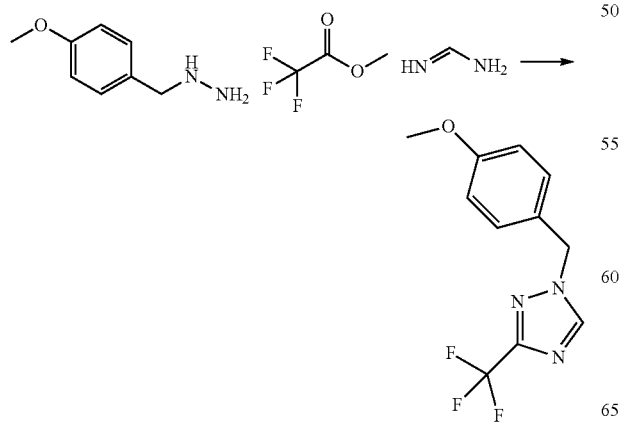

Step 1: 1-(4-Methoxybenzyl)-3-(trifluoromethyl)-1H-1,2,4-triazole

To a stirred mixture of (4-methoxybenzyl)hydrazine, hydrochloride (50.0 g, 265 mmol) in methanol (500 mL) was added sodium methoxide 25 wt % in methanol (60.0 g, 278 mmol). After stirring the white suspension for 15 minutes methyl 2,2,2-trifluoroacetate (36.0 g, 281 mmol) was added dropwise over 30 minutes. The reaction was stirred for an additional 2 hr. (LCMS showed a new peak 92% (UV) at t$_{RET}$ 0.75 min. Weak M+Na$^+$ 271.2 seen for the acylated PMB hydrazine. PMB hydrazine SM t$_{RET}$ 0.33 min. MS(ES) [M+H]$^+$121.0.) The reaction was treated with formamidine acetate acetic acid salt (30.0 g, 288 mmol), heated to reflux 85° C., and stirred for 24 hr. (LCMS showed a new peak 47% (UV) at t$_{RET}$ 0.95 min with a weak MS(ES) [M+H]$^+$258.2) The reaction was evaporated to dryness, taken up in EtOAc, washed with aq. NaHCO$_3$, dried (Na$_2$SO$_4$), filtered and evaporated to dryness. Purified by silica gel chromatography (Isco RediSep Rf Gold 330 g, 0% for 4 minutes to 30% over 2 minutes then to 70% over 15 minutes EtOAc in heptane). The pure fractions were combined and evaporated to dryness to give the product 1-(4-methoxybenzyl)-3-(trifluoromethyl)-1H-1,2,4-triazole (45.4 g) as a yellow oil, which solidified under vacuum to a yellow solid. This material was used without further purification in the next reaction. The reaction was repeated five more times to give a total of 260.5 g product. $^1$H NMR (400 MHz, CDCl$_3$) δ 8.06 (s, 1H), 7.35-7.30 (m, 2H), 6.97 (d, J=8.9 Hz, 2H), 5.36 (s, 2H), 3.87 (s, 3H). LCMS m/z 258.2 [M+H]$^+$

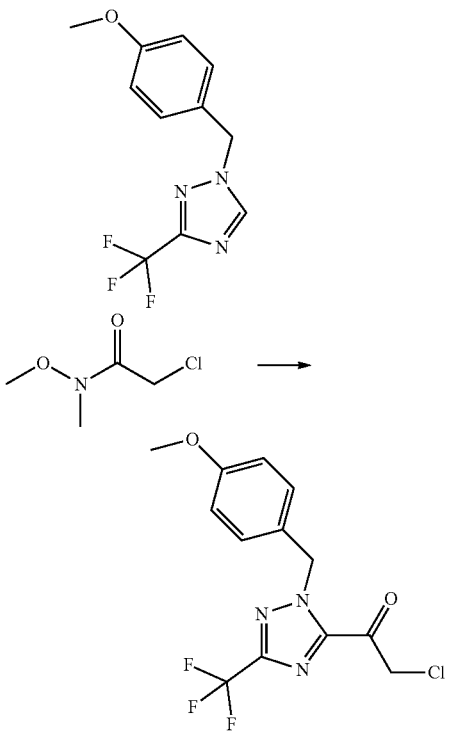

Step 2

The reaction below was done at half scale two times then combined after purification.

To a stirred solution of 1-(4-methoxybenzyl)-3-(trifluoromethyl)-1H-1,2,4-triazole (64.0 g, 249 mmol) in tetrahydrofuran (THF) (400 mL) under nitrogen at −10° C. (ice, NaCl) was added dropwise 2,2,6,6-tetramethylpiperidinyl magnesium chloride lithium chloride complex 1.0 N (400 mL, 400 mmol) over 30 minutes. The reaction was stirred for 30 min then treated with a solution of 2-chloro-N-methoxy-N-methylacetamide (58.0 g, 422 mmol) in tetrahydrofuran (THF) (140 mL). The reaction was stirred for 1 hr then carefully quenched with 1 N aq. HCl (500 mL). (pH ~4) The reaction was extracted with EtOAc (300 mL), washed with brine, dried (Na$_2$SO$_4$), filtered and concentrated under vacuum. Purified by silica gel chromatography (Isco RediSep Rf Gold 330 g, 25 to 60% CH$_2$Cl$_2$ in heptane; solid was loaded with 30 g Isolute HM-N). The pure fractions were combined and evaporated to dryness to give the product 2-chloro-1-(1-(4-methoxybenzyl)-3-(trifluoromethyl)-1H-1,2,4-triazol-5-yl)ethan-1-one (53.21 g, 159 mmol, 64.1% yield) as a white solid. $^1$H NMR (400 MHz, CDCl$_3$) δ 7.44 (d, J=8.9 Hz, 2H), 6.91 (d, J=8.6 Hz, 2H), 5.78 (s, 2H), 4.97 (s, 2H), 3.83 (s, 3H).

Intermediate 4

2-chloro-1-(3-(difluoromethyl)-1-(4-methoxybenzyl)-1H-1,2,4-triazol-5-yl)ethan-1-one

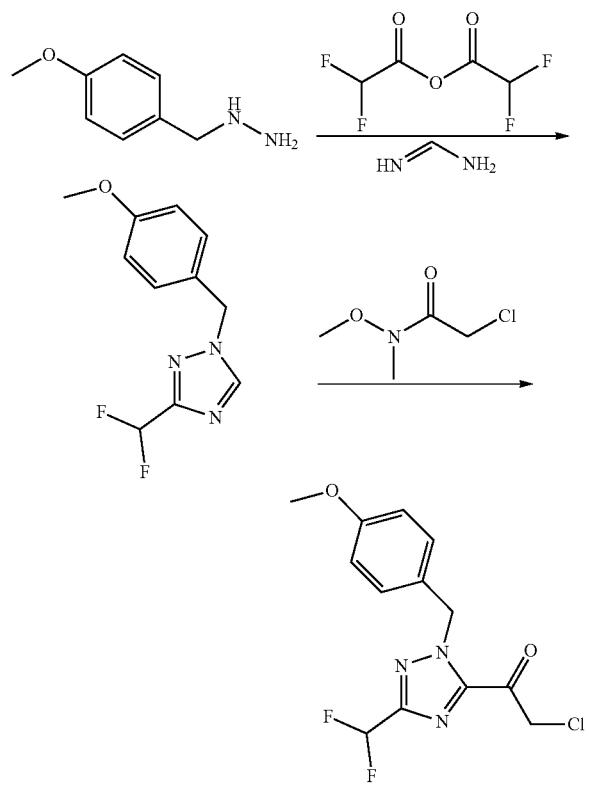

Step 1

To a mixture of (4-methoxybenzyl)hydrazine, hydrochloride (25 g, 133 mmol) and potassium carbonate (37.5 g, 271 mmol) in 2-methyltetrahydrofuran (2-MeTHF) (250 mL) was added 2,2-difluoroacetic anhydride (25 mL, 201 mmol) dropwise over 30 min. The reaction stirred for 30 min then was diluted with EtOAc (300 mL) and water (500 mL). The ethyl acetate phase was removed, washed with brine, dried (Na$_2$SO$_4$), filtered and evaporated in vacuo. The residue was taken up in ethanol (250 mL) and treated with formamidine acetate acetic acid salt (20 g, 192 mmol) at 100° C. for 24 hr with acetic acid (75 mL, 1310 mmol) added after 4 hr. The reaction was cooled to rt and was evaporated in vacuo. The residue was taken up in EtOAc, washed with aq. NaHCO$_3$, dried (Na$_2$SO$_4$), filtered and evaporated in vacuo. Purification by silica gel chromatography (Isco RediSep Rf Gold 220 g, 20 to 80% EtOAc in heptane) afforded 3-(difluoromethyl)-1-(4-methoxybenzyl)-1H-1,2,4-triazole (26 g, 75% yield) as a light yellow oil. $^1$H NMR (400 MHz, CHLOROFORM-d) δ 8.06 (s, 1H), 7.28-7.31 (m, 2H), 6.93-6.99 (m, 2H), 6.75 (t, J=53.7 Hz, 1H), 5.33 (s, 2H), 3.86 (s, 3H). LCMS m/z 240.2 [M+H]$^+$ Step 2

To a stirred solution of 3-(difluoromethyl)-1-(4-methoxybenzyl)-1H-1,2,4-triazole (25 g, 105 mmol) in tetrahydrofuran (200 mL) under nitrogen at −10° C. (ice, NaCl) was added dropwise 2,2,6,6-tetramethylpiperidinyl magnesium chloride lithium chloride complex 1.0 N in THF/toluene (180 mL, 180 mmol) over 30 min. The reaction mixture was stirred for 30 min then was treated with a solution of 2-chloro-N-methoxy-N-methylacetamide (25 g, 182 mmol) in tetrahydrofuran (50 mL). The reaction was stirred for 1 hr then carefully quenched with 1 N aq. HCl (450 mL) (pH ~4). The reaction was extracted with EtOAc (300 mL), washed (brine), dried (Na$_2$SO$_4$), filtered and concentrated in vacuo. The crude was purified by silica gel chromatography (Isco RediSep Rf Gold 330 g, 10 to 50% EtOAc in heptane). The desired fractions were combined and concentrated in vacuo to afford 2-chloro-1-(3-(difluoromethyl)-1-(4-methoxybenzyl)-1H-1,2,4-triazol-5-yl)ethan-1-one (19.6 g, 59.4% yield) as a white solid. $^1$H NMR (400 MHz, CHLOROFORM-d) δ 7.42 (d, J=8.87 Hz, 2H), 6.90 (d, J=8.87 Hz, 2H), 6.76 (t, J=53.3 Hz, 1H), 5.76 (s, 2H), 4.98 (s, 2H), 3.83 (s, 3H). LCMS m/z 316.0 [M+H]$^+$ (weak).

Intermediate 5

6-bromo-2-(1-(4-methoxybenzyl)-3-(trifluoromethyl)-1H-1,2,4-triazol-5-yl)imidazo[1,2-a]pyrimidine

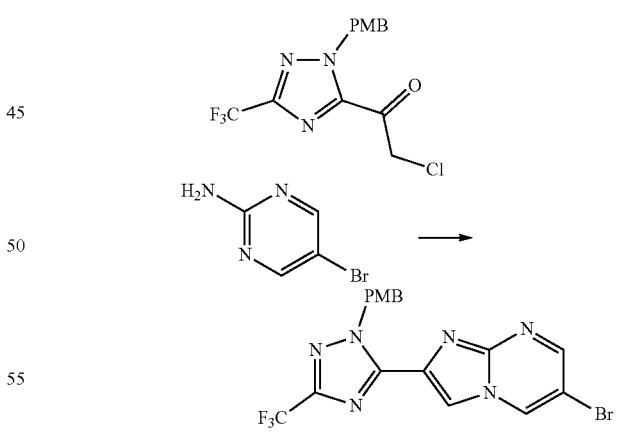

A mixture of 2-chloro-1-(1-(4-methoxybenzyl)-3-(trifluoromethyl)-1H-1,2,4-triazol-5-yl)ethan-1-one (4.0 g, 11.99 mmol, Intermediate 3), 5-bromopyrimidin-2-amine (4.2 g, 24.14 mmol) and isopropanol (60 mL) was refluxed for 3 days. The reaction was cooled to room temperature. The resulting suspension was basified with aq. sat. NaHCO$_3$, filtered, washed with water and dried under vacuum to give the crude product. The crude product was purified by silica gel chromatography (Isco RediSep Rf Gold 120 g, 0 to 20%

EtOAc in DCM). The desired fractions were combined and evaporated in vacuo. The remaining was triturated with hexanes, filtered and dried under vacuum to give 6-bromo-2-(1-(4-methoxybenzyl)-3-(trifluoromethyl)-1H-1,2,4-triazol-5-yl)imidazo[1,2-a]pyrimidine (1.85 g, 32.3% yield) as a light tan solid. $^1$H NMR (400 MHz, DMSO-d6) δ 9.40 (d, J=2.45 Hz, 1H), 8.78 (d, J=2.45 Hz, 1H), 8.55 (s, 1H), 7.36 (d, J=8.80 Hz, 2H), 6.86-6.93 (m, 2H), 6.11 (s, 2H), 3.71 (s, 3H). LCMS m/z 453.1, 455.1 [M+H]$^+$ Intermediate 6

2-(2-aminopyrimidin-4-yl)-2,2-difluoroethan-1-ol

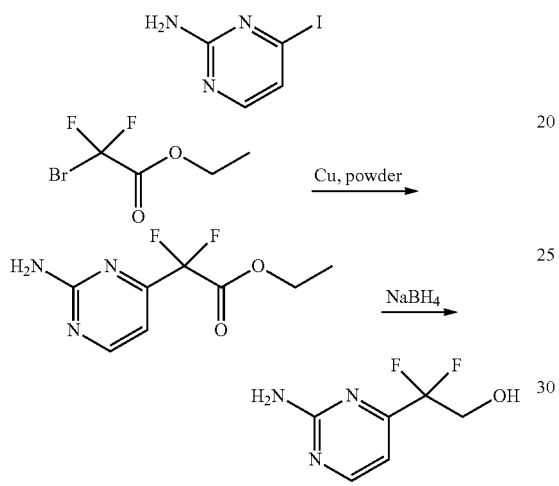

Step 1

A mixture of 4-iodopyrimidin-2-amine (5.0 g, 22.62 mmol), Copper powder (3.8 g, 59.8 mmol), DMSO (10 mL) and ethyl 2-bromo-2,2-difluoroacetate (4.4 mL, 34.3 mmol) was heated to 60° C. for 18 hr. The reaction was cooled to rt, diluted with EtOAc (200 mL), neutralized with aq. sat. NH$_4$Cl (200 mL) and stirred for 15 minutes. The mixture was filtered to remove insolubles and rinsed with EtOAc. The clear filtrate was transferred to a separatory funnel, and the aqueous phase was removed. The organic phase was washed with brine, dried (Na$_2$SO$_4$), filtered, and concentrated in vacuo. The resulting material was purified by silica gel chromatography (Isco RediSep Rf Gold 80 g, 0 to 100% EtOAc in CH$_2$Cl$_2$). The desired fractions were combined and concentrated in vacuo to afford ethyl 2-(2-aminopyrimidin-4-yl)-2,2-difluoroacetate (2.3 g, 44.5% yield) as an off-white solid. $^1$H NMR (400 MHz, DMSO-d$_6$) δ ppm 8.49 (d, J=4.89 Hz, 1H), 7.16 (s, 2H), 6.88 (d, J=4.89 Hz, 1H), 4.32 (q, J=6.85 Hz, 2H), 1.18-1.26 (m, 3H). LCMS m/z 218.2 [M+H]$^+$ Step 2

To a stirred solution of ethyl 2-(2-aminopyrimidin-4-yl)-2,2-difluoroacetate (2.0 g, 9.21 mmol) in ethanol (50 mL) at 0° C. was added portionwise sodium borohydride (400 mg, 10.57 mmol). The reaction was stirred at 0° C. for 30 min then allowed to warm to rt. The reaction was stirred for 1.5 hr then slowly quenched with 1N aq HCl (25 mL). The reaction was concentrated to near dryness in vacuo, basified with sat. NaHCO$_3$ and filtered to remove the insolubles. The product remained in the aqueous filtrate. The aqueous solution was evaporated to dryness in vacuo. The resulting solid was triturated with 20% MeOH in CHCl$_3$ (100 mL), filtered and rinsed with 20% MeOH in CHCl$_3$. The filtrate was evaporated to dryness in vacuo to give the crude product as a yellow solid. The crude was purified by silica gel chromatography (Isco RediSep Rf Gold 80 g, 0 to 20% MeOH in DCM). The desired fractions were combined and evaporated in vacuo to afford 2-(2-aminopyrimidin-4-yl)-2,2-difluoroethan-1-ol (1.1 g, 64.8% yield) as a white solid. $^1$H NMR (400 MHz, DMSO-d$_6$) δ ppm 8.40 (d, J=4.89 Hz, 1H), 6.98 (s, 2H), 6.78 (d, J=4.89 Hz, 1H), 5.58 (t, J=6.48 Hz, 1H), 3.89 (dt, J=6.48, 14.12 Hz, 2H). LCMS m/z 176.1 [M+H]$^+$ Intermediate 7

4-(difluoromethyl)pyrimidin-2-amine

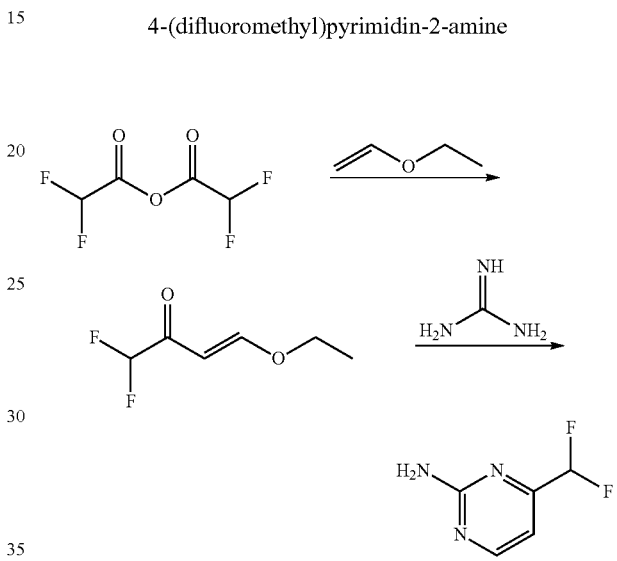

Step 1

To a stirred solution of ethyl vinyl ether (15.99 mL, 167 mmol) and pyridine (16.4 mL, 203 mmol) in DCM (160 mL) at −70° C. (CO$_2$, iPrOH) was add dropwise 2,2-difluoroacetic anhydride (25.8 mL, 208 mmol). The reaction warmed to rt and stirred overnight. The reaction was quenched with water. The organic was separated, dried (Na$_2$SO$_4$), filtered and concentrated in vacuo to afford (E)-4-ethoxy-1,1-difluorobut-3-en-2-one (25.4 g, 87% yield) as an orange oil. $^1$H NMR (400 MHz, CHLOROFORM-d) δ 7.84 (d, J=12.23 Hz, 1H), 5.85-5.91 (m, 1H), 5.62 (t, J=54 Hz, 1H), 4.07 (q, J=7.17 Hz, 2H), 1.39 (t, J=7.09 Hz, 3H). LCMS m/z 151.1 [M+H]$^+$ Step 2

A mixture of guanidine hydrochloride (19.6 g, 205 mmol) and ethanol (80 mL) was stirred for 1 hr then treated with sodium hydroxide (8.0 g, 200 mmol) and stirred overnight. To this stirred suspension was added dropwise a solution of the above intermediate, (E)-4-ethoxy-1,1-difluorobut-3-en-2-one (25.4 g, 146 mmol,) in DCM (80 mL) over 1 hr. The combined stirred 2 hr then was evaporated in vacuo. The residue was taken up in water (100 mL) and stirred vigorously. The resulting solids were filtered, washed with water and heptane then dried under vacuum to afford 4-(difluoromethyl)pyrimidin-2-amine (14.02 g, 55.0% yield) as a white solid. $^1$H NMR (400 MHz, DMSO-d$_6$) δ 8.43 (d, J=4.89 Hz, 1H), 7.01 (br. s., 2H), 6.76 (d, J=4.89 Hz, 1H), 6.67 (t, J=54.8 Hz, 1H). LCMS m/z 146.0 [M+H]$^+$

Intermediate 8 tert-butyl 2-amino-8,8-difluoro-7,8-dihydropyrido[4,3-d]pyrimidine-6(5H)-carboxylate

Example 1

5-[3-(1H-imidazol-4-yl)imidazo[1,2-a]pyrimidin-2-yl]-3-(trifluoromethyl)-1H-1,2,4-triazole

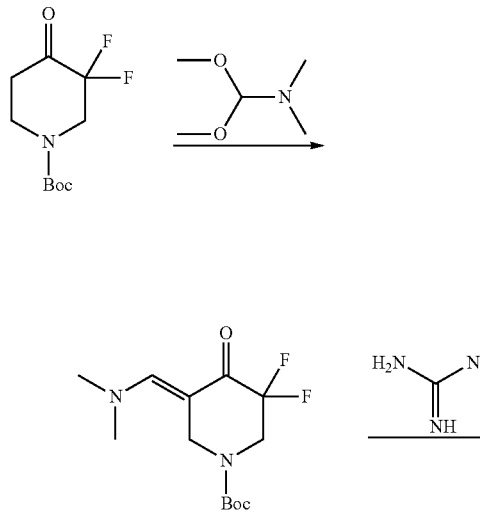

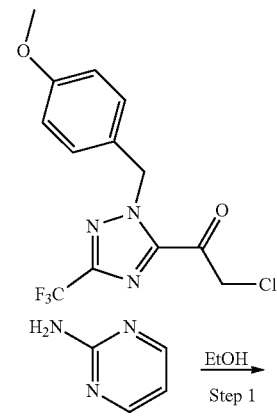

Step 1 tert-Butyl 3,3-difluoro-4-oxopiperidine-1-carboxylate (855 mg, 3.63 mmol) was mixed with 1,1-dimethoxy-N,N-dimethylmethanamine (10 mL, 74.7 mmol) and the mixture was heated to 100 C for 16 hr. The reaction was cooled to rt and was neutralized slowly with sat. aq. sodium bicarbonate. The mixture was extracted with EtOAc (6×) and the combined organics were washed (brine), dried (MgSO$_4$), filtered and concentrated in vacuo to afford crude tert-butyl (E)-5-((dimethylamino)methylene)-3,3-difluoro-4-oxopiperidine-1-carboxylate (1055 mg, 100% yield). LCMS m/z 291.2 [M+H]$^+$

Step 2 tert-Butyl (E)-5-((dimethylamino)methylene)-3,3-difluoro-4-oxopiperidine-1-carboxylate (1050 mg, 3.62 mmol), guanidine hydrochloride (930 mg, 9.74 mmol), and K$_2$CO$_3$ (1353 mg, 9.79 mmol) were suspended in N-methyl-2-pyrrolidone (NMP) (15 mL) and heated to 75 C for 3 hr. The solution was cooled to rt then slowly neutralized with sat. aq. sodium bicarbonate. The mixture was extracted with EtOAc (4×) and the combined organics were washed (brine), dried (MgSO$_4$), filtered and concentrated in vacuo. The crude material was purified by silica gel chromatography (Isco RediSep Rf Gold 80 g, 0-100% EtOAc in Heptane). The desired fractions were concentrated in vacuo to afford, tert-butyl 2-amino-8,8-difluoro-7,8-dihydropyrido[4,3-d]pyrimidine-6(5H)-carboxylate (695 mg, 67.1% yield) LCMS m/z 287.2 [M+H]$^+$ -continued

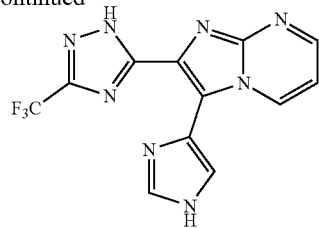

Step 1

2-Chloro-1-(1-(4-methoxybenzyl)-3-(trifluoromethyl)-1H-1,2,4-triazol-5-yl)ethan-1-one (Intermediate 3) (6.20 g, 18.6 mmol) and pyrimidin-2-amine (3.71 g, 39.0 mmol) in EtOH (80 mL) were heated at 90° C. overnight. The reaction was allowed to cool to rt, and the resulting precipitate was collected by filtration and washed with EtOH to yield 2-(1-(4-methoxybenzyl)-3-(trifluoromethyl)-1H-1,2,4-triazol-5-yl)imidazo[1,2-a]pyrimidine hydrochloride (3.85 g, 9.37 mmol, 50% yield) as a white solid. LCMS m/z 375.2 [M+H]$^+$ Step 2

To 2-(1-(4-methoxybenzyl)-3-(trifluoromethyl)-1H-1,2,4-triazol-5-yl)imidazo[1,2-a]pyrimidine hydrochloride (6.07 g, 14.8 mmol) in chloroform (200 mL) was added N-bromosuccinimide (3.68 g, 20.7 mmol), and the mixture was heated to 60° C. for 2 h. The reaction was washed with 1:1 sat'd Na$_2$S$_2$O$_3$ (aq)/sat'd NaHCO$_3$ (aq) and brine, dried over MgSO$_4$, and concentrated. The residue was triturated with 10% DCM in hexanes, and the resulting solid was washed with hexanes to yield 3-bromo-2-(1-(4-methoxybenzyl)-3-(trifluoromethyl)-1H-1,2,4-triazol-5-yl)imidazo[1,2-a]pyrimidine (6.22 g, 13.7 mmol, 93% yield) as a white solid. $^1$H NMR (400 MHz, CDCl$_3$) δ ppm 8.76 (dd, J=4.1, 2.0 Hz, 1H), 8.61 (dd, J=6.8, 2.0 Hz, 1H), 7.48 (d, J=8.8 Hz, 2H), 7.18 (dd, J=7.0, 4.2 Hz, 1H), 6.86 (d, J=8.9 Hz, 2H), 6.17 (s, 2H), 3.79 (s, 3H). LCMS m/z 455.3 [M+H]$^+$ Step 3

A mixture of 3-bromo-2-(1-(4-methoxybenzyl)-3-(trifluoromethyl)-1H-1,2,4-triazol-5-yl)imidazo[1,2-a]pyrimidine (4.51 g, 9.95 mmol), N,N-dimethyl-4-(4,4,5,5-tetramethyl-1,3,2-dioxaborolan-2-yl)-1H-imidazole-1-sulfonamide (Intermediate 2) (5.99 g, 19.9 mmol), PdCl$_2$(dppf)-CH$_2$Cl$_2$-adduct (1.63 g, 1.99 mmol) and potassium phosphate (3.17 g, 14.9 mmol) in dioxane (20 mL) and water (4 mL) was purged with nitrogen and heated at 100° C. for 10 h. The reaction was concentrated, and the residue was partitioned between sat'd aq NaHCO$_3$ and DCM. The organic layer was isolated, washed with brine, dried over MgSO$_4$ and concentrated. The residue was purified by silica gel chromatography (ISCO 330 g RediSep Rf column, eluting with 20-100% [3:1 EtOAc:EtOH] in hexane) to yield 4-(2-(1-(4-methoxybenzyl)-3-(trifluoromethyl)-1H-1,2,4-triazol-5-yl)imidazo[1,2-a]pyrimidin-3-yl)-N,N-dimethyl-1H-imidazole-1-sulfonamide (4.02 g, 74%). $^1$H NMR (400 MHz, CDCl$_3$) δ ppm 9.82 (dd, J=7.1, 2.0 Hz, 1H), 8.76 (dd, J=4.1, 2.0 Hz, 1H), 8.71 (d, J=1.5 Hz, 1H), 8.08 (d, J=1.3 Hz, 1H), 7.49 (d, J=8.9 Hz, 2H), 7.09 (dd, J=7.1, 4.1 Hz, 1H), 6.85 (d, J=8.9 Hz, 2H), 6.23 (s, 2H), 3.79 (s, 3H), 3.01 (s, 6H). LCMS m/z 548.3 [M+H]$^+$ Step 4

4-(2-(1-(4-Methoxybenzyl)-3-(trifluoromethyl)-1H-1,2,4-triazol-5-yl)imidazo[1,2-a]pyrimidin-3-yl)-N,N-dimethyl-1H-imidazole-1-sulfonamide (4.02 g, 7.34 mmol) in TFA (40 mL) was heated to 90° C. for 2 h and concentrated. The residue was taken up in water (5 mL), adjusted to pH=7 with the addition of sat'd aq NaHCO$_3$, and stirred in a mixture of EtOAc (200 mL) and sat'd aq NaHCO$_3$ for 1 h. The resulting precipitate was collected by filtration and suspended in EtOH at 100° C. for 1 h. The solid was collected by filtration and suspended again in EtOH at 100° C. for 1 h and collected by filtration to yield 3-(1H-imidazol-4-yl)-2-(3-(trifluoromethyl)-1H-1,2,4-triazol-5-yl)imidazo[1,2-a]pyrimidine (1.42 g, 4.43 mmol, 60%). $^1$H NMR (400 MHz, DMSO-d$_6$) δ ppm 15.78 (br s, 1H), 9.87 (d, J=5.6 Hz, 1H), 8.75 (dd, J=1.9, 3.9 Hz, 1H), 8.49 (s, 1H), 8.33 (br s, 1H), 7.27 (dd, J=4.1, 6.8 Hz, 1H). LCMS m/z 321.2 [M+H]$^+$ Example 2

5-[6-fluoro-3-(1H-imidazol-5-yl)imidazo[1,2-a]pyrimidin-2-yl]-3-(trifluoromethyl)-1H-1,2,4-triazole

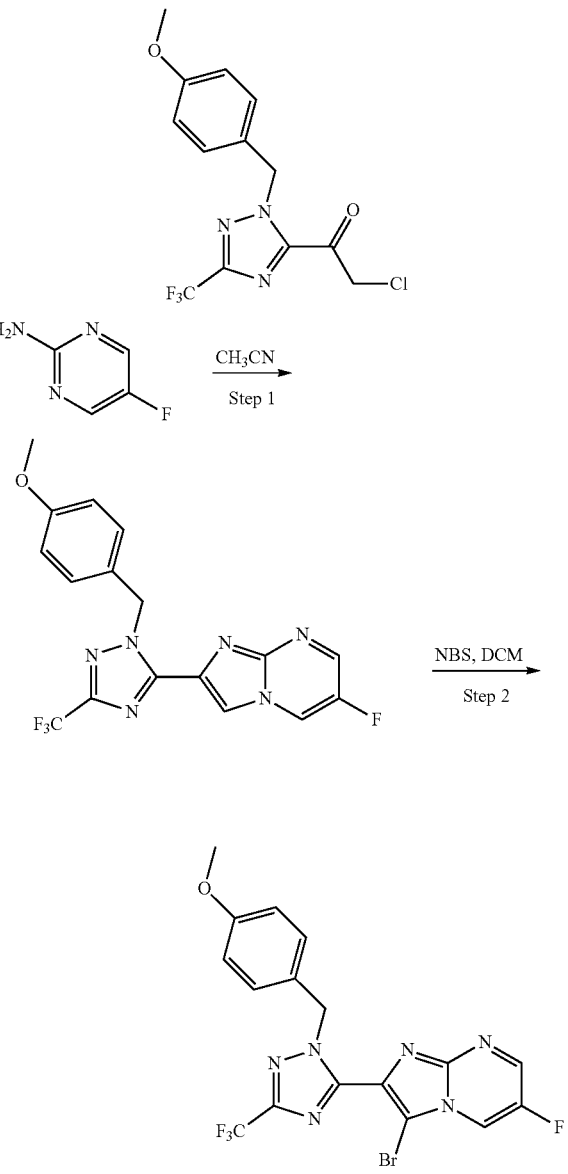

-continued

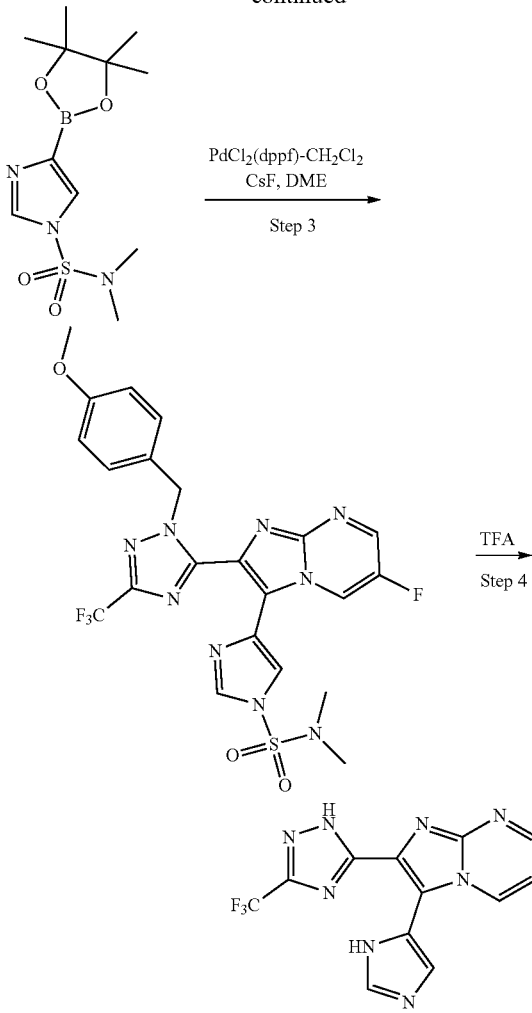

Step 1

In each of nine separate vessels, a mixture of 2-chloro-1-(1-(4-methoxybenzyl)-3-(trifluoromethyl)-1H-1,2,4-triazol-5-yl)ethan-1-one (1.00 g, 3.00 mmol) (Intermediate 3) and 5-fluoropyrimidin-2-amine (508 mg, 4.50 mmol) in MeCN (10 mL) was heated in a microwave reactor at 170° C. for 4 h. The nine reaction mixtures were combined and filtered. The filtrate was evaporated and purified by silica gel chromatography (330 g Isco RediSep Rf Gold column, 10-80% [3:1:0.01 EtOAc/EtOH/Et$_3$N] in hexanes). The fractions were combined and concentrated in vacuo to afford 6-fluoro-2-(1-(4-methoxybenzyl)-3-(trifluoromethyl)-1H-1,2,4-triazol-5-yl)imidazo[1,2-a]pyrimidine (7.07 g, 18.0 mmol, 67% yield) as a yellow solid. $^1$H NMR (400 MHz, CHLOROFORM-d) δ ppm 8.72 (d, J=2.9 Hz, 1H), 8.55-8.43 (m, 1H), 8.33 (s, 1H), 7.52 (d, J=8.8 Hz, 2H), 6.86 (d, J=8.8 Hz, 2H), 6.20 (s, 2H), 3.80 (s, 3H). LCMS m/z 393.1 [M+H]$^+$ Step 2

To a mixture of 6-fluoro-2-(1-(4-methoxybenzyl)-3-(trifluoromethyl)-1H-1,2,4-triazol-5-yl)imidazo[1,2-a]pyrimidine (7.07 g, 18.02 mmol) in DCM (400 mL) was added NBS (4.17 g, 23.4 mmol), and the reaction mixture was stirred at rt for 3 h. The reaction mixture was partitioned between 1:1 sat. aq Na$_2$S$_2$O$_3$/sat. aq NaHCO$_3$ and DCM. The organic layer was washed with brine, dried over MgSO$_4$, and concentrated in vacuo. The resulting residue was purified by silica gel chromatography (330 g Isco RediSep Rf Gold column, 10 to 50% [3:1:0.01 EtOAc/EtOH/Et$_3$N] in hexanes) to afford 3-bromo-6-fluoro-2-(1-(4-methoxybenzyl)-3-(trifluoromethyl)-1H-1,2,4-triazol-5-yl)imidazo[1,2-a]pyrimidine (5.76 g, 12.2 mmol, 68% yield) as a yellow solid. $^1$H NMR (400 MHz, CHLOROFORM-d) δ ppm 8.74 (d, J=2.7 Hz, 1H), 8.53 (t, J=3.1 Hz, 1H), 7.46 (d, J=8.8 Hz, 2H), 6.86 (d, J=8.8 Hz, 2H), 6.14 (s, 2H), 3.80 (s, 3H). LCMS m/z 473.0 [M+H]$^+$ Step 3

A mixture of 3-bromo-6-fluoro-2-(1-(4-methoxybenzyl)-3-(trifluoromethyl)-1H-1,2,4-triazol-5-yl)imidazo[1,2-a]pyrimidine (5.76 g, 12.2 mmol), N,N-dimethyl-4-(4,4,5,5-tetramethyl-1,3,2-dioxaborolan-2-yl)-1H-imidazole-1-sulfonamide (5.52 g, 18.34 mmol) (Intermediate 2), CsF (4.09 g, 26.9 mmol) and PdCl$_2$(dppf)-CH$_2$Cl$_2$ adduct (0.998 g, 1.222 mmol) in DME (5 mL) under N$_2$ was heated and stirred at 100° C. for 16 h. The reaction mixture was filtered and the filtrate was concentrated in vacuo. The resulting residue was purified by silica gel chromatography (220 g Isco RediSep Rf Gold column, 20-80% 3:1 EtOAc:EtOH in hexanes with 2% NH$_4$OH) to afford 4-(6-fluoro-2-(1-(4-methoxybenzyl)-3-(trifluoromethyl)-1H-1,2,4-triazol-5-yl)imidazo[1,2-a]pyrimidin-3-yl)-N,N-dimethyl-1H-imidazole-1-sulfonamide (4.88 g, 8.63 mmol, 70% yield). $^1$H NMR (400 MHz, CHLOROFORM-d) δ ppm 9.95 (dd, J=4.4, 2.9 Hz, 1H), 8.86-8.66 (m, 2H), 8.09 (d, J=1.2 Hz, 1H), 7.47 (d, J=8.6 Hz, 2H), 6.85 (d, J=8.8 Hz, 2H), 6.21 (s, 2H), 3.79 (s, 3H), 3.02 (s, 6H). LCMS m/z 566.1 [M+H]$^+$ Step 4

4-(6-Fluoro-2-(1-(4-methoxybenzyl)-3-(trifluoromethyl)-1H-1,2,4-triazol-5-yl)imidazo[1,2-a]pyrimidin-3-yl)-N,N-dimethyl-1H-imidazole-1-sulfonamide (565 mg, 0.999 mmol) in TFA (10 mL) was heated and stirred at 90° C. for 4 h. The reaction mixture was concentrated, and the residue was purified by preparative HPLC (MDAP Method A) to give 5-[6-fluoro-3-(1H-imidazol-5-yl)imidazo[1,2-a]pyrimidin-2-yl]-3-(trifluoromethyl)-1H-1,2,4-triazole as a yellow solid (233 mg, 0.69 mmol, 69%). $^1$H NMR (400 MHz, DMSO-d$_6$) δ ppm 15.75 (br s, 1H), 12.73 (br s, 1H), 10.30 (dd, J=5.0, 3.1 Hz, 1H), 8.93 (d, J=2.9 Hz, 1H), 8.64 (s, 1H), 8.06 (d, J=1.2 Hz, 1H). LCMS: t$_{RET}$=0.41 min (gradient of 1-100% of 0.1% v/v solution of TFA in acetonitrile to 0.1% v/v solution of TFA in water over 1.85 min), m/z 339.2 [M+H]$^+$ Example 3

5-[3-(1H-imidazol-5-yl)-7-(trifluoromethyl)imidazo[1,2-a]pyrimidin-2-yl]-3-(trifluoromethyl)-1H-1,2,4-triazole

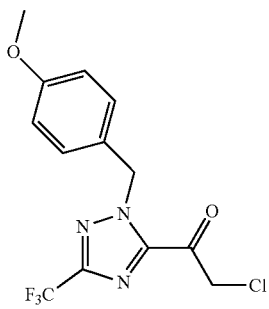

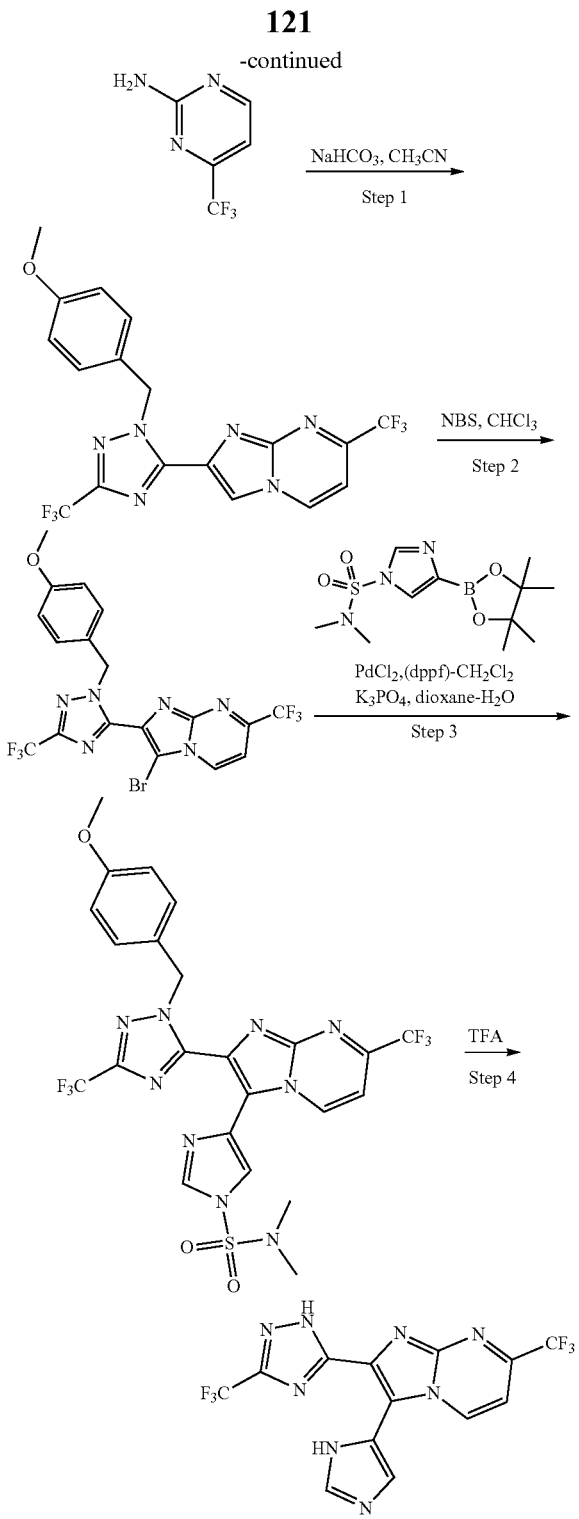

Step 1

2-Chloro-1-(1-(4-methoxybenzyl)-3-(trifluoromethyl)-1H-1,2,4-triazol-5-yl)ethan-1-one (Intermediate 3) (2.46 g, 7.36 mmol), 4-(trifluoromethyl)pyrimidin-2-amine (1.00 g, 6.13 mmol) and sodium bicarbonate (0.515 g, 6.13 mmol) in CH₃CN (20 mL) were heated in a capped vessel at 115° C. overnight. Another portion of 2-chloro-1-(1-(4-methoxybenzyl)-3-(trifluoromethyl)-1H-1,2,4-triazol-5-yl)ethan-1-one (500 mg) was added, heating was continued another night, then more 2-chloro-1-(1-(4-methoxybenzyl)-3-(trifluorom- ethyl)-1H-1,2,4-triazol-5-yl)ethan-1-one (500 mg) was added. The temperature was increased to 120° C., and the reaction was stirred over another night and cooled. The resulting precipitate was removed by filtration and washed with aq. citric acid and MeOH. The filtrate was concentrated until only aqueous remained, which was extracted with EtOAc. The organic layer was dried over Na₂SO₄, concentrated and purified by silica gel chromatography (120 g Isco RediSep Rf Gold column, eluting with 0-50% EtOAc in hexanes) to give crude product. This material was sonicated with MeOH and filtered. The filtrate was treated with water until a solid precipitated. The solid was collected by filtration and washed with hexane followed by 10% Et₂O in hexane to yield 2-(1-(4-methoxybenzyl)-3-(trifluoromethyl)-1H-1,2,4-triazol-5-yl)-7-(trifluoromethyl)imidazo[1,2-a]pyrimidine (980 mg, 1.88 mmol, 31%) as a tan solid. $^1$H NMR (400 MHz, DMSO-d₆) δ ppm 9.36 (d, J=6.8 Hz, 1H), 8.90 (s, 1H), 7.71 (d, J=6.8 Hz, 1H), 7.36-7.40 (m, 2H), 6.90-6.94 (m, 2H), 6.15 (s, 2H), 3.72 (s, 3H). LCMS m/z 443.2 [M+H]⁺

Step 2

To 2-(1-(4-methoxybenzyl)-3-(trifluoromethyl)-1H-1,2,4-triazol-5-yl)-7-(trifluoromethyl)imidazo[1,2-a]pyrimidine (500 mg, 1.13 mmol) in chloroform (15 mL) was added N-bromosuccinimide (225 mg, 1.27 mmol), and the mixture was stirred at rt for 90 min., 55° C. for 1 h, then 45° C. overnight. The reaction was concentrated, taken up in DCM, washed with sat'd aq NaHCO₃, dried over Na₂SO₄, and concentrated. The resulting residue was triturated with 1:4 Et₂O:hexanes to yield 3-bromo-2-(1-(4-methoxybenzyl)-3-(trifluoromethyl)-1H-1,2,4-triazol-5-yl)-7-(trifluoromethyl)imidazo[1,2-a]pyrimidine (385 mg, 0.687 mmol, 61%) as an off-white solid. $^1$H NMR (400 MHz, DMSO-d₆) δ ppm 9.29 (d, J=7.1 Hz, 1H), 7.77 (d, J=7.1 Hz, 1H), 7.35-7.40 (m, 2H), 6.90-6.95 (m, 2H), 6.05 (s, 2H,) 3.73 (s, 3H). LCMS m/z 523.2 [M+H]⁺

Step 3

A mixture of 3-bromo-2-(1-(4-methoxybenzyl)-3-(trifluoromethyl)-1H-1,2,4-triazol-5-yl)-7-(trifluoromethyl)imidazo[1,2-a]pyrimidine (380 mg, 0.729 mmol) and N,N-dimethyl-4-(4,4,5,5-tetramethyl-1,3,2-dioxaborolan-2-yl)-1H-imidazole-1-sulfonamide (Intermediate 2) (439 mg, 1.46 mmol) in dioxane (8 mL) was stirred for several minutes. Water (400 μL), PdCl₂(dppf)-CH₂Cl₂-adduct (107 mg, 0.131 mmol) and potassium phosphate (232 g, 1.09 mmol) were added, and the mixture was purged with nitrogen. The reaction was capped, heated to 100° C. for 3 h and partitioned between EtOAc and water. The organic layer was isolated, concentrated and purified by silica gel chromatography (120 g Isco RediSep Rf Gold column, eluting with 5-55% EtOAc in hexanes) to yield 4-(2-(1-(4-methoxybenzyl)-3-(trifluoromethyl)-1H-1,2,4-triazol-5-yl)-7-(trifluoromethyl)imidazo[1,2-a]pyrimidin-3-yl)-N,N-dimethyl-1H-imidazole-1-sulfonamide (350 mg, 0.512 mmol, 70%) as a yellow solid. $^1$H NMR (400 MHz, DMSO-d₆) δ ppm 9.98 (d, J=7.3 Hz, 1H), 8.55 (dd, J=20.0, 1.4 Hz, 2H), 7.77 (d, J=7.3 Hz, 1H), 7.42 (d, J=8.8 Hz, 2H), 6.90-6.98 (m, 2H), 5.96 (s, 2H), 3.73 (s, 3H), 2.88 (s, 6H). LCMS m/z 616.3 [M+H]⁺

Step 4

4-(2-(1-(4-Methoxybenzyl)-3-(trifluoromethyl)-1H-1,2,4-triazol-5-yl)-7-(trifluoromethyl)imidazo[1,2-a]pyrimidin-3-yl)-N,N-dimethyl-1H-imidazole-1-sulfonamide (350 mg, 0.569 mmol) in TFA (12 mL) was stirred at 68° C. overnight. The reaction was concentrated, azeotroped with MeOH and purified by preparative HPLC (MDAP Method B). Fractions containing desired product were treated with sodium citrate buffer and concentrated until only aqueous remained. The resulting solid was collected by filtration and washed with water and hexane to yield 3-(1H-imidazol-4-yl)-7-(trifluoromethyl)-2-(3-(trifluoromethyl)-1H-1,2,4-triazol-5-yl)imidazo[1,2-a]pyrimidine (100 mg, 0.245 mmol, 43%) as a yellow solid. $^1$H NMR (400 MHz, DMSO-d$_6$) δ ppm 15.88 (br s, 1H), 12.81 (br s, 1H), 10.48 (d, J=7.4 Hz, 1H), 8.68 (s, 1H), 8.08 (d, J=1.0 Hz, 1H), 7.69 (d, J=7.4 Hz, 1H). LCMS m/z 389.1 [M+H]$^+$ Examples 4-12 were synthesized in an analogous manner to Example 2.

| Ex. | Name | Structure | $^1$H NMR | MS (M + H)$^+$ |
|---|---|---|---|---|
| 4 | 5-[6-chloro-3-(1H-imidazol-4-yl)imidazo[1,2-a]pyrimidin-2-yl]-3-(difluoromethyl)-1H-1,2,4-triazole | 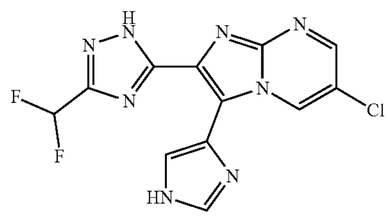 [SMILES: FC(F)c1n[nH]c(-c2nc3ncc(Cl)cn3c2-c2c[nH]cn2)n1] | (DMSO-d$_6$) δ ppm 15.34 (br s, 1 H), 12.82 (br s, 1 H), 10.35 (br s, 1 H), 8.75 (d, J = 2.5 Hz, 2 H), 8.12 (s, 1 H), 7.21 (t, J = 53.2 Hz, 1 H) | 337.1 |
| 5 | 3-(difluoromethyl)-5-[6-fluoro-3-(1H-imidazol-4-yl)imidazo[1,2-a]pyrimidin-2-yl]-1H-1,2,4-triazole | 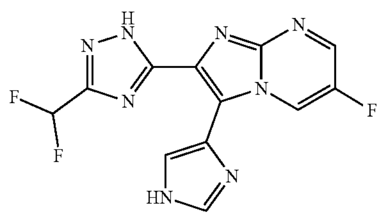 [SMILES: Fc1cnc2nc(-c3nc(C(F)F)n[nH]3)c(-c3c[nH]cn3)n2c1] | (DMSO-d$_6$) δ ppm 15.36 (br s, 1 H), 10.02 (br s, 1 H), 8.94 (d, J = 2.5 Hz, 1 H), 8.59 (s, 1 H), 8.42 (br s, 1 H), 7.17 (t, J = 53 Hz, 1 H), 1H not observed | 321.0 |
| 6 | 2,2-difluoro-2-[3-(1H-imidazol-5-yl)-2-[3-(trifluoromethyl)-1H-1,2,4-triazol-5-yl]imidazo[1,2-a]pyrimidin-7-yl]ethan-1-ol | 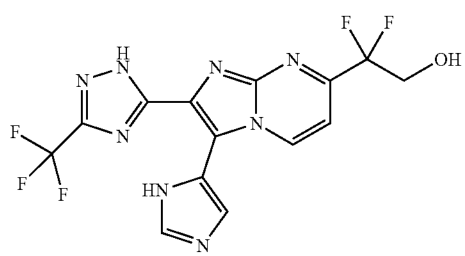 [SMILES: OCC(F)(F)c1ccn2c(-c3cnc[nH]3)c(-c3nc(C(F)(F)F)n[nH]3)nc2n1] | (DMSO-d$_6$) δ ppm 15.79 (br s, 1H), 12.75 (br s, 1H), 10.31 (d, J = 5.4 Hz, 1H), 8.62 (br s, 1H), 8.06 (s, 1H), 7.51 (d, J = 7.3 Hz, 1H), 4.28-3.94 (m, 2H) | 401.2 |
| 7 | 5-[7-chloro-3-(1H-imidazol-5-yl)imidazo[1,2-a]pyrimidin-2-yl]-3-(trifluoromethyl)-1H-1,2,4-triazole, trifluoroacetic acid salt | 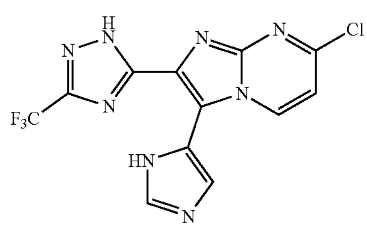 | (DMSO-d$_6$) δ ppm 15.77 (br s, 1H) 13.3-12.9 (m, 1H) 9.99 (br s, 1H) 8.55 (s, 1H) 8.26 (br s, 1H) 7.39 (d, J = 7.3 Hz, 1 H) | 355.1, 357.1 |
| 8 | 3-(difluoromethyl)-5-[7-(difluoromethyl)-3-(1H-imidazol-5-yl)imidazo[1,2-a]pyrimidin-2-yl]-1H-1,2,4-triazole | 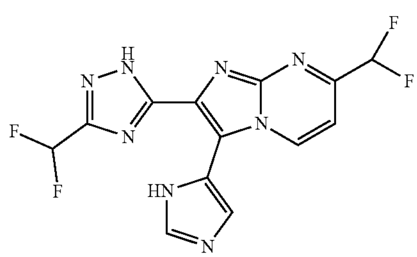 [SMILES: FC(F)c1ccn2c(-c3cnc[nH]3)c(-c3nc(C(F)F)n[nH]3)nc2n1] | (DMSO-d$_6$) δ 15.37 (br s, 1H), 12.77 (br s, 1H), 10.36 (d, J = 7.3 Hz, 1H), 8.73 (s, 1H), 8.07 (s, 1H), 7.50 (d, J = 7.3 Hz, 1H), 7.22 (t, J = 53 Hz, 1H), 7.07 (t, J = 54 Hz, 1H) | 353.1 |
| 9 | [3-(1H-imidazol-5-yl)-2-[3-(trifluoromethyl)-1H-1,2,4-triazol-5-yl]imidazo[1,2-a]pyrimidin-7-yl]methanol, 0.3 trifluoroacetic acid salt | 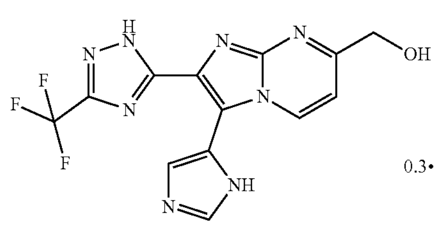 [SMILES: OCc1ccn2c(-c3cnc[nH]3)c(-c3nc(C(F)(F)F)n[nH]3)nc2n1] | (DMSO-d$_6$) δ ppm 15.69 (br s, 1H), 12.82 (br s, 1H), 9.99 (br s, 1H), 8.54-8.47 (m, 1H), 8.12 (br s, 1H), 7.36 (d, J = 7.1 Hz, 1H), 6.55 (br s, 0.3H), 5.75 (br s, 1H), 4.65 (s, 2H) | 351.0 |

-continued

| Ex. | Name | Structure | $^1$H NMR | MS (M + H)$^+$ |
|---|---|---|---|---|
| 10 | 12-(1H-imidazol-4-yl)-11-[3-(trifluoromethyl)-1H-1,2,4-triazol-5-yl]-5-oxa-1,8,10-triazatricyclo[7.3.0.0$^3$,$^7$]dodeca-2,7,9,11-tetraene, 0.2 trifluoroacetic acid salt | 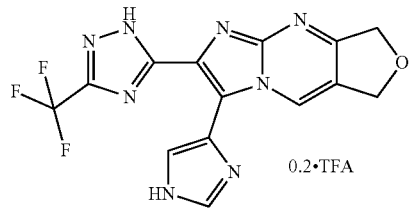 [SMILES: FC(F)(F)c1n[nH]c(-c2nc3nc4c(cn3c2-c2c[nH]cn2)COC4)n1] | (DMSO-d$_6$) δ ppm 15.63 (br s, 1 H), 12.71 (br s, 1 H), 10.04 (s, 1 H), 8.50 (s, 1 H), 8.03-8.01 (m, 1 H), 6.55-6.53 (m, 0.3 H), 5.17 (s, 2 H), 4.99 (s, 2 H) | 363.1 |
| 11 | 5-[3-(1H-pyrazol-4-yl)imidazo[1,2-a]pyrimidin-2-yl]-3-(trifluoromethyl)-1H-1,2,4-triazole, trifluoroacetic acid salt | 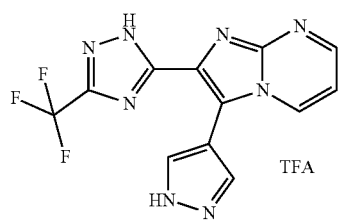 [SMILES: FC(F)(F)c1n[nH]c(-c2nc3ncccn3c2-c2cn[nH]c2)n1] | (DMSO-d$_6$) δ ppm 15.61 (br s, 1H), 8.90 (dd, J = 7.0, 1.9 Hz, 1H), 8.72 (dd, J = 4.1, 1.8 Hz, 1H), 8.26 (br s, 2H), 7.19 (dd, J = 6.8, 4.1 Hz, 1H), 2H not observed | 321.0 |
| 12 | 5-[3-(1H-imidazol-5-yl)-7-(2,2,2-trifluoroethoxy)imidazo[1,2-a]pyrimidin-2-yl]-3-(trifluoromethyl)-1H-1,2,4-triazole | 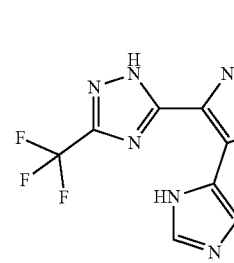 | $^1$H NMR (400 MHZ, DMSO-d6) δ ppm 15.54 (br s, 1H), 12.66 (br s, 1H), 10.04 (d, J = 7.3 Hz, 1H), 8.56 (s,1H), 8.00 (d, J = 1.0 Hz, 1H), 6.96 (d, J = 7.8 Hz, 1H), 5.14 (q, J = 8.8 Hz, 2H) | 419.2 |

The following example was prepared in an analogous manner to Example 2, except additional Steps 3a and 3b were performed after Step 3.

Example 13

1-[3-(1H-imidazol-5-yl)-2-[3-(trifluoromethyl)-1H-1,2,4-triazol-5-yl]imidazo[1,2-a]pyrimidin-7-yl]ethan-1-ol

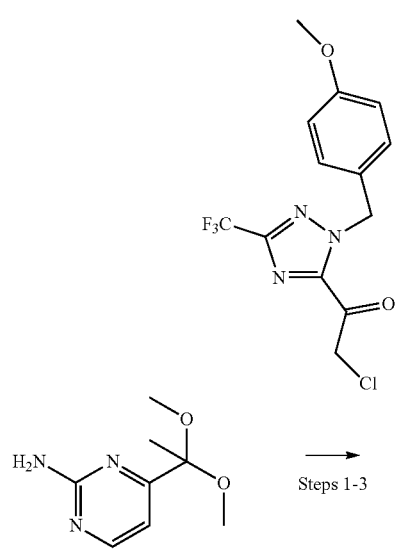

-continued

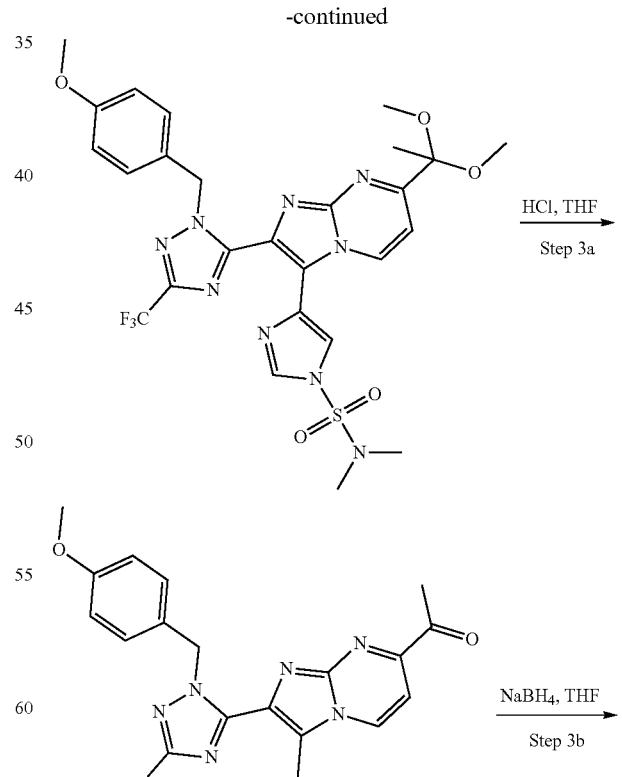

-continued

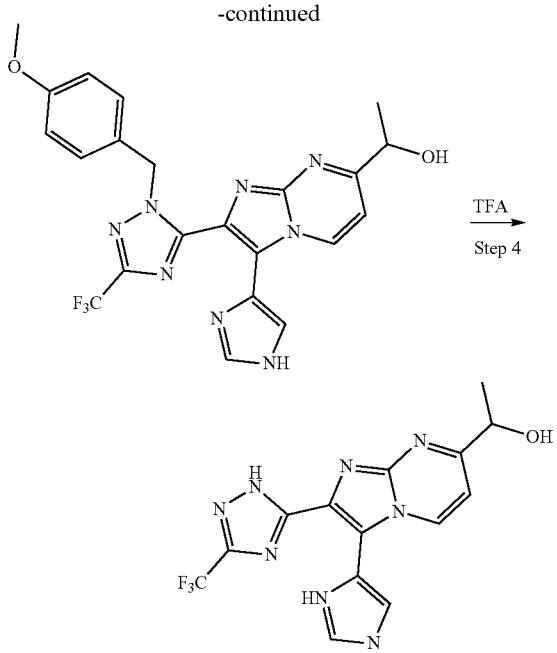

Step 3a 4-(7-(1,1-Dimethoxyethyl)-2-(1-(4-methoxybenzyl)-3-(trifluoromethyl)-1H-1,2,4-triazol-5-yl)imidazo[1,2-a]pyrimidin-3-yl)-N,N-dimethyl-1H-imidazole-1-sulfonamide (70.4 mg, 0.11 mmol) was dissolved in THF (4 mL). HCl (2 mL, 8.00 mmol, 4 N in dioxane) was added and the reaction was stirred at rt for 3 h. As no reaction was observed thus far, six drops of 6 N aq HCl was added and the reaction was stirred at rt for 20 h and then at 60° C. for 4 h. The reaction was cooled and concentrated in vacuo. The resultant residue was partitioned between sat. aq NaHCO₃ and EtOAc. The organic layer was washed with brine, dried (MgSO₄), filtered and concentrated to provide 1-(3-(1H-imidazol-4-yl)-2-(1-(4-methoxybenzyl)-3-(trifluoromethyl)-1H-1,2,4-triazol-5-yl)imidazo[1,2-a]pyrimidin-7-yl)ethan-1-one (39.8 mg, 0.082 mmol, 74% yield) as a crude yellow residue, which was used in the next step without purification. LCMS m/z 483.2 [M+H]⁺

Step 3b 1-(3-(1H-Imidazol-4-yl)-2-(1-(4-methoxybenzyl)-3-(trifluoromethyl)-1H-1,2,4-triazol-5-yl)imidazo[1,2-a]pyrimidin-7-yl)ethan-1-one (39.8 mg, 0.08 mmol) was dissolved in THF (4 mL). NaBH₄ (9.36 mg, 0.24 mmol) was added and the reaction mixture was stirred at rt for 4 h. The reaction was quenched by adding 0.5 mL sat. aq NaHCO₃. The reaction mixture was extracted with EtOAc. The organic layer was washed with brine, dried (MgSO₄), filtered and concentrated in vacuo to provide a crude yellow residue of 1-(3-(1H-imidazol-4-yl)-2-(1-(4-methoxybenzyl)-3-(trifluoromethyl)-1H-1,2,4-triazol-5-yl)imidazo[1,2-a]pyrimidin-7-yl)ethan-1-ol (39.2 mg, 0.08 mmol, 98% yield), which was used in the next step without purification. LCMS m/z 485.2 [M+H]⁺

Step 4

1-(3-(1H-Imidazol-4-yl)-2-(1-(4-methoxybenzyl)-3-(trifluoromethyl)-1H-1,2,4-triazol-5-yl)imidazo[1,2-a]pyrimidin-7-yl)ethan-1-ol (39.2 mg, 0.08 mmol) was dissolved in trifluoroacetic acid (2 mL, 26.0 mmol). The mixture was stirred at 60° C. for 6 h. The reaction mixture was cooled and concentrated to a yellow residue. The residue was dissolved in 2 mL THF and 6 drops of 16 N aq NaOH were added. The mixture was stirred 1 h then was concentrated to a yellow residue. This residue was purified by preparative HPLC (Xselect CSH C₁₈ column (150 mm×30 mm i.d. 5 μm packing diameter), 30-85% 10 mM ammonium bicarbonate in water with acetonitrile). The desired fractions were concentrated to afford 1-(3-(1H-imidazol-5-yl)-2-(3-(trifluoromethyl)-1H-1,2,4-triazol-5-yl)imidazo[1,2-a]pyrimidin-7-yl)ethan-1-ol (3.5 mg, 0.009 mmol, 12% yield) as a yellow solid. ¹H NMR (400 MHz, METHANOL-d₄) δ ppm 9.44 (d, J=7.1 Hz, 1H), 7.89 (d, J=0.98 Hz, 1H), 7.61 (s, 1H), 7.34 (d, J=7.1 Hz, 1H), 5.08-4.85 (m, 1H), 1.57 (d, J=6.8 Hz, 3H). LCMS m/z 365.1 [M+H]⁺

The following example was prepared in an analogous manner to Example 2, except Step 4a was performed after Step 3.

Example 14

1-[3-(1H-imidazol-5-yl)-2-[3-(trifluoromethyl)-1H-1,2,4-triazol-5-yl]imidazo[1,2-a]pyrimidin-7-yl]ethan-1-one

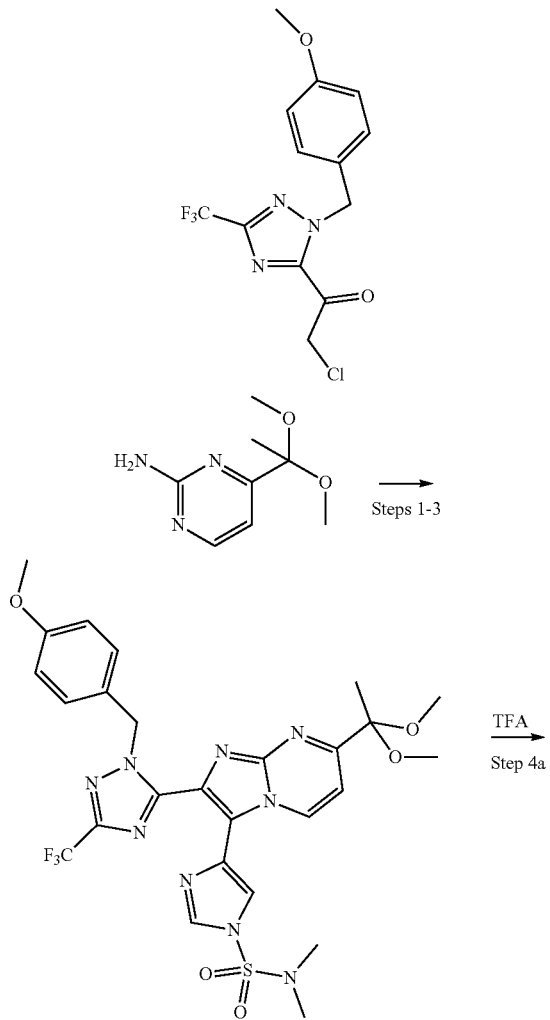

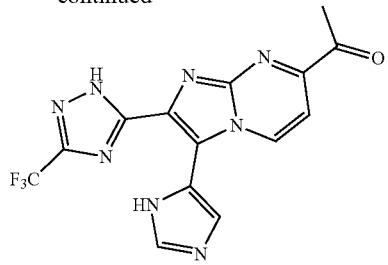

Step 4a 4-(7-(1,1-dimethoxyethyl)-2-(1-(4-methoxybenzyl)-3-(trifluoromethyl)-1H-1,2,4-triazol-5-yl)imidazo[1,2-a]pyrimidin-3-yl)-N,N-dimethyl-1H-imidazole-1-sulfonamide (58.1 mg, 0.091 mmol) was dissolved in trifluoroacetic acid (2 mL, 26.0 mmol). The reaction mixture was heated at 70° C. for 16 h. The reaction mixture was cooled and the mixture was concentrated to a brown residue. This residue was purified by reverse phase HPLC (Xselect CSH $C_{18}$ column (150 mm×30 mm i.d. 5 μm packing diameter), 15-50% acetonitrile/water, each with 0.1% formic acid). The desired fractions were concentrated to afford 1-(3-(1H-imidazol-5-yl)-2-(3-(trifluoromethyl)-1H-1,2,4-triazol-5-yl)imidazo[1,2-a]pyrimidin-7-yl)ethan-1-one (15 mg, 0.041 mmol, 45% yield) as a yellow solid. $^1$H NMR (400 MHz, METHANOL-$d_4$) δ ppm 9.82 (d, J=7.3 Hz, 1H), 8.39 (s, 1H), 8.00 (d, J=0.98 Hz, 1H), 7.72 (d, J=7.1 Hz, 1H), 2.79 (s, 3H). LCMS m/z 363.1 [M+H]$^+$ Examples 15-17 were synthesized in an analogous manner to Example 2, except additional Step 3c was performed after Step 3.

Example 15

5-[6-(cyclohexylmethyl)-3-(1H-imidazol-5-yl)imidazo[1,2-a]pyrimidin-2-yl]-3-(trifluoromethyl)-1H-1,2,4-triazole, trifluoroacetic acid salt

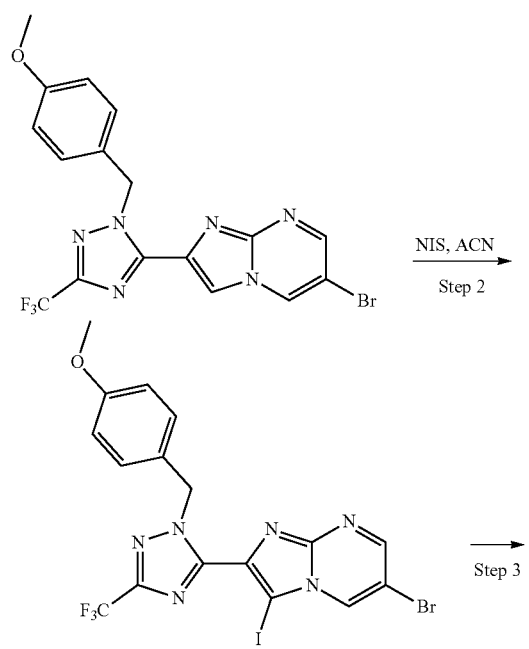

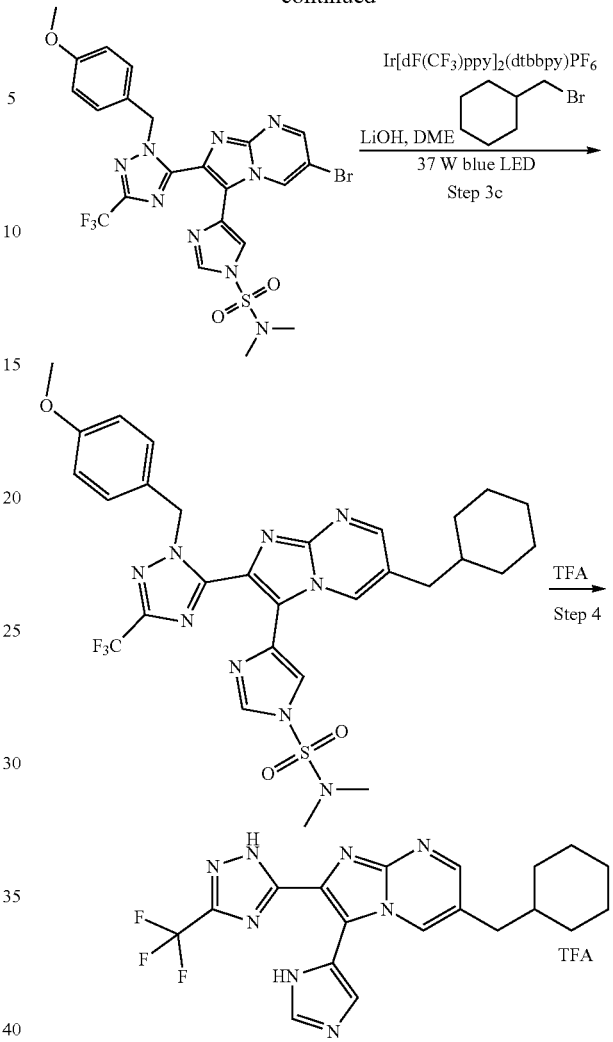

Step 2

To a solution of 6-bromo-2-(1-(4-methoxybenzyl)-3-(trifluoromethyl)-1H-1,2,4-triazol-5-yl)imidazo[1,2-a]pyrimidine (1 g, 2.21 mmol) (Intermediate 5) in acetonitrile (50 mL) was added NIS (0.596 g, 2.65 mmol). The reaction was stirred at rt for 2 h. The mixture was concentrated to dryness. The residue was purified by silica gel chromatography (220 g column, 2:1, PE:EtOAc) to afford 6-bromo-3-iodo-2-(1-(4-methoxybenzyl)-3-(trifluoromethyl)-1H-1,2,4-triazol-5-yl)imidazo[1,2-a]pyrimidine (1.1 g, 1.823 mmol, 83% yield) as a yellow solid. LCMS m/z 578.9 [M+H]$^+$

Step 3c

To a solution of 4-(6-bromo-2-(1-(4-methoxybenzyl)-3-(trifluoromethyl)-1H-1,2,4-triazol-5-yl)imidazo[1,2-a]pyrimidin-3-yl)-N,N-dimethyl-1H-imidazole-1-sulfonamide (100 mg, 0.16 mmol), Ir[dF(CF$_3$)ppy]$_2$(dtbbpy)PF$_6$ (8.96 mg, 7.98 μmol), NiCl$_2$ glyme (3.51 mg, 0.02 mmol), 4,4-di-tert-butyl-2,2-bipyridine (4.28 mg, 0.02 mmol) and LiOH (7.65 mg, 0.32 mmol) in DME (10 mL) was added (Me$_3$Si)$_3$SiH (0.05 mL, 0.16 mmol) and (bromomethyl)cyclohexane (42.4 mg, 0.24 mmol) under N$_2$ with stirring. The reaction was stirred at rt, 3 h with 37 W blue LED. The mixture was concentrated to dryness. The residue was purified by silica gel chromatography (100 g column, 1:1, PE:EtOAc) to afford 4-(6-(cyclohexylmethyl)-2-(1-(4-methoxybenzyl)-3-

(trifluoromethyl)-1H-1,2,4-triazol-5-yl)imidazo[1,2-a]pyrimidin-3-yl)-N,N-dimethyl-1H-imidazole-1-sulfonamide (80 mg, 0.123 mmol, 77% yield) as a yellow solid. LCMS m/z 644.2 [M+H]+

Step 4

A solution of 4-(6-(cyclohexylmethyl)-2-(1-(4-methoxybenzyl)-3-(trifluoromethyl)-1H-1,2,4-triazol-5-yl)imidazo[1,2-a]pyrimidin-3-yl)-N,N-dimethyl-1H-imidazole-1-sulfonamide (80 mg, 0.124 mmol) in TFA (4 mL) was stirred at 80° C. for 3 h. The mixture was cooled to rt and concentrated to remove TFA. The residue was dissolved in DMF (2.0 mL), filtered, and purified by preparative HPLC (SunFire C18 OBD Prep Column, 100 Å, 5 μm, 19 mm×250 mm; Mobile Phase A:Water [0.05% TFA], Mobile Phase B: MeCN; Flow rate: 25 mL/min; Gradient: 28% B to 45% B over 7 min). The product was collected, concentrated and lyophilized to afford 6-(cyclohexylmethyl)-3-(1H-imidazol-5-yl)-2-(3-(trifluoromethyl)-1H-1,2,4-triazol-5-yl)imidazo[1,2-a]pyrimidine, trifluoroacetic acid salt (9.4 mg, 0.018 mmol, 14% yield) as a yellow solid. ¹H NMR (400 MHz, DMSO-d₆) δ 9.15 (s, 1H), 8.64 (s, 1H), 8.61 (s, 1H), 8.26 (s, 1H), 2.52 (d, J=6.8 Hz, 2H), 1.61-1.58 (m, 6H), 1.09-1.07 (m, 3H), 1.02-0.83 (m, 2H). LCMS m/z 417.1 [M+H]+

Example 16

5-[6-cyclopentyl-3-(1H-imidazol-5-yl)imidazo[1,2-a]pyrimidin-2-yl]-3-(trifluoromethyl)-1H-1,2,4-triazole, trifluoroacetic acid salt

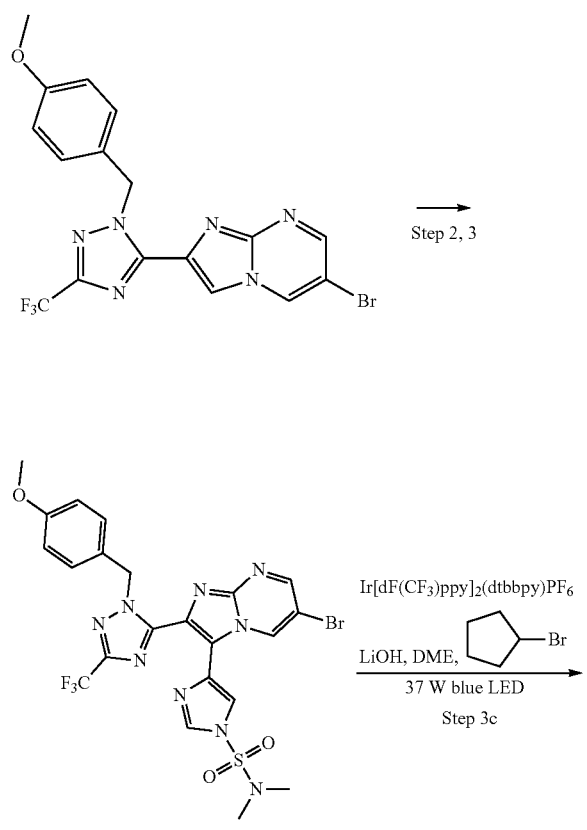

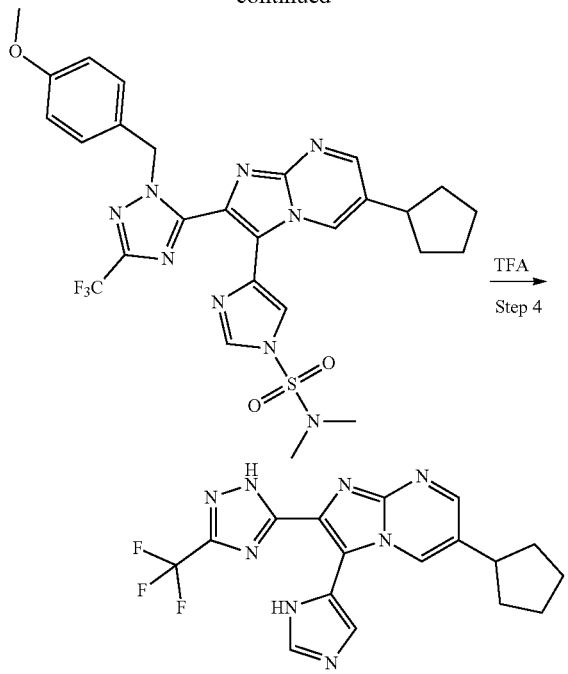

Step 3c

To a solution of 4-(6-bromo-2-(1-(4-methoxybenzyl)-3-(trifluoromethyl)-1H-1,2,4-triazol-5-yl)imidazo[1,2-a]pyrimidin-3-yl)-N,N-dimethyl-1H-imidazole-1-sulfonamide (100 mg, 0.16 mmol) Ir[dF(CF₃)ppy]₂(dtbbpy)PF₆ (8.96 mg, 7.98 μmol), NiCl₂ glyme (3.51 mg, 0.02 mmol), 4,4-di-tert-butyl-2,2-bipyridine (4.28 mg, 0.02 mmol) and LiOH (7.65 mg, 0.32 mmol) in DME (8 mL) was added (Me₃Si)₃SiH (0.05 mL, 0.160 mmol) and bromocyclopentane (0.03 mL, 0.24 mmol) under N₂ with stirring. The reaction was stirred at rt for 3 h with 37 W blue LED. The mixture was concentrated to dryness. The residue was purified by silica gel chromatography (100 g column, 1:1, PE:EtOAc) to afford 4-(6-cyclopentyl-2-(1-(4-methoxybenzyl)-3-(trifluoromethyl)-1H-1,2,4-triazol-5-yl)imidazo[1,2-a]pyrimidin-3-yl)-N,N-dimethyl-1H-imidazole-1-sulfonamide (40 mg, 0.062 mmol, 39% yield) as a yellow solid. LCMS m/z 616.15 [M+H]+

Step 4

A solution of 4-(6-cyclopentyl-2-(1-(4-methoxybenzyl)-3-(trifluoromethyl)-1H-1,2,4-triazol-5-yl)imidazo[1,2-a]pyrimidin-3-yl)-N,N-dimethyl-1H-imidazole-1-sulfonamide (40 mg, 0.065 mmol) in (TFA) (4 mL) was stirred at 80° C. for 3 h. The mixture was cooled and concentrated to remove TFA. The residue was dissolved in DMF (2.0 mL) filtered, and purified by preparative HPLC (SunFire C18 OBD Prep Column, 100 Å, 5 μm, 19 mm×250 mm; Mobile Phase A:Water [0.05% TFA], Mobile Phase B: MeCN; Flow rate: 25 mL/min; Gradient: 20% B to 33% B over 10 min). The product was collected, concentrated and lyophilized to afford 6-cyclopentyl-3-(1H-imidazol-5-yl)-2-(3-(trifluoromethyl)-1H-1,2,4-triazol-5-yl)imidazo[1,2-a]pyrimidine, trifluoroacetic acid salt (10.4 mg, 0.020 mmol, 31% yield) as a white solid. ¹H NMR (400 MHz, DMSO-d₆) δ 9.20 (s, 1H), 8.78 (s, 1H), 8.67 (s, 1H), 8.32 (s, 1H), 3.16-3.11 (m, 1H), 2.12-2.10 (m, 2H), 1.82-1.81 (m, 2H), 1.72-1.64 (m, 4H). LCMS m/z 389.05 [M+H]+

Example 17

5-[6-(cyclopentylmethyl)-3-(1H-imidazol-5-yl)imidazo[1,2-a]pyrimidin-2-yl]-3-(trifluoromethyl)-1H-1,2,4-triazole, trifluoroacetic acid salt

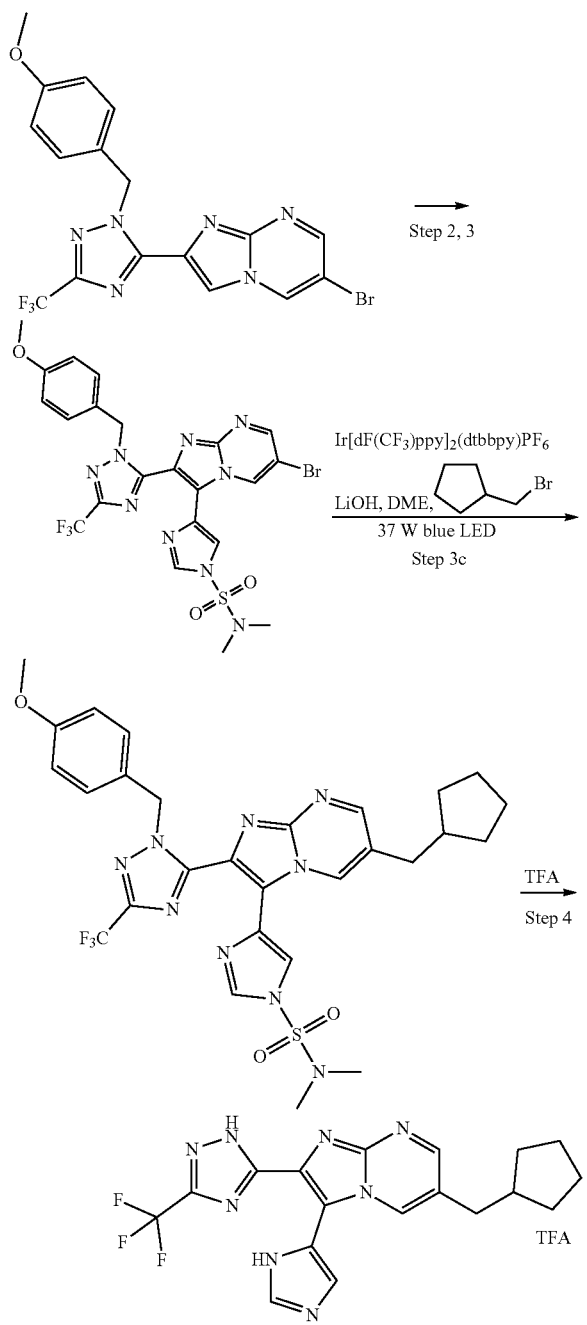

Step 3c

To a solution of 4-(6-bromo-2-(1-(4-methoxybenzyl)-3-(trifluoromethyl)-1H-1,2,4-triazol-5-yl)imidazo[1,2-a]pyrimidin-3-yl)-N,N-dimethyl-1H-imidazole-1-sulfonamide (150 mg, 0.239 mmol) Ir[dF(CF$_3$)ppy]$_2$(dtbbpy)PF$_6$ (13.43 mg, 0.012 mmol), NiCl$_2$ glyme (5.26 mg, 0.024 mmol), LiOH (11.47 mg, 0.479 mmol) and 4,4-di-tert-butyl-2,2-bipyridine (6.43 mg, 0.024 mmol) in DME (14 mL) was added (bromomethyl)cyclopentane (0.044 mL, 0.359 mmol) and (Me$_3$Si)$_3$SiH (0.074 mL, 0.239 mmol) at rt under N$_2$. The reaction was stirred at rt for 3 h with a 34 W blue LED. The mixture was concentrated to dryness. The residue was purified by silica gel chromatography (100 g column, 1:1, PE:EtOAc) to afford 4-(6-(cyclopentylmethyl)-2-(1-(4-methoxybenzyl)-3-(trifluoromethyl)-1H-1,2,4-triazol-5-yl)imidazo[1,2-a]pyrimidin-3-yl)-N,N-dimethyl-1H-imidazole-1-sulfonamide (80 mg, 0.119 mmol, 49.9% yield) as a yellow solid. LCMS m/z 630.3 [M+H]$^+$

Step 4

A solution of 4-(6-(cyclopentylmethyl)-2-(1-(4-methoxybenzyl)-3-(trifluoromethyl)-1H-1,2,4-triazol-5-yl)imidazo[1,2-a]pyrimidin-3-yl)-N,N-dimethyl-1H-imidazole-1-sulfonamide (80 mg, 0.127 mmol) in TFA (4 mL) was stirred at 80° C. for 3 h. The mixture was cooled to rt and concentrated to remove TFA. The residue was dissolved in DMF (2.0 mL), filtered, and purified by preparative HPLC (SunFire C18 OBD Prep Column, 100 Å, 5 μm, 19 mm×250 mm; Mobile Phase A:Water [0.05% TFA], Mobile Phase B: MeCN; Flow rate: 25 mL/min; Gradient: 30% B to 35% B over 7 min). The product was collected, concentrated and lyophilized to afford 6-(cyclopentylmethyl)-3-(1H-imidazol-5-yl)-2-(3-(trifluoromethyl)-1H-1,2,4-triazol-5-yl)imidazo[1,2-a]pyrimidine, trifluoroacetic acid salt (8.9 mg, 0.017 mmol, 14% yield) as a yellow solid. $^1$H NMR (400 MHz, DMSO-d$_6$) δ 9.30 (s, 1H), 8.64 (s, 1H), 8.57 (s, 1H), 8.30 (s, 1H), 2.64 (d, J=7.6 Hz, 2H), 2.13-2.05 (m, 1H), 1.65-1.52 (m, 4H), 1.48-1.43 (m, 2H), 1.20-1.11 (m, 2H). LCMS m/z 403.1 [M+H]$^+$ The following example was synthesized in an analogous manner to Example 2, except additional Steps 3d and 3e were performed after Step 3.

Example 18

13,13-difluoro-6-(1H-imidazol-5-yl)-11-methyl-5-[3-(trifluoromethyl)-1H-1,2,4-triazol-5-yl]-2,4,7,11-tetraazatricyclo[7.4.0.0$^{3,7}$]trideca-1,3,5,8-tetraene, trifluoroacetic acid salt

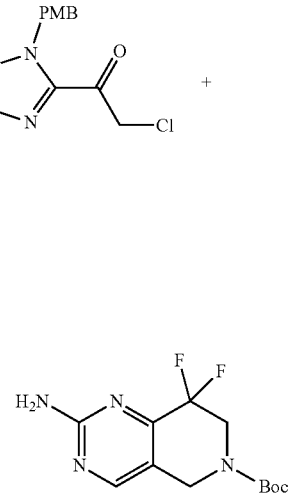

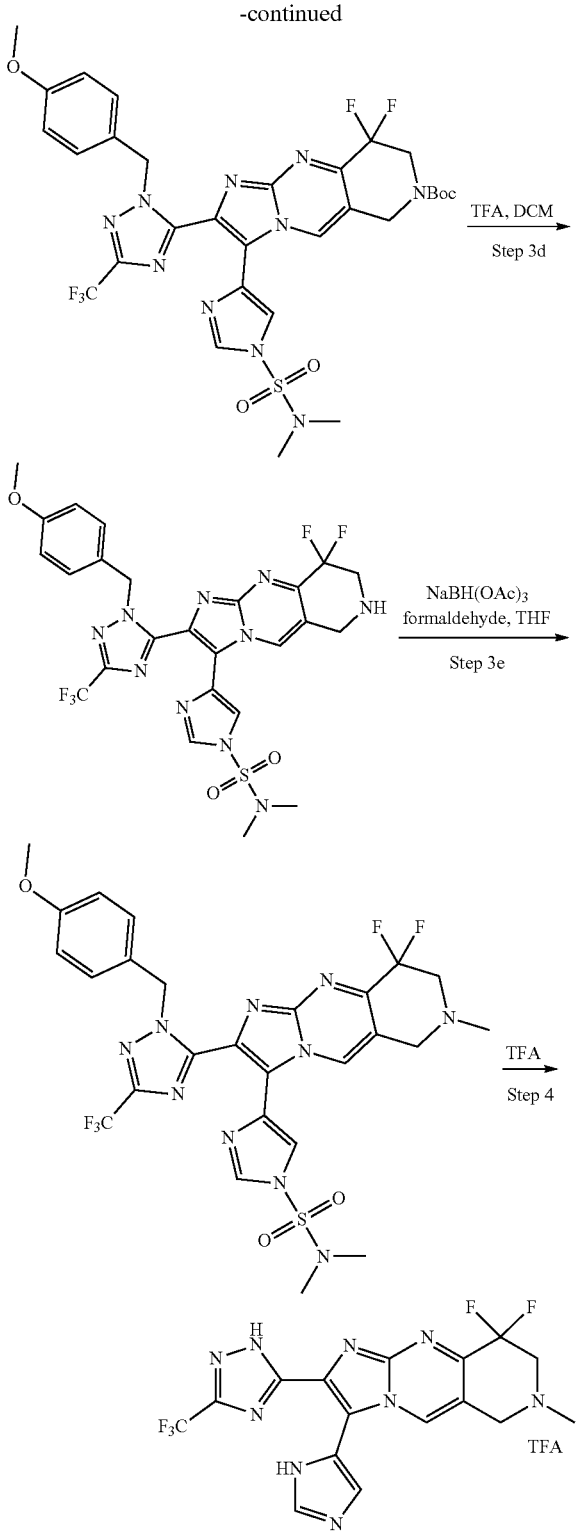

Step 3d tert-Butyl 3-(1-(N,N-dimethylsulfamoyl)-1H-imidazol-4-yl)-9,9-difluoro-2-(1-(4-methoxybenzyl)-3-(trifluoromethyl)-1H-1,2,4-triazol-5-yl)-8,9-dihydroimidazo[1,2-a]pyrido[4,3-d]pyrimidine-7(6H)-carboxylate (90 mg, 0.122 mmol) was dissolved in DCM (15 mL) followed by the addition of TFA (2 mL, 26.0 mmol). The solution was stirred at rt for 5 h. The solution was concentrated in vacuo. The resultant was dissolved (MeOH, 5 mL), neutralized with aq. NH$_4$OH (5 drops) and concentrated in vacuo to afford 4-(9,9-difluoro-2-(1-(4-methoxybenzyl)-3-(trifluoromethyl)-1H-1,2,4-triazol-5-yl)-6,7,8,9-tetrahydroimidazo[1,2-a]pyrido[4,3-d]pyrimidin-3-yl)-N,N-dimethyl-1H-imidazole-1-sulfonamide (88 mg, 0.138 mmol) which was used in the next step without purification. LCMS m/z 639.3 [M+H]$^+$ Step 3e 4-(9,9-Difluoro-2-(1-(4-methoxybenzyl)-3-(trifluoromethyl)-1H-1,2,4-triazol-5-yl)-6,7,8,9-tetrahydroimidazo[1,2-a]pyrido[4,3-d]pyrimidin-3-yl)-N,N-dimethyl-1H-imidazole-1-sulfonamide (53 mg, 0.083 mmol) was dissolved in THF (3 mL). Acetic acid (0.095 mL, 1.660 mmol) and formaldehyde (0.025 mL, 0.332 mmol) were added and the mixture was stirred 20 min. Sodium triacetoxyborohydride (48 mg, 0.226 mmol) was added. The reaction mixture was stirred for several minutes then additional formaldehyde (0.1 mL) and NaBH(OAc)$_3$ (10 mg) were added in multiple batches until LCMS indicated complete conversion to product. Lastly, MeOH (1 mL) was added and the mixture was stirred for 20 min. The reaction was diluted with EtOAc. Sat. aq. NaHCO$_3$ was added and the combined mixture was extracted with EtOAc (3×). The combined organics were washed with brine, dried (MgSO$_4$), filtered and concentrated. The resulting residue was purified by silica gel chromatography (Isco RediSep Rf Gold 24 g column, 25-100% EtOAc in Heptane). Product fractions were concentrated to afford 4-(9,9-difluoro-2-(1-(4-methoxybenzyl)-3-(trifluoromethyl)-1H-1,2,4-triazol-5-yl)-7-methyl-6,7,8,9-tetrahydroimidazo[1,2-a]pyrido[4,3-d]pyrimidin-3-yl)-N,N-dimethyl-1H-imidazole-1-sulfonamide (27 mg, 0.041 mmol, 50% yield). LCMS m/z 653.2 [M+H]$^+$ Step 4

4-(9,9-Difluoro-2-(1-(4-methoxybenzyl)-3-(trifluoromethyl)-1H-1,2,4-triazol-5-yl)-7-methyl-6,7,8,9-tetrahydroimidazo[1,2-a]pyrido[4,3-d]pyrimidin-3-yl)-N,N-dimethyl-1H-imidazole-1-sulfonamide (27 mg, 0.041 mmol) was dissolved in TFA (5 mL, 64.9 mmol). The reaction was heated at 60° C. overnight. The reaction was cooled to rt, concentrated in vacuo and then evaporated (3×) from DCM/EtOAc/MeOH. The residue was suspended in IPA (5 mL) and was neutralized with aq. NH$_4$OH then concentrated. The resulting solid was purified by ISCO reverse phase prep HPLC (30-100%, MeCN in water, +0.1% TFA in each solvent, Gemini Prep C18 5 μM, 50×30 mm, AXIA packed column). The product fractions were concentrated in vacuo then lyopholized to afford 9,9-difluoro-3-(1H-imidazol-5-yl)-7-methyl-2-(3-(trifluoromethyl)-1H-1,2,4-triazol-5-yl)-6,7,8,9-tetrahydroimidazo[1,2-a]pyrido[4,3-d]pyrimidine, trifluoroacetic acid salt (3.4 mg, 6.30 μmol, 15% yield) as a yellow solid. $^1$H NMR (400 MHz, DMSO-d$_6$) δ ppm 9.23-9.22 (m, 1H), 9.21-9.20 (m, 1H), 8.22-8.20 (m, 1H), 4.28 (s, 2H), 2.84 (s, 3H), 2H obscured by solvent. LCMS m/z 426.2 [M+H]$^+$The following example was synthesized in an analogous manner to Example 2, except additional Step 1a was performed after Step 1.

Example 19

5-[7-(1,1-difluoro-2-methoxyethyl)-3-(1H-imidazol-5-yl)imidazo[1,2-a]pyrimidin-2-yl]-3-(trifluoromethyl)-1H-1,2,4-triazole

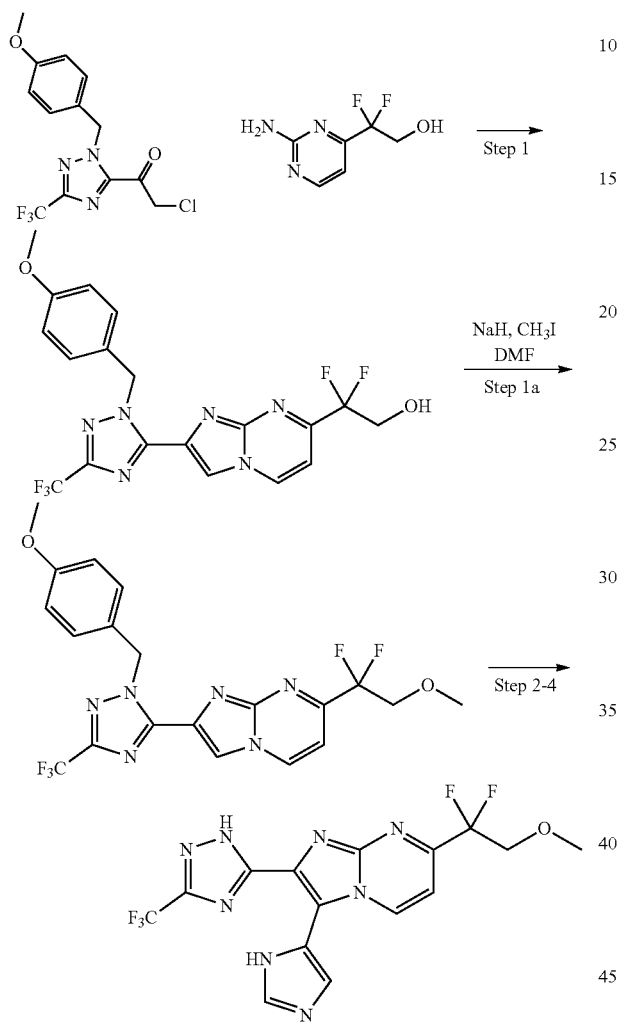

Step 1a

A stirred solution of 2,2-difluoro-2-(2-(1-(4-methoxybenzyl)-3-(trifluoromethyl)-1H-1,2,4-triazol-5-yl)imidazo[1,2-a]pyrimidin-7-yl)ethan-1-ol (1.0 g, 2.201 mmol) in N,N-dimethylformamide (15 mL) was treated with 60% dispersion sodium hydride (100 mg, 2.50 mmol) portionwise at 0° C. for 15 min. Iodomethane (170 μL, 2.72 mmol) was added and the reaction stirred at 0° C. for 15 min then was allowed to warm to rt before quenching with water. The reaction was extracted with EtOAc and the organic layer was washed with aq. $Na_2S_2O_3$, dried ($Na_2SO_4$), filtered and concentrated in vacuo. The crude material was purified by silica gel chromatography (80 g Isco RediSep Rf Gold column, 0-60% EtOAc in $CH_2Cl_2$). The desired fractions were combined and concentrated in vacuo to afford 7-(1,1-difluoro-2-methoxyethyl)-2-(1-(4-methoxybenzyl)-3-(trifluoromethyl)-1H-1,2,4-triazol-5-yl)imidazo[1,2-a]pyrimidine (0.67 g, 1.359 mmol, 62% yield) as an off-white solid. $^1$H NMR (400 MHz, DMSO-$d_6$) δ 9.24 (d, J=6.9 Hz, 1H), 8.81 (s, 1H), 7.53 (d, J=6.9 Hz, 1H), 7.38-7.32 (m, 2H), 6.94-6.88 (m, 2H), 6.14 (s, 2H), 4.15 (t, J=13.9 Hz, 2H), 3.71 (s, 3H), 3.38 (s, 3H). LCMS m/z 468.8 [M+H]$^+$ Final product 7-(1,1-difluoro-2-methoxyethyl)-3-(1H-imidazol-5-yl)-2-(3-(trifluoromethyl)-1H-1,2,4-triazol-5-yl)imidazo[1,2-a]pyrimidine: $^1$H NMR (400 MHz, DMSO-d6) δ 15.77 (br s, 1H), 12.73 (br s, 1H), 10.34 (d, J=7.3 Hz, 1H), 8.63 (br s, 1H), 8.05 (s, 1H), 7.53 (d, J=7.3 Hz, 1H), 4.16 (t, J=13.7 Hz, 2H), 3.39 (s, 3H). LCMS m/z 415.1 [M+H]$^+$ The following example was synthesized in an analogous manner to Example 2, except Step 1b was performed instead of Step 2.

Example 20

3-(1H-Imidazol-5-yl)-2-(3-(trifluoromethyl)-1H-1,2,4-triazol-5-yl)imidazo[1,2-a]pyrimidin-6-yl methanesulfonate

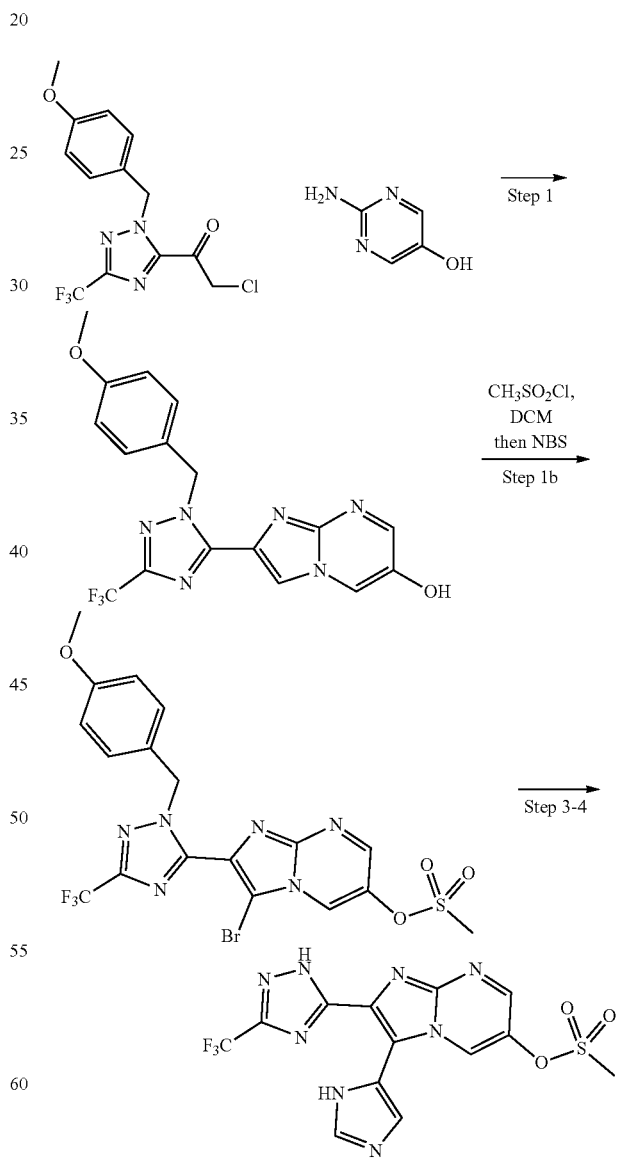

Step 1b

To a solution of 2-(1-(4-methoxybenzyl)-3-(trifluoromethyl)-1H-1,2,4-triazol-5-yl)imidazo[1,2-a]pyrimidin-6-ol (0.120 g, 0.307 mmol) and triethylamine (0.043 mL, 0.307 mmol) in DCM (2 mL) was added methanesulfonyl chloride (0.024 mL, 0.307 mmol) dropwise. The reaction was stirred at room temperature for 30 min. NBS (0.082 g, 0.461 mmol) was added and the reaction stirred for 1 h. The reaction was partitioned between DCM and saturated aq sodium carbonate. The organic layer was concentrated under reduced pressure to provide crude material. The crude material was purified by silica gel chromatography (Combiflash, 0-30% [3:1 EtOAc:EtOH] in DCM). Product fractions were concentrated to afford 3-bromo-2-(1-(4-methoxybenzyl)-3-(trifluoromethyl)-1H-1,2,4-triazol-5-yl)imidazo[1,2-a]pyrimidin-6-yl methanesulfonate (0.137 g, 0.250 mmol, 81% yield) as a light yellow solid. $^1$H NMR (400 MHz, CHLOROFORM-d) δ ppm 8.66 (d, J=2.4 Hz, 1H), 8.62 (d, J=2.4 Hz, 1H), 7.44-7.38 (m, 2H), 6.84-6.78 (m, 2H), 6.10 (s, 2H), 3.75 (s, 3H), 3.39 (s, 3H). LCMS m/z 547.0, 548.9 [M+H]$^+$ Final product 3-(1H-imidazol-5-yl)-2-(3-(trifluoromethyl)-1H-1,2,4-triazol-5-yl)imidazo[1,2-a]pyrimidin-6-yl methanesulfonate: $^1$H NMR (400 MHz, DMSO-d$_6$) δ=15.77 (br s, 1H), 12.73 (br s, 1H), 10.39 (d, J=2.0 Hz, 1H), 8.82 (d, J=2.9 Hz, 1H), 8.66 (s, 1H), 8.06 (d, J=1.0 Hz, 1H), 3.60 (s, 3H). LMCS m/z 415.0 [M+H]$^+$ The following example was synthesized in an analogous manner to Example 2, except Step 5 was performed instead of Step 1.

Example 21

5-[3-(1H-imidazol-5-yl)-7-(methylsulfanyl)imidazo[1,2-a]pyrimidin-2-yl]-3-(trifluoromethyl)-1H-1,2,4-triazole

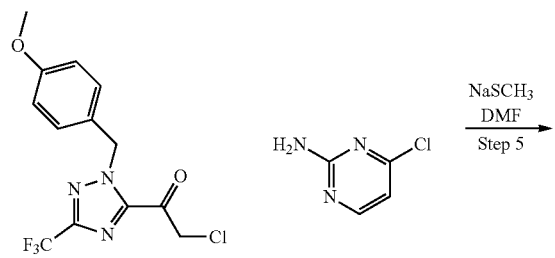

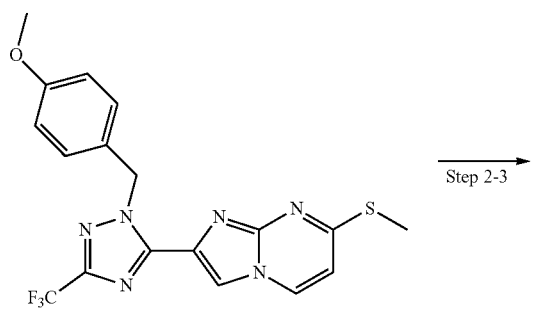

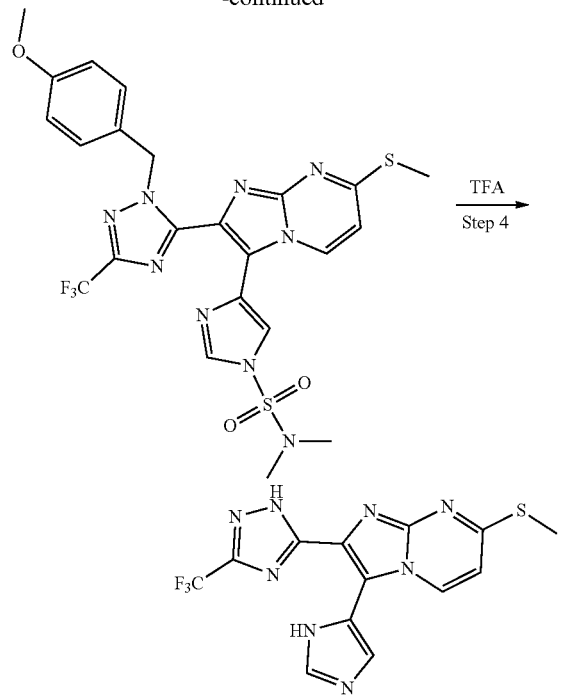

Step 5

To a stirred solution of 4-chloropyrimidin-2-amine (1.0 g, 7.72 mmol) in DMF (20 mL) was added portionwise sodium thiomethoxide (0.55 g, 7.85 mmol) over 10 minutes. The reaction was stirred at room temperature for 1 h. The reaction was treated with 2-chloro-1-(1-(4-methoxybenzyl)-3-(trifluoromethyl)-1H-1,2,4-triazol-5-yl)ethan-1-one (1.5 g, 4.50 mmol) and stirred at 100° C. for 18 h. The mixture was triturated with sat. aq. NaHCO$_3$, filtered, washed with water and dried under vacuum to afford 2-(1-(4-methoxybenzyl)-3-(trifluoromethyl)-1H-1,2,4-triazol-5-yl)-7-(methylthio)imidazo[1,2-a]pyrimidine (1.6 g, 3.58 mmol, 80% yield) as a beige solid. $^1$H NMR (400 MHz, DMSO-d$_6$) δ 8.78-8.73 (m, 1H), 8.49 (s, 1H), 7.31 (d, J=8.8 Hz, 2H), 7.17-7.13 (m, 1H), 6.91 (d, J=8.8 Hz, 2H), 6.13 (s, 2H), 3.71 (s, 3H), 2.62 (s, 3H). LCMS m/z 421.2 [M+H]$^+$ Step 4

4-(2-(1-(4-Methoxybenzyl)-3-(trifluoromethyl)-1H-1,2,4-triazol-5-yl)-7-(methylthio)imidazo[1,2-a]pyrimidin-3-yl)-N,N-dimethyl-1H-imidazole-1-sulfonamide (500 mg, 0.842 mmol) in TFA (15 mL) was heated at 70° C. for 12 h. The reaction was concentrated in vacuo. The crude material was suspended in water (5 mL) and adjusted close to pH 7 with sat. NaHCO$_3$. The mixture was treated with ammonium citrate buffer (0.2 M) then was triturated and filtered. The resultant filtered solid was washed with water followed by a small volume of EtOH and dried. Next, solid was washed with DCM and dried under vacuum to afford 3-(1H-imidazol-5-yl)-7-(methylthio)-2-(3-(trifluoromethyl)-1H-1,2,4-triazol-5-yl)imidazo[1,2-a]pyrimidine (273 mg, 0.711 mmol, 84%) as a light orange solid. $^1$H NMR (400 MHz, DMSO-d$_6$) δ ppm 15.60 (br s, 1H), 12.72 (br s, 1H), 9.84 (d, J=7.3 Hz, 1H), 8.57 (s, 1H), 8.03 (s, 1H), 7.14 (d, J=7.3 Hz, 1H), 2.62 (s, 3H). LCMS m/z 367.1 [M+H]$^+$ The following example was synthesized in an analogous manner to Example 2, except Step 1c was performed after Step 1 and Step 3f was performed after Step 3.

Example 22

5-[3-(1H-imidazol-5-yl)-6-methanesulfonylimidazo[1,2-a]pyrimidin-2-yl]-3-(trifluoromethyl)-1H-1,2,4-triazole

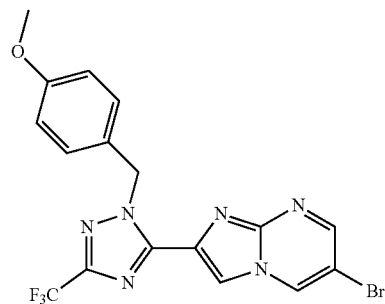

NaSCH₃
DMSO
Step 1c

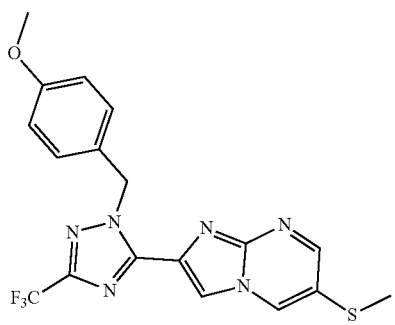

Step 2-3

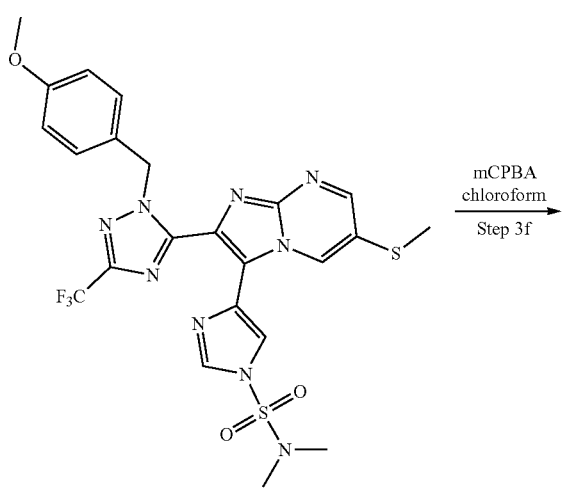

mCPBA
chloroform
Step 3f

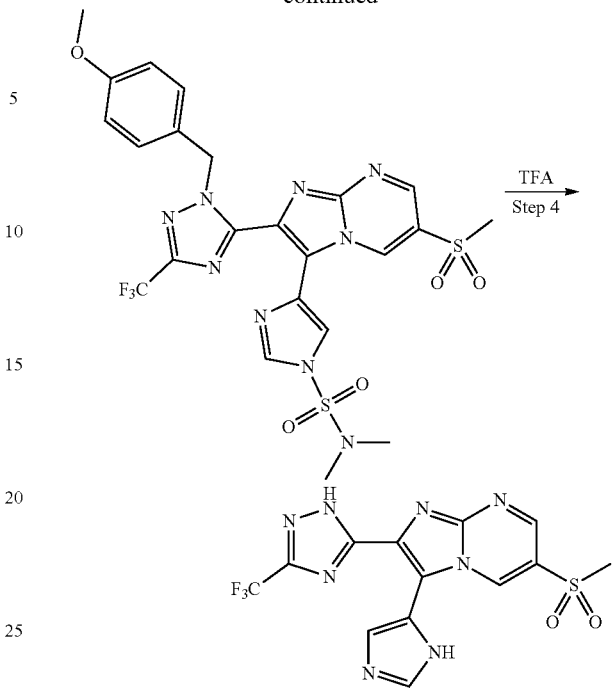

TFA
Step 4

Step 1c

Sodium thiomethoxide (310 mg, 4.42 mmol) was added to a mixture of 6-bromo-2-(1-(4-methoxybenzyl)-3-(trifluoromethyl)-1H-1,2,4-triazol-5-yl)imidazo[1,2-a]pyrimidine (1.8 g, 3.97 mmol) and dimethyl sulfoxide (DMSO) (20 mL) under nitrogen. The reaction was sealed and stirred at 100° C. for 4 h. The reaction was cooled to room temperature and was diluted with EtOAc. The organic phase was washed with water and brine then dried (Na₂SO₄), filtered and evaporated in vacuo. The crude material was purified by silica gel chromatography (Isco RediSep Rf Gold 120 g column, 30-100% EtOAc in heptane). The fractions were combined and concentrated in vacuo to afford 2-(1-(4-methoxybenzyl)-3-(trifluoromethyl)-1H-1,2,4-triazol-5-yl)-6-(methylthio)imidazo[1,2-a]pyrimidine (0.70 g, 1.582 mmol, 40% yield) as a light tan solid. ¹H NMR (400 MHz, DMSO-d₆) δ 8.92 (d, J=2.93 Hz, 1H), 8.64 (d, J=2.45 Hz, 1H), 8.44 (s, 1H), 7.27 (d, J=8.80 Hz, 2H), 6.79-6.84 (m, 2H), 6.03 (s, 2H), 3.62 (s, 3H), 2.50 (s, 3H). LCMS m/z 421.2 [M+H]⁺.

Step 3f

To a stirred solution of 4-(2-(1-(4-methoxybenzyl)-3-(trifluoromethyl)-1H-1,2,4-triazol-5-yl)-6-(methylthio)imidazo[1,2-a]pyrimidin-3-yl)-N,N-dimethyl-1H-imidazole-1-sulfonamide (350 mg, 0.590 mmol) in chloroform (20 mL) at 0° C. in an ice bath was added mCPBA 77 wt % (470 mg, 2.72 mmol). The reaction was allowed to warm to room temperature and stirred overnight. The reaction was washed with aq. Na₂CO₃, dried (Na₂SO₄), filtered and concentrated under vacuum. The resulting residue was purified by silica gel chromatography (Isco RediSep Rf Gold 40 g, 0 to 60% EtOAc in CH₂Cl₂). The pure fractions were combined and evaporated to dryness to give the product 4-(2-(1-(4-methoxybenzyl)-3-(trifluoromethyl)-1H-1,2,4-triazol-5-yl)-6-(methylsulfonyl)imidazo[1,2-a]pyrimidin-3-yl)-N,N-dimethyl-1H-imidazole-1-sulfonamide (249 mg, 0.382 mmol, 64.8% yield) as a yellow solid. ¹H NMR (400 MHz, DMSO-d₆) δ 10.29 (s, 1H), 9.19-9.15 (m, 1H), 8.64 (d, J=1.5

Hz, 1H), 8.61-8.60 (m, 1H), 7.41 (d, J=8.8 Hz, 2H), 6.94-6.87 (m, 2H), 5.98 (s, 2H), 3.72 (s, 3H), 3.47 (s, 3H), 2.88 (s, 6H). LCMS m/z 626.1 [M+H]+.

Step 4

4-(2-(1-(4-Methoxybenzyl)-3-(trifluoromethyl)-1H-1,2,4-triazol-5-yl)-6-(methylsulfonyl)imidazo[1,2-a]pyrimidin-3-yl)-N,N-dimethyl-1H-imidazole-1-sulfonamide (240 mg, 0.384 mmol) in TFA (10 mL) was stirred at 70° C. for 12 h. The reaction was concentrated in vacuo and suspended in water (5 mL). The mixture was brought to pH 7 with the addition of sat'd aq NaHCO3, and then treated with ammonium citrate (0.2 M) buffer (50 mL). The resulting solid was filtered and washed with water, EtOH, DCM and dried to afford 3-(1H-imidazol-5-yl)-6-(methylsulfonyl)-2-(3-(trifluoromethyl)-1H-1,2,4-triazol-5-yl)imidazo[1,2-a]pyrimidine (128 mg, 0.302 mmol, 79%) as a light yellow solid. $^1$H NMR (400 MHz, DMSO-d$_6$) δ ppm 13.27 (br s, 1H), 10.45 (d, J=2.5 Hz, 1H), 9.13 (d, J=2.5 Hz, 1H), 8.38 (s, 1H), 8.19 (s, 1H), 3.48 (s, 3H), 1H not observed. LCMS m/z 399.0 [M+H]+

Example 23

4-oxo-4-[(4-{2-[3-(trifluoromethyl)-1H-1,2,4-triazol-5-yl]imidazo[1,2-a]pyrimidin-3-yl}-1H-imidazol-1-yl)methoxy]butanoic acid

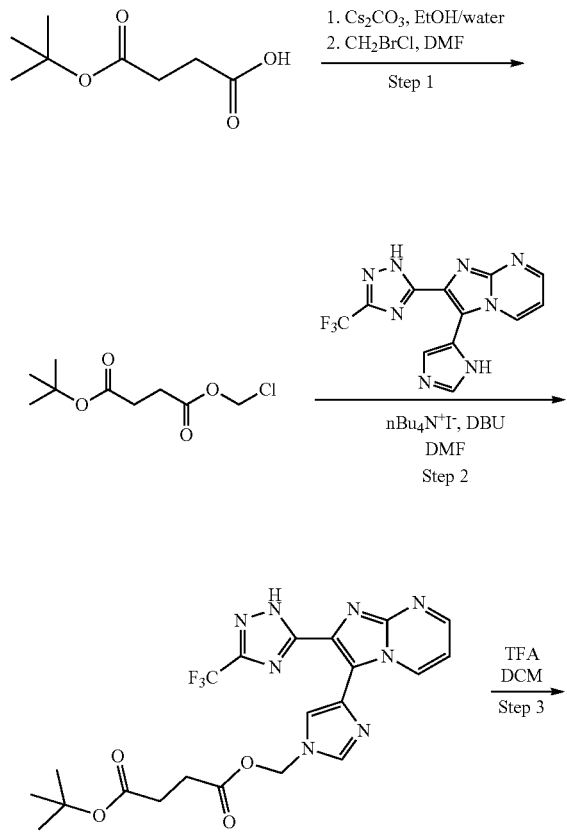

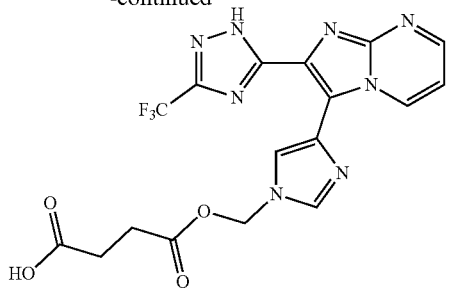

Step 1

To a solution of 4-(tert-butoxy)-4-oxobutanoic acid (3 g, 17.22 mmol) in a solvent mixture of ethanol (75 mL) and water (11 mL) was added cesium carbonate (2.81 g, 8.61 mmol). The mixture was briefly sonicated then was stirred for 15 minutes. The solvents were evaporated and the residue was dried overnight under high vacuum.

The dry Cs-salt was dissolved in DMF (55.00 mL), bromochloromethane (72.8 mL, 1119 mmol) was added and the solution was stirred at RT overnight. The resulting precipitate was filtered off, and the solution was concentrated to afford a residue. The residue was partitioned between water and EtOAc. The organic phase was washed with water (1×) and brine (2×), dried over sodium sulfate and was evaporated to afford tert-butyl (chloromethyl) succinate (3.484 g, 15.65 mmol, 91% yield) as a colorless oil. $^1$H NMR (400 MHz, DMSO-d$_6$) δ ppm 5.86 (s, 2H), 2.58-2.66 (m, 2H), 2.48-2.53 (m, 2H), 1.39 (s, 9H).

Step 2

A solution of 3-(1H-imidazol-5-yl)-2-(3-(trifluoromethyl)-1H-1,2,4-triazol-5-yl)imidazo[1,2-a]pyrimidine (100 mg, 0.312 mmol, Example 1), tert-butyl (chloromethyl) succinate (87 mg, 0.390 mmol), tetrabutylammonium iodide (144 mg, 0.390 mmol), and DBU (0.059 mL, 0.390 mmol) in DMF (2 mL) was stirred at room temperature overnight. The major product was isolated by MDAP preparative HPLC (MDAP Method F) to afford tert-butyl ((4-(2-(3-(trifluoromethyl)-1H-1,2,4-triazol-5-yl)imidazo[1,2-a]pyrimidin-3-yl)-1H-imidazol-1-yl)methyl) succinate (49 mg, 0.097 mmol, 31.0% yield) as a yellow lyophile. LCMS m/z 507.4 [M+H]+. $^1$H NMR (400 MHz, DMSO-d$_6$) δ 15.66 (br s, 1H), 10.00 (dd, J=2.01, 7.03 Hz, 1H), 8.74 (dd, J=2.01, 4.02 Hz, 1H), 8.67 (d, J=1.26 Hz, 1H), 8.18 (d, J=1.25 Hz, 1H), 7.26 (dd, J=4.02, 7.03 Hz, 1H), 6.13 (s, 2H), 2.54-2.61 (m, 2H), 2.44-2.49 (m, 2H), 1.29 (s, 9H).

Step 3

To a solution of tert-butyl ((4-(2-(3-(trifluoromethyl)-1H-1,2,4-triazol-5-yl)imidazo[1,2-a]pyrimidin-3-yl)-1H-imidazol-1-yl)methyl) succinate (46 mg, 0.091 mmol) in DCM (4 mL) was added TFA (4 mL, 51.9 mmol), and the mixture was stirred at room temperature for 2 h then evaporated to dryness. The oily residue was triturated with ether to afford 4-oxo-4-((4-(2-(3-(trifluoromethyl)-1H-1,2,4-triazol-5-yl)imidazo[1,2-a]pyrimidin-3-yl)-1H-imidazol-1-yl)methoxy) butanoic acid (41 mg, 0.091 mmol, 100% yield) as a pale yellow solid. LCMS m/z 451.2 [M+H]+. $^1$H NMR (400 MHz, DMSO-d$_6$) δ ppm 15.71 (br s, 1H), 12.26 (br s, 1H), 9.98 (dd, J=2.03, 7.10 Hz, 1H), 8.74 (dd, J=2.03, 4.06 Hz, 1H), 8.65 (d, J=1.27 Hz, 1H), 8.19 (d, J=1.27 Hz, 1H), 7.26 (dd, J=4.06, 7.10 Hz, 1H), 6.13 (s, 2H), 2.55-2.65 (m, 2H), 2.45-2.50 (m, 2H).

Example 24

(4-{2-[1-({[(2S)-2-amino-3-methylbutanoyl]oxy}methyl)-3-(trifluoromethyl)-1H-1,2,4-triazol-5-yl]imidazo[1,2-a]pyrimidin-3-yl}-1H-imidazol-1-yl)methyl (2S)-2-amino-3-methylbutanoate, 2 trifluoroacetic acid salt

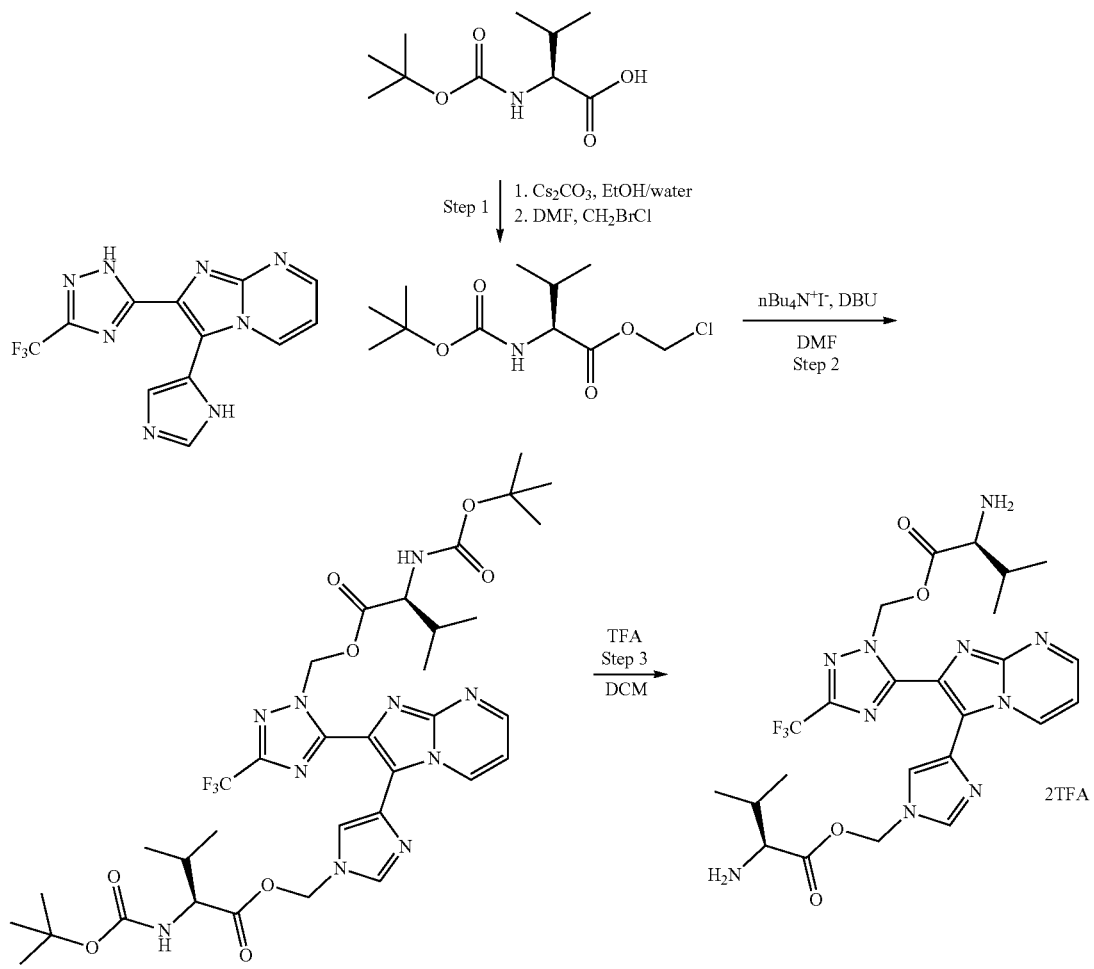

Step 1

To a solution of (S)-2-((tert-butoxycarbonyl)amino)-3-methylbutanoic acid (3 g, 13.81 mmol) in the solvent mixture of ethanol (75 mL) and water (11 mL), cesium carbonate (2.249 g, 6.90 mmol) was added and stirred until the carbonate dissolved and the gas evolution seized (about 15 minutes). The solvents were evaporated and the residue dried overnight in high vacuum.

The dry Cs-salt was dissolved in DMF (55.00 mL), bromochloromethane (58.4 mL, 898 mmol) was added and the solution was stirred at RT overnight. The CsBr precipitate was filtered off, and the solution was evaporated. The residue was partitioned between water and EtOAc, the organic phase washed with water (1×), brine (1×), dried over sodium sulfate and was evaporated. The residue was purified by silica gel chromatography (80 g Isco RediSep Rf Gold column, eluting with 0-20% (EtOAc in hexanes) to afford (S)-chloromethyl 2-((tert-butoxycarbonyl)amino)-3-methylbutanoate (2.817 g, 10.60 mmol, 77% yield) as a clear oil.

LCMS m/z 288 [M+Na]$^+$. $^1$H NMR (400 MHz, DMSO-$d_6$) δ 7.40 (d, J=7.86 Hz, 1H), 5.96 (d, J=6.08 Hz, 1H), 5.85 (d, J=6.34 Hz, 1H), 3.90 (dd, J=6.59, 7.60 Hz, 1H), 1.94-2.12 (m, 1H), 1.39 (s, 9H), 0.86-0.96 (m, 6H).

Step 2

A solution of 3-(1H-imidazol-5-yl)-2-(3-(trifluoromethyl)-1H-1,2,4-triazol-5-yl)imidazo[1,2-a]pyrimidine (27.7 mg, 0.086 mmol, Example 1), chloromethyl (tert-butoxycarbonyl)-L-valinate (28.7 mg, 0.108 mmol), tetrabutylammonium iodide (39.9 mg, 0.108 mmol), and DBU (0.016 mL, 0.108 mmol) in DMF (0.5 mL) was stirred at room temperature for 4 h. More chloromethyl (tert-butoxycarbonyl)-L-valinate (5.74 mg, 0.022 mmol) and DBU (0.003 mL, 022 mmol) were added and the mixture stirred for 28 h. More chloromethyl (tert-butoxycarbonyl)-L-valinate (22.96 mg, 0.086 mmol) and DBU (0.013 mL, 0.086 mmol) were added and the mixture stirred over weekend (~2.5 days). The product was isolated by preparative HPLC (MDAP Method G) to afford (5-(3-(1-(((((tert-butoxycarbonyl)-L-valyl)oxy)

methyl)-1H-imidazol-4-yl)imidazo[1,2-a]pyrimidin-2-yl)-3-(trifluoromethyl)-1H-1,2,4-triazol-1-yl)methyl (tert-butoxycarbonyl)-L-valinate (32 mg, 0.041 mmol, 47.5% yield) as an off-white lyophile. LCMS m/z 779.3 [M+H]+.

Step 3

To a solution of (5-(3-(1-((((tert-butoxycarbonyl)-L-valyl)oxy)methyl)-1H-imidazol-4-yl)imidazo[1,2-a]pyrimidin-2-yl)-3-(trifluoromethyl)-1H-1,2,4-triazol-1-yl)methyl (tert-butoxycarbonyl)-L-valinate (30 mg, 0.039 mmol) in DCM (4 mL), TFA (4 mL, 51.9 mmol) was added and the mixture was stirred at room temperature for 1 hr and then evaporated to dryness. The residue was dissolved in 5 mL water and was lyophilized to afford (5-(3-(1-(((L-valyl)oxy)methyl)-1H-imidazol-4-yl)imidazo[1,2-a]pyrimidin-2-yl)-3-(trifluoromethyl)-1H-1,2,4-triazol-1-yl)methyl L-valinate, 2 trifluoroacetic acid salt (30 mg, 0.037 mmol, 97% yield) as a pale yellow lyophile. LCMS m/z 579.2 [M+H]+; 1H NMR (400 MHz, DMSO-$d_6$) δ 9.82 (dd, J=1.88, 7.15 Hz, 1H), 8.79 (dd, J=2.01, 4.02 Hz, 1H), 8.34-8.45 (m, 7H), 8.24 (d, J=1.00 Hz, 1H), 7.32 (dd, J=4.02, 7.03 Hz, 1H), 7.06 (d, J=10.54 Hz, 1H), 6.83 (d, J=10.54 Hz, 1H), 6.34 (d, J=10 Hz, 1H), 6.26 (d, J=10 Hz, 1H), 4.03 (dd, J=4.52, 9.03 Hz, 2H), 2.02-2.24 (m, 2H), 0.80-0.91 (m, 12H).

Example 25

{2-[methyl({[1-(5-{2-[3-(trifluoromethyl)-1H-1,2,4-triazol-5-yl]imidazo[1,2-a]pyrimidin-3-yl}-1H-imidazol-1-yl)ethoxy]carbonyl})amino]pyridin-3-yl}methyl 2-(methylamino)acetate, hydrochloride salt Step 1

A mixture of 3-(1H-imidazol-5-yl)-2-(3-(trifluoromethyl)-1H-1,2,4-triazol-5-yl)imidazo[1,2-a]pyrimidine (75 mg, 0.234 mmol, Example 1), (2-(((1-chloroethoxy)carbonyl)(methyl)amino)pyridin-3-yl)methyl N-(tert-butoxycarbonyl)-N-methylglycinate (107 mg, 0.258 mmol), tetrabutylammonium iodide (95 mg, 0.258 mmol), and DBU (0.044 mL, 0.293 mmol) in DMF (2 mL) was heated overnight at 60° C. The main product was isolated by preparative HPLC (MDAP Method E) to afford (2-(methyl((1-(5-(2-(3-(trifluoromethyl)-1H-1,2,4-triazol-5-yl)imidazo[1,2-a]pyrimidin-3-yl)-1H-imidazol-1-yl)ethoxy)carbonyl)amino)pyridin-3-yl)methyl N-(tert-butoxycarbonyl)-N-methylglycinate (64 mg, 0.091 mmol, 39.1% yield). LCMS m/z 700.5 [M+H]+.

Step 2

To a solution of (2-(methyl((1-(5-(2-(3-(trifluoromethyl)-1H-1,2,4-triazol-5-yl)imidazo[1,2-a]pyrimidin-3-yl)-1H-imidazol-1-yl)ethoxy)carbonyl)amino)pyridin-3-yl)methyl N-(tert-butoxycarbonyl)-N-methylglycinate (64 mg, 0.091 mmol) in DCM (2 mL), TFA (2 mL, 26.0 mmol) was added and the mixture was stirred for 15 minutes. The solvent was evaporated and the product was isolated by preparative HPLC (MDAP Method A) to afford 24 mg of an off-white lyophile. The lyophile was dissolved in a minimal volume of ACN, 4M HCl in dioxane (0.114 mL, 0.457 mmol) was added and the solvents were evaporated. The HCl treatment was repeated one more time then the residue was dissolved in 3 mL water and was lyophilized to afford (2-(methyl((1-(5-(2-(3-(trifluoromethyl)-1H-1,2,4-triazol-5-yl)imidazo[1,2-a]pyrimidin-3-yl)-1H-imidazol-1-yl)ethoxy)carbonyl)amino)pyridin-3-yl)methyl methylglycinate, hydrochloride

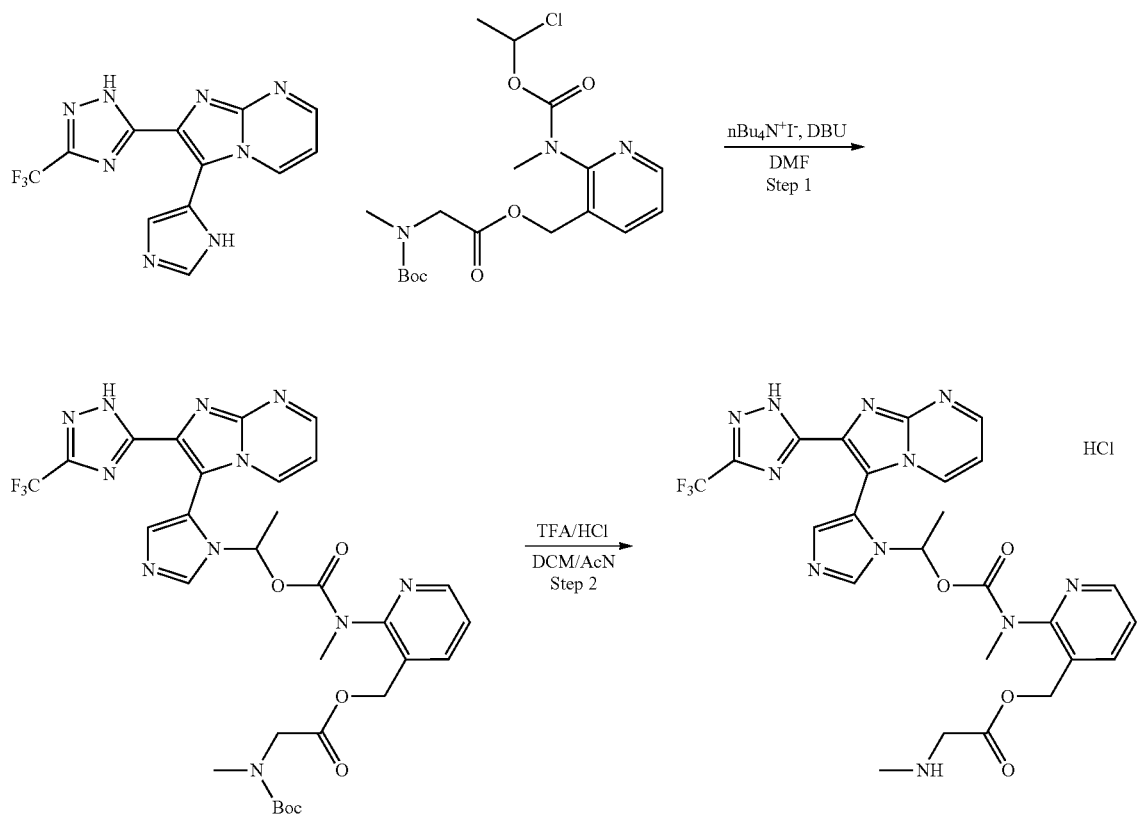

(20 mg, 0.031 mmol, 34.4% yield) as an off-white lyophile. LCMS m/z 600.2 [M+H]+. The structure was confirmed by 2D NMR (HMBC).

Example 26, Example 27, and Example 28

2-(methylamino)ethyl (4-{2-[3-(trifluoromethyl)-1H-1,2,4-triazol-5-yl]imidazo[1,2-a]pyrimidin-3-yl}-1H-imidazol-1-yl)methyl carbonate, 2 trifluoroacetic acid salt
[4-(2-{1-[({[2-(methylamino)ethoxy]carbonyl}oxy)methyl]-3-(trifluoromethyl)-1H-1,2,4-triazol-5-yl}imidazo[1,2-a]pyrimidin-3-yl)-1H-imidazol-1-yl] methyl 2-(methylamino)ethyl carbonate, 2 trifluoroacetic acid salt
{5-[3-(1H-imidazol-5-yl)imidazo[1,2-a]pyrimidin-2-yl]-3-(trifluoromethyl)-1H-1,2,4-triazol-1-yl}methyl 2-(methylamino)ethyl carbonate, 2 trifluoroacetic acid salt Step 1

To an ice cold solution of tert-butyl (2-hydroxyethyl)(methyl)carbamate (0.986 g, 5.63 mmol), TEA (0.863 mL, 6.19 mmol), and pyridine (0.501 mL, 6.19 mmol) in DCM (40 mL), chloromethyl carbonochloridate (0.500 mL, 5.63 mmol) was added dropwise over 1 minute. The mixture was stirred at room temperature overnight. 1N HCl (20 mL, 20.00 mmol) was added, stirred vigorously for 2 minutes then the layers were separated. The aqueous layer was further extracted with DCM (2×5 mL), the combined organic layer was washed with sat. aq sodium bicarbonate (1×), brine (1×), dried over sodium sulfate and was evaporated to afford tert-butyl (2-(((chloromethoxy)carbonyl)oxy)ethyl)(methyl)carbamate (1.098 g, 2.71 mmol, 48.1% yield) as a colorless oil. The product was contaminated with 33% starting material (by 1H-NMR), but was used in the next step without further purification.

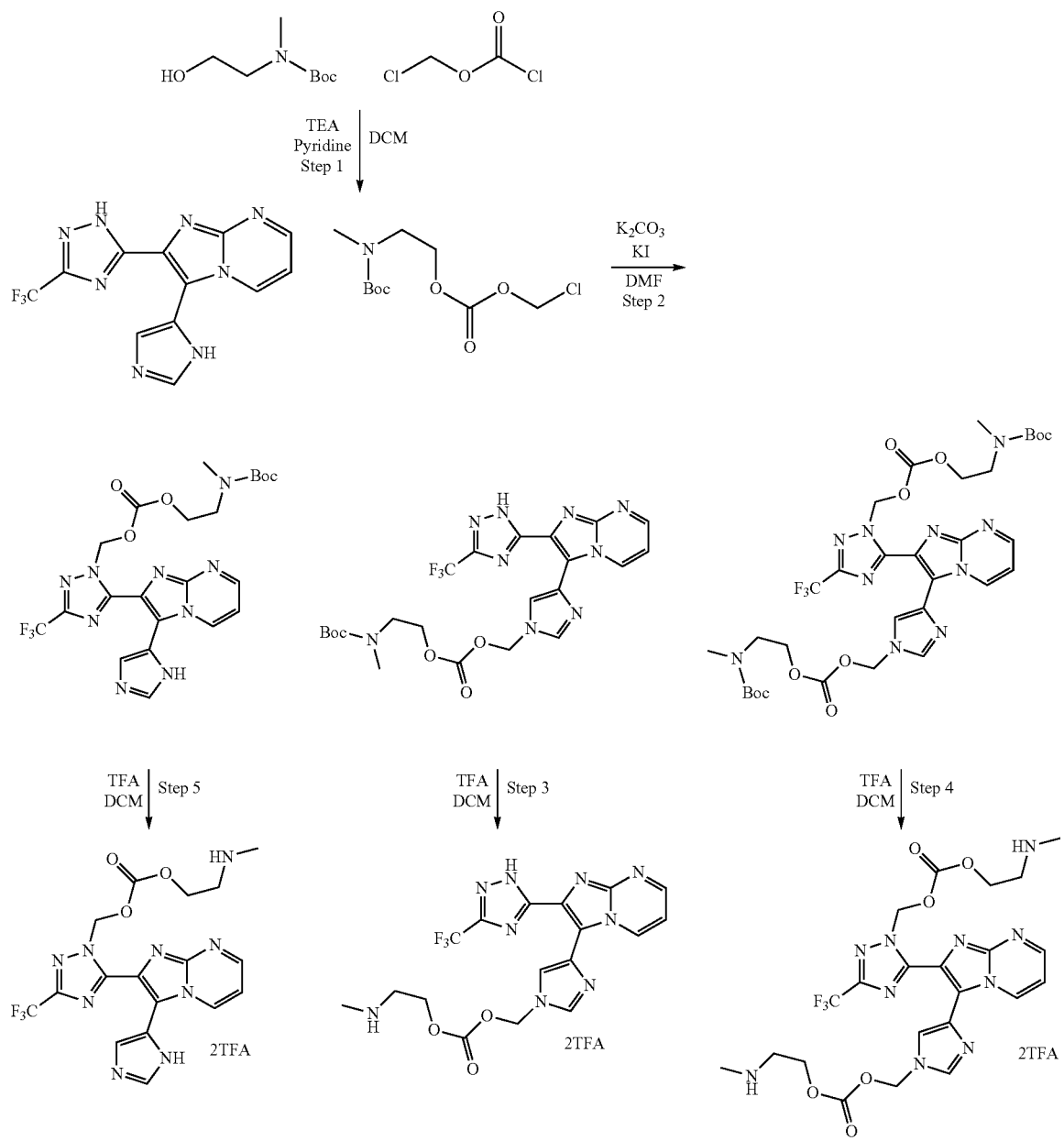

¹H NMR (400 MHz, CHLOROFORM-d) δ 5.75 (s, 2H), 4.29-4.43 (m, 2H), 3.50-3.61 (m, 2H), 2.94 (s, 3H), 1.48 (s, 9H)

Step 2

3-(1H-imidazol-5-yl)-2-(3-(trifluoromethyl)-1H-1,2,4-triazol-5-yl)imidazo[1,2-a]pyrimidine (100 mg, 0.312 mmol, Example 1), tert-butyl (2-(((chloromethoxy)carbonyl)oxy)ethyl)(methyl)carbamate (158 mg, 0.390 mmol), potassium carbonate (64.7 mg, 0.468 mmol), and potassium iodide (51.8 mg, 0.312 mmol) in DMF (2 mL) was stirred overnight at room temperature. The mixture was filtered and the products were isolated by preparative HPLC (MDAP Method H) to afford tert-butyl (2-(((((5-(3-(1H-imidazol-5-yl)imidazo[1,2-a]pyrimidin-2-yl)-3-(trifluoromethyl)-1H-1,2,4-triazol-1-yl)methoxy)carbonyl)oxy)ethyl)(methyl)carbamate (22 mg, 12.8% yield). LCMS m/z 552.1 [M+H]⁺. The structure was confirmed after deprotection in Step 5.

tert-butyl methyl(2-(((((4-(2-(3-(trifluoromethyl)-1H-1,2,4-triazol-5-yl)imidazo[1,2-a]pyrimidin-3-yl)-1H-imidazol-1-yl)methoxy)carbonyl)oxy)ethyl)carbamate (24 mg, 13.9% yield). LCMS m/z 552.09 [M+H]⁺. The structure was confirmed after deprotection in Step 3.

tert-butyl methyl(2-(((((3-(trifluoromethyl)-5-(3-(1-(7,10,10-trimethyl-3,8-dioxo-2,4,9-trioxa-7-azaundecyl)-1H-imidazol-4-yl)imidazo[1,2-a]pyrimidin-2-yl)-1H-1,2,4-triazol-1-yl)methoxy)carbonyl)oxy)ethyl)carbamate (35 mg, 14.3% yield). LCMS m/z 783.28 [M+H]⁺. The structure was confirmed after deprotection in Step 4. Step 3

A solution of tert-butyl methyl(2-(((((4-(2-(3-(trifluoromethyl)-1H-1,2,4-triazol-5-yl)imidazo[1,2-a]pyrimidin-3-yl)-1H-imidazol-1-yl)methoxy)carbonyl)oxy)ethyl)carbamate (24 mg, 0.044 mmol), and TFA (2 mL) in DCM (2 mL) was stirred at room temperature for 10 minutes. The mixture was evaporated to dryness, the residue was dissolved in water and was lyophilized to afford 2-(methylamino)ethyl ((4-(2-(3-(trifluoromethyl)-1H-1,2,4-triazol-5-yl)imidazo[1,2-a]pyrimidin-3-yl)-1H-imidazol-1-yl)methyl) carbonate, 2 trifluoroacetic acid salt (Example 26) (26 mg, 0.038 mmol, 88% yield). LCMS m/z 452.3 [M+H]⁺; ¹H NMR (400 MHz, DMSO-d₆) δ 10.04 (dd, J=2.01, 7.03 Hz, 1H), 8.72-8.79 (m, 2H), 8.51-8.66 (m, 2H), 8.24 (d, J=1.25 Hz, 1H), 7.28 (dd, J=4.02, 7.03 Hz, 1H), 6.21 (s, 2H), 4.35-4.43 (m, 3H), 3.21-3.32 (m, 2H), 2.58 (t, J=5.27 Hz, 2H). The structure was confirmed with 2D NMR (HMBC).

Step 4

A solution of tert-butyl methyl(2-(((((3-(trifluoromethyl)-5-(3-(1-(7,10,10-trimethyl-3,8-dioxo-2,4,9-trioxa-7-azaundecyl)-1H-imidazol-4-yl)imidazo[1,2-a]pyrimidin-2-yl)-1H-1,2,4-triazol-1-yl)methoxy)carbonyl)oxy)ethyl)carbamate (35 mg, 0.045 mmol), and TFA (2 mL, 26.0 mmol) in DCM (2 mL) was stirred at room temperature for 10 minutes. The mixture was evaporated to dryness, the residue was dissolved in water and was lyophilized to afford (5-(3-(1-(((2-(methylamino)ethoxy)carbonyl)oxy)methyl)-1H-imidazol-4-yl)imidazo[1,2-a]pyrimidin-2-yl)-3-(trifluoromethyl)-1H-1,2,4-triazol-1-yl)methyl (2-(methylamino)ethyl) carbonate, 2 trifluoroacetic acid salt (Example 27) (37 mg, 0.046 mmol, 102% yield). LCMS m/z 583.1 [M+H]⁺; ¹H NMR (400 MHz, DMSO-d₆) δ 9.82 (dd, J=2.01, 7.28 Hz, 1H), 8.79 (dd, J=2.01, 4.02 Hz, 1H), 8.54-8.71 (m, 4H), 8.40 (d, J=1.25 Hz, 1H), 8.24 (d, J=1.25 Hz, 1H), 7.31 (dd, J=4.02, 7.03 Hz, 1H), 6.79 (s, 2H), 6.18 (s, 2H), 4.34-4.43 (m, 4H), 3.22-3.31 (m, J=1.00 Hz, 4H), 2.54-2.64 (m, 6H). The structure was confirmed with 2D NMR (HMBC).

Step 5

A solution of tert-butyl (2-(((((5-(3-(1H-imidazol-5-yl)imidazo[1,2-a]pyrimidin-2-yl)-3-(trifluoromethyl)-1H-1,2,4-triazol-1-yl)methoxy)carbonyl)oxy)ethyl)(methyl)carbamate (22 mg, 0.040 mmol), and TFA (2 mL, 26.0 mmol) in DCM (2 mL) was stirred at room temperature for 10 minutes. The mixture was evaporated to dryness, the residue was dissolved in water (a little ACN was needed) and was lyophilized to afford (5-(3-(1H-imidazol-5-yl)imidazo[1,2-a]pyrimidin-2-yl)-3-(trifluoromethyl)-1H-1,2,4-triazol-1-yl)methyl (2-(methylamino)ethyl) carbonate, 2 trifluoroacetic acid salt (Example 28) (21 mg, 0.031 mmol, 77% yield) LCMS m/z 452.3 [M+H]⁺. ¹H NMR (400 MHz, DMSO-d₆) δ 9.74-9.85 (m, 1H), 8.78 (dd, J=2.01, 4.02 Hz, 1H), 8.45-8.58 (m, 2H), 8.20 (s, 2H), 7.30 (dd, J=4.02, 7.03 Hz, 1H), 6.81 (s, 2H), 4.35-4.42 (m, 2H), 3.22-3.30 (m, 2H), 2.54-2.60 (m, 3H). The structure was confirmed with 2D NMR (HMBC, 15N HMBC).

Example 29 and Example 30

{4-oxo-4-[(4-{2-[3-(trifluoromethyl)-1H-1,2,4-triazol-5-yl]imidazo[1,2-a]pyrimidin-3-yl}-1H-imidazol-1-yl)methoxy]butoxy}phosphonic acid, trifluoroacetic acid salt {4-oxo-4-[(5-{3-[1-({[4-(phosphonooxy)butanoyl]oxy}methyl)-1H-imidazol-4-yl]imidazo[1,2-a]pyrimidin-2-yl}-3-(trifluoromethyl)-1H-1,2,4-triazol-1-yl)methoxy]butoxy}phosphonic acid, trifluoroacetic acid salt

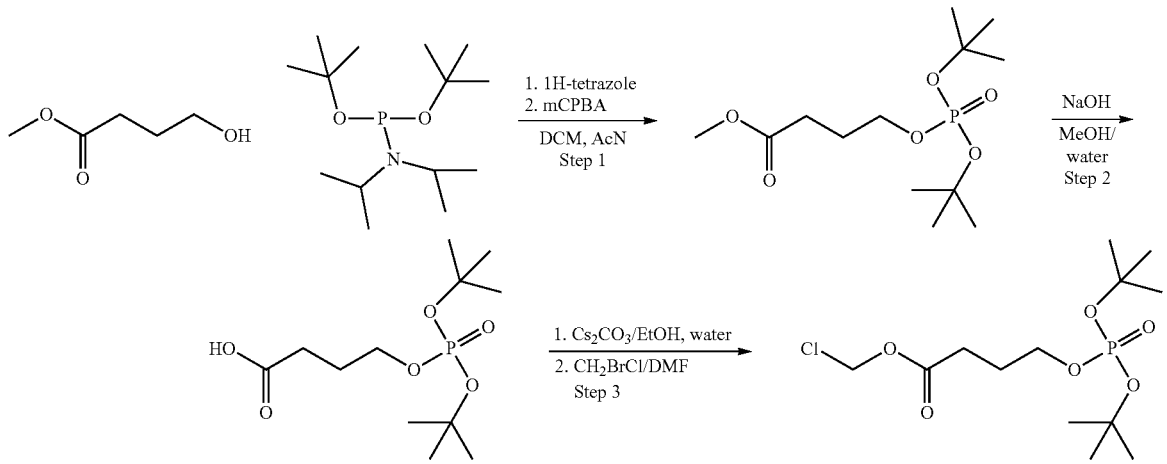

153

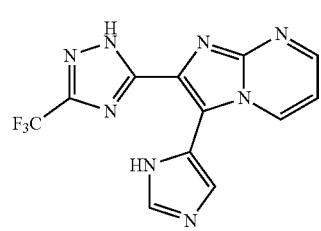

-continued

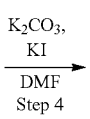

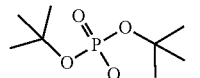

154

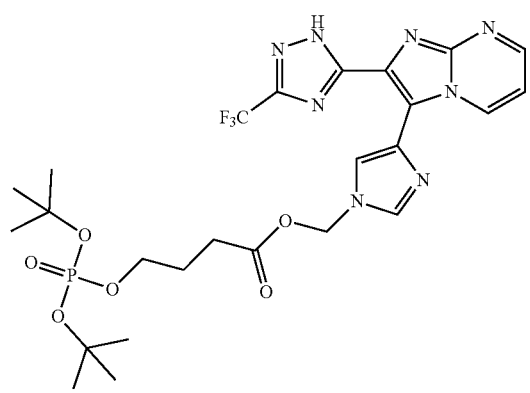

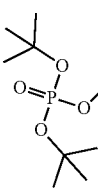

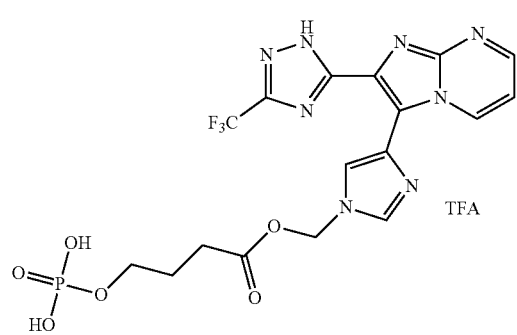

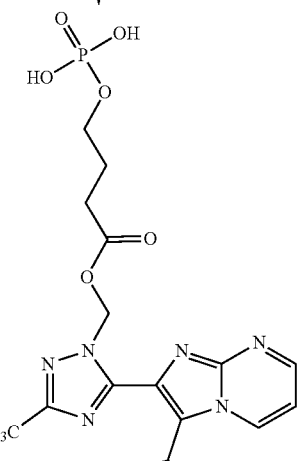

Step 1

A solution of methyl 4-hydroxybutanoate (1.170 g, 9.90 mmol) and di-tert-butyl diisopropylphosphoramidite (4.69 mL, 14.86 mmol) in DCM (20 mL) was evaporated to dryness and was dried under high vacuum for 30 minutes. The mixture was azeotroped with acetonitrile (20 mL) then was dissolved in acetonitrile (60.00 mL) and evaporated to about half its volume. A solution of 0.45M 1H-tetrazole in acetonitrile (44.0 mL, 19.81 mmol) was added. Immediately, a white precipitate started to form. The mixture was stirred at room temperature for 1.5 hr and then it was cooled to 0° C. and mCPBA (5.55 g, 24.76 mmol) (77% purity) was introduced. The mixture was stirred at 0° C. for 10 minutes then 1 hr at room temperature. Sodium sulfite (3.12 g, 24.76 mmol), dissolved in 40 mL water, was added to quench the excess mCPBA; the acetonitrile was distilled off. The residue was partitioned between water (30 mL) and EtOAc (50 mL), the organic phase was washed with water (1×), saturated aq sodium bicarbonate (2×), water (1×), brine (1×), dried over sodium sulfate and was evaporated to afford the crude product as an oil (3.4 g). The crude product was purified in two batches (0.5 g/2.9 g) by silica gel chromatography (24 g/120 g Isco RediSep Rf Gold column, eluting with 0-20% (EtOAC/EtOH 3/1 in hexanes) to afford methyl 4-((di-tert-butoxyphosphoryl)oxy)butanoate (1.043 g, 33.9% yield). $^1$H NMR (400 MHz, DMSO-$d_6$) δ 3.88 (q, J=6.36 Hz, 2H), 3.60 (s, 3H), 2.40 (t, J=7.28 Hz, 2H), 1.80-1.89 (m, 2H), 1.41 (s, 18H).

Step 2

To a stirred cold solution of methyl 4-((di-tert-butoxyphosphoryl)oxy)butanoate (1.043 g, 3.36 mmol) in methanol (15 mL) and water (3 mL) was added 5M aq NaOH (2.017 mL, 10.08 mmol) and the stirring was continued at 0° C. for 5 hrs. A solution of 6M aq HCl (1.680 mL, 10.08 mmol) was added then the MeOH was distilled off. The residue was extracted with EtOAc (2×), the organic phase washed with brine (1×), dried over sodium sulfate and was evaporated to afford 4-((di-tert-butoxyphosphoryl)oxy)butanoic acid (876 mg, 2.96 mmol, 88% yield) as a colorless oil. $^1$H NMR (400 MHz, DMSO-$d_6$) δ 12.11 (br s, 1H), 3.88 (q, J=6.53 Hz, 2H), 2.31 (t, J=7.28 Hz, 2H), 1.81 (quin, J=6.84 Hz, 2H), 1.41 (s, 18H). $^{31}$P NMR (162 MHz, DMSO-$d_6$) δ −9.89 (br t, J=5.87 Hz, 1P).

Step 3

To a solution of 4-((di-tert-butoxyphosphoryl)oxy)butanoic acid (680 mg, 2.295 mmol) in ethanol (12 mL) was added cesium carbonate (374 mg, 1.147 mmol) dissolved in water (2 mL), and the mixture was stirred until the gas evolution seized (about 15 minutes). The solvents were evaporated and the residue dried overnight in high vacuum to afford cesium 4-((di-tert-butoxyphosphoryl)oxy)butanoate (976 mg, 2.279 mmol, 99% yield) as a colorless oil.

The dry Cs-salt was dissolved in DMF (9 mL), bromochloromethane (9.70 mL, 149 mmol) was added and the solution was stirred at RT overnight. The CsBr precipitate was filtered off, and the solution was evaporated. The residue was partitioned between water and EtOAc, the organic phase washed with water (1×), brine (1×), dried over sodium sulfate and was evaporated to afford chloromethyl 4-((di-tert-butoxyphosphoryl)oxy)butanoate (723 mg, 2.097 mmol, 91% yield) as a colorless oil; $^1$H NMR (400 MHz, DMSO-$d_6$) δ 5.86 (s, 2H), 3.89 (q, J=6.36 Hz, 2H), 1.80-1.93 (m, 2H), 1.41 (m, 20H).

Step 4

A suspension of 3-(1H-imidazol-5-yl)-2-(3-(trifluoromethyl)-1H-1,2,4-triazol-5-yl)imidazo[1,2-a]pyrimidine (100 mg, 0.312 mmol, Example 1), chloromethyl 4-((di-tert-butoxyphosphoryl)oxy)butanoate (118 mg, 0.343 mmol), potassium iodide (51.8 mg, 0.312 mmol), and potassium carbonate (86 mg, 0.625 mmol) in DMF (1 mL) was stirred at RT overnight. The mixture was filtered and separated by preparative HPLC (MDAP Method H) to afford (4-(2-(3-(trifluoromethyl)-1H-1,2,4-triazol-5-yl)imidazo[1,2-a]pyrimidin-3-yl)-1H-imidazol-1-yl)methyl 4-((di-tert-butoxyphosphoryl)oxy)butanoate (78 mg, 0.124 mmol, 39.7% yield) as a pale yellow oil. LCMS m/z 629.3 [M+H]$^+$ and (5-(3-(1-(((4-((di-tert-butoxyphosphoryl)oxy)butanoyl)oxy)methyl)-1H-imidazol-4-yl)imidazo[1,2-a]pyrimidin-2-yl)-3-(trifluoromethyl)-1H-1,2,4-triazol-1-yl)methyl 4-((di-tert-butoxyphosphoryl)oxy)butanoate (53 mg, 0.057 mmol, 18.12% yield) as a pale yellow oil. LCMS m/z 937.4 [M+H]$^+$.

Step 5

(4-(2-(3-(Trifluoromethyl)-1H-1,2,4-triazol-5-yl)imidazo[1,2-a]pyrimidin-3-yl)-1H-imidazol-1-yl)methyl 4-((di-tert-butoxyphosphoryl)oxy)butanoate ((4-(2-(3-(trifluoromethyl)-1H-1,2,4-triazol-5-yl)imidazo[1,2-a]pyrimidin-3-yl)-1H-imidazol-1-yl)methyl 4-((di-tert-butoxyphosphoryl)oxy)butanoate (78 mg, 0.124 mmol) was dissolved in TFA (2 mL, 26.0 mmol), let stand for 10 minutes then was evaporated, was co-evaporated with 3 mL ACN (2×) and was dried. The residue was dissolved in water and was lyophilized to afford (4-(2-(3-(trifluoromethyl)-1H-1,2,4-triazol-5-yl)imidazo[1,2-a]pyrimidin-3-yl)-1H-imidazol-1-yl)methyl 4-(phosphonooxy)butanoate, trifluoroacetic acid salt (Example 29) (66 mg, 0.105 mmol, 33.5% yield) as a beige lyophile. LCMS m/z 517.2 [M+H]$^+$. $^1$H NMR (400 MHz, DMSO-$d_6$) δ 15.70 (br s, 1H), 9.95 (dd, J=1.96, 7.09 Hz, 1H), 8.75 (dd, J=2.08, 4.03 Hz, 1H), 8.64 (d, J=1.22 Hz, 1H), 8.25 (d, J=1.22 Hz, 1H), 7.26 (dd, J=4.16, 7.09 Hz, 1H), 6.13 (s, 2H), 3.78-3.89 (m, 2H), 2.43-2.49 (m, J=7.50, 7.50 Hz, 2H), 1.84 (quin, J=6.91 Hz, 2H). The two phosphate H were not observed. The structure was confirmed with 2D NMR (ROESY).

Step 6

(5-(3-(1-(((4-((Di-tert-butoxyphosphoryl)oxy)butanoyl)oxy)methyl)-1H-imidazol-4-yl)imidazo[1,2-a]pyrimidin-2-yl)-3-(trifluoromethyl)-1H-1,2,4-triazol-1-yl)methyl 4-((di-tert-butoxyphosphoryl)oxy)butanoate (53 mg, 0.057 mmol) was dissolved in TFA (2 mL, 26.0 mmol), let stand for 10 minutes then was evaporated, was co-evaporated with 3 mL ACN (2×) and was dried. The residue was dissolved in water and was lyophilized to afford (5-(3-(1-(((4-(phosphonooxy)butanoyl)oxy)methyl)-1H-imidazol-4-yl)imidazo[1,2-a]pyrimidin-2-yl)-3-(trifluoromethyl)-1H-1,2,4-triazol-1-yl)methyl 4-(phosphonooxy)butanoate, trifluoroacetic acid salt (Example 30) (39 mg, 0.047 mmol, 15.11% yield) as a beige lyophile. LCMS m/z 713.05 [M+H]$^+$. $^1$H NMR (400 MHz, DMSO-$d_6$) δ 9.76 (dd, J=2.20, 7.09 Hz, 1H), 8.77 (dd, J=1.96, 4.16 Hz, 1H), 8.26 (d, J=1.47 Hz, 1H), 8.21 (d, J=1.22 Hz, 1H), 7.28 (dd, J=4.03, 6.97 Hz, 1H), 6.69 (s, 2H), 6.09 (s, 2H), 3.75-3.89 (m, 4H), 2.39-2.48 (m, 4H), 1.73-1.90 (m, 4H). The four phosphate H were not observed. The structure was confirmed with 2D NMR (ROESY, HMBC, 15N HMBC)

Example 31, Example 32, and Example 33

3-({[(4-{2-[1-({[(2-carboxyethoxy)carbonyl]oxy}methyl)-3-(trifluoromethyl)-1H-1,2,4-triazol-5-yl]imidazo[1,2-a]pyrimidin-3-yl}-1H-imidazol-1-yl)methoxy]carbonyl}oxy)propanoic acid, trifluoroacetic acid salt 3-({[(4-{2-[3-(trifluoromethyl)-1H-1,2,4-triazol-5-yl]imidazo[1,2-a]pyrimidin-3-yl}-1H-imidazol-1-yl)methoxy]carbonyl}oxy)propanoic acid, 0.5 trifluoroacetic acid salt 3-{[({5-[3-(1H-imidazol-5-yl)imidazo[1,2-a]pyrimidin-2-yl]-3-(trifluoromethyl)-1H-1,2,4-triazol-1-yl}methoxy)carbonyl]oxy}propanoic acid, 2 trifluoroacetic acid salt

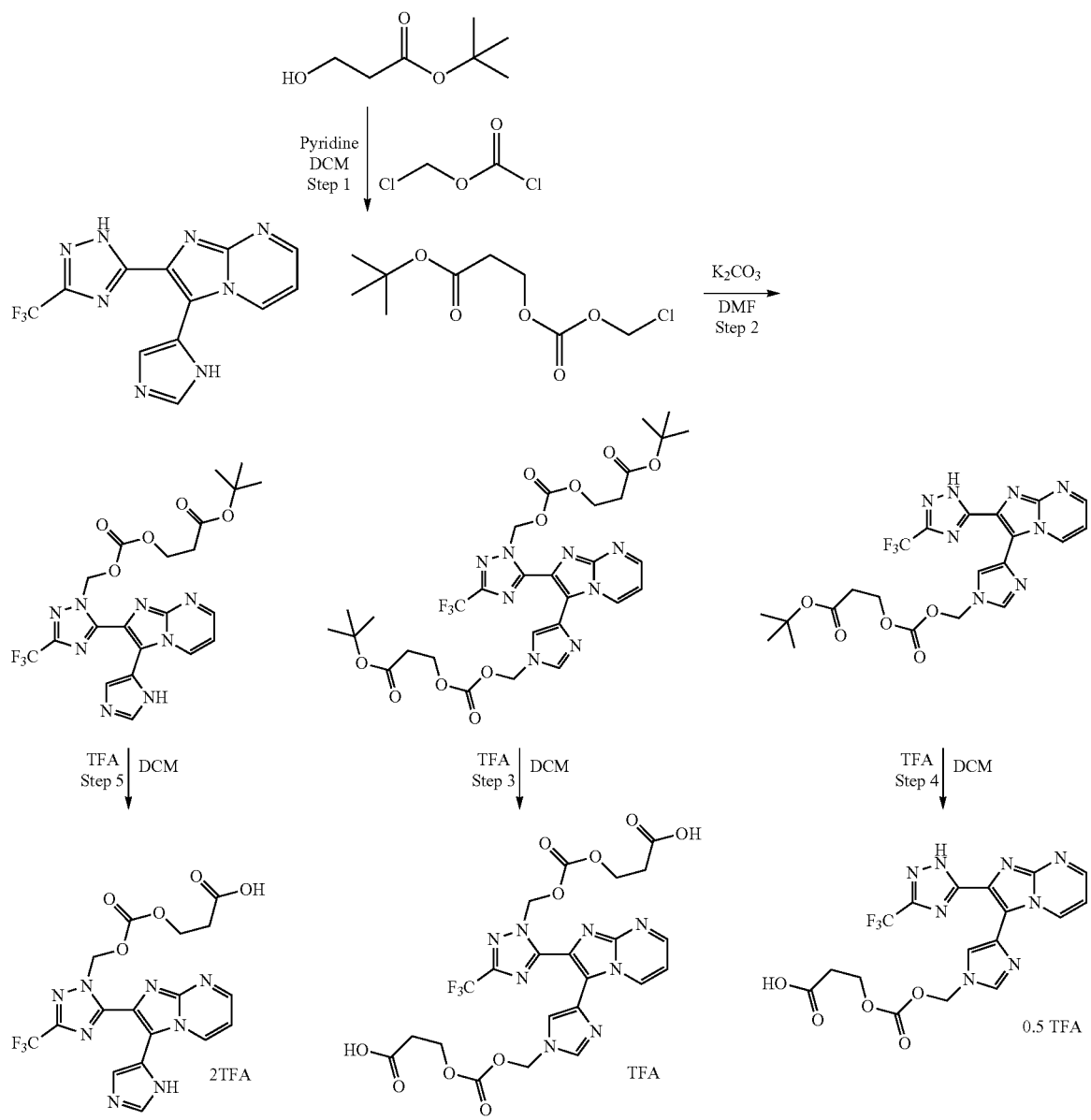

Step 1

To an ice-cold solution of tert-butyl 3-hydroxypropanoate (1 g, 6.84 mmol) and pyridine (0.609 mL, 7.52 mmol) in DCM (25 mL), chloromethyl carbonochloridate (0.608 mL, 6.84 mmol) was added dropwise over about 1 minute. The mixture was stirred at room temperature overnight. A solution of 1N aq HCl (20 mL, 658 mmol) was added, the mixture was stirred vigorously for 2 minutes and then the layers were separated. The aqueous layer was further extracted with DCM (2×5 mL), the combined organic layer was washed with sat. aq sodium bicarbonate (1×), brine (1×), dried over sodium sulfate and was evaporated to afford tert-butyl 3-(((chloromethoxy)carbonyl)oxy)propanoate (1.468 g, 6.15 mmol, 90% yield) as a colorless oil.

$^1$H NMR (400 MHz, CHLOROFORM-d) δ 5.77 (s, 2H), 4.50 (t, J=6.46 Hz, 2H), 2.68 (t, J=6.34 Hz, 2H), 1.50 (s, 9H).

Step 2

A suspension of 3-(1H-imidazol-5-yl)-2-(3-(trifluoromethyl)-1H-1,2,4-triazol-5-yl)imidazo[1,2-a]pyrimidine (100 mg, 0.312 mmol, Example 1), tert-butyl 3-(((chloromethoxy)carbonyl)oxy)propanoate (93 mg, 0.390 mmol), potassium carbonate (64.7 mg, 0.468 mmol) in DMF (2 mL) was stirred overnight. The mixture was filtered and the products were isolated by preparative HPLC (MDAP Method H) to afford tert-butyl 3-((((5-(3-(1H-imidazol-5-yl)imidazo[1,2-a]pyrimidin-2-yl)-3-(trifluoromethyl)-1H-1,2,4-triazol-1-yl)methoxy)carbon yl)oxy)propanoate (14 mg, 8.6% yield). MS ES+ m/z 523.1 [M+H]$^+$. The structure was confirmed after deprotection in Step 5.

Tert-butyl 3-(((((5-(3-(1-((((3-(tert-butoxy)-3-oxopropoxy)carbonyl)oxy)methyl)-1H-imidazol-4-yl)imidazo[1,2-a]pyrimidin-2-yl)-3-(trifluoromethyl)-1H-1,2,4-triazol-1-yl)methoxy)carbonyl)oxy)propanoate (73 mg, 32.3% yield). MS ES+ m/z 725.2 [M+H]$^+$. The structure was confirmed after deprotection in Step 3.

Tert-butyl 3-((((4-(2-(3-(trifluoromethyl)-1H-1,2,4-triazol-5-yl)imidazo[1,2-a]pyrimidin-3-yl)-1H-imidazol-1-yl)

methoxy)carbonyl)oxy)propanoate (25 mg, 15.3% yield). MS ES+ m/z 523.1 [M+H]⁺. The structure was confirmed after deprotection in Step 4.

Step 3

A solution of tert-butyl 3-(((((5-(3-(1-((((3-(tert-butoxy)-3-oxopropoxy)carbonyl)oxy)methyl)-1H-imidazol-4-yl)imidazo[1,2-a]pyrimidin-2-yl)-3-(trifluoromethyl)-1H-1,2,4-triazol-1-yl)methoxy)carbonyl)oxy)propanoate (73 mg, 0.101 mmol), and TFA (2 mL, 26.0 mmol) in DCM (2 mL) was stirred at room temperature for 1 hr. The mixture was evaporated to dryness, the residue was dissolved in water (a little ACN was needed) and was lyophilized to afford 3-(((((5-(3-(1-((((2-carboxyethoxy)carbonyl)oxy)methyl)-1H-imidazol-4-yl)imidazo[1,2-a]pyrimidin-2-yl)-3-(trifluoromethyl)-1H-1,2,4-triazol-1-yl)methoxy)carbonyl)oxy)propanoic acid, trifluoroacetic acid salt (Example 31) (75 mg, 0.103 mmol, 100% yield). LCMS m/z 613.1; ¹H NMR (400 MHz, DMSO-d₆) δ 9.77 (dd, J=2.01, 7.03 Hz, 1H), 8.77 (dd, J=2.01, 4.02 Hz, 1H), 8.32 (d, J=1.25 Hz, 1H), 8.24 (d, J=1.25 Hz, 1H), 7.29 (dd, J=4.14, 7.15 Hz, 1H), 6.73 (s, 2H), 6.12 (s, 2H), 4.25-4.35 (m, 4H), 2.56-2.67 (m, 4H). The two carboxyl protons were not observed.

Step 4

A solution of tert-butyl 3-(((((4-(2-(3-(trifluoromethyl)-1H-1,2,4-triazol-5-yl)imidazo[1,2-a]pyrimidin-3-yl)-1H-imidazol-1-yl)methoxy)carbonyl)oxy)propanoate (25 mg, 0.048 mmol), and TFA (2 mL, 26.0 mmol) in DCM (2 mL) was stirred at room temperature for 1 hr. The mixture was evaporated to dryness, the residue was dissolved in water (a little ACN was needed) and was lyophilized to afford 3-(((((4-(2-(3-(trifluoromethyl)-1H-1,2,4-triazol-5-yl)imidazo[1,2-a]pyrimidin-3-yl)-1H-imidazol-1-yl)methoxy)carbonyl)oxy)propanoic acid, 0.5 trifluoroacetic acid salt (Example 32) (25 mg, 0.047 mmol, 97% LCMS m/z 467.2 [M+H]⁺. ¹H NMR (400 MHz, DMSO-d₆) δ 15.71 (br s, 1H), 9.99 (dd, J=2.01, 7.03 Hz, 1H), 8.75 (dd, J=2.01, 4.02 Hz, 1H), 8.69 (d, J=1.26 Hz, 1H), 8.24 (d, J=1.25 Hz, 1H), 7.26 (dd, J=4.02, 7.03 Hz, 1H), 6.16 (s, 2H), 4.32 (t, J=6.15 Hz, 2H), 2.63 (t, J=6.15 Hz, 2H). The triazole NH was not observed.

Step 5

A solution of tert-butyl 3-(((((5-(3-(1H-imidazol-5-yl)imidazo[1,2-a]pyrimidin-2-yl)-3-(trifluoromethyl)-1H-1,2,4-triazol-1-yl)methoxy)carbonyl)oxy)propanoate (14 mg, 0.027 mmol), and TFA (2 mL, 26.0 mmol) in DCM (2 mL) was stirred at room temperature for 1 hr. The mixture was evaporated to dryness, the residue was dissolved in water (a little ACN was needed) and was lyophilized to afford 3-(((((5-(3-(1H-imidazol-5-yl)imidazo[1,2-a]pyrimidin-2-yl)-3-(trifluoromethyl)-1H-1,2,4-triazol-1-yl)methoxy)carbonyl)oxy)propanoic acid, 2 trifluoroacetic acid salt (Example 33) (14 mg, 0.020 mmol, 75% yield). LCMS m/z 467.16 [M+H]⁺; ¹H NMR (400 MHz, DMSO-d₆) δ 9.39-9.51 (m, 1H), 8.82 (dd, J=2.03, 4.06 Hz, 1H), 8.63-8.77 (m, 1H), 8.20 (d, J=1.27 Hz, 1H), 7.29-7.37 (m, 1H), 6.81 (s, 2H), 4.30 (t, J=6.21 Hz, 2H), 2.60 (t, J=6.08 Hz, 2H). The carboxyl and imidazole H were not observed.

Example 34

({5-[6-fluoro-3-(1H-imidazol-5-yl)imidazo[1,2-a]pyrimidin-2-yl]-3-(trifluoromethyl)-1H-1,2,4-triazol-1-yl}methoxy)phosphonic acid

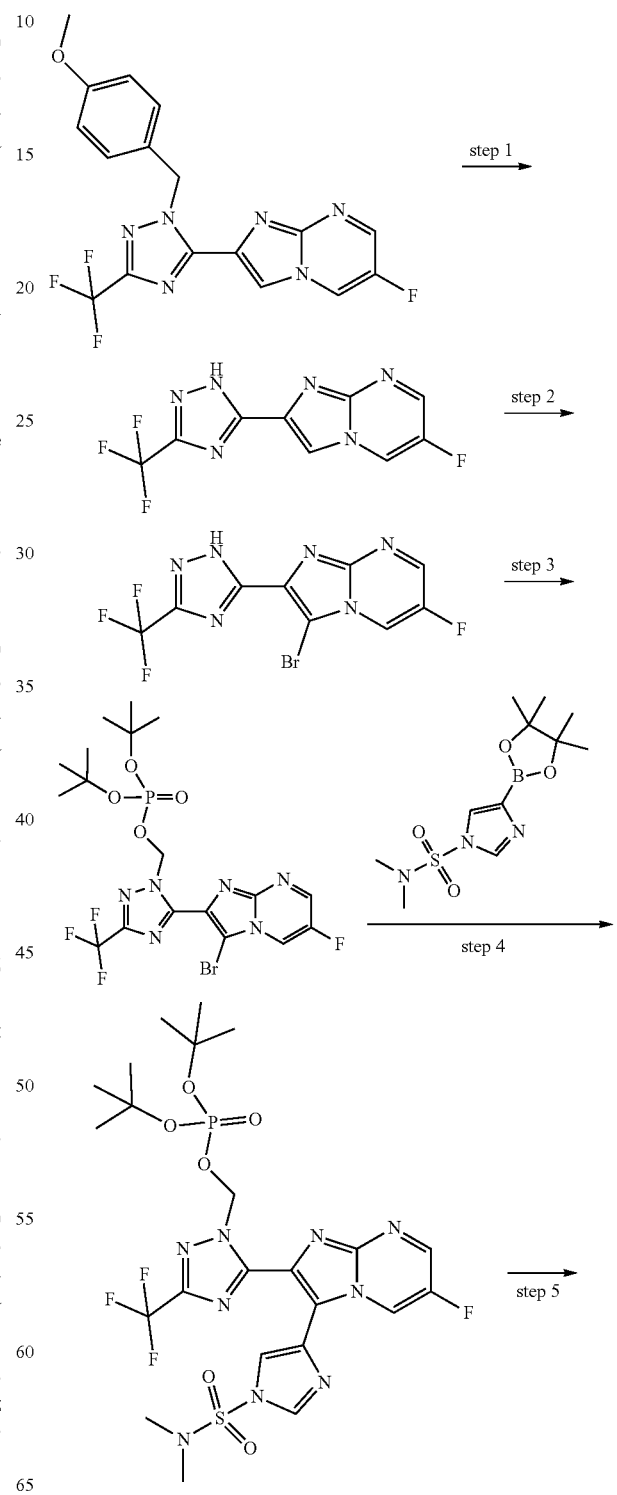

-continued

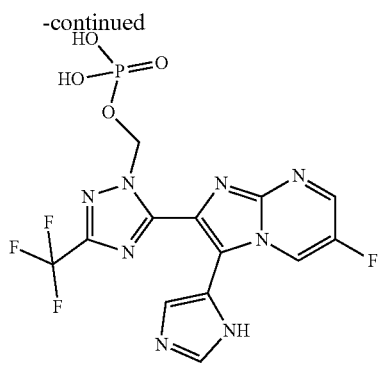

Step 1

A mixture of 6-fluoro-2-(1-(4-methoxybenzyl)-3-(trifluoromethyl)-1H-1,2,4-triazol-5-yl)imidazo[1,2-a]pyrimidine (24 g, 61.2 mmol, prepared for example according to Step 1 of Example 2) and TFA (90 ml, 1168 mmol) was heated at 70° C. for 10 hours. The mixture was cooled, poured onto ice, and then carefully neutralized with potassium carbonate to ~pH 7.

The aqueous layer was extracted with ethyl acetate (3×200 mL) and the combined extracts were washed with water and brine then dried (anhydrous $Na_2SO_4$) and evaporated onto ISOLUTE® HM-N absorbent and purified by flash chromatography (CombiFlash® RF using a 330 g Redisep RF Gold® silica gel column, 0-10% ethyl acetate in dichloromethane) to give the crude product.

Trituration with TBME (200 mL) gave a tan solid that was collected and washed with TBME and hexanes to give 6-fluoro-2-(3-(trifluoromethyl)-1H-1,2,4-triazol-5-yl)imidazo[1,2-a]pyrimidine (13.2 g, 48.5 mmol, 79% yield). LCMS electrospray, me/z 273.1 (M+H$^+$); $^1$H NMR (400 MHz, DMSO-d6) δ ppm 15.76 (br s, 1H) 9.32 (dd, J=4.40, 2.93 Hz, 1H) 8.90 (d, J=2.93 Hz, 1H) 8.55 (s, 1H).

Step 2

A suspension of 6-fluoro-2-(3-(trifluoromethyl)-1H-1,2,4-triazol-5-yl)imidazo[1,2-a]pyrimidine (11.5 g, 42.3 mmol) and NBS (8.27 g, 46.5 mmol) in chloroform (200 mL) was stirred at ambient temperature for 2 hours. The mixture was filtered through a porcelain filter with a paper filter using vacuum filtration and the cake washed with dichloromethane and hexanes to give 3-bromo-6-fluoro-2-(3-(trifluoromethyl)-1H-1,2,4-triazol-5-yl)imidazo[1,2-a]pyrimidine (12.0 g, 34.2 mmol, 81% yield) product as a yellow solid. 1H NMR (400 MHz, DMSO-d6) δ ppm 15.87 (s, 1H) 9.32 (dd, J=3.91, 2.93 Hz, 1H) 8.96 (d, J=2.45 Hz, 1H); LCMS m/e 351.0.

Step 3

A suspension of 3-bromo-6-fluoro-2-(3-(trifluoromethyl)-1H-1,2,4-triazol-5-yl)imidazo[1,2-a]pyrimidine (11.6 g, 33.0 mmol) and potassium carbonate (13.70 g, 99 mmol) in N,N-dimethylformamide (120 mL) was stirred vigorously at 55° C. and di-tert-butyl (chloromethyl) phosphate (15.54 mL, 66.1 mmol) was added and the mixture stirred overnight.

The mixture was poured into water (1 L) and extracted with ethyl acetate (×3). The combined organic extracts were washed with water (×2) and brine, dried over anhydrous $Na_2SO_4$, and evaporated.

The product was adsorbed onto Isolute® HM-N absorbent and purified by flash chromatography (CombiFlash® RF using a 330 g Redisep RF Gold® silica gel column, 0-30% ethyl acetate in dichloromethane) to give (5-(3-bromo-6-fluoroimidazo[1,2-a]pyrimidin-2-yl)-3-(trifluoromethyl)-1H-1,2,4-triazol-1-yl)methyl di-tert-butyl phosphate (8.6 g, 15.00 mmol, 45% yield). $^1$H NMR (400 MHz, CHLOROFORM-d) δ ppm 8.71 (d, J=2.93 Hz, 1H) 8.51 (t, J=2.93 Hz, 1H) 6.69-6.75 (m, 2H) 1.45 (s, 18H); LCMS: [M+H]$^+$ 573.0, 575.0 Br pattern.

Step 4

A mixture of (5-(3-bromo-6-fluoroimidazo[1,2-a]pyrimidin-2-yl)-3-(trifluoromethyl)-1H-1,2,4-triazol-1-yl)methyl di-tert-butyl phosphate (1.0 g, 1.75 mmol), N,N-dimethyl-4-(4,4,5,5-tetramethyl-1,3,2-dioxaborolan-2-yl)-1H-imidazole-1-sulfonamide (788 mg, 2.62 mmol, Intermediate 2), cesium fluoride (530 mg, 3.5 mmol) and PdCl$_2$(dppf) (192 mg, 0.26 mmol) in 1,2-dimethoxyethane (DME) (15 mL) was sealed in a 45 mL microwave vial, stirred and heated thermally at 130° C. for 90 mins.

This reaction was performed 7 other times, and then the reaction mixtures were combined and purified as shown below.

The reaction mixture was filtered through a pad of Celite®, washed with ethyl acetate, and evaporated in vacuo. The residue was taken up in dichloromethane (50 mL) and adsorbed onto a silica gel (35 g) pre-column. Flash chromatography (CombiFlash® RF using a 40 g Redisep RF Gold® silica gel column, 0-40% ethyl acetate in dichloromethane) afforded di-tert-butyl ((5-(3-(1-(N,N-dimethylsulfamoyl)-1H-imidazol-4-yl)-6-fluoroimidazo[1,2-a]pyrimidin-2-yl)-3-(trifluoromethyl)-1H-1,2,4-triazol-1-yl)methyl) phosphate (5.6 g, 8.39 mmol, 60% yield).

$^1$H NMR (400 MHz, CHLOROFORM-d) δ ppm 9.94 (dd, J=4.40, 2.93 Hz, 1H) 8.77 (d, J=1.47 Hz, 1H) 8.72 (d, J=2.94 Hz, 1H) 8.09 (d, J=1.47 Hz, 1H) 6.78 (s, 1H) 6.76 (s, 1H) 3.00 (s, 6H) 1.42 (s, 18H); LCMS: m/e 668.2 (M+H$^+$).

Step 5

A solution of di-tert-butyl ((5-(3-(1-(N,N-dimethylsulfamoyl)-1H-imidazol-4-yl)-6-fluoroimidazo[1,2-a]pyrimidin-2-yl)-3-(trifluoromethyl)-1H-1,2,4-triazol-1-yl)methyl) phosphate (6.0 g, 8.99 mmol) in dichloromethane (5 mL) in a 250 mL round bottom flask was treated with 4M HCl in dioxane (25 mL, 100 mmol). The flask was stoppered and the reaction mixture stirred at ambient temperature for 18 hours. The reaction mixture was neutralized to ~pH 7 with 20% aqueous potassium carbonate solution and the mixture was evaporated in vacuo and azeotroped twice with ethanol to give a crude solid.

The solid was desalted by Prep HPLC as shown below.

| Purification Details: Technique: Reverse Phase |
| --- |
| Gradient (Initial % B to Final % B) |
| 3 min hold at 0% B |
| 0% to 35% B over 4.5 min |
| 2 min hold at 100% B |
| Overall Runtime: 10.5 min |
| Column: Phenomenex Gemini C18, 5 μm, 50 × 30 mm |
| Mobile Phase: |
| A: Water with 0.1% Formic Acid |
| B: Acetonitrile with 0.1% Formic Acid |
| Flow Rate: 43(mL/min) |

The product was freeze dried to give ({5-[6-fluoro-3-(1H-imidazol-5-yl)imidazo[1,2-a]pyrimidin-2-yl]-3-(trifluoromethyl)-1H-1,2,4-triazol-1-yl}methoxy)phosphonic acid (2.02 g, 4.37 mmol, 49% yield).

$^1$H NMR (400 MHz, DMSO-d$_6$) δ ppm 9.98 (dd, J=4.89, 2.93 Hz, 1H) 8.96 (d, J=2.93 Hz, 1H) 8.16 (d, J=0.98 Hz, 1H) 8.11 (s, 1H) 6.44 (d, J=10.76 Hz, 2H) (2 OH and 1 NH were not observed); LCMS: t$_{RET}$=0.41 min (gradient of 1-100% of 0.1% v/v solution of formic acid in acetonitrile to 0.1% v/v solution of formic acid in water over 1.85 min), m/e 449.1 (M+H⁺).

Example 35 and Example 36 methyl 2-(3-bromo-1H-1,2,4-triazol-5-yl)-3-(1H-pyrazol-4-yl)imidazo[1,2-a]pyrimidine-7-carboxylate methyl 2-(3-bromo-1H-1,2,4-triazol-5-yl)-3-(1H-imidazol-4-yl)imidazo[1,2-a]pyrimidine-7-carboxylate

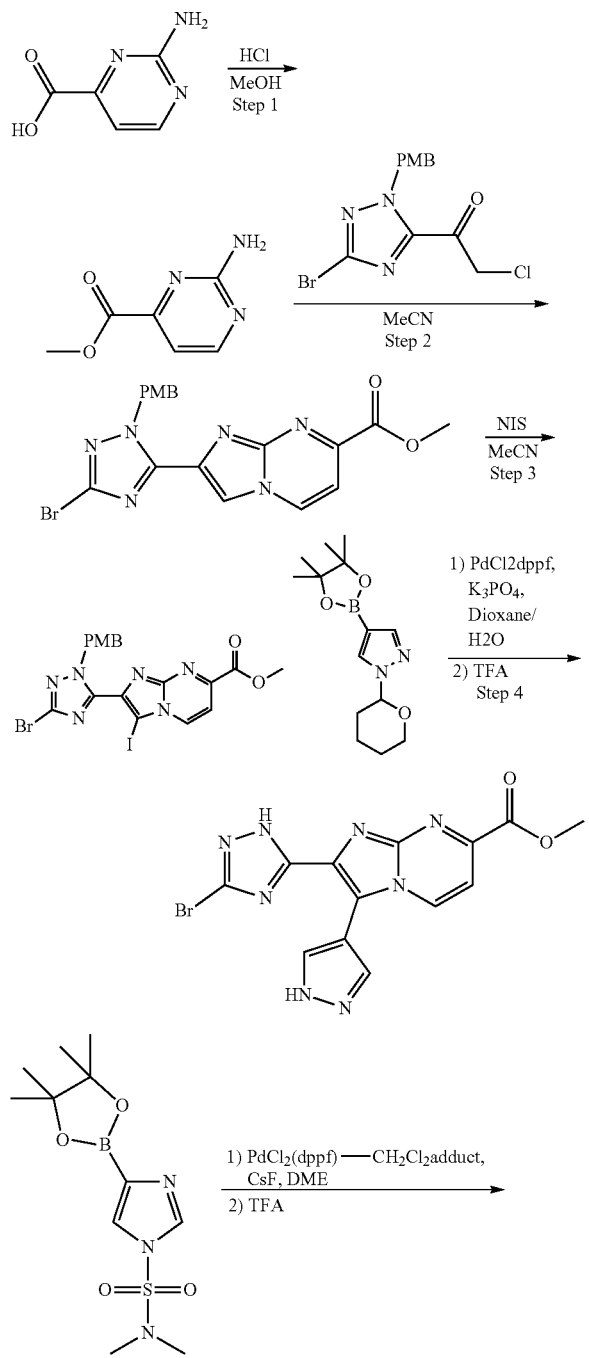

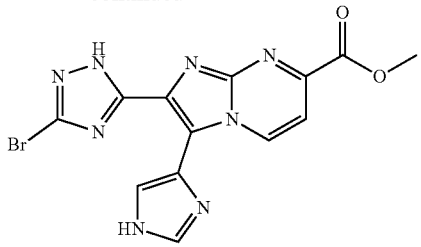

Step 1: Methyl 2-aminopyrimidine-4-carboxylate

A mixture of 2-aminopyrimidine-4-carboxylic acid (5.3 g, 38.1 mmol), 4M HCl in dioxane (20.0 mL, 80 mmol), and methanol (80.0 mL) was heated to 64° C. for 4 hrs. The reaction mixture was cooled to rt, and then an excess amount of diethylether was added to the reaction mixture. The resulting precipitate was collected by filtration, and then dried in a vacuum oven to give the desired product as a HCl salt. This material was stirred and sonicated in 160 mL of sat. aq NaHCO₃ for 20 min. Gas evolution was observed. The suspended solid was collected by filtration and washed with deionized water. The solid was dried overnight in a vacuum oven at 50° C. to yield the title compound (4.97 g, 32.5 mmol, 85% yield). 1H NMR (400 MHz, DMSO-d6) δ=8.48 (d, J=4.8 Hz, 1H), 7.05-7.10 (br s, 2H), 7.06 (d, J=5.1 Hz, 1H), 3.85 (s, 3H). LCMS: [M+H]⁺=154.0

Step 2: Methyl 2-(3-bromo-1-(4-methoxybenzyl)-1H-1,2,4-triazol-5-yl)imidazo[1,2-a]pyrimidine-7-carboxylate A mixture of 1-(3-bromo-1-(4-methoxybenzyl)-1H-1,2,4-triazol-5-yl)-2-chloroethan-1-one (520.0 mg, 1.509 mmol, Intermediate 1), and methyl 2-aminopyrimidine-4-carboxylate (462 mg, 3.02 mmol) in acetonitrile (20 mL) was heated to 115° C. overnight in a sealed reaction tube. The reaction showed very little conversion to the desired product. Another batch of methyl 2-aminopyrimidine-4-carboxylate (462 mg, 3.02 mmol) was added to the reaction mixture. The mixture was heated to 115° C. overnight in a sealed reaction tube. The reaction mixture was cooled to rt and the resulting precipitate was collected by filtration and washed with acetonitrile. The solid was vigorously stirred in 1:1 mixture of EtOAc/1 N aq HCl for 20 min to remove residual methyl 2-aminopyrimidine-4-carboxylate. The suspended solid was collected by filtration to give the title compound (423 mg, 0.96 mmol, 63% yield). 1H NMR (400 MHz, DMSO-d6) δ=9.21 (d, J=7.1 Hz, 1H), 8.78 (s, 1H), 7.75 (d, J=7.1 Hz, 1H), 7.37 (d, J=8.9 Hz, 2H), 6.91 (d, J=8.9 Hz, 2H), 6.05 (s, 2H), 3.97 (s, 3H), 3.72 (s, 3H). LCMS: [M+H]⁺=443.2, 445.2 (Br isotope peak).

Step 3: Methyl 2-(3-bromo-1-(4-methoxybenzyl)-1H-1,2,4-triazol-5-yl)-3-iodoimidazo[1,2-a]pyrimidine-7-carboxylate A mixture of methyl 2-(3-bromo-1-(4-methoxybenzyl)-1H-1,2,4-triazol-5-yl)imidazo[1,2-a]pyrimidine-7-carboxylate (379.0 mg, 0.855 mmol), catalytic amount of TFA (0.066 μl, 0.855 μmol) and NIS (289 mg, 1.283 mmol) in acetonitrile (20.0 mL) was heated to 60° C. for 1 h. The reaction mixture was cooled to rt and the resulting precipitate was collected by filtration to give the title compound (320 mg, 0.56 mmol, 66% yield). The filterate was concentrated, and then DCM (40 mL) was added. The organic solution was washed with sat. aq NaHCO$_3$ and brine. The organic layer was dried over Na$_2$SO$_4$, filtered and concentrated to a residue. The residue was purified over silica, eluting with 0-50% EtOAc in DCM to give another batch of the title compound (129 mg, 0.23 mmol, 26% yield). 1H NMR (400 MHz, DMSO-d6) δ=9.10 (d, J=7.4 Hz, 1H), 7.75 (d, J=7.1 Hz, 1H), 7.35 (d, J=8.9 Hz, 2H), 6.91 (d, J=8.9 Hz, 2H), 5.92 (s, 2H), 3.98 (s, 3H), 3.72 (s, 3H). LCMS: [M+H]$^+$=569.0, 571.0 (Br isotope peak).

Step 4: methyl 2-(3-bromo-1H-1,2,4-triazol-5-yl)-3-(1H-pyrazol-4-yl)imidazo[1,2-a]pyrimidine-7-carboxylate A mixture of methyl 2-(3-bromo-1-(4-methoxybenzyl)-1H-1,2,4-triazol-5-yl)-3-iodoimidazo[1,2-a]pyrimidine-7-carboxylate (121 mg, 0.213 mmol), PdCl$_2$(dppf)-CH$_2$Cl$_2$ adduct (27.8 mg, 0.034 mmol), K$_3$PO$_4$ (61.3 mg, 0.289 mmol) and 1-(tetrahydro-2H-pyran-2-yl)-4-(4,4,5,5-tetramethyl-1,3,2-dioxaborolan-2-yl)-1H-pyrazole (95 mg, 0.34 mmol) in DMF (9 mL) and water (3 mL) was sonicated for 3 min in a microwave vial and heated in a Biotage microwave unit at 75° C. for 8 min. To the reaction mixture was added EtOAc (10 mL), and the mixture was washed with water and brine. The organic layer was dried over Na$_2$SO$_4$ and concentrated. The residue was purified over silica (12 g column), eluting with 10-50% EtOAc in hexanes to give the protected intermediate methyl 2-(3-bromo-1-(4-methoxybenzyl)-1H-1,2,4-triazol-5-yl)-3-(1-(tetrahydro-2H-pyran-2-yl)-1H-pyrazol-4-yl)imidazo[1,2-a]pyrimidine-7-carboxylate (48 mg). This material was suspended in TFA (4 mL), and the reaction mixture was heated to 60° C. for >2 h until protecting groups were removed, as monitored by LCMS. The reaction was cooled to RT and concentrated to a residue. The residue was stirred in hot MeOH and collected by filtration to yield the title compound (Example 35) (37 mg, 0.095 mmol, 45%) as a yellow solid. $^1$H NMR (600 MHz, DMSO-d$_6$) δ ppm 15.23 (br. s., 1H), 13.42 (br. s., 1H), 8.98-9.07 (m, 1H), 8.25 (br. s., 2H), 7.57-7.66 (m, 1H), 3.96 (s, 3H). LCMS: [M+H]$^+$=389.0, 391.0 (Br isotope peak)

Step 4: methyl 2-(3-bromo-1H-1,2,4-triazol-5-yl)-3-(1H-imidazol-4-yl)imidazo[1,2-a]pyrimidine-7-carboxylate A mixture of methyl 2-(3-bromo-1-(4-methoxybenzyl)-1H-1,2,4-triazol-5-yl)-3-iodoimidazo[1,2-a]pyrimidine-7-carboxylate (122 mg, 0.214 mmol), PdCl$_2$(dppf)-CH$_2$Cl$_2$ adduct (18 mg, 0.021 mmol), CsF (81 mg, 0.54 mmol) and N,N-dimethyl-4-(4,4,5,5-tetramethyl-1,3,2-dioxaborolan-2-yl)-1H-imidazole-1-sulfonamide (103 mg, 0.343 mmol, Intermediate 2) in DME (10 mL) was sonicated for 5 min in a microwave vial and heated in a Biotage microwave unit at 130° C. for 40 min. The reaction mixture was cooled to rt, diluted with EtOAc, and then washed with water. The organic layer was dried over Na$_2$SO$_4$ and concentrated, and the residue was purified over silica (24 g column), eluting with 35-40% EtOAc in hexanes. Fractions containing the protected intermediate methyl 2-(3-bromo-1-(4-methoxybenzyl)-1H-1,2,4-triazol-5-yl)-3-(1-(N,N-dimethylsulfamoyl)-1H-imidazol-4-yl)imidazo[1,2-a]pyrimidine-7-carboxylate were concentrated, and the residue was recrystallized from EtOAc to yield the protected intermediate methyl 2-(3-bromo-1-(4-methoxybenzyl)-1H-1,2,4-triazol-5-yl)-3-(1-(N,N-dimethylsulfamoyl)-1H-imidazol-4-yl)imidazo[1,2-a]pyrimidine-7-carboxylate (43 mg). This material was suspended in TFA (4 mL), and the reaction mixture was heated to 61° C. for 16 hr. The reaction mixture was concentrated to a residue. The residue was suspended in DCM, and the partially pure product was collected by filtration. The collected solid was stirred in refluxing EtOH for five minutes, and was collected by filtration to yield the title compound (Example 36) (14 mg, 0.036 mmol, 17%) as a yellowish solid. 1H NMR (700 MHz, DMSO-d6) δ 15.61-15.25 (br s, 1H), 13.66-12.19 (br s, 1H), 10.21-9.93 (m, 1H), 8.53 (br s, 1H), 8.39-8.19 (m, 1H), 7.75 (d, J=7.3 Hz, 1H), 3.97 (s, 3H) LCMS: [M+H]$^+$=389.1, 391.1 (Br isotope peak)

Example 37

3-bromo-5-[3-(1H-imidazol-4-yl)imidazo[1,2-a]pyrimidin-2-yl]-1H-1,2,4-triazole, trifluoroacetic acid salt

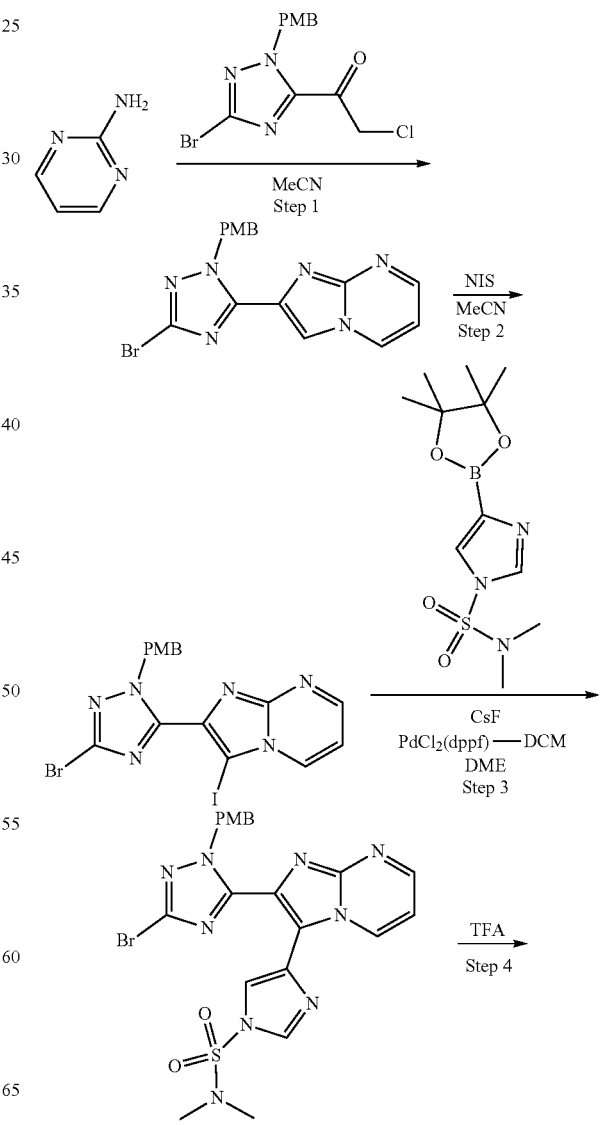

-continued

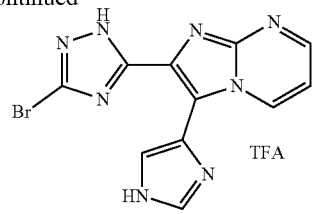

Step 2: 2-(3-Bromo-1-(4-methoxybenzyl)-1H-1,2,4-triazol-5-yl)-3-iodoimidazo[1,2-a]pyrimidine A mixture of 2-(3-bromo-1-(4-methoxybenzyl)-1H-1,2,4-triazol-5-yl)imidazo[1,2-a]pyrimidine (274.0 mg, 0.711 mmol), catalytic amount of TFA (0.055 µl, 0.711 µmol) and NIS (208 mg, 0.925 mmol) in acetonitrile (10.0 mL) was heated to 60° C. for 15 min. The reaction mixture was cooled to rt and the resulting precipitate was collected by filtration to give the title compound (307.0 mg, 0.60 mmol, 84% yield). 1H NMR (400 MHz, DMSO-d6) δ=8.94 (dd, J=1.9, 7.0 Hz, 1H), 8.71 (dd, J=1.9, 4.2 Hz, 1H), 7.39-7.21 (m, 3H), 6.90 (d, J=8.9 Hz, 2H), 5.91 (s, 2H), 3.72 (s, 3H). LCMS: M+H]$^+$=510.8, 512.8 (Br isotope peak)

Step 3: 4-(2-(3-Bromo-1-(4-methoxybenzyl)-1H-1,2,4-triazol-5-yl)imidazo[1,2-a]pyrimidin-3-yl)-N,N-dimethyl-1H-imidazole-1-sulfonamide A mixture of 2-(3-bromo-1-(4-methoxybenzyl)-1H-1,2,4-triazol-5-yl)-3-iodoimidazo[1,2-a]pyrimidine (212.0 mg, 0.415 mmol), N,N-dimethyl-4-(4,4,5,5-tetramethyl-1,3,2-dioxaborolan-2-yl)-1H-imidazole-1-sulfonamide (200 mg, 0.664 mmol, Intermediate 2), CsF (158 mg, 1.037 mmol), PdCl2(dppf)-CH2Cl2adduct (33.9 mg, 0.041 mmol) in DME (9 mL) was well sonicated for 5 min and then heated at 130° C. for 20 min using an Anton-Parr microwave unit. The reaction mixture was cooled to rt and the resulting precipitate was collected by filtration. The collected solid was diluted with DCM and washed with water and brine. The organic layer was dried over Na2SO4, filtered and concentrated to a residue. The residue was purified over silica, eluting with 15%-70% 3:1 EtOAc-EtOH in DCM to give the title compound (110 mg, 0.20 mmol, 48% yield). 1H NMR (400 MHz, DMSO-d6) δ=9.56 (dd, J=2.0, 7.1 Hz, 1H), 8.79 (dd, J=2.0, 4.1 Hz, 1H), 8.52 (d, J=1.3 Hz, 1H), 8.43 (d, J=1.3 Hz, 1H), 7.42-7.36 (m, 2H), 7.31 (dd, J=4.1, 7.1 Hz, 1H), 6.95-6.85 (m, 2H), 5.87 (s, 2H), 3.72 (s, 3H), 2.91 (s, 6H). LCMS: [M+H]$^+$=558.2, 560.1 (Br isotope peak).

Step 4: 3-bromo-5-[3-(1H-imidazol-4-yl)imidazo[1,2-a]pyrimidin-2-yl]-1H-1,2,4-triazole, trifluoroacetic acid salt A suspension of 4-(2-(3-bromo-1-(4-methoxybenzyl)-1H-1,2,4-triazol-5-yl)imidazo[1,2-a]pyrimidin-3-yl)-N,N-dimethyl-1H-imidazole-1-sulfonamide (107 mg, 0.192 mmol) in TFA (5 mL) was heated at 60° C. until complete by LCMS. The reaction mixture was concentrated, and the residue was suspended in warm DCM with sonication. The resulting solid was collected by filtration and still showed traces of protected intermediate. The material was treated with TFA and heated to 64° C. for 4 hr to complete deprotection. The reaction mixture was concentrated, and the residue was suspended in DCM with sonication. The solid was collected by filtration to yield the title compound (50.0 mg, 0.112 mmol, 59%) as a white solid. 1H NMR (400 MHz, DMSO-d6) δ=9.42 (br d, J=2.3 Hz, 1H), 8.87-8.72 (m, 2H), 8.35 (d, J=1.0 Hz, 1H), 7.28 (dd, J=4.1, 6.8 Hz, 1H). 2 NH protons were not observed. LCMS: [M+H]$^+$=331.0, 333.0 (Br isotope peak)

Example 38

5-[6-fluoro-3-(1H-pyrazol-4-yl)imidazo[1,2-a]pyrimidin-2-yl]-3-(trifluoromethyl)-1H-1,2,4-triazole

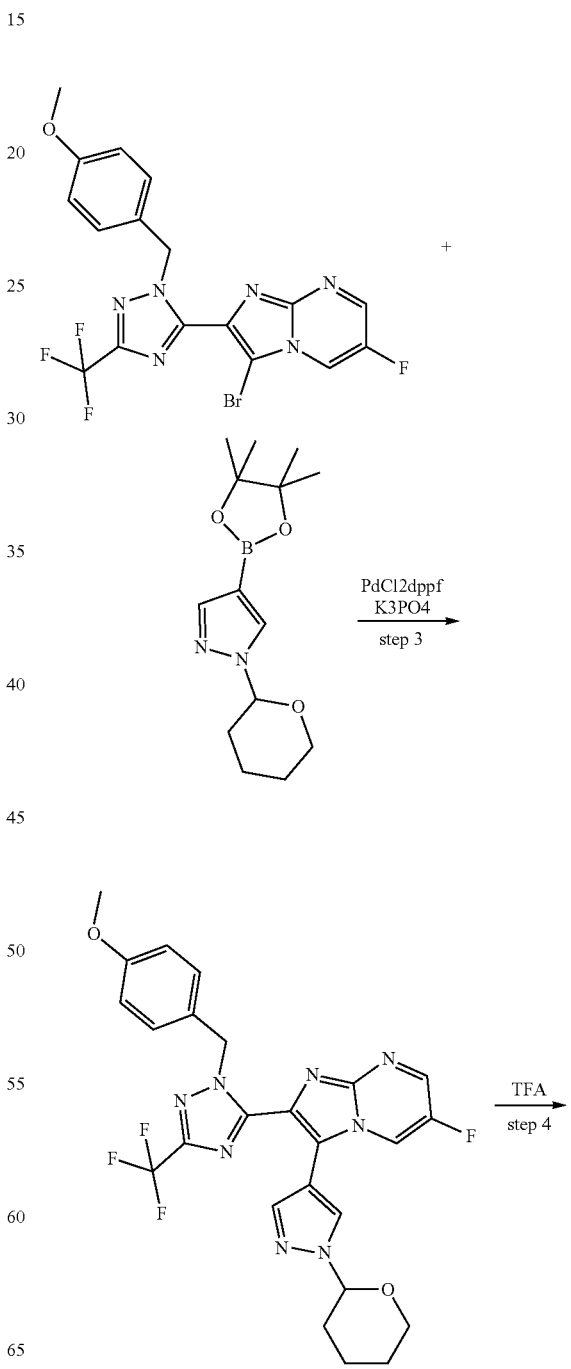

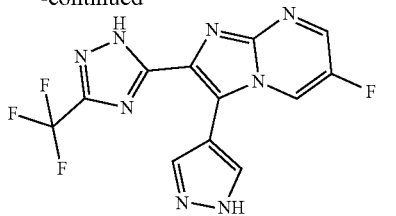

Step 3: 6-Fluoro-2-(1-(4-methoxybenzyl)-3-(trifluoromethyl)-1H-1,2,4-triazol-5-yl)-3-(1-(tetrahydro-2H-pyran-2-yl)-1H-pyrazol-4-yl)imidazo[1,2-a]pyrimidine To a mixture of 3-bromo-6-fluoro-2-(1-(4-methoxybenzyl)-3-(trifluoromethyl)-1H-1,2,4-triazol-5-yl)imidazo[1,2-a]pyrimidine (150 mg, 0.318 mmol), 1-(tetrahydro-2H-pyran-2-yl)-4-(4,4,5,5-tetramethyl-1,3,2-dioxaborolan-2-yl)-1H-pyrazole (133 mg, 0.477 mmol), potassium phosphate (203 mg, 0.955 mmol) in dioxane (2 mL) was added $PdCl_2$(dppf)-$CH_2Cl_2$ adduct (26.0 mg, 0.032 mmol). The reaction mixture was heated in a microwave vial at 120° C. for 10 min in an Anton-Parr microwave unit. The reaction mixture was cooled to rt and filtered. The filtrate was concentrated to a brown residue. This residue was purified by Isco Combiflash (20%-100% (3:1 EtOAc/EtOH)/Hexane; 40 g RediSep column). Collected fractions containing the product were combined and concentrated to give the title compound as a yellow solid (147 mg, 0.27 mmol, 85% yield). LCMS: $[M+H]^+$=543.3.

Step 4: 5-[6-fluoro-3-(1H-pyrazol-4-yl)imidazo[1,2-a]pyrimidin-2-yl]-3-(trifluoromethyl)-1H-1,2,4-triazole A suspension of 6-fluoro-2-(1-(4-methoxybenzyl)-3-(trifluoromethyl)-1H-1,2,4-triazol-5-yl)-3-(1-(tetrahydro-2H-pyran-2-yl)-1H-pyrazol-4-yl)imidazo[1,2-a]pyrimidine (147 mg, 0.271 mmol) in TFA (5 mL) was heated to 80° C. for 8 hr. The reaction mixture was concentrated and the residue was purified by reverse-phase HPLC (Xselect CSH $C_{18}$ column (150 mm×30 mm i.d. 5 µm packing diameter), eluting with 15-55% $CH_3CN$ in water (each with 0.1% formic acid) to yield the title compound (35.5 mg, 0.105 mmol, 39%). $^1$H NMR (400 MHz, DMSO-$d_6$) δ ppm 15.62 (br s, 1H), 13.38 (br s, 1H), 9.10 (dd, J=4.4, 2.9 Hz, 1H), 8.90 (d, J=2.9 Hz, 1H), 8.44 (s, 1H), 8.11 (s, 1H). LCMS: $[M+H]^+$=339.1.

Examples 39-165 were prepared using methods similar to those described herein and knowledge known in the art. The table below shows the general synthetic methods by which these compounds were prepared, and their theoretical and observed molecular weight.

| Example | General Method | pMW | [M + H]⁺ |
|---|---|---|---|
| 39 | 1 | 347.14 | 347.1, 349.1 |
| 40 | 5 | 389.22 | 389.2, 391.1 |
| 41 | 1 | 334.27 | 335.0 |
| 42 | 1 | 405.35 | 406.2 |
| 43 | 1 | 363.31 | 364.2 |
| 44 | 1 | 350.26 | 351.3 |
| 45 | 1 | 354.68 | 355.2 |
| 46 | 1 | 423.34 | 424.3 |
| 47 | 1 | 362.32 | 363.2 |
| 48 | 1 | 362.28 | 363.1 |
| 49 | 1 | 380.29 | 381.2 |
| 50 | 1 | 302.25 | 303.15 |
| 51 | 1 | 364.29 | 365.2 |
| 52 | 1 | 348.29 | 349.0 |
| 53 | 1 | 405.35 | 406.3 |
| 54 | 1 | 334.27 | 335.2 |
| 55 | 1 | 362.32 | 363.1 |
| 56 | 1 | 419.37 | 420.2 |
| 57 | 1 | 373.17 | 373.0, 375.1 |
| 58 | 1 | 350.26 | 351.0 |
| 59 | 1 | 364.29 | 365.1 |
| 60 | 1 | 336.24 | 337.0 |
| 61 | 1 | 350.26 | 351.2 |
| 62 | Prodrug | 362.28 | 363.1 |
| 63 | 1 | 361.29 | 362.3 |
| 64 | 1 | 388.24 | 389.2 |
| 65 | 4 | 434.38 | 435.3 |
| 66 | 1 | 390.33 | 391.3 |
| 67 | 3 | 439.38 | 440.1 |
| 68 | 3 | 403.33 | 404.2 |
| 69 | 4 | 364.29 | 365.2 |
| 70 | 4 | 419.37 | 420.3 |
| 71 | 4 | 376.3 | 377.1 |
| 72 | 1 | 376.3 | 377.3 |
| 73 | 3 | 389.35 | 390.2 |
| 74 | 1 | 375.32 | 376.2 |
| 75 | 4 | 363.31 | 364.3 |
| 76 | 4 | 405.35 | 406.2 |
| 77 | 1 | 399.13 | 401.2 |
| 78 | 4 | 420.36 | 421.3 |
| 79 | 4 | 378.32 | 379.3 |
| 80 | 4 | 419.37 | 420.3 |
| 81 | Prodrug | 404.36 | 405.2 |
| 82 | 5 | 390.33 | 391.1 |
| 83 | 1 | 411.3 | 412.2 |
| 84 | Prodrug | 464.37 | 465.2 |
| 85 | 4 | 360.33 | 361.2 |
| 86 | 4 | 346.3 | 347.2 |
| 87 | 3 | 453.34 | 454.1 |
| 88 | 1 | 370.25 | 371.1 |
| 89 | 1 | 410.36 | 411.2 |
| 90 | 1 | 302.25 | 303.2 |
| 91 | 1 | 399.13 | 398.9, 400.9 |
| 92 | 1 | 378.27 | 379.2 |
| 93 | 1 | 388.24 | 389.1 |
| 94 | 3 | 433.4 | 434.20 |
| 95 | 1 | 370.25 | 371.1 |
| 96 | 5 | 424.39 | 425.20 |
| 97 | 6 | 320.24 | 321.0 |
| 98 | 6 | 334.27 | 335.1 |
| 99 | 4 | 456.4 | 457.0 |
| 100 | 5 | 378.27 | 379.2 |
| 101 | 4 | 414.3 | 415.1 |
| 102 | 5 | 364.25 | 365.2 |
| 103 | 1 | 392.36 | 393.1 |
| 104 | 3 | 424.36 | 425.1 |
| 105 | 4 | 403.33 | 404.0 |
| 106 | 4 | 441.38 | 442.1 |
| 107 | 5 | 335.25 | 336.1 |
| 108 | 3 | 439.35 | 440.1 |
| 109 | 1 | 376.35 | 377.2 |
| 110 | 1 | 345.25 | 346.0 |
| 111 | 4 | 432.29 | 433.0 |
| 112 | 4 | 438.37 | 439.0 |
| 113 | 1 | 318.25 | 319.0 |
| 114 | 4 | 432.29 | 433.0 |
| 115 | 4 | 446.32 | 447.0 |
| 116 | 3 | 408.36 | 409.1 |
| 117 | 4 | 428.33 | 429.1 |
| 118 | 5 | 445.33 | 446.0 |
| 119 | 4 | 427.35 | 428.1 |
| 120 | 2 | 370.25 | 371.0 |
| 121 | 4 | 414.3 | 415.2 |
| 122 | 5 | 433.4 | 434.1 |
| 123 | 4 | 532.31 | 533.30 |

-continued

| Example | General Method | pMW | [M + H]+ |
|---|---|---|---|
| 124 | 1 | 345.25 | 346.0 |
| 125 | 1 | 406.23 | 407.1 |
| 126 | 4 | 434.38 | 435.1 |
| 127 | 4 | 436.4 | 437.3 |
| 128 | 1 | 422.68 | 423.1, 425.1 |
| 129 | 4 | 422.37 | 423.3 |
| 130 | 1 | 334.27 | 335.0 |
| 131 | 1 | 334.27 | 335.1 |
| 132 | 1 | 433.4 | 434.1 |
| 133 | 1 | 360.3 | 361.1 |
| 134 | 1 | 374.33 | 375.1 |
| 135 | 3 | 420.36 | 421.2 |
| 136 | 1 | 402.34 | 403.1 |
| 137 | 1 | 404.36 | 405.1 |
| 138 | 1 | 348.29 | 349.0 |
| 139 | 4 | 448.41 | 449.2 |
| 140 | 4 | 462.44 | 463.2 |
| 141 | 4 | 448.41 | 449.2 |
| 142 | 4 | 436.4 | 437.2 |
| 143 | 4 | 458.41 | 459.2 |
| 144 | 2 | 428.3 | 429.1 |
| 145 | 4 | 464.41 | 465.3 |
| 146 | 4 | 444.38 | 445.2 |
| 147 | 4 | 461.41 | 462.2 |
| 148 | 4 | 458.41 | 459.2 |
| 149 | 4 | 475.44 | 476.2 |
| 150 | 4 | 472.44 | 473.2 |
| 151 | 4 | 478.82 | 479.3 |
| 152 | 4 | 475.44 | 476.2 |
| 153 | 4 | 436.4 | 437.2 |
| 154 | 5 | 378.32 | 379.1 |
| 155 | 4 | 460.42 | 461.2 |
| 156 | 4 | 448.41 | 449.2 |
| 157 | 4 | 404.36 | 405.2 |
| 158 | 4 | 458.41 | 459.1 |
| 159 | 1 | 349.13 | 350.9 |
| 160 | 5 | 418.26 | 419.1 |
| 161 | 5 | 406.33 | 407.1 |
| 162 | 5 | 455.35 | 456.1 |
| 163 | 5 | 364.29 | 365.1 |
| 164 | 4 | 419.37 | 420.2 |
| 165 | 1 | 378.32 | 379.1 |

Solubility Data

The solubility of certain compounds in FASSIF (Fasted State Simulated Intestinal Fluid) was measured and is listed in Table 2 below.

The solubility of solid compounds was determined in FaSSIF at pH 6.5 after 4 h equilibration at room temperature. 1 mL of FaSSIF buffer (3 mM sodium taurocholate, 0.75 mM lecithin in sodium phosphate buffer at pH 6.5) was added to manually weighed 1 mg of the solid compound in a 4 mL vial. The resulting suspension was shaken at 900 rpm for 4 h at room temperature and then transferred to a Multiscreen HTS, 96-well solubility filter plate. The residual solid was removed by filtration. The supernatant solution was quantified by HPLC-UV using single point calibration of a known concentration of the compound in DMSO. The dynamic range of the assay was 1-1000 µg/mL.

TABLE 2

| Example No. | FASSIF Solubility (µg/mL) |
|---|---|
| 1 | 4 |
| 2 | 5 |
| 23 | 455 |
| 24 | 324 |
| 25 | >1000 |
| 27 | 298 |

TABLE 2-continued

| Example No. | FASSIF Solubility (µg/mL) |
|---|---|
| 28 | 208 |
| 29 | >1000 |
| 34 | >1000 |

Biological Data

Recombinant Human CGAS Production.

Human cGAS (157-522) was purified from *E. coli* (BL21 (DE3)*) expressing an amino-terminal His-MBP-tev tag by Ni-IDA affinity chromatography in lysis buffer ((20 mM HEPES, pH 7.5, 400 mM NaCl, 10% glycerol, 30 mM Imidazole, 1 mM PMSF, 1 mM TCEP, 100 mM Arginine, 100 mM Glutamic Acid, and protease inhibitors (Roche complete EDTA-free)) and eluted step-wise using 50 and 500 mM imidazole in wash buffer (20 mM HEPES, pH 7.5, 400 mM NaCl, 10% glycerol, 1 mM TCEP). The eluted protein was further purified by size exclusion chromatography using Superdex 75 equilibrated in 20 mM HEPES, pH 7.5, 400 mM NaCl, 1 mM TCEP, 1 mM PMSF.

RapidFire 300 Mass Spectrometric (RF-MS 300) Assay.

Compounds were resuspended in 10 mM stock concentration using DMSO and tested to determine their IC50 values against human CGAS (157-522) using a RapidFire Mass spectrometry assay. Compounds were serially diluted 2, 3, or 4-fold in neat DMSO to generate 11-point dose response curves and then 250 nL compound or DMSO solution was transferred to Greiner 384-well V-bottom assay plates (Catalog #781280) using an Echo acoustic dispenser (Labcyte). A solution of 150 µM ATP, 150 µM GTP, 20 µM pppGpA (GTP-2'5'-AMP, custom synthesis from Chem-Genes), and 10 µg/mL sheared salmon sperm DNA (Sigma, Catalog #D1626) in assay buffer (20 mM Trizma, pH 7.5, 10 mM magnesium chloride, 0.3 mM CHAPS, and 0.01% (w/v) bovine serum albumin) was added to columns 1-17, 19-24 of the plate at 12.5 µL/well using a Combi liquid handler (ThermoFisher). A 12.5 µL/well low control solution containing 150 µM ATP, 150 µM GTP, 20 µM pppGpA in assay buffer was added to column 18 using the Combi. A 12.5 µL/well solution of 10-100 nM human CGAS (157-522) in assay buffer was then added to all wells of the plate using the Combi. Plates were centrifuged to mix the solutions and then incubated for 1-2 hr at room temperature. Reactions were quenched by added 50 µL/well of 0.5% (v/v) trifluoroacetic acid (TFA) in mass spectrometry grade deionized water containing 5 µM cyclic-di-UMP (ci-di-UMP; Invivogen Catalog #tlrl-cdu) as the internal standard (IS). Plates were centrifuged for 1 min and then quenched reactions were analyzed using a RF-MS 300 system operating in a Multiple Reaction Monitoring (MRM) detection mode.

Samples (10 µL injection volume) were passed over a silica $C_{18}$/type C solid phase extraction (SPE) cartridge for analyte (2'3'-cyclic guanosine monophosphate adenosine monophosphate (2'3'-cGAMP), product of biochemical reaction)/pppGpA/c-di-UMP IS adsorption. Adsorbed samples were desalted for 3000 ms using a 100% water eluent A/desalting solution. Afterwards, desalted samples were eluted using a 0.5% TFA in 20%/80% acetonitrile/water eluent B/elution solution directly into either a Sciex 4000, 5000 or 5500 triple quadrupole mass spectrometer (QQQ-MS) for MRM analyte/IS detection. QQQ-MS detection conditions were as follow: scan type: MRM; curtain (CUR) gas: 30 psi; nebulizer (GS1) gas: 50 psi; drying (GS2) gas: 60 psi; collisionally activated dissociation (CAD) gas: 12 relative setting; precursor ion (Q1) masses: 2'3'- cGAMP: m/z 675.1 Da/pppGpA: m/z 853.0 Da/c-di-UMP: m/z 613.1 Da; fragment ion (Q3) masses: 2'3'-cGAMP: m/z 524.1 Da/pppGpA: m/z 702.0 Da/c-di-UMP: 307.1 Da; declustering potentials (DPs): 2'3'-cGAMP: +81 V/pppGpA: +85 V/c-di-UMP: +85 V; entrance potential: +10 V (all analytes); collision energies (CEs): 2'3'-cGAMP: +33 V/pppGpA: +36 V/c-di-UMP: +35 V; collision cell exit potential (CXP): +10 V (all analytes); interface heater (Sciex 4000/5000 only): on; Q1 resolution: unit (all analyte); Q3 resolution: unit (all analytes). The area under the curve (AUC) for all analytes was obtained using the RapidFire Integrator software application to calculate AUC-2'3'-cGAMP/AUC-c-di-UMP intensity ratio. Percent product formation was calculated by comparison to column 6 (high control)/column 18 (low control) responses. The % product inhibition was calculated as follows:

$$\% \text{ inhibition} = 100 \times [(\text{sample} - \text{average low control})/$$
$$(\text{average high control} - \text{average low control})]$$

Curve fitting was performed using the equation $Y = A + \left[\dfrac{(B-A)}{1+\left(\dfrac{10^x}{10^C}\right)^D}\right]$, where A is the minimum response, B is the maximum response, C is the $\log_{10}$*XC50, D is the slope factor, and x is the $\log_{10}$ compound concentration [M] in ABASE XE.

CGAS Whole Blood Cytokine Release Assay

Blood collection: Blood was collected in a tube containing 10% Sodium Heparin (5 ml/45 ml blood final).

Protocol for CGAS Whole Blood Cytokine Release Assay: Compounds serial diluted at 1:3 were provided at 150 nL per well, in a 384 well polypropylene microplate (cat. 781280; Greiner Bio-One, Frickenhausen, Germany). 5 µL of PBS/20% Null BacMam was dispensed to all wells except for column 18 on a Multidrop Combi (Thermo Scientific, Waltham, MA). 5 uL of PBS was dispensed into column 18. The Bravo (Agilent, Santa Clara, CA) was used to transfer 45 uL of donor derived blood into the compound plates. The Bravo protocol mixed the blood and compound/PBS 5 times. The plates were incubated at 37° C., 5% CO2, for 6 hours. At the 6 hour mark the plates were removed and centrifuged for 10 minutes at 3000 RPM. 3 uL of supernatant was transferred from the plate to a 384 well NBS microplate (cat. 4513; Corning Life Sciences, Corning, NY). These plates were sealed with adhesive foil and stored in a −80 freezer until ready for analysis.

For cytokine detection, Human IP-10 BD cytometric bead array (CBA) beads (BD Biosciences, Franklin Lakes, NJ) were used. Capture bead solution was prepared by performing a 1:50 dilution of the IP-10 capture bead stock solution in BD diluent for serum/plasma (cat. 51-9003991 BD Biosciences, Franklin Lakes, NJ). 2 µL of this solution was added per well to the assay microplates which were then sealed with adhesive foil and incubated at room temperature for 2 h in the dark. Detection reagent was further prepared by performing a 1:50 dilution of the detection reagent stock solution. 2 µL of detection reagent was added per well and microplates were sealed with adhesive foil and incubated at room temperature in the dark for 1 h. After the 1 h incubation 3 uL of BD CBA wash buffer was added per well of the microplates. Data were acquired on an iQue Screener flow cytometer. The iQue used fluorescence detection to quantify the inhibition of IP-10 present in the sample wells. A sip time of 1 second per sample was used. The blue laser with excitation of 488 nm and emission filters 585/40 nm were used to capture the mean and median of IP-10 with the detector in logarithmic mode (FL2-H).

All data analysis was carried out in IDBS ActivityBase XE. Percent inhibition is determined using the formula 100−(100(U−C2)/(C1−C2)), where U is the unknown value, C1 is the average high control response of the mixture in DMSO only, and C2 is the average of minimum response of column 18 no BacMam stimulation control.

Curve fitting was performed using the equation $Y = A + \left[\dfrac{(B-A)}{1+\left(\dfrac{10^x}{10^C}\right)^D}\right]$, where A is the minimum response, B is the maximum response, C is the $\log_{10}$*XC50, D is the slope factor, and x is the $\log_{10}$ compound concentration [M] in ABASE XE.

The biological data from the RF-MS 300 assay and the whole blood (hWB) cytokine release assay for the compounds are shown in Table 3 below.

TABLE 3

| Example No | RF-MS pXC50 | hWB pXC50 |
|---|---|---|
| 1 | 8.8 | 6.8 |
| 2 | 8.4 | 6.5 |
| 3 | 8.2 | 6.1 |
| 4 | 8.4 | 7.2 |
| 5 | 8.6 | 6.7 |
| 6 | 8.4 | 6.3 |
| 7 | 8.2 | 5.8 |
| 8 | 8.5 | 6.7 |
| 9 | 8.4 | 7 |
| 10 | 8.2 | 6.9 |
| 11 | 8 | — |
| 12 | 7.9 | 5.2 |
| 13 | 8 | 6 |
| 14 | 8 | 7.2 |
| 15 | 8 | <4.5 |
| 16 | 8.4 | 5.5 |
| 17 | 8.1 | 5.9 |
| 18 | 7.9 | — |
| 19 | 8.2 | 6.4 |
| 20 | 8.7 | — |
| 21 | 8.3 | 6.2 |
| 22 | 7.6 | 5.1 |
| 23 | 6.6 | 6.1 |
| 24 | 7.2 | — |
| 25 | 7.6 | 6.5 |
| 26 | 8.3 | 7.4 |
| 27 | 8.3 | 6.8 |
| 28 | 8.5 | 6.5 |
| 29 | 7.5 | 6.5 |
| 30 | 6.5 | 5.9 |
| 31 | 5.7 | 5.3 |
| 32 | 6.1 | 5.5 |
| 33 | 6.5 | 6.3 |
| 34 | 6.1 | — |
| 35 | 8.5 | — |
| 36 | 8.5 | — |
| 37 | 8.5 | — |
| 38 | 8.1 | 6 |
| 39 | 8.6 | — |
| 40 | 7.6 | — |
| 41 | 8.1 | — |
| 42 | 7.6 | — |
| 43 | 7.8 | — |
| 44 | 8.1 | — |
| 45 | 8.5 | — |
| 46 | 7.2 | — |
| 47 | 8.8 | — |
| 48 | 8.7 | — |
| 49 | 7.9 | — |

TABLE 3-continued

| Example No | RF-MS pXC50 | hWB pXC50 |
|---|---|---|
| 50 | 8.5 | 7.1 |
| 51 | 8 | — |
| 52 | 8.3 | — |
| 53 | 7.8 | — |
| 54 | 8.2 | — |
| 55 | 8.1 | 6 |
| 56 | 7.7 | — |
| 57 | 8.3 | 7.2 |
| 58 | 8 | 6.5 |
| 59 | 7.9 | — |
| 60 | 9.1 | — |
| 61 | 7.9 | 6.4 |
| 62 | 8.6 | 6.9 |
| 63 | 8.2 | 6.1 |
| 64 | 8 | 6.4 |
| 65 | 8 | 6.3 |
| 66 | 8.6 | 6.5 |
| 67 | 8.3 | 5.6 |
| 68 | 8.3 | 5.9 |
| 69 | 8.6 | 6.9 |
| 70 | 8.5 | 5.7 |
| 71 | 8.3 | 6.9 |
| 72 | 7.9 | 4.8 |
| 73 | 8.2 | 6.1 |
| 74 | 8.1 | 5.9 |
| 75 | 8 | 6.2 |
| 76 | 8.5 | 5.3 |
| 77 | 8.7 | 6.4 |
| 78 | 8.1 | 6.4 |
| 79 | 8.5 | 7 |
| 80 | 8.5 | 4.9 |
| 81 | 8.4 | 6.8 |
| 82 | 8.3 | 6.7 |
| 83 | 8.1 | 6.5 |
| 84 | 4.8 | 6.8 |
| 85 | 8.4 | 7.3 |
| 86 | 8.4 | 7.3 |
| 87 | 5.7 | <4.5 |
| 88 | 8.3 | 6.3 |
| 89 | 8.6 | 5.8 |
| 90 | 8 | 6 |
| 91 | 8.4 | 6 |
| 92 | 8 | — |
| 93 | 7.7 | 5.6 |
| 94 | 5.8 | — |
| 95 | 8 | 6.4 |
| 96 | 8.2 | — |
| 97 | 5.1 | — |
| 98 | 6.1 | — |
| 99 | 8.3 | — |
| 100 | 8.3 | 6.4 |
| 101 | 8.8 | 6.9 |
| 102 | 8.5 | — |
| 103 | 8.9 | 6.6 |
| 104 | 8.4 | 5.2 |
| 105 | 8.5 | 6 |
| 106 | 8.5 | — |
| 107 | 8.6 | 6.2 |
| 108 | 8.1 | 6.2 |
| 109 | 8.3 | 5.9 |
| 110 | 7.3 | 6.4 |
| 111 | 8.4 | 6.4 |
| 112 | 8.1 | — |
| 113 | 8.3 | 6 |
| 114 | 8.4 | 6 |
| 115 | 8.3 | 5.8 |
| 116 | 8.3 | — |
| 117 | 8.2 | 5.5 |
| 118 | 7.9 | 6.2 |
| 119 | 6.8 | — |
| 120 | 8.2 | 6.2 |
| 121 | 8.1 | 5.8 |
| 122 | 8.3 | — |
| 123 | 8.2 | 5.9 |
| 124 | 8.2 | 6.8 |
| 125 | 7.8 | 5.5 |
| 126 | 8.1 | 6.3 |
| 127 | 8.1 | 6.6 |
| 128 | 7.9 | 5.5 |
| 129 | 8.1 | 6.5 |
| 130 | 5.7 | — |
| 131 | 4.8 | — |
| 132 | 7.4 | — |
| 133 | 8.5 | 6.7 |
| 134 | 8.4 | 6.4 |
| 135 | 8.5 | 6.2 |
| 136 | 8.1 | 6.5 |
| 137 | 7.8 | 6.2 |
| 138 | 6.3 | — |
| 139 | 8.1 | 6.4 |
| 140 | 7.9 | 6.1 |
| 141 | 8.4 | 6.5 |
| 142 | 8.4 | 6.1 |
| 143 | 8.4 | 5.6 |
| 144 | 7.9 | 6.1 |
| 145 | 8 | 6 |
| 146 | 8.2 | 5.7 |
| 147 | 8 | 5.3 |
| 148 | 8 | 5.4 |
| 149 | 8 | 5 |
| 150 | 8.3 | 5.3 |
| 151 | 8.1 | 5.4 |
| 152 | 8 | 5.6 |
| 153 | 7.8 | 6.1 |
| 154 | 8.4 | 6.3 |
| 155 | 8.1 | 6.3 |
| 156 | 8 | 6.2 |
| 157 | 8.6 | 6.6 |
| 158 | 8.1 | — |
| 159 | 8.3 | 6.7 |
| 160 | 8.3 | 6.4 |
| 161 | 8.3 | 6.6 |
| 162 | 8.1 | 6 |
| 163 | 8 | 6.1 |
| 164 | 7.8 | 5.2 |
| 165 | 8.2 | 6.7 |

It is believed that for the prodrug compounds, the activity in the RF-MS assay is due to the parent compound from impurity in the sample. For the hWB assay, some prodrugs are unstable under the assay conditions, so the activity of the prodrugs could be due to the parent compound from impurity or due to prodrug moiety removal.

Additional Data

Certain compounds disclosed in WO 2022/137082 and WO 2022/137085 were tested and the biological data from the RF-MS 300 assay and the whole blood (hWB) cytokine release assay for the compounds are shown in Table 4 below. An exemplary compound of the invention was shown to have an improved profile relative to certain compounds disclosed in WO 2022/137082 and WO 2022/137085.

The whole blood (hWB) cytokine release assay was performed as follows.

Human whole blood was collected from individual healthy donors into a 60 ml syringe containing sodium heparin (5 ml sodium heparin per syringe; Cat #309653, Becton-Dickinson, NJ, US). In a biosafety cabinet, 140 ul of the collected blood was transferred to each well of a 96-well flat bottom plate (Cat #167008, VWR, PA, US). The DMSO stock solution of small molecule cGAS inhibitor (10 mM stock solution) was diluted in PBS to prepare 10× solutions (3-fold dilutions) and 20 ul of the prepared 10× solutions was added to appropriate wells. Plates were shaken for 5 minutes at room temperature then incubated at 37° C. for 30 minutes. The stock solution of purified Bacmam was diluted with PBS+0.1% BSA to prepare a 4% (v/v) solution (10×). To activate the cGAS pathway, 20 uL of Bacmam was added to the blood, and the plates were shaken for 10 minutes at room temperature. PBS was added to achieve a final volume of 200 ul. Plates were then incubated at 37° C. for 6 hours.

Plates were removed from incubator and 100 uL/well PBS added. Plates were gently shaken for 10 minutes at room temperature and centrifuged (3000 rpm, 10 minutes) at room temperature. The plasma layer was removed and transferred to a separate 96-well plate and maintained at −80° C.

Plasma samples were measured for IP-10 levels using the IP-10 detection (U-plex or V-plex) plates (Cat #K151-UFK-4; Cat #K151-NVD-4; Meso-Scale Discovery, Inc.).

The invention claimed is:
1. A compound of Formula (I) or a tautomer thereof, or a pharmaceutically acceptable salt of said compound or tautomer thereof,

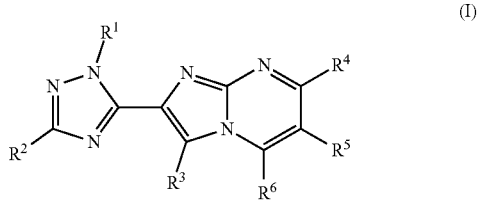

(I)

wherein
$R^1$ is hydrogen or a prodrug moiety;
$R^2$ is selected from the group consisting of hydrogen, halo, cyano, nitro, $C_{1-3}$ alkyl, halo ($C_{1-3}$) alkyl, halo

TABLE 4

| Compound | Structure | RF-MS pXC50 | hWB pXC50 |
|---|---|---|---|
| Example 2 | 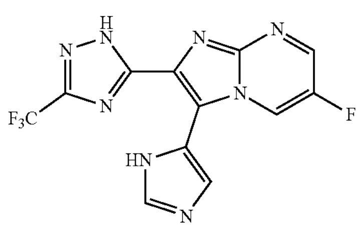 [SMILES: Fc1cnc2nc(-c3nc(C(F)(F)F)n[nH]3)c(-c3cnc[nH]3)n2c1] | 8.4 | 6.6 |
| WO 2022/137085 Example 11 | 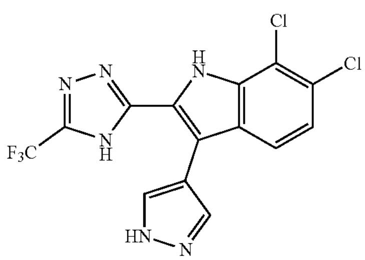 [SMILES: FC(F)(F)c1nnc(-c2[nH]c3c(Cl)c(Cl)ccc3c2-c2cn[nH]c2)[nH]1] | 7.4 | <4.5, 4.6 |
| WO 2022/137085 Example 109 | 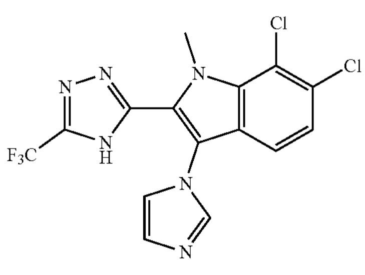 [SMILES: Cn1c(-c2nnc(C(F)(F)F)[nH]2)c(-n2ccnc2)c2ccc(Cl)c(Cl)c21] | 6.6 | <4.5, <4.5 |
| WO 2022/137082 Example 46 | 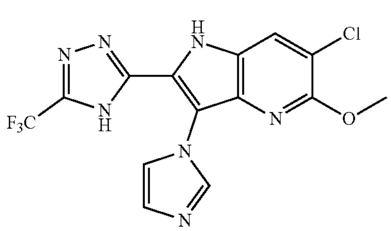 [SMILES: COc1nc2c(-n3ccnc3)c(-c3nnc(C(F)(F)F)[nH]3)[nH]c2cc1Cl] | 7.2 | <4.5, 5.0 |

($C_{1-3}$) alkoxy, —S(O) $R^7$, —SO$_2$R$^7$, —C(O) NR$^7$R$^8$, —NR$^7$C(O) R$^8$, —CO$_2$R$^7$, wherein $C_{1-3}$ alkyl, halo ($C_{1-3}$) alkyl, and halo ($C_{1-3}$) alkoxy is optionally substituted by hydroxyl or —NR$^7$R$^8$;

R$^3$ is a 5- or 6-membered heteroaryl optionally substituted by $C_{1-3}$ alkyl, —C(O) R$^8$ or a prodrug moiety;

each R$^4$, R$^5$ and R$^6$ is independently-L-Y;
  each L is independently selected from a bond, —(CR$^a$R$^b$)$_n$—, —O—, —(CR$^a$R$^b$)$_n$O—, —O(CR$^a$R$^b$)$_n$—, or —(CR$^a$R$^b$)$_n$O(CR$^a$R$^b$)$_m$—;
  wherein each n or m is independently 1, 2 or 3;
  each R$^a$ and R$^b$ is independently selected from hydrogen, halo and methyl;
  each Y is independently selected from the group consisting of hydrogen, halo, hydroxyl, cyano, $C_{1-4}$ alkyl, $C_{1-4}$ alkoxy, $C_{3-7}$cycloalkyl, $C_{2-4}$ alkenyl, $C_{1-4}$ thioalkyl, $C_{1-6}$ hydroxyalkyl, $C_{1-4}$ cyanoalkyl, halo ($C_{1-4}$) alkyl, halo ($C_{2-4}$) alkenyl, —NR$^9$R$^{10}$, —C(O) NR$^9$R$^{10}$, —CO$_2$R$^{10}$, —C(O) R$^{10}$, —SO$_2$R$^{10}$, —OSO$_2$R$^{10}$, —S(O) R$^{10}$, —SO$_2$NR$^9$R$^{10}$, —N(R$^{10}$)SO$_2$R$^{10}$, —CF$_2$CH$_2$OR$^{10}$, phenyl, 5- or 6-membered heteroaryl, and 4- to 10-membered heterocycloalkyl ring containing one, two or three heteroatoms independently selected from N, O and S, wherein the $C_{3-7}$cycloalkyl, phenyl, heteroaryl and heterocycloalkyl groups are optionally substituted with one, two or three substituents independently selected from halo, hydroxyl, —C(O) R$^{10}$, oxo, $C_{1-4}$ alkyl, halo ($C_{1-4}$) alkyl and $C_{1-4}$ hydroxyalkyl; or R$^4$ and R$^5$ taken together with the carbon atoms to which they are attached form a 5- to 8-membered monocyclic or bicyclic ring which optionally contains one or two heteroatoms independently selected from N, O and S, wherein the ring is optionally substituted with one, two or three substituents independently selected from halo, $C_{1-4}$ alkyl, oxo, —C(O) R$^{10}$ and —SO$_2$R$^{10}$;

R$^7$ and R$^8$ are independently selected from hydrogen and $C_{1-4}$ alkyl;

R$^9$ is independently selected from the group consisting of hydrogen, $C_1$-4 alkyl, —C(O) $C_{1-4}$ alkyl and halo ($C_{1-4}$) alkyl; and R$^{10}$ is independently selected from hydrogen and $C_{1-6}$ alkyl; or wherein R$^9$ and R$^{10}$ taken together with the nitrogen atom to which they are attached form a 5- to 8-membered heterocycloalkyl ring containing one or two heteroatoms independently selected from N, O and S, wherein the heterocycloalkyl is optionally substituted with oxo;

wherein each prodrug moiety is independently selected from the group consisting of —CH(R$^c$)O—P(O)(OR$^d$)(OR$^e$), —CH(R$^c$)O—C(O)—$C_{1-6}$ alkylene-O—P(O)(OR$^d$) (OR$^e$), —CH(R$^c$)O—C(O)—$C_{1-6}$ alkylene-P(O)(OR$^d$) (OR$^e$), —CH(R$^c$)O—C(O)—$C_{1-6}$ alkylene-CO$_2$H, —CH(R$^c$)O—C(O) R$^d$, —CH(R$^c$)O—C(O) O—$C_{1-6}$ alkylene-CO$_2$H, —CH(R$^c$)O—C(O)—$C_{1-6}$ alkylene-NR$^d$R$^e$, —CH(R$^c$)O—C(O)O—$C_{1-6}$ alkylene-NR$^d$R$^e$, —C(O) R$^d$, —CH(R$^c$)O—C(O)—$C_{1-6}$ alkylene-heterocycloalkyl, —CH(R$^c$)O—C(O)—$C_{1-6}$ alkylene-heterocycloalkyl and —CR$^d$R$^e$—O—(C(O)—NR$^d$-heteroarylene-CH$_2$O—C(O)—CH$_2$—NR$^d$R$^e$, wherein each heterocycloalkyl is 4- to 6-membered and contains one or two heteroatoms independently selected from N, O and S, and each heteroarylene is 5- or 6-membered and contains one or two heteroatoms independently selected from N, O and S;

wherein R$^c$ is independently selected from hydrogen and methyl; and

R$^d$ and R$^e$ are each independently hydrogen or $C_{1-6}$ alkyl.

2. A compound or a tautomer thereof, or a pharmaceutically acceptable salt of said compound or tautomer thereof according to claim 1, wherein R$^3$ is a 5-membered heteroaryl.

3. A compound of Formula (I) or a tautomer thereof, or a pharmaceutically acceptable salt of said compound or tautomer thereof,

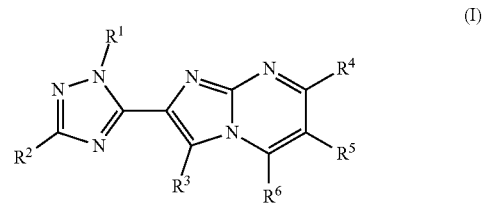

(I)

wherein
R$^1$ is hydrogen or a prodrug moiety;
R$^2$ is selected from the group consisting of hydrogen, halo, cyano, nitro, $C_{1-3}$ alkyl, halo ($C_{1-3}$) alkyl, halo ($C_{1-3}$) alkoxy, —S(O) R$^7$, —SO$_2$R$^7$, —C(O) NR$^7$R$^8$, —NR$^7$C(O) R$^8$, —CO$_2$R$^7$, wherein $C_{1-3}$ alkyl, halo ($C_{1-3}$) alkyl, and halo ($C_{1-3}$) alkoxy is optionally substituted by hydroxyl or —NR$^7$R$^8$;

R$^3$ is imidazolyl or pyrazolyl, where R$^3$ is optionally substituted by $C_{1-3}$ alkyl, —C(O) R$^8$ or a prodrug moiety;

each R$^4$, R$^5$ and R$^6$ is independently-L-Y;
  each L is independently selected from a bond, —(CR$^a$R$^b$)$_n$—, —O—, —(CR$^a$R$^b$)$_n$O—, —O(CR$^a$R$^b$)$_n$—, or —(CR$^a$R$^b$)$_n$O(CR$^a$R$^b$)$_m$—;
  wherein each n or m is independently 1, 2 or 3;
  each R$^a$ and R$^b$ is independently selected from hydrogen or methyl;
  each Y is independently selected from the group consisting of hydrogen, halo, hydroxyl, cyano, $C_{1-4}$ alkyl, $C_{1-4}$ alkoxy, $C_{3-7}$cycloalkyl, $C_{2-4}$ alkenyl, $C_{1-4}$ thioalkyl, $C_{1-6}$ hydroxyalkyl, $C_{1-4}$ cyanoalkyl, halo ($C_1$-4) alkyl, halo ($C_{2-4}$) alkenyl, —NR$^9$R$^{10}$, —C(O) NR$^9$R$^{10}$, —CO$_2$R$^{10}$, —C(O) R$^{10}$, —SO$_2$R$^{10}$, —OSO$_2$R$^{10}$, —S(O) R$^{10}$, —SO$_2$NR$^9$R$^{10}$, —N(R$^{10}$)SO$_2$R$^{10}$, —CF$_2$CH$_2$OR$^{10}$, phenyl, 5- or 6-membered heteroaryl, and 4- to 10-membered heterocycloalkyl ring containing one, two or three heteroatoms independently selected from N, O and S, wherein the $C_{3-7}$cycloalkyl, phenyl, heteroaryl and heterocycloalkyl groups are optionally substituted with one, two or three substituents independently selected from halo, hydroxyl, —C(O) R$^{10}$, oxo, $C_{1-4}$ alkyl, halo ($C_{1-4}$) alkyl and $C_{1-4}$ hydroxyalkyl; or R$^4$ and R$^5$ taken together with the carbon atoms to which they are attached form a 5- to 8-membered monocyclic or bicyclic ring which optionally contains one or two heteroatoms independently selected from N, O and S, wherein the ring is optionally substituted with one, two or three substituents independently selected from halo, $C_{1-4}$ alkyl, oxo, —C(O) R$^{10}$ and —SO$_2$R$^{10}$;

R$^7$ and R$^8$ are independently selected from hydrogen and $C_{1-3}$ alkyl;

R$^9$ is independently selected from the group consisting of hydrogen, $C_{1-4}$ alkyl, —C(O) $C_{1-4}$ alkyl and halo ($C_{1-4}$) alkyl; and $R^{10}$ is independently selected from hydrogen and $C_{1-6}$ alkyl; or
wherein $R^9$ and $R^{10}$ taken together with the nitrogen atom to which they are attached form a 5- to 8-membered heterocycloalkyl ring containing one or two heteroatoms independently selected from N, O and S, wherein the heterocycloalkyl is optionally substituted with oxo;
wherein each prodrug moiety is independently selected from the group consisting of —CH($R^c$)O—P(O)(O$R^d$) (O$R^e$), —CH($R^c$)O—C(O)—$C_{1-6}$ alkylene-O—P(O) (O$R^d$) (O$R^e$), —CH($R^c$)O—C(O)—$C_{1-6}$ alkylene-P(O)(O$R^d$) (O$R^e$), —CH($R^c$)O—C(O)—$C_{1-6}$ alkylene-CO$_2$H, —CH($R^c$)O—C(O) $R^d$, —CH($R^c$)O—C(O)O—$C_{1-6}$ alkylene-CO$_2$H, —CH($R^c$)O—C(O)—$C_{1-6}$ alkylene-N$R^dR^e$, —CH($R^c$)O—C(O)O—$C_{1-6}$ alkylene-N$R^dR^e$, —C(O) $R^d$, —CH($R^c$)O—C(O)—$C_{1-6}$ alkylene-heterocycloalkyl, —CH($R^c$)O—C(O)—$C_{1-6}$ alkylene-heterocycloalkyl and —C$R^dR^e$—O—(C(O)—N$R^d$-heteroarylene-CH$_2$O—C(O)—CH$_2$—N$R^dR^e$, wherein each heterocycloalkyl is 4- to 6-membered and contains one or two heteroatoms independently selected from N, O and S, and each heteroarylene is 5- or 6-membered and contains one or two heteroatoms independently selected from N, O and S;
wherein $R^c$ is independently selected from hydrogen and methyl; and
$R^d$ and $R^e$ are each independently hydrogen or $C_{1-6}$ alkyl.

4. A compound or a tautomer thereof, or a pharmaceutically acceptable salt of said compound or tautomer thereof according to claim 1, wherein $R^a$ and $R^b$ are hydrogen.

5. A compound or a tautomer thereof, or a pharmaceutically acceptable salt of said compound or tautomer thereof according to claim 1, wherein each prodrug moiety is independently selected from the group consisting of —CH$_2$O—P(O)(O$R^d$) (O$R^e$), —CH$_2$O—C(O)—$C_{1-6}$ alkylene-O—P(O)(O$R^d$) (O$R^e$), —CH$_2$O—C(O)—$C_{1-6}$ alkylene-P(O)(O$R^d$) (O$R^e$), —CH$_2$O—C(O)—$C_{1-6}$ alkylene-CO$_2$H, —CH$_2$O—C(O)$R^d$, —CH$_2$O—C(O)O—$C_{1-6}$ alkylene-CO$_2$H, —CH$_2$O—C(O)—$C_{1-6}$ alkylene-N$R^dR^e$, —CH$_2$O—C(O)O—$C_{1-6}$ alkylene-N$R^dR^e$, —C(O) $R^d$, —CH$_2$O—C(O)—$C_{1-6}$ alkylene-heterocycloalkyl, —CH$_2$O—C(O)—$C_{1-6}$ alkylene-heterocycloalkyl and —C$R^dR^e$—O—(C(O)—N$R^d$-heteroarylene-CH$_2$O—C(O)—CH$_2$—N$R^dR^e$;
wherein $R^d$ and $R^e$ are each independently hydrogen or $C_{1-6}$ alkyl;
each heterocycloalkyl is 4- to 6-membered and contains one or two heteroatoms independently selected from N, O and S; and
each heteroarylene is 5- or 6-membered and contains one or two heteroatoms independently selected from N, O and S.

6. A compound or a tautomer thereof, or a pharmaceutically acceptable salt of said compound or tautomer thereof according to claim 5, wherein each prodrug moiety is independently selected from —CH$_2$O—P(O)(O$R^d$) (O$R^e$), —CH$_2$O—C(O)—$C_{1-6}$ alkylene-O—P(O)(O$R^d$) (O$R^e$), —CH$_2$O—C(O)—$C_{1-6}$ alkylene-P(O)(O$R^d$) (O$R^e$), —CH$_2$O—C(O)—$C_{1-6}$ alkylene-CO$_2$H, —CH$_2$O—C(O) $R^d$, —CH$_2$O—C(O)O—$C_{1-6}$ alkylene-CO$_2$H, —CH$_2$O—C(O)—$C_{1-6}$ alkylene-N$R^dR^e$, —CH$_2$O—C(O)O—$C_{1-6}$ alkylene-N$R^dR^e$ and —C(O) $R^d$.

7. A compound or a tautomer thereof, or a pharmaceutically acceptable salt of said compound or tautomer thereof according to claim 6, wherein each prodrug moiety is independently selected from

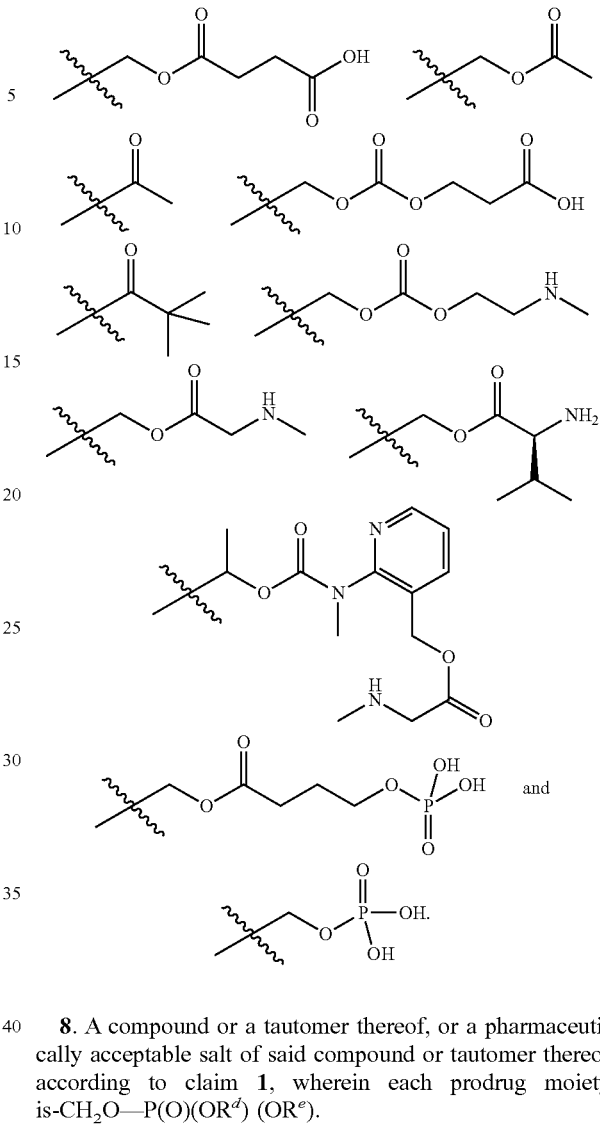

8. A compound or a tautomer thereof, or a pharmaceutically acceptable salt of said compound or tautomer thereof according to claim 1, wherein each prodrug moiety is-CH$_2$O—P(O)(O$R^d$) (O$R^e$).

9. A compound or a tautomer thereof, or a pharmaceutically acceptable salt of said compound or tautomer thereof according to claim 8, wherein each prodrug moiety is

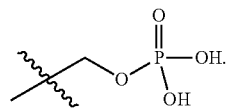 [SMILES: *COP(=O)(O)O]

10. A compound or a tautomer thereof, or a pharmaceutically acceptable salt of said compound or tautomer thereof according to claim 1, wherein $R^3$ is imidazolyl.

11. A compound or a tautomer thereof, or a pharmaceutically acceptable salt of said compound or tautomer thereof according to claim 1, wherein $R^1$ is a prodrug moiety selected from the group consisting of —CH($R^c$)O—P(O)(O$R^d$) (O$R^e$), —CH($R^c$)O—C(O)—$C_{1-6}$ alkylene-O—P(O)(O$R^d$) (O$R^e$), —CH($R^c$)O—C(O)—$C_{1-6}$ alkylene-P(O)(OR) (O$R^e$), —CH($R^c$)O—C(O)—$C_{1-6}$ alkylene-CO$_2$H, —CH($R^c$)O—C(O) $R^d$, —CH($R^c$)O—C(O)O—$C_{1-6}$ alkylene-CO$_2$H, —CH($R^c$)O—C(O)—$C_{1-6}$ alkylene-N$R^dR^e$, —CH($R^c$)O—C(O)O—$C_{1-6}$ alkylene-N$R^dR^e$;

wherein $R^c$ is independently selected from hydrogen and methyl;

$R^d$ and $R^e$ are each independently hydrogen or $C_{1-6}$ alkyl;

each heterocycloalkyl is 4- to 6-membered and contains one or two heteroatoms independently selected from N, O and S; and each heteroarylene is 5- or 6-membered and contains one or two heteroatoms independently selected from N, O and S;

and $R^3$ is imidazolyl.

12. A compound or a tautomer thereof, or a pharmaceutically acceptable salt of said compound or tautomer thereof according to claim 11, wherein $R^1$ is

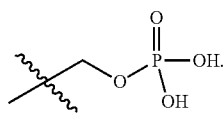

13. A compound or a tautomer thereof, or a pharmaceutically acceptable salt of said compound or tautomer thereof according to claim 1, wherein $R^1$ is hydrogen and $R^3$ is imidazolyl.

14. A compound or a tautomer thereof, or a pharmaceutically acceptable salt of said compound or tautomer thereof according to claim 1, wherein $R^2$ is selected from the group consisting of Br, cyano, —C(O) $NH_2$, —$CF_2CH_2NH_2$, —$CF_2CH_2OH$, —$CH_2F$, —$CHF_2$, —$CF_3$, —$CF_2CF_3$, —$CF_2CH_3$, —$CF_2CHF_2$, —$OCHF_2$ and —$S(O)CH_3$.

15. A compound or a tautomer thereof, or a pharmaceutically acceptable salt of said compound or tautomer thereof according to claim 14, wherein $R^2$ is -$CF_3$.

16. A compound or a tautomer thereof, or a pharmaceutically acceptable salt of said compound or tautomer thereof according to claim 1, wherein each L is a bond.

17. A compound or a tautomer thereof, or a pharmaceutically acceptable salt of said compound or tautomer thereof according to claim 16, wherein each Y is independently selected from the group consisting of hydrogen, halo, cyano, $C_{1-4}$ alkyl, $C_{1-4}$ alkoxy, $C_{3-7}$cycloalkyl, $C_{1-4}$ thioalkyl, $C_{1-6}$ hydroxyalkyl, $C_{1-4}$ cyanoalkyl, halo ($C_{1-4}$) alkyl, —$NR^9R^{10}$, —$CO_2R^{10}$, —C(O) $R^{10}$, —$CF_2CH_2OR^{10}$, and 4- to 10-membered heterocycloalkyl ring containing one or two heteroatoms independently selected from N, O and S where the heterocycloalkyl and $C_{3-7}$cycloalkyl are optionally substituted with up to three substituents independently selected from halo, hydroxyl, —C(O) $R^{10}$, oxo, $C_{1-4}$ alkyl, halo ($C_{1-4}$) alkyl and $C_{1-4}$ hydroxyalkyl; or $R^4$ and $R^5$ taken together with the carbon atoms to which they are attached form a 5- to 8-membered monocyclic or bicyclic ring which optionally contains one or two heteroatoms independently selected from N, O and S, wherein the ring is optionally substituted with up to three substituents independently selected from halo, $C_{1-4}$ alkyl, oxo, —C(O) $R^{10}$ and —$SO_2R^{10}$.

18. A compound or a tautomer thereof, or a pharmaceutically acceptable salt of said compound or tautomer thereof according to claim 1, wherein each Y is independently selected from hydrogen, halogen, $CO_2R^{10}$ and halo ($C_{1-4}$) alkyl.

19. A compound or a tautomer thereof, or a pharmaceutically acceptable salt of said compound or tautomer thereof according to claim 1, wherein $R^6$ is hydrogen.

20. A compound or a tautomer thereof, or a pharmaceutically acceptable salt of said compound or tautomer thereof according to claim 1, wherein $R^4$ and $R^6$ are hydrogen and $R^5$ is fluoro.

21. A compound or a tautomer thereof, or a pharmaceutically acceptable salt of said compound or tautomer thereof selected from the group consisting of:

5-[3-(1H-imidazol-4-yl) imidazo[1,2-a]pyrimidin-2-yl]-3-(trifluoromethyl)-1H-1,2,4-triazole;

5-[6-fluoro-3-(1H-imidazol-5-yl) imidazo[1,2-a]pyrimidin-2-yl]-3-(trifluoromethyl)-1H-1,2,4-triazole;

5-[3-(1H-imidazol-5-yl)-7-(trifluoromethyl) imidazo[1,2-a]pyrimidin-2-yl]-3-(trifluoromethyl)-1H-1,2,4-triazole;

5-[6-chloro-3-(1H-imidazol-4-yl) imidazo[1,2-a]pyrimidin-2-yl]-3-(difluoromethyl)-1H-1,2,4-triazole;

3-(difluoromethyl)-5-[6-fluoro-3-(1H-imidazol-4-yl) imidazo[1,2-a]pyrimidin-2-yl]-1H-1,2,4-triazole;

5-[7-chloro-3-(1H-imidazol-5-yl) imidazo[1,2-a]pyrimidin-2-yl]-3-(trifluoromethyl)-1H-1,2,4-triazole;

3-(difluoromethyl)-5-[7-(difluoromethyl)-3-(1H-imidazol-5-yl) imidazo[1,2-a]pyrimidin-2-yl]-1H-1,2,4-triazole;

5-[3-(1H-pyrazol-4-yl) imidazo[1,2-a]pyrimidin-2-yl]-3-(trifluoromethyl)-1H-1,2,4-triazole;

{4-oxo-4-[(4-{2-[3-(trifluoromethyl)-1H-1,2,4-triazol-5-yl]imidazo[1,2-a]pyrimidin-3-yl}-1H-imidazol-1-yl) methoxy]butoxy}phosphonic acid;

{4-oxo-4-[(5-{3-[1-({[4-(phosphonooxy) butanoyl] oxy}methyl)-1H-imidazol-4-yl]imidazo[1,2-a]pyrimidin-2-yl}-3-(trifluoromethyl)-1H-1,2,4-triazol-1-yl) methoxy]butoxy}phosphonic acid;

({5-[6-fluoro-3-(1H-imidazol-5-yl) imidazo[1,2-a]pyrimidin-2-yl]-3-(trifluoromethyl)-1H-1,2,4-triazol-1-yl}methoxy) phosphonic acid;

methyl 2-(3-bromo-1H-1,2,4-triazol-5-yl)-3-(1H-pyrazol-4-yl) imidazo[1,2-a]pyrimidine-7-carboxylate;

methyl 2-(3-bromo-1H-1,2,4-triazol-5-yl)-3-(1H-imidazol-4-yl) imidazo[1,2-a]pyrimidine-7-carboxylate;

3-bromo-5-[3-(1H-imidazol-4-yl) imidazo[1,2-a]pyrimidin-2-yl]-1H-1,2,4-triazole;

5-[6-fluoro-3-(1H-pyrazol-4-yl) imidazo[1,2-a]pyrimidin-2-yl]-3-(trifluoromethyl)-1H-1,2,4-triazole;

5-[6-chloro-3-(1H-imidazol-5-yl) imidazo[1,2-a]pyrimidin-2-yl]-3-(trifluoromethyl)-1H-1,2,4-triazole;

3-(difluoromethyl)-5-[3-(1H-imidazol-5-yl) imidazo[1,2-a]pyrimidin-2-yl]-1H-1,2,4-triazole;

5-[3-(1H-imidazol-5-yl)-6-(trifluoromethyl) imidazo[1,2-a]pyrimidin-2-yl]-3-(trifluoromethyl)-1H-1,2,4-triazole;

5-[6-bromo-3-(1H-imidazol-5-yl) imidazo[1,2-a]pyrimidin-2-yl]-3-(trifluoromethyl)-1H-1,2,4-triazole;

3-(difluoromethyl)-5-[3-(1H-imidazol-5-yl)-7-(trifluoromethyl) imidazo[1,2-a]pyrimidin-2-yl]-1H-1,2,4-triazole;

3-bromo-5-[3-(1H-imidazol-5-yl)-7-(trifluoromethyl) imidazo[1,2-a]pyrimidin-2-yl]-1H-1,2,4-triazole;

5-[3-(1H-pyrazol-4-yl)-7-(trifluoromethyl) imidazo[1,2-a]pyrimidin-2-yl]-3-(trifluoromethyl)-1H-1,2,4-triazole;

5-[7-(difluoromethyl)-3-(1H-imidazol-5-yl) imidazo[1,2-a]pyrimidin-2-yl]-3-(trifluoromethyl)-1H-1,2,4-triazole;

5-[3-(1H-imidazol-5-yl)-7-(trifluoromethyl) imidazo[1,2-a]pyrimidin-2-yl]-1H-1,2,4-triazole;

5-[3-(1H-imidazol-5-yl)-7-(trifluoromethyl) imidazo[1,2-a]pyrimidin-2-yl]-3-methyl-1H-1,2,4-triazole;

methyl 3-(1H-imidazol-4-yl)-2-[3-(trifluoromethyl)-1H-1,2,4-triazol-5-yl]imidazo[1,2-a]pyrimidine-7-carboxylate;

3-(1H-imidazol-4-yl)-2-[3-(trifluoromethyl)-1H-1,2,4-triazol-5-yl]imidazo[1,2-a]pyrimidine-7-carboxylic acid;

3-(difluoromethoxy)-5-[3-(1H-imidazol-5-yl) imidazo[1,2-a]pyrimidin-2-yl]-1H-1,2,4-triazole;

5-[6-(difluoromethyl)-3-(1H-imidazol-4-yl) imidazo[1,2-a]pyrimidin-2-yl]-3-(trifluoromethyl)-1H-1,2,4-triazole;

5-[6-fluoro-3-(1H-imidazol-5-yl)-7-(trifluoromethyl) imidazo[1,2-a]pyrimidin-2-yl]-3-(trifluoromethyl)-1H-1,2,4-triazole;

5-[6-chloro-3-(1H-imidazol-5-yl)-7-(trifluoromethyl) imidazo[1,2-a]pyrimidin-2-yl]-3-(trifluoromethyl)-1H-1,2,4-triazole;

5-[3-(2-methyl-1H-imidazol-4-yl) imidazo[1,2-a]pyrimidin-2-yl]-3-(trifluoromethyl)-1H-1,2,4-triazole;

5-[3-(1-methyl-1H-pyrazol-4-yl) imidazo[1,2-a]pyrimidin-2-yl]-3-(trifluoromethyl)-1H-1,2,4-triazole; and 3-bromo-5-[6-fluoro-3-(1H-imidazol-4-yl) imidazo[1,2-a]pyrimidin-2-yl]-1H-1,2,4-triazole.

22. A compound according to claim 1, which is

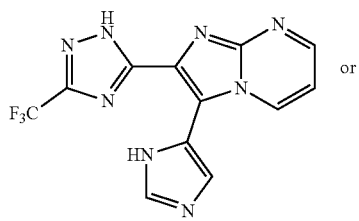 or

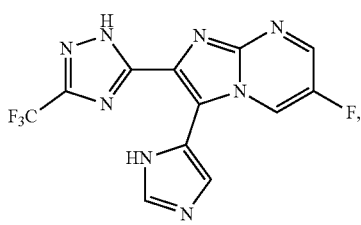

or a tautomer thereof, or a pharmaceutically acceptable salt of said compound or tautomer thereof.

23. A compound according to claim 1, which is

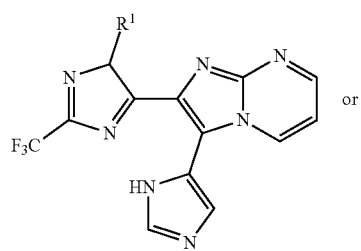 or

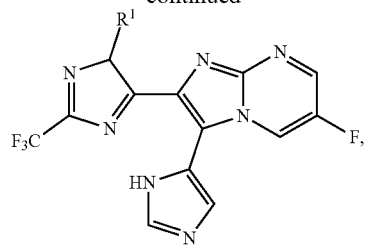

wherein $R^1$ is a prodrug moiety selected from the group consisting of —CH($R^c$)O—P(O)(O$R^d$) (O$R^e$), —CH($R^c$)O—C(O)—$C_{1-6}$ alkylene-O—P(O)(O$R^d$) (O$R^e$), —CH($R^c$)O—C(O)—$C_{1-6}$ alkylene-P(O)(O$R^d$) (O$R^e$), —CH($R^c$)O—C(O)—$C_{1-6}$ alkylene-CO$_2$H, —CH($R^c$)O—C(O) $R^d$, —CH($R^c$)O—C(O)O—$C_{1-6}$ alkylene-CO$_2$H, —CH($R^c$)O—C(O)—$C_{1-6}$ alkylene-N$R^d R^e$, —CH($R^c$)O—C(O)O—$C_{1-6}$ alkylene-N$R^d R^e$, —C(O) $R^d$, —CH($R^c$)O—C(O)—$C_{1-6}$ alkylene-heterocycloalkyl, —CH($R^c$)O—C(O)—$C_{1-6}$ alkylene-heterocycloalkyl and —C$R^d R^e$—O—(C(O)—N$R^d$-heteroarylene-CH$_2$O—C(O)—CH$_2$—N$R^d R^e$;

wherein $R^c$ is independently selected from hydrogen and methyl;

$R^d$ and $R^e$ are each independently hydrogen or $C_{1-6}$ alkyl;

each heterocycloalkyl is 4- to 6-membered and contains one or two heteroatoms independently selected from N, O and S; and each heteroarylene is 5- or 6-membered and contains one or two heteroatoms independently selected from N, O and S;

or a tautomer thereof, or a pharmaceutically acceptable salt of said compound or tautomer thereof.

24. A compound according to claim 23, which is

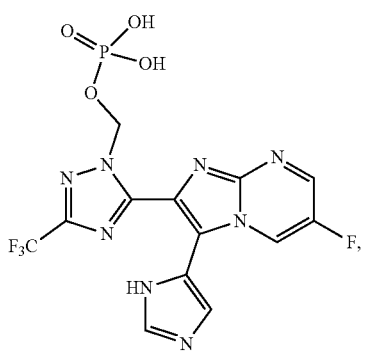 [SMILES: O=P(O)(O)OCn1nc(C(F)(F)F)nc1-c1nc2ncc(F)cn2c1-c1cnc[nH]1]

or a tautomer thereof, or a pharmaceutically acceptable salt of said compound or tautomer thereof.

25. A pharmaceutical composition comprising (a) a compound or a tautomer thereof, or a pharmaceutically acceptable salt of said compound or tautomer thereof according to claim 1; and (b) a pharmaceutically acceptable excipient.

26. The compound according to claim 22, which is

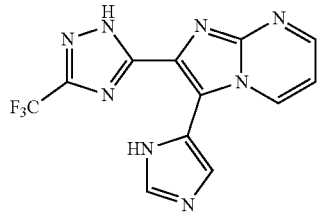 or

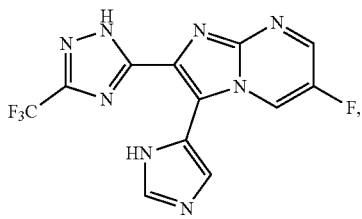

or a tautomer thereof.

27. The compound according to claim 22, which is

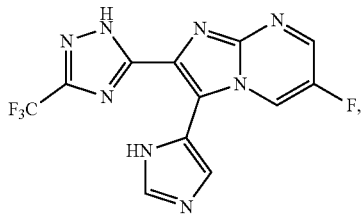

or a tautomer thereof.

28. A compound according to claim 24, which is

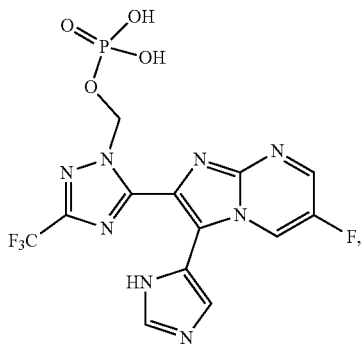 [SMILES: O=P(O)(O)OCn1nc(C(F)(F)F)nc1-c1nc2ncc(F)cn2c1-c1cnc[nH]1]

or a tautomer thereof.

* * * * *